United States Patent
Ravinder et al.

(10) Patent No.: US 9,879,283 B2
(45) Date of Patent: Jan. 30, 2018

(54) CRISPR OLIGONUCLEOTIDES AND GENE EDITING

(71) Applicants: LIFE TECHNOLOGIES CORPORATION, Carlsbad, CA (US); THERMO FISHER SCIENTIFIC GENEART GMBH, Regensburg (DE)

(72) Inventors: Namritha Ravinder, San Diego (CA); Korbinian Heil, Munich (DE); Yizhu Guo, Castro Valley, CA (US); Xiquan Liang, Escondido, CA (US); Robert Potter, San Marcos, CA (US); Sanjay Kumar, Carlsbad, CA (US)

(73) Assignees: Life Technologies Corporation, Carlsbad, CA (US); Thermo Fisher Scientific GENEART GmbH, Regensburg (DE)

( * ) Notice: Subject to any disclaimer, the term of this patent is extended or adjusted under 35 U.S.C. 154(b) by 0 days.

(21) Appl. No.: 14/879,872

(22) Filed: Oct. 9, 2015

(65) Prior Publication Data

US 2016/0102322 A1 Apr. 14, 2016

Related U.S. Application Data

(60) Provisional application No. 62/061,961, filed on Oct. 9, 2014, provisional application No. 62/101,787, filed on Jan. 9, 2015, provisional application No. 62/218,826, filed on Sep. 15, 2015.

(51) Int. Cl.
| | | |
|---|---|---|
| *C12Q 1/68* | (2006.01) | |
| *C12N 15/90* | (2006.01) | |
| *C12N 15/10* | (2006.01) | |
| *C12P 19/34* | (2006.01) | |
| *C12N 15/11* | (2006.01) | |

(52) U.S. Cl.
CPC ......... *C12N 15/907* (2013.01); *C12N 15/102* (2013.01); *C12N 15/11* (2013.01); *C12P 19/34* (2013.01); *C12Q 1/686* (2013.01); *C12N 2310/3519* (2013.01)

(58) Field of Classification Search
CPC ....................................................... C12P 19/34
See application file for complete search history.

(56) References Cited

U.S. PATENT DOCUMENTS

| | | | |
|---|---|---|---|
| 5,334,575 A | 8/1994 | Noonan et al. | |
| 5,888,795 A | 3/1999 | Hamilton | |
| 7,070,941 B2 | 7/2006 | Zhao et al. | |
| 7,375,234 B2 | 5/2008 | Sharpless et al. | |
| 2002/0031762 A1* | 3/2002 | Merryman | C12N 15/1062 435/6.16 |
| 2011/0059502 A1 | 3/2011 | Chalasani | |
| 2013/0046084 A1 | 2/2013 | Brown et al. | |
| 2015/0225773 A1* | 8/2015 | Farmer | C12N 15/1003 506/26 |

FOREIGN PATENT DOCUMENTS

| | | |
|---|---|---|
| WO | WO1992/007949 | 5/1992 |
| WO | WO1994/012632 | 6/1994 |

OTHER PUBLICATIONS

Corey et al. Primary structure of a methionine tranfer RNA from *Escherichia coli*. Nature, vol. 220, pp. 1039-1040, Dec. 1968.*
Paetzold et al. In situ overlap and sequence synthesis during DNA assembly. ACS Synthetic Biology, vol. 2, No. 12, pp. 750-755, 2013, Epub Nov. 6, 2013, including pp. 1/11-11/11 Supporting Information.*
Cho, et al., "Heritable Gene Knockout in Caenorhabditis elegans by Direct Injection of Cas9-sgRNA Ribonucleoproteins", *Genetics*, vol. 195, No. 3, Nov. 2013, 1177-1180.
Cho, et al., "Targeted genome engineering in human cells with the Cas9 RNA-guided endonuclease", *Nature Biotechnology*, vol. 31, 2013, 230-232.
Cong, et al., "Multiplex genome engineering using CRISPR/Cas systems", *Science*, vol. 339, No. 6121, Feb. 15, 2013, 819-823.
Fu, et al., "High-frequency off-target mutagenesis induced by CRISPR-Cas nucleases in human cells", *Nature Biotechnology*, vol. 31, 2013, 822-826.
Geu-Flores, et al., "USER fusion: a rapid and efficient method for simultaneous fusion and cloning of multiple PCR products", *Nucleic Acids Research*, vol. 35, No. 7, Mar. 27, 2007, e55 (1-6).
Guilinger, et al., "Fusion of catalytically inactive Cas9 to FokI nuclease improves the specificity of genome modification", *Nature Biotechnology*, vol. 32, 2014, 577-582.
Heckman, et al., "Gene splicing and mutagenesis by PCR-driven overlap extension", *Nature Protocols*, vol. 2, No. 4, 924-932, 2007.
Jiang, et al., "RNA-guided editing of bacterial genomes using CRISPR-Cas systems", *Nature Biotechnology*, vol. 31, No. 3, Mar. 2013, 233-239.
Kabadi, et al., "Multiplex CRISPR/Cas9-based genome engineering from a single lentiviral vector", *Nucleic Acids Research*, vol. 42, No. 19, Oct. 29, 2014, e147 (1-11).
Kearns, et al., "Cas9 effector-mediated regulation of transcription and differentiation in human pluripotent stem cells", *Development*, vol. 141, 2014, 219-223.
Kim, et al., "Highly efficient RNA-guided genome editing in human cells via delivery of purified Cas9 ribonucleoproteins", *Genome Research*, vol. 24, No. 6, Jun. 2014, 1012-1019.
Lanar, et al., "Expression-PCR (E-PCR): Overview and Applications", *Genome Research*, vol. 4, Jan. 1, 1994, S92-S96.
Lieber, et al., "High level gene expression in mammalian cells by a nuclear T7-phage RNA polymerase", *Nucleic Acids Research*, vol. 17, No. 21, 1989, 8485-8493.
Logel, et al., "Synthesis of CRNA Probes from PCR-Generated DNA", *Biotechniques*, vol. 13, No. 4, Jan. 1, 1992, 604-606, 608.
Mali, et al., "RNA-guided human genome engineering via Cas9.", *Science*, vol. 339, No. 6121, Feb. 15, 2013, 823-826.
PCT/US2015/054986, Invitation to Pay Additional Fees mailed Jan. 13, 2016, 1-14.

(Continued)

*Primary Examiner* — Jennifer Dunston

(57) ABSTRACT

The present disclosure generally relates to compositions and methods for the genetic modification of cells. In particular, the disclosure relates to CRISPR reagents and the use of such reagents.

9 Claims, 43 Drawing Sheets

(56) References Cited

OTHER PUBLICATIONS

Roche, "Generation of linear expression elements by PCR", *Roche Applied Science, Rapid Translation System Application Note No. 9/2002*, www.5prime.com/media/434179/app_09.pdf, Sep. 1, 2002, 1-6.

Rouillard, et al., "Gene2Oligo: Oligonucleotide Design for in Vitro Gene Synthesis", *Nucleic Acids Research*, vol. 32, Jul. 2004, W176-W180.

Sakuma, et al., "Multiplex genome engineering in human cells using all-in-one CRISPR/Cas9 vector system", *Scientific Reports*, vol. 4, 2014, 5400 (1-6).

Sander, et al., "CRISPR-Cas systems for editing, regulating and targeting genomes", *Nature Biotechnology*, vol. 32, No. 4, Apr. 2014, 347-355.

Shao, et al., "CRISPR/Cas-mediated genome editing in the rat via direct injection of one-cell embryos", *Nature Protocols*, vol. 9, No. 10, 2014, 2493-2512.

Sung, et al., "Highly efficient gene knockout in mice and zebrafish with RNA-guided endonucleases", *Genome Research*, vol. 24, Nov. 2014, 125-131.

Tsai, et al., "Dimeric CRISPR RNA-guided FokI nucleases for highly specific genome editing", *Nature Biotechnology*, vol. 32, 2014, 569-576.

Tsai, et al., "Multiplex genome engineering in human cells using all-in-one CRISPR/Cas9 vector system", *Nature Biotechnology*, vol. 33, Feb. 2015, 187-197.

Wang, et al., "One-Step Generation of Mice Carrying Mutations in Multiple Genes by CRISPR/Cas-Mediated Genome Engineering", *Cell*, vol. 153, No. 4, May 9, 2013, 910-918.

Zuris, et al., "Cationic lipid-mediated delivery of proteins enables efficient protein-based genome editing in vitro and in vivo", *Nature Biotechnology*, vol. 33, No. 1, Jan. 2015, 73-80.

Clontech Laboratories, Inc., "Guide-it sgRNA In Vitro Transcription and Screening System User Manual" Cat. Nos. 631438, 631439 & 631440, 2014, 12 pages.

Morrell, M. et al. "Manipulating the Genome: Advanced Tools for CRISPR/Cas9 Genome Editing and Analysis" Takara Clontech, Scientific Poster, Jan. 2015, 1 page.

Quinn, et al. "A Streamline method for production, screening, and application of sRNAs for CRISPR/Cas gene editing", The American Society of Gene and Cell Therapy, Molecular Therapy, vol. 22, Supp. 1, #336, May 2014, 1 page.

* cited by examiner

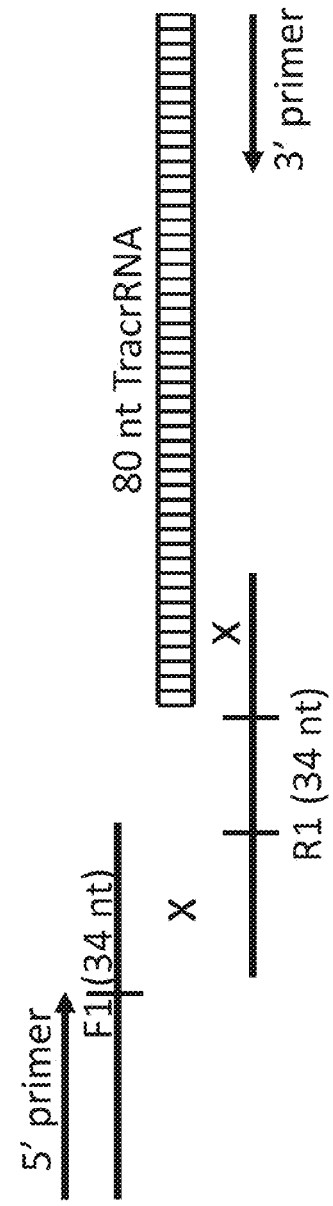
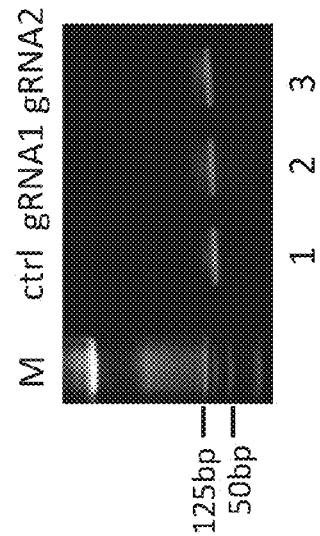
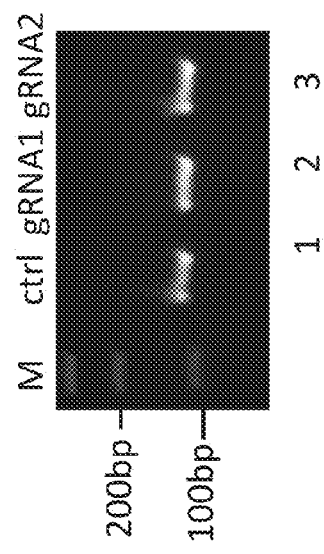
FIG. 20A
FIG. 20B
FIG. 20C

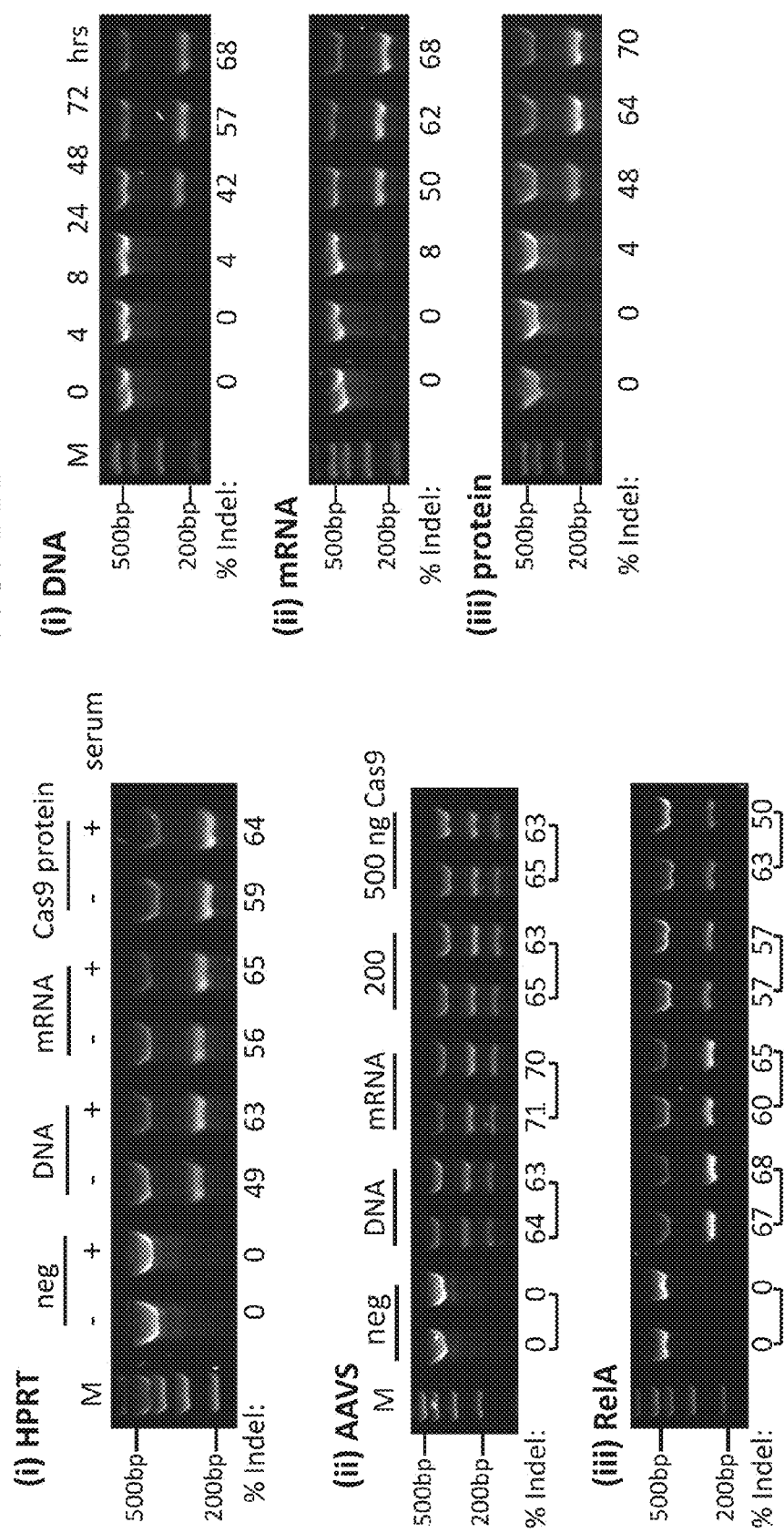

CRISPR OLIGONUCLEOTIDES AND GENE EDITING

PRIORITY

This application claims the benefit of U.S. Provisional Application Nos. 62/061,961, filed Oct. 9, 2014, 62/101,787, filed Jan. 9, 2015 and 62/218,826 filed Sep. 15, 2015, whose disclosure is incorporated by reference in its entirety.

SEQUENCE LISTING

The instant application contains a Sequence Listing which has been submitted electronically in ASCII format and is hereby incorporated by reference in its entirety. Said ASCII copy, created on Oct. 7, 2015, is named LT00948_SL.txt and is 98,513 bytes in size.

FIELD

The present disclosure generally relates to compositions and methods for the genetic modification of cells. In particular, the disclosure relates to CRISPR reagents and the use of such reagents.

BACKGROUND

A number of genome-editing systems, such as designer zinc fingers, transcription activator-like effectors (TALEs), CRISPRs, and homing meganucleases, have been developed. One issue with these systems is that they require a both the identification of target sites for modification and the designing of a reagents specific for those sites, which is often laborious and time consuming. In one aspect, the invention allows for the efficient design, preparation, and use of genome editing reagents.

SUMMARY

The present disclosure relates, in part, to compositions and methods for editing of nucleic acid molecules. There exists a substantial need for efficient systems and techniques for modifying genomes. This invention addresses this need and provides related advantages.

CRISPR systems do not require the generation of customized proteins to target specific sequences but rather a single Cas enzyme that can be directed to a target nucleotide sequence (a target locus) by a short RNA molecule with sequence complementarity to the target.

The present disclosure is directed, in part, to CRISPR editing system modifications that increase the usefulness of these systems. One problem associated with gene editing systems is the amount of time and labor required to design and produce target locus specific gene editing reagents. The invention provides, in part, compositions and methods for the efficient, cost-effective production of CRISPR components.

In some specific aspects, the invention is directed to three types of sequence specific nucleic acid binding activities. Using the Cas9 proteins as an example, these three systems include those where Cas9 proteins are employed with (1) double-stranded cutting activity (e.g., one Cas9 protein gene editing systems), (2) nickase activity (e.g., two Cas9 protein gene editing systems, referred to as "dual nickase" systems), and (3) no cutting activity but with the retention of nucleic acid binding activity (e.g., "dead" Cas9, referred to as dCas9, useful, for example, for gene repression, gene activation, DNA methylation, etc.).

In some aspects, the invention provides methods for producing nucleic acid molecules, including methods comprising performing polymerase chain reactions (PCR) in reaction mixtures containing (i) a double-stranded nucleic acid segment and (ii) at least one oligonucleotide capable of hybridizing to nucleic acid at one terminus of the double-stranded nucleic acid segment, wherein the nucleic acid molecule is produced by the PCR reaction, and wherein the product nucleic acid molecule contains at or near one terminus a promoter suitable for in vitro transcription. In some instances, nucleic acid molecules produced by PCR reaction encode RNA molecules of lengths from about 20 to about 300 (e.g., from about 20 to about 250, from about 20 to about 200, from about 35 to about 150, from about 70 to about 150, from about 40 to about 200, from about 50 to about 200, from about 60 to about 200, from about 60 to about 125, etc.) nucleotides.

RNA molecules generated by methods of the invention (e.g., ligation) or encoded by nucleic acid molecules produced by methods of the invention may contain a region (e.g., from about 10 to about 50, from about 20 to about 50, from about 30 to about 50, from about 15 to about 40, from about 15 to about 30, etc. nucleotides) of sequence complementarity to a target locus. Such RNA molecules may also form one or more (e.g., two, three, four, five, etc.) hairpin turn under physiological conditions (e.g., 37° C., 10 mM Tris-HCl, pH 7.0, 0.9% sodium chloride). Further, such RNA molecules may be a CRISPR RNA such as a guide RNA molecule.

In additional aspects, the invention includes methods for producing nucleic acid molecules, these methods comprising performing polymerase chain reactions (PCR) in reaction mixtures comprising (i) a double-stranded nucleic acid segment comprising a first terminus and a second terminus, (ii) a first oligonucleotide comprising a first terminus and a second terminus, wherein the second terminus of the first oligonucleotide is capable of hybridizing to the first terminus of the double-stranded nucleic acid segment, and (iii) a second oligonucleotide comprising a first terminus and a second terminus, wherein the second terminus of the second oligonucleotide is capable of hybridizing to the first terminus of the first oligonucleotide, to produce the nucleic acid molecule. In some instances, the product nucleic acid molecule will contains one or more (e.g., one, two, three, etc.) promoter suitable for in vitro transcription at or near one terminus. Also, in some instances, the product nucleic acid molecule will encode one or more CRISPR RNA (e.g., a crRNA molecule, a tracrRNA molecule, a guide RNA molecule, etc.). In some instances, reaction mixtures further comprises a first primer and a second primer, wherein the first primer is capable of hybridizing at or near the first terminus of the second oligonucleotide and the second primer is capable of hybridizing at or near the second terminus of the double-stranded nucleic acid segment.

The invention also includes methods for producing nucleic acid molecules, the methods comprising performing polymerase chain reactions in reaction mixtures containing (i) a first double-stranded nucleic acid segment comprising a first terminus and a second terminus, (ii) a second double-stranded nucleic acid segment comprising a first terminus and a second terminus, and (iii) at least one oligonucleotide comprising a first terminus and a second terminus, wherein the first terminus of the oligonucleotide is capable of hybridizing to nucleic acid at the first terminus of the first double-stranded nucleic acid segment to produce the nucleic acid molecule, and wherein the second terminus of the oligonucleotide is capable of hybridizing to nucleic acid at the second terminus of the second double-stranded nucleic acid segment to produce the nucleic acid molecule. In some instances, the product nucleic acid molecule will contain one or more promoter suitable for in vitro transcription at or near one terminus.

The invention further includes methods for producing nucleic acid molecules, these method comprising performing polymerase chain reactions in reaction mixtures containing (i) a first double-stranded nucleic acid segment comprising a first terminus and a second terminus, (ii) a second double-stranded nucleic acid segment comprising a first terminus and a second terminus, (iii) a first oligonucleotide comprising a first terminus and a second terminus, and (iv) a second oligonucleotide comprising a first terminus and a second terminus, wherein the second terminus of the first oligonucleotide is capable of hybridizing to nucleic acid at the first terminus of the second double-stranded nucleic acid segment, wherein the second terminus of the second oligonucleotide is capable of hybridizing to the first terminus of the first oligonucleotide, wherein the second terminus of the second oligonucleotide is capable of hybridizing to the first terminus of the second double-stranded nucleic acid segment. In some instances, the product nucleic acid molecules contain one or more promoter suitable for in vitro transcription at or near (e.g., within 10 base pairs) one terminus.

The invention also includes methods for producing CRISPR RNA molecules, these methods comprise contacting two or more linear RNA segments with each other under conditions that allow for the 5' terminus of a first RNA segment to be covalently linked with the 3' terminus of a second RNA segment to form the CRISPR RNA. In some instances, the CRISPR RNA molecules are separated from reaction mixture components (e.g., by column chromatography, such as by high-performance liquid chromatography).

The invention additionally includes methods for producing a guide RNA molecules, these method comprise: (a) separately producing a crRNA molecule and a tracrRNA molecule and (b) contacting the crRNA molecule and the tracrRNA molecule with each other under conditions that allow for the covalently linking of the 3' terminus of the crRNA to the 5' terminus of the tracrRNA to produce the guide RNA molecule. Guide RNA molecules may have a region of sequence complementarity of at least 10 (e.g., from about 10 to about 50, from about 10 to about 40, from about 10 to about 35, from about 10 to about 30, from about 10 to about 25, from about 15 to about 25, from about 17 to about 22, etc.) nucleotides to a target locus. In many instances, the target locus is a naturally occurring chromosomal locus in a eukaryotic cell.

The invention also includes compositions comprising two RNA molecules connected by a triazole group, wherein one of the RNA molecules has a region of sequence complementarity of at least 10 nucleotides to a target locus.

In some aspects, the invention is directed to methods for gene editing at a target locus within a cell, these methods comprise introducing into the cell at least one CRISPR protein and at least one CRISPR RNA, wherein the at least one CRISPR RNA has a region of sequence complementarity of at least 10 base pairs to the target locus. In some instances, a linear DNA segment that has sequence homology at both termini to the target locus is also introduced into the cell. In some instances, one of the at least one CRISPR proteins is a Cas9 protein. This Cas9 protein may have the ability to make a double-stranded cut in DNA or to nick double-stranded DNA. In some instances, two Cas9 proteins are introduced into the cells, where one Cas9 protein has a mutation that renders to HNH domain inactive and the other Cas9 protein has a mutation that renders to RuvC domain rendering that domain inactive. In some instances, two RNA molecules (e.g., CRISPR RNA molecules), each with sequence complementarity to different target sequences, are introduced into the cell. Further, these different target sequences may be located within forty (e.g., from about 2 to about 40, from about 2 to about 25, from about 2 to about 20, from about 2 to about 15, from about 2 to about 10, from about 2 to about 8, from about 4 to about 20, from about 4 to about 15, from about 4 to about 10, from about 6 to about 20, etc.) base pairs of each other. Distances between sequences may be measured in reference to the double-stranded cut or nick site. In such instances, target sequences may overlap.

The invention further includes cells containing one or more CRISPR system components and cells made by methods set out herein. For example, the invention includes cells into which CRISPR complexes have been introduced (e.g., cells that contain (1) plasmids encoding Cas9 and guide RNA, (2) Cas9 mRNA and guide RNA, etc.). The invention further includes cells containing mRNA encoding dCas9 and fusion proteins thereof, as well as cells that have been modified by methods of the invention (e.g., cells that have undergone cleavage and relegation of cellular DNA with and without inserts at the cleavage site) that either contain or no longer contain one or more CRISPR system component.

BRIEF DESCRIPTION OF THE DRAWINGS

For a more complete understanding of the principles disclosed herein, and the advantages thereof, reference is now made to the following descriptions taken in conjunction with the accompanying drawings, in which:

FIG. 3 discloses SEQ ID NOS 58-60, respectively, in order of appearance.

FIG. 6 guide RNA disclosed as SEQ ID NO: 58.

FIG. 8 guide RNA disclosed as SEQ ID NO: 58.

Figure 12A:
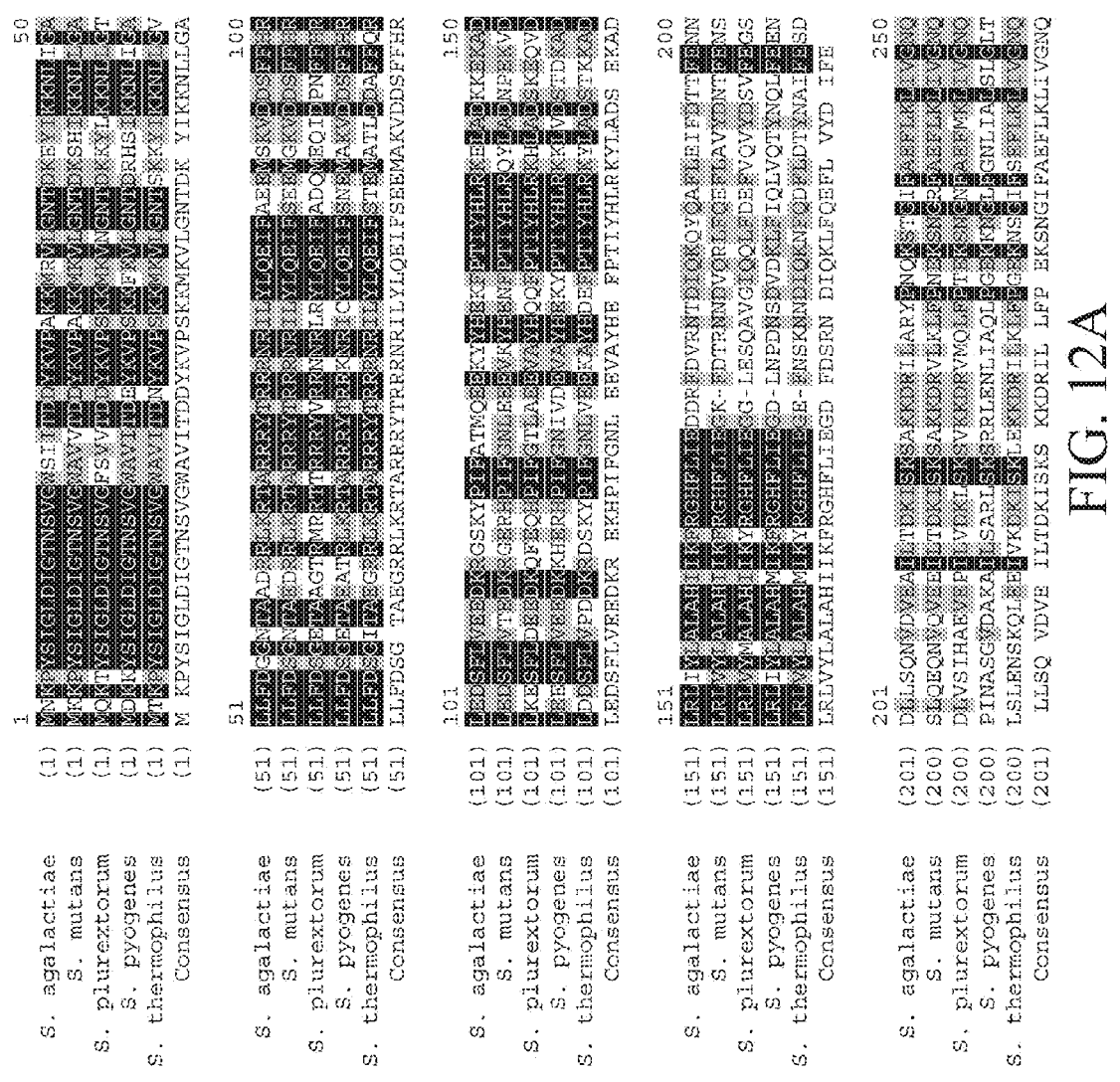
Figure 12B:
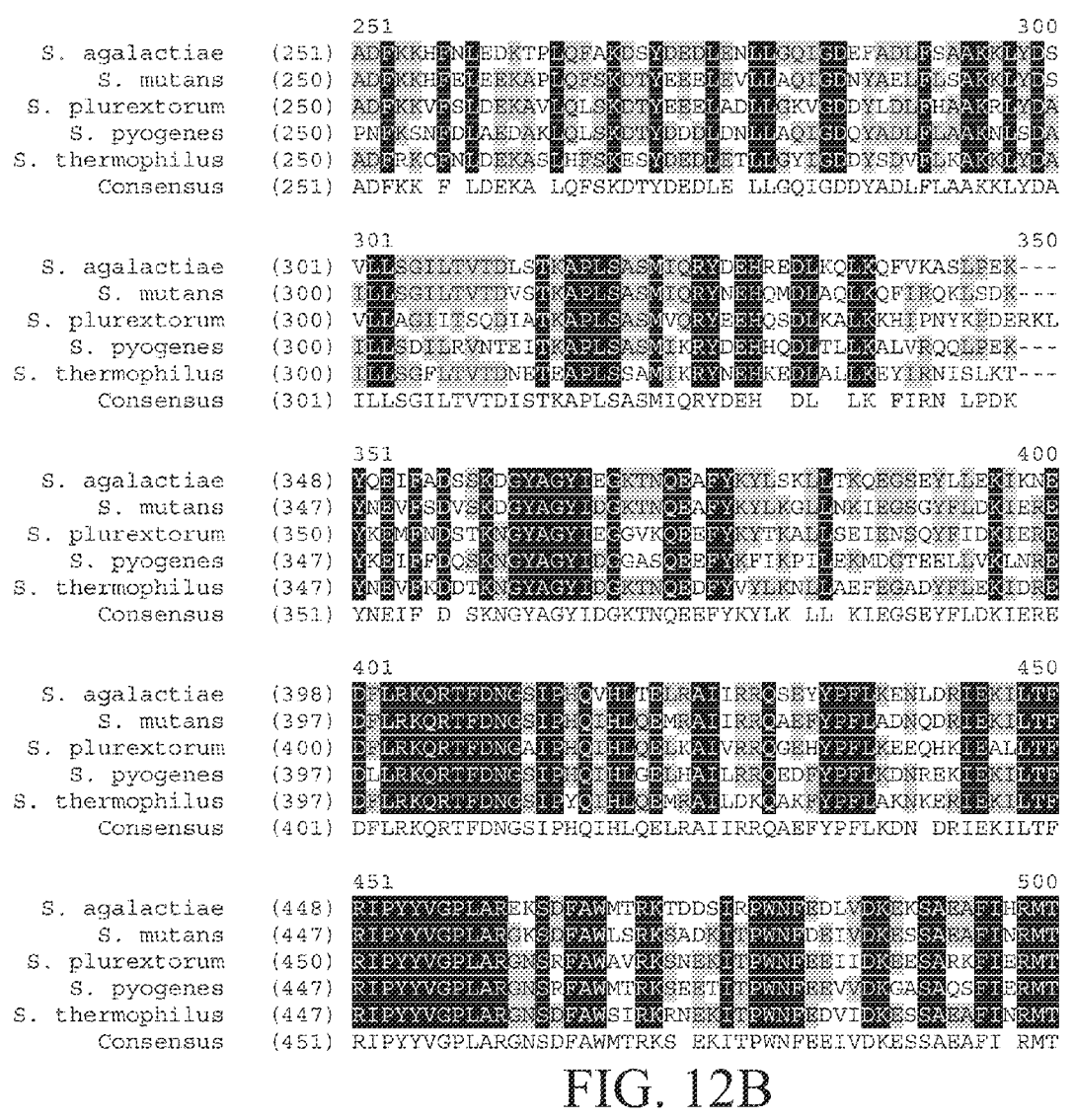
Figure 12C:
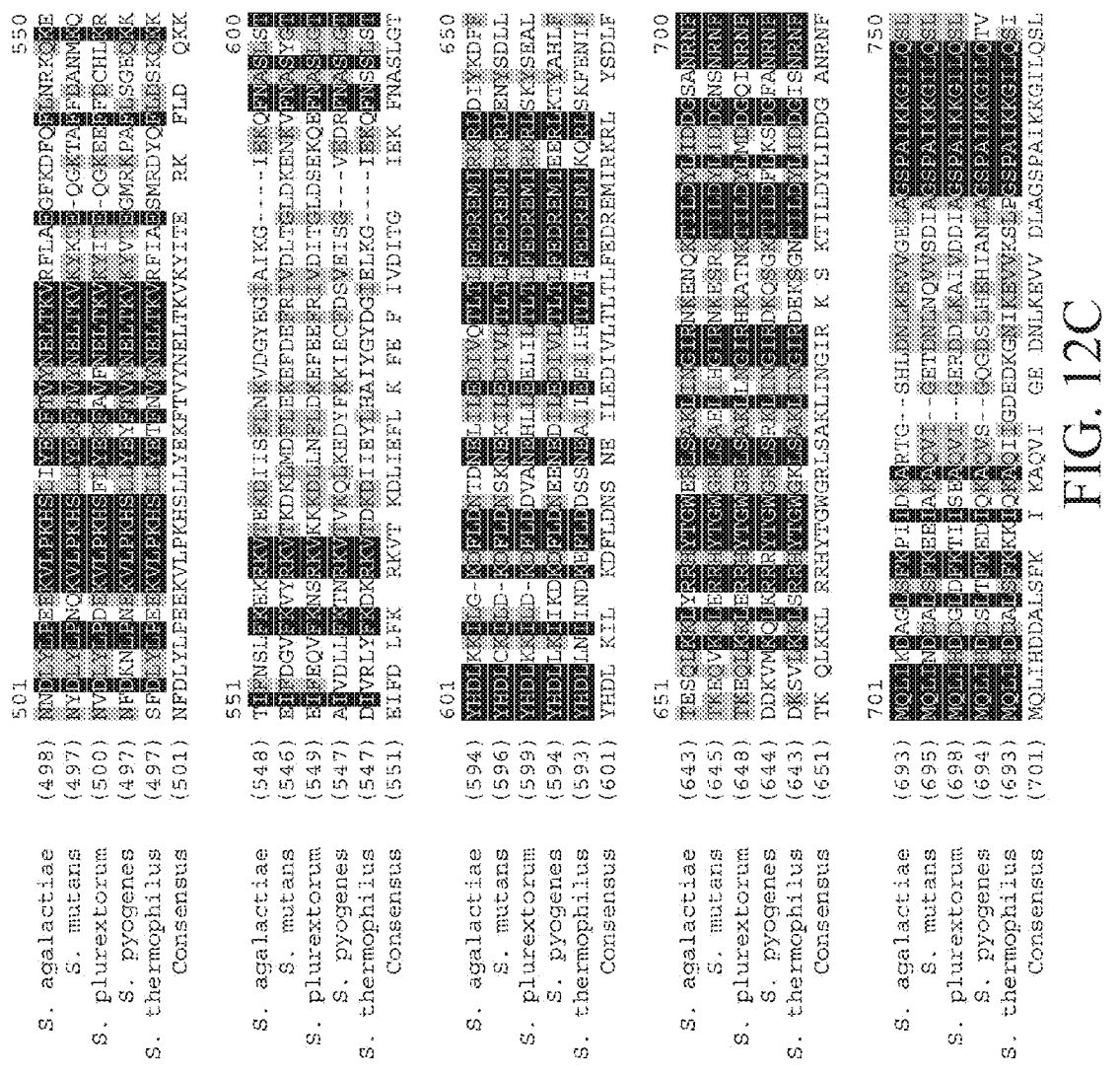
Figure 12D:
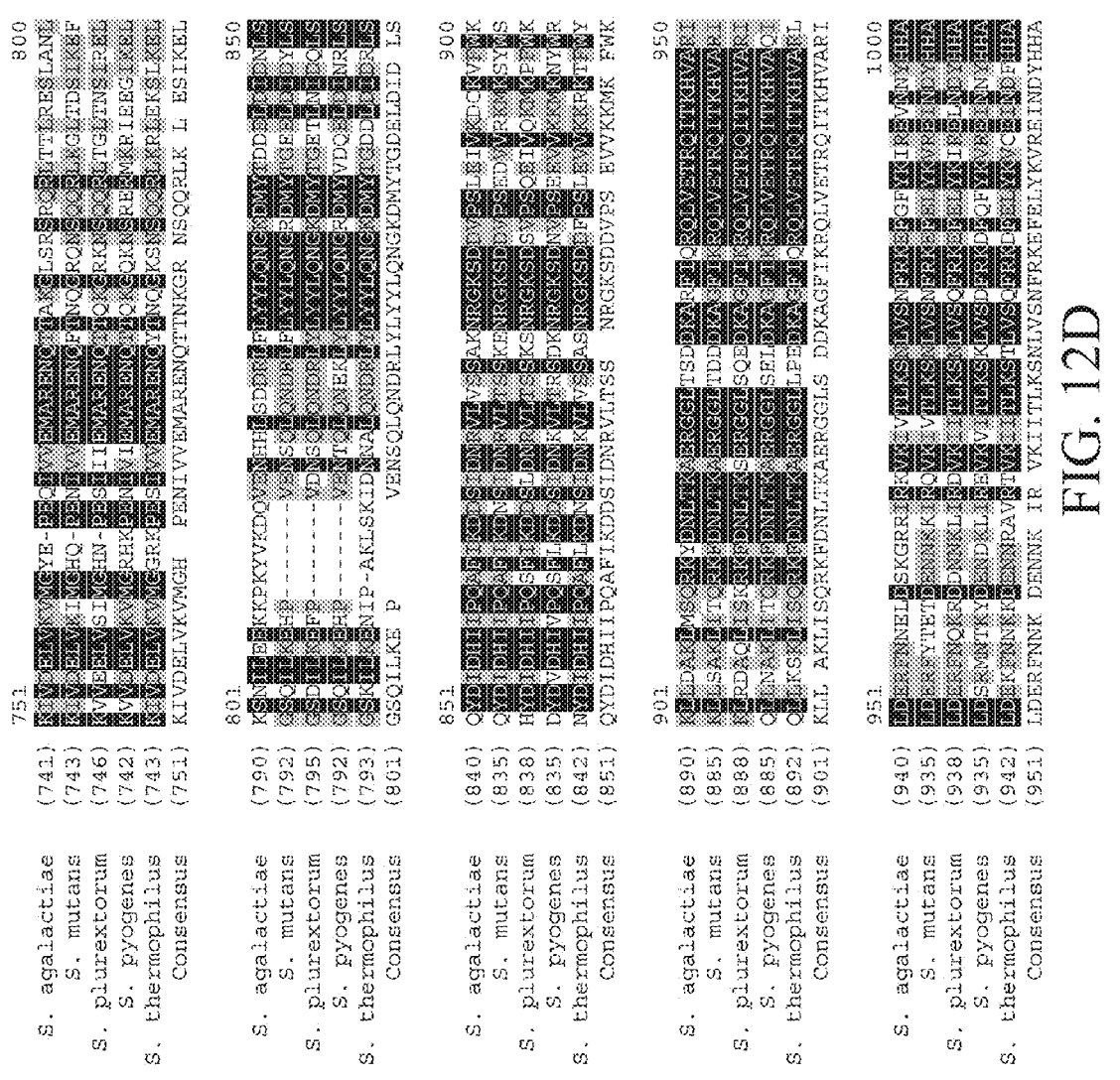
Figure 12E:
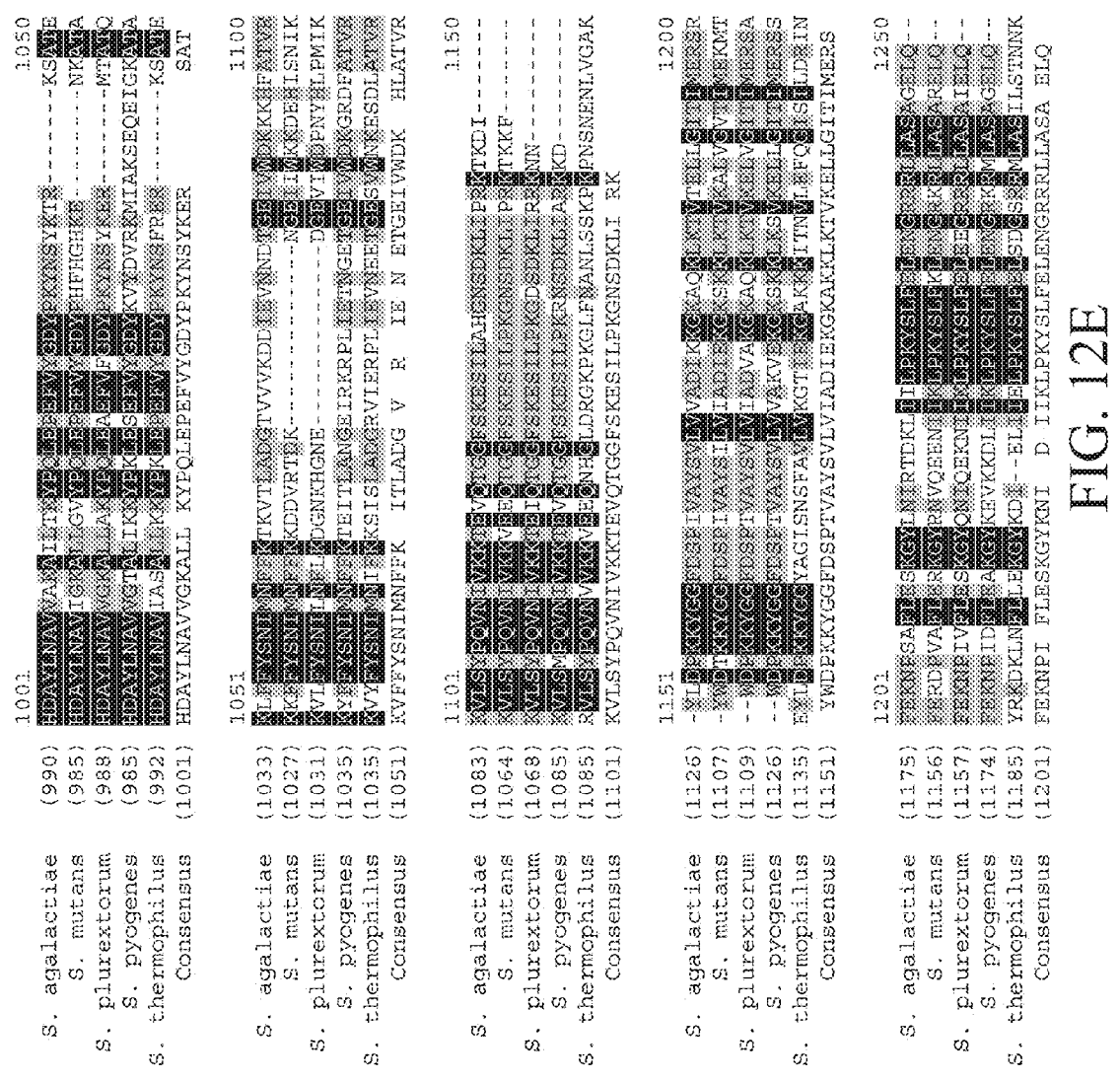
Figure 12F:
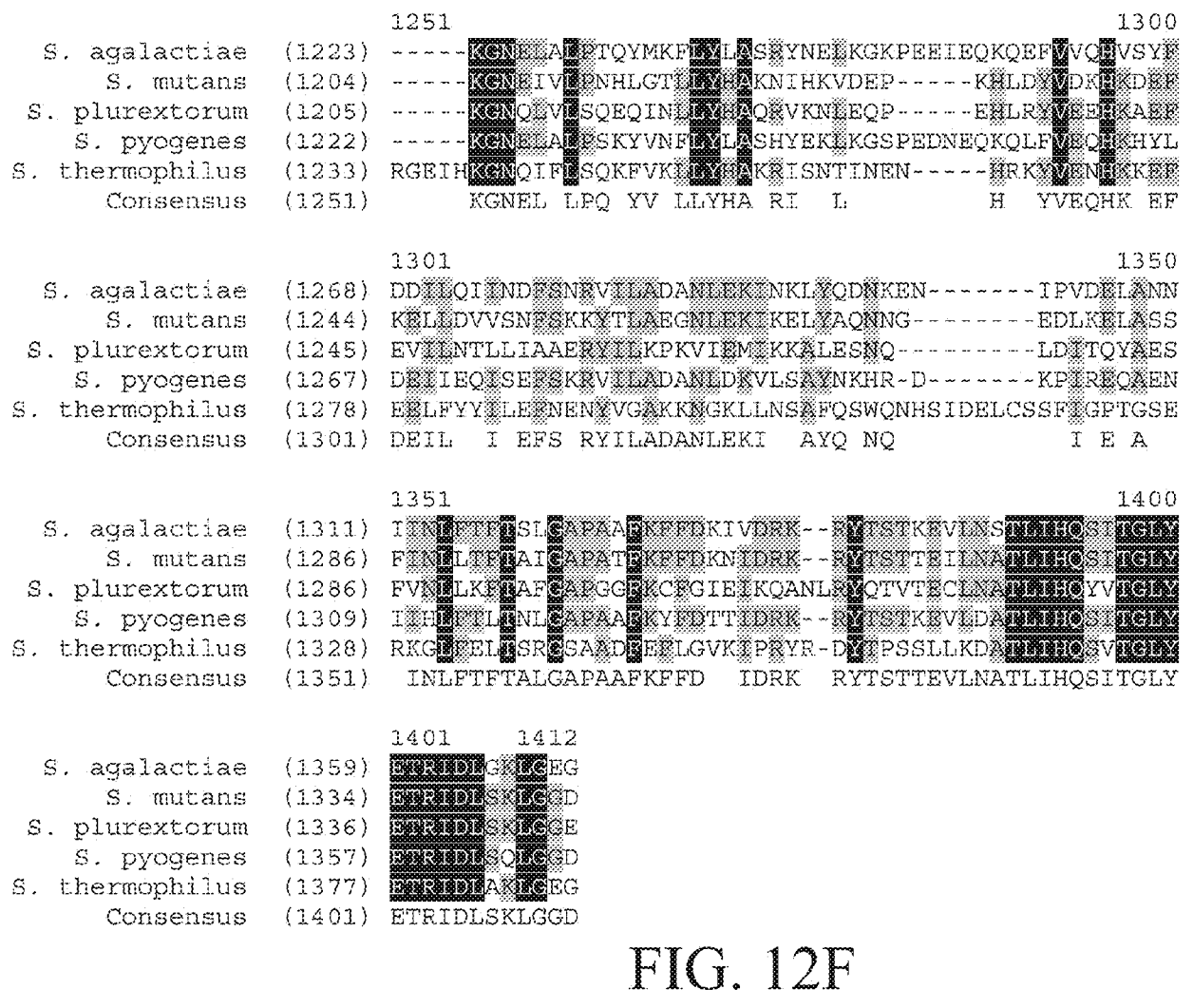

FIGS. 12A-12F shows an alignment of Cas9 proteins of from five *Streptococcus* species (SEQ ID NOS 61-63, 1 and 64, respectively, in order of appearance). Identical amino acids are shown as white characters on a black background. Conservative amino acid alterations are shown as black letters on a gray background.

FIG. 19 discloses SEQ ID NO: 65.

FIGS. 20A-20D. Design and synthesis of gRNA. (FIG. 20A) Design of oligonucleotide pool. The pool consists of one 80 nucleotide tracerRNA PCR fragment, two end primers, and two 34 bp oligonucleotides with 15 bp overlap. (FIG. 20B) One-step synthesis of gRNA template. Four DNA oligonucleotides and one PCR fragment were assembled in a single tube and the PCR product was analyzed by agarose gel electrophoresis (Lanes 2 and 3). A gRNA template prepared from all-in-one plasmid served as control (Lane 1). (FIG. 20C) In vitro transcription. Aliquots of PCR product (Lanes 2 and 3) along with the control (Lane 1) were subjected to in vitro transcription. The resulting product was analyzed by denaturing gel. (FIG. 20D: Error rates in synthetic gRNA templates) The DNA template of gRNA was synthesized using the standard gene synthesis approach with a set of short oligonucleotides (GS). Alternatively, the oligonucleotide pool described above was used for PCR assembly. Two standard desalted end primers (15 bp) and HPLC or PAGE-purified end primers (15 bp*) were tested in assembly PCR reaction. The synthetic gRNA templates as well as control gRNA template from the 'all-in-one' plasmid (plasmid) were cloned into a TOPO vector. For each individual template, 96 colonies were randomly picked for sequencing.

FIGS. 21A-21D. Lipid-mediated transfection. (FIG. 21A: DNA vs. mRNA vs. Protein) Three separate genomic loci (HPRT, AAVS or RelA) were edited via Cas9 plasmid DNA, mRNA or protein transfection of HEK293FT cells. For the HPRT target, transfection was performed in the presence or absence of serum. The efficiency of genome modification was determined by Genomic Cleavage assay. (FIG. 21B: Time course of editing) HEK293FT cells were transfected with either plasmid DNA, Cas9 mRNA/gRNA or Cas9 RNPs directed to the HPRT loci. Cell samples were taken at different time points and analyzed by genomic cleavage assays. (FIG. 21C) Western Blot analysis of samples taken at different time points. (FIG. 21D) Off-target mutation of VEGFA T3 target caused by Cas9 plasmid DNA, mRNA or protein transfection. Percentages of on-target mutation as well as OT3-2 and OT3-18 off-target mutations were determined by DNA sequencing.

(FIG. 22A: Electroporation-mediated transfection) Mastermixes of plasmid DNA, Cas9 mRNA/gRNA or Cas9 protein/gRNA were used to electroporate Jurkat T cells using the Neon 24 optimized protocol, which varies in pulse voltage, pulse width and number of pulses. The percentage of locus-specific genome cleavage was estimated 48-hour post transfection using a genomic cleavage assay. The letter "P" has been positioned at the top of each protein lane for ease of data review. The two bars to the right of each "P" are DNA and mRNA, respectively. (FIG. 22B: Electroporation-mediated transfection) Dose-dependent effect of genome editing. While keeping the ratio of Cas9 protein/gRNA constant, different amounts of Cas9 RNPs were used for electroporation using protocol 5. Experiments were done in triplicate. The percentage of cleavage was confirmed by sequencing.

Oligonucleotides were designed in a manner to correct an alteration in nucleic acid encoding GFP resulting in the generation of fluorescence upon correction. Thus, homologous recombination corrects the alteration resulting in expression active GFP. "% of GFP+ cells" refers to the percentage of cells that were found to contain functionally active GFP. The same assay was used to score homologous recombination in a number of additional experiments set out herein.

Figure 27:
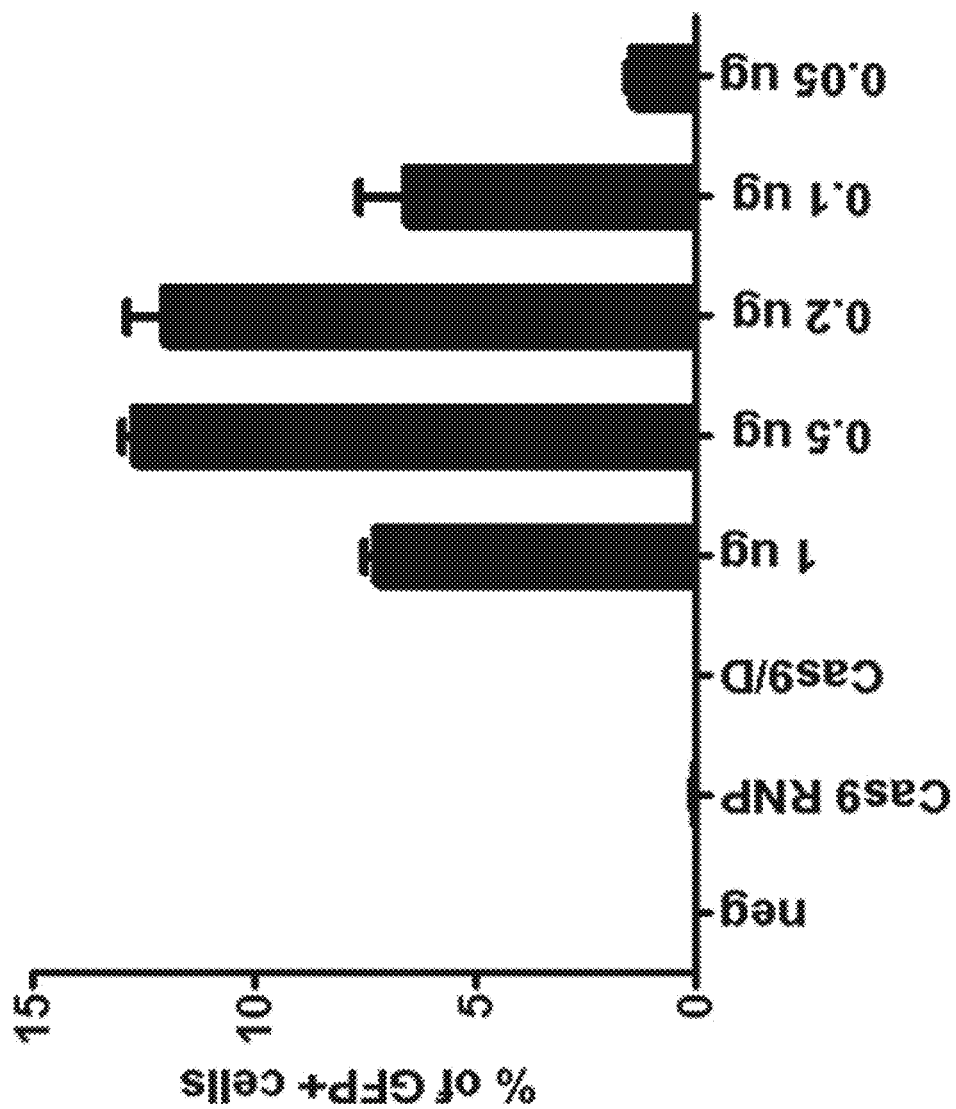

FIG. 27 shows data for the effect of the amount of oligonucleotide on homologous recombination. Under the conditions tested, the optimal amount of oligonucleotide is between 0.2 to 0.5 µg of single-stranded donor DNA in 10 µl of Suspension Buffer R.

Figure 28:
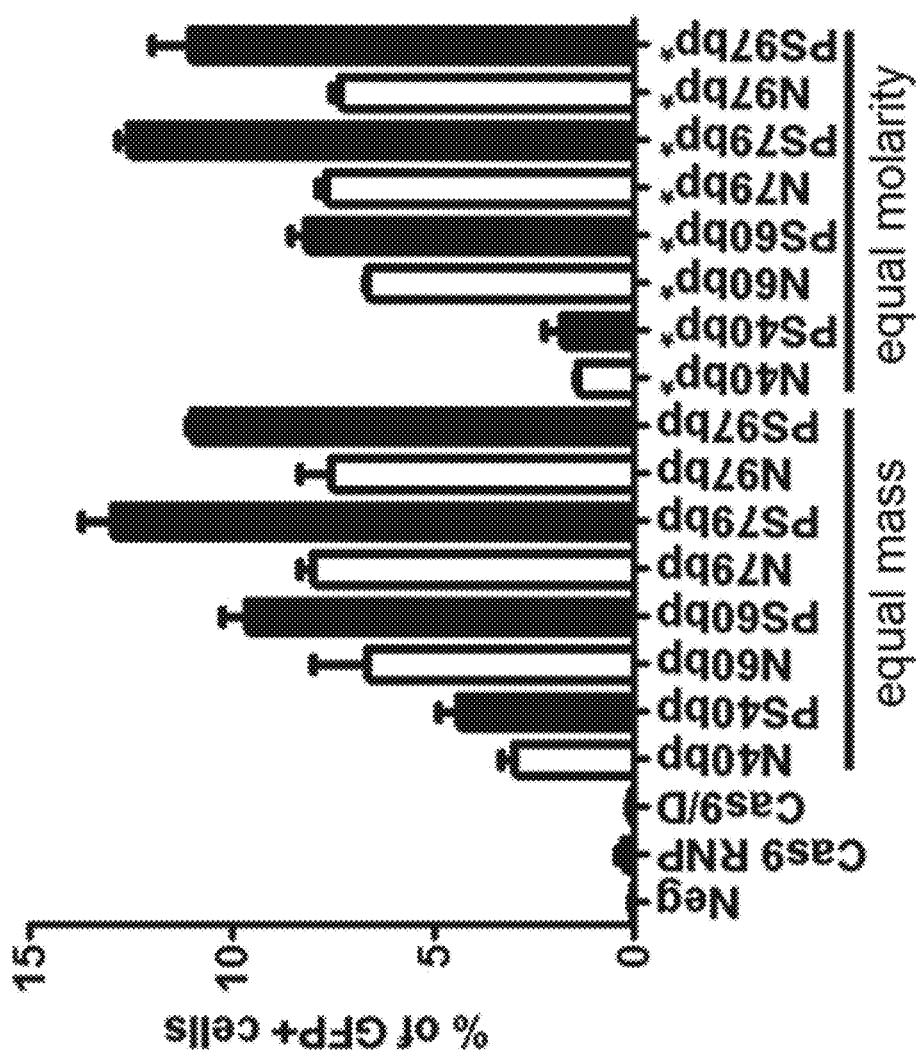

FIG. 28 shows data for the effect of oligonucleotide length and phosphorothioate modifications on homologous recombination. The amount of oligonucleotide for the equal mass experiments was 0.33 µg per 10 µl reaction. For equal molarity experiments, 10 pmoles per 10 µl reaction (1 µM final concentration) was used. "N" refers to no chemical modifications. "PS" refers to phosphorothioate chemical modifications at both termini.

Figure 29:
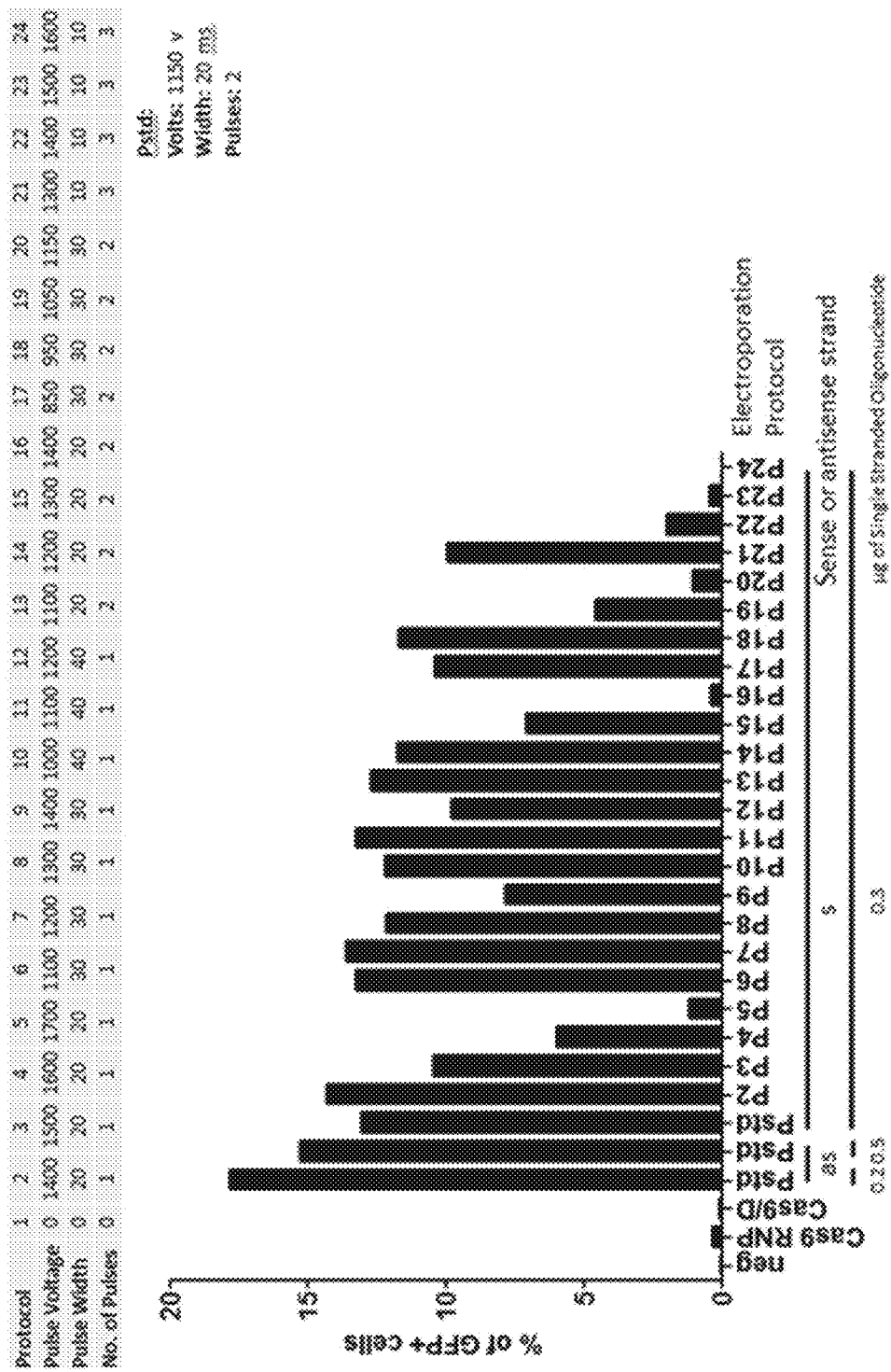

FIG. 29 shows a number of electroporation conditions and data resulting from their use. The data was generated using sequential delivery in the HEK 293 cells, first using Pstd electroporation conditions to deliver Cas9 RNP and the second using the indicated conditions for delivery of donor DNA. The data for Pstd with 0.2 µg of antisense donor DNA shows about a 147-fold induction of homologous recombination over the HR background induced by Cas9/donor without gRNA and about 47-fold induction over Cas9 RNP background. The data for Pstd with 0.5 µg of antisense donor DNA shows about a 126-fold induction of homologous recombination over Cas9/donor background and about 40-fold induction over Cas9 RNP background.

Figure 30:
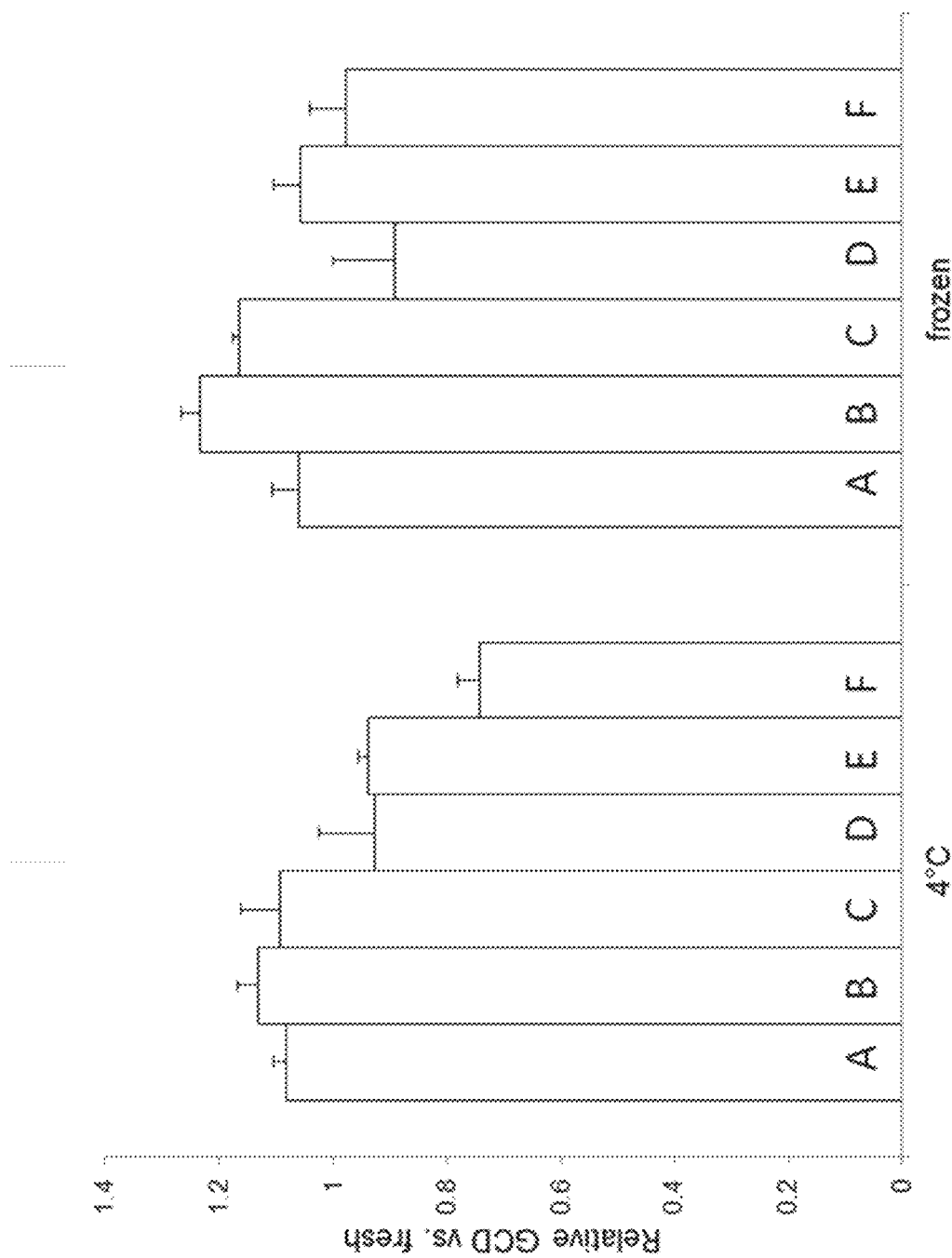

FIG. 30 shows the results of an experiment to determine gRNA/Cas9 complex stability. 50 µg of gRNA was combined with 150 µg of Cas9 protein, left at room temperature for 5 minutes, and then samples were stored either at 4° C. or frozen at −20° C. for the following lengths of time: 1 week (A), 2 weeks (B), 1 month (C), 2 months (D), 3 months (E), or 6 months (F). After the designated length of time, the samples were then screened using 293FT cells for cleavage activity using GENEART® Genomic Cleavage Detection Kits (Thermo Fisher Scientific, Cat. No. A24372). Cleavage activity was compared to freshly prepared gRNA/Cas9 complexes and relative activity was calculated with 1 being the same activity for both the stored sample and the freshly prepared sample. The errors bars indicated one standard deviation.

Figure 31:
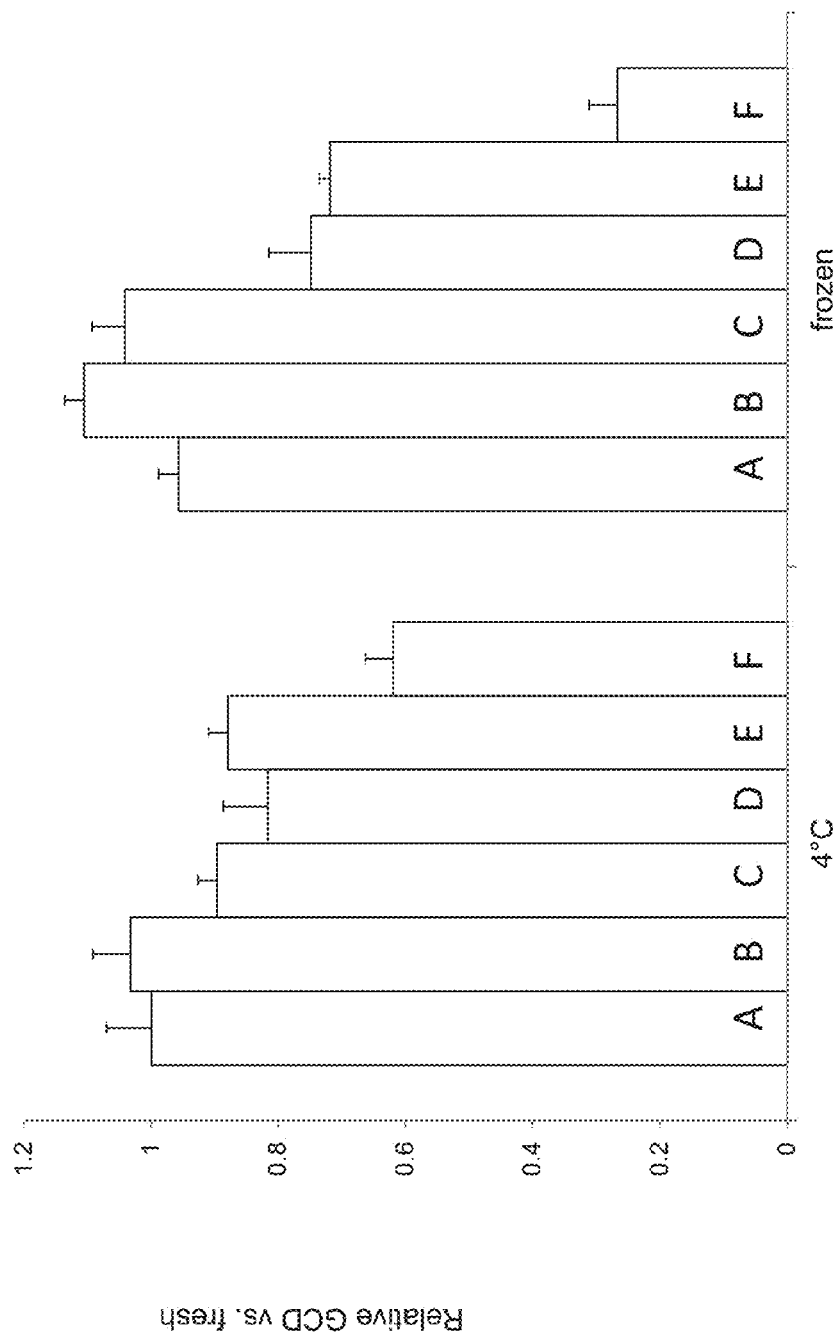

FIG. 31 shows the results of an experiment to determine gRNA/Cas9 complex stability and OPTI-MEM® culture medium (Thermo Fisher Scientific, cat. no. 31985-070) Complex preparation and storage conditions were as set out in the legend to FIG. 30 with 50 µg of gRNA was combined with 150 µg of Cas9 protein and 10 µl of OPTI-MEM®.

Figure 32:
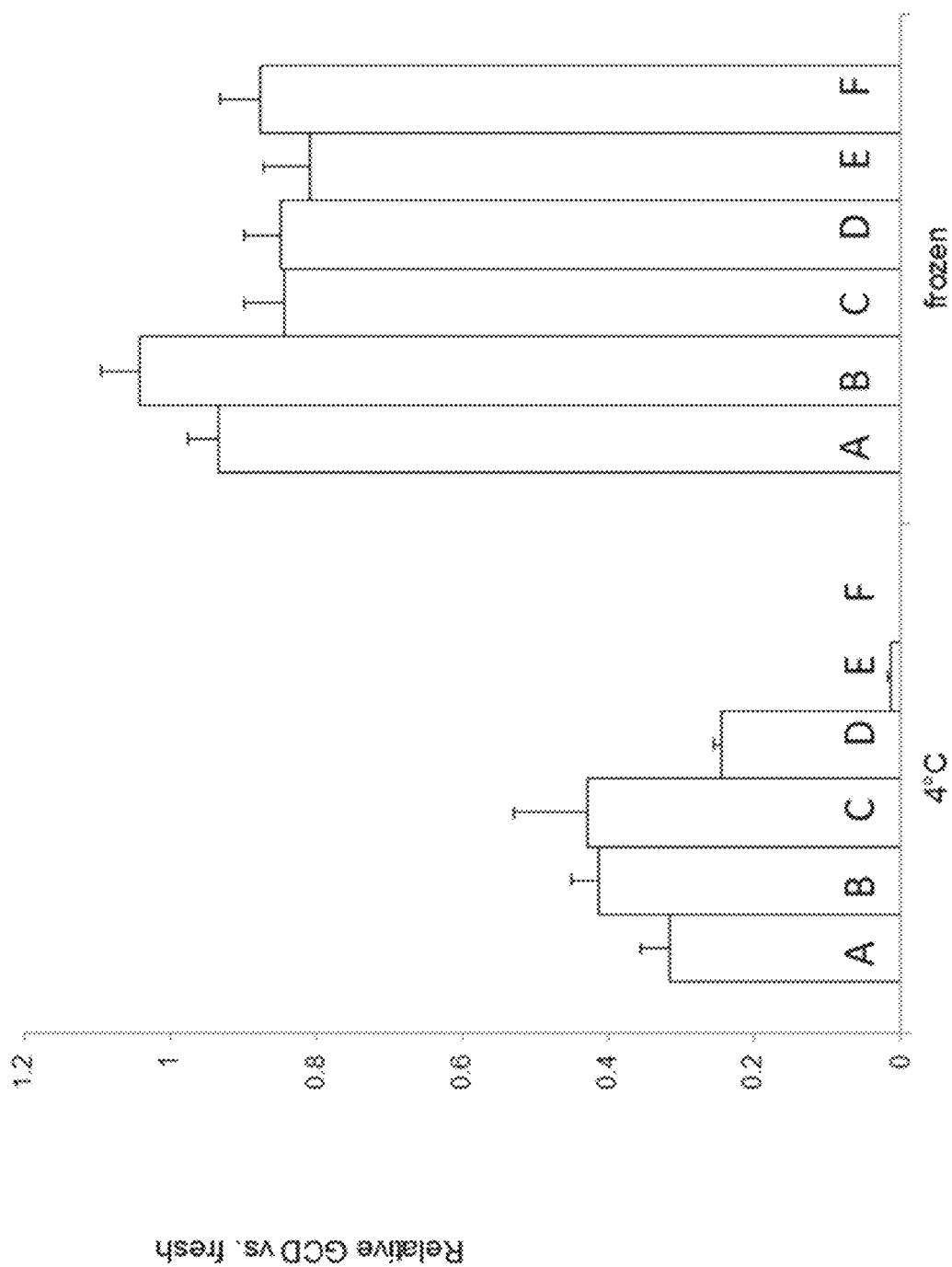

FIG. 32 shows the results of an experiment to determine Cas9 protein and LIPOFECTAMINE® RNAiMax transfection reagent (Thermo Fisher Scientific, cat. no. 13778-150) stability Complex preparation and storage conditions were as set out in the legend to FIG. 30 with 150 ng of Cas9 protein and 1.5 µl of LIPOFECTAMINE® RNAiMax at stored at 4 C or −20° C. 50 ng of gRNA mix with Opti-MEM.

DETAILED DESCRIPTION

Definitions

As used herein the term "CRISPR activity" refers to an activity associated with a CRISPR system. Examples of such activities are double-stranded nuclease, nickase, transcriptional activation, transcriptional repression, nucleic acid methylation, nucleic acid demethylation, and recombinase.

As used herein the term "CRISPR system" refers to a collection of CRISPR proteins and nucleic acid that, when combined, result in at least CRISPR associated activity (e.g., the target locus specific, double-stranded cleavage of double-stranded DNA).

As used herein the term "CRISPR complex" refers to the CRISPR proteins and nucleic acid (e.g., RNA) that associate with each other to form an aggregate that has functional activity. An example of a CRISPR complex is a wild-type Cas9 (sometimes referred to as Csn1) protein that is bound to a guide RNA specific for a target locus.

As used herein the term "CRISPR protein" refers to a protein comprising a nucleic acid (e.g., RNA) binding domain nucleic acid and an effector domain (e.g., Cas9, such as *Streptococcus pyogenes* Cas9). The nucleic acid binding domains interact with a first nucleic acid molecules either having a region capable of hybridizing to a desired target nucleic acid (e.g., a guide RNA) or allows for the association with a second nucleic acid having a region capable of hybridizing to the desired target nucleic acid (e.g., a crRNA). CRISPR proteins can also comprise nuclease domains (i.e., DNase or RNase domains), additional DNA binding domains, helicase domains, protein-protein interaction domains, dimerization domains, as well as other domains.

CRISPR protein also refers to proteins that form a complex that binds the first nucleic acid molecule referred to above. Thus, one CRISPR protein may bind to, for example, a guide RNA and another protein may have endonuclease activity. These are all considered to be CRISPR proteins because they function as part of a complex that performs the same functions as a single protein such as Cas9.

In many instances, CRISPR proteins will contain nuclear localization signals (NLS) that allow them to be transported to the nucleus.

The amino acid sequence of a representative Cas9 protein is set out below in Table 1.

TABLE 1

*Streptococcus pyogenes* Cas9
(GenBank Accession No. WP_010922251) (SEQ ID NO: 1)

```
  1 MDKKYSIGLD IGTNSVGWAV ITDEYKVPSK KFKVLGNTDR HSIKKNLIGA LLFDSGETAE

61 ATRLKRTARR RYTRRKNRIC YLQEIFSNEM AKVDDSFFHR LEESFLVEED KKHERHPIFG

121 NIVDEVAYHE KYPTIYHLRK KLVDSTDKAD LRLIYLALAH MIKFRGHFLI EGDLNPDNSD

181 VDKLFIQLVQ TYNQLFEENP INASGVDAKA ILSARLSKSR RLENLIAQLP GEKKNGLFGN

241 LIALSLGLTP NFKSNFDLAE DAKLQLSKDT YDDDLDNLLA QIGDQYADLF LAAKNLSDAI

301 LLSDILRVNT EITKAPLSAS MIKRYDEHHQ DLTLLKALVR QQLPEKYKEI FFDQSKNGYA

361 GYIDGGASQE EFYKFIKPIL EKMDGTEELL VKLNREDLLR KQRTFDNGSI PHQIHLGELH

421 AILRRQEDFY PFLKDNREKI EKILTFRIPY YVGPLARGNS RFAWMTRKSE ETITPWNFEE

481 VVDKGASAQS FIERMTNFDK NLPNEKVLPK HSLLYEYFTV YNELTKVKYV TEGMRKPAFL

541 SGEQKKAIVD LLFKTNRKVT VKQLKEDYFK KIECFDSVEI SGVEDRFNAS LGTYHDLLKI

601 IKDKDFLDNE ENEDILEDIV LTLTLFEDRE MIEERLKTYA HLFDDKVMKQ LKRRRYTGWG

661 RLSRKLINGI RDKQSGKTIL DFLKSDGFAN RNFMQLIHDD SLTFKEDIQK AQVSGQGDSL
```

TABLE 1-continued

Streptococcus pyogenes Cas9
(GenBank Accession No. WP_010922251) (SEQ ID NO: 1)

```
 721 HEHIANLAGS PAIKKGILQT VKVVDELVKV MGRHKPENIV IEMARENQTT QKGQKNSRER

781 MKRIEEGIKE LGSQILKEHP VENTQLQNEK LYLYYLQNGR DMYVDQELDI NRLSDYDVDH

841 IVPQSFLKDD SIDNKVLTRS DKNRGKSDNV PSEEVVKKMK NYWRQLLNAK LITQRKFDNL

901 TKAERGGLSE LDKAGFIKRQ LVETRQITKH VAQILDSRMN TKYDENDKLI REVKVITLKS

961 KLVSDFRKDF QFYKVREINN YHHAHDAYLN AVVGTALIKK YPKLESEFVY GDYKVYDVRK

1021 MIAKSEQEIG KATAKYFFYS NIMNFFKTEI TLANGEIRKR PLIETNGETG EIVWDKGRDF

1081 ATVRKVLSMP QVNIVKKTEV QTGGFSKESI LPKRNSDKLI ARKKDWDPKK YGGFDSPTVA

1141 YSVLVVAKVE KGKSKKLKSV KELLGITIME RSSFEKNPID FLEAKGYKEV KKDLIIKLPK

1201 YSLFELENGR KRMLASAGEL QKGNELALPS KYVNFLYLAS HYEKLKGSPE DNEQKQLFVE

1261 QHKHYLDEII EQISEFSKRV ILADANLDKV LSAYNKHRDK PIREQAENII HLFTLTNLGA

1321 PAAFKYFDTT IDRKRYTSTK EVLDATLIHQ SITGLYETRI DLSQLGGD
```

As used herein, the term "transcriptional regulatory sequence" refers to a functional stretch of nucleotides contained on a nucleic acid molecule, in any configuration or geometry, that act to regulate the transcription of (1) one or more structural genes (e.g., two, three, four, five, seven, ten, etc.) into messenger RNA or (2) one or more genes into untranslated RNA. Examples of transcriptional regulatory sequences include, but are not limited to, promoters, enhancers, repressors, and the like.

As used herein, the term "promoter" is an example of a transcriptional regulatory sequence, and is specifically a nucleic acid generally described as the 5' region of a gene located proximal to the start codon or nucleic acid which encodes untranslated RNA. The transcription of an adjacent nucleic acid segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

As used herein, the terms "vector" refers to a nucleic acid molecule (e.g., DNA) that provides a useful biological or biochemical property to an insert. Examples include plasmids, phages, autonomously replicating sequences (ARS), centromeres, and other sequences which are able to replicate or be replicated in vitro or in a host cell, or to convey a desired nucleic acid segment to a desired location within a host cell. A vector can have one or more restriction endonuclease recognition sites (e.g., two, three, four, five, seven, ten, etc.) at which the sequences can be cut in a determinable fashion without loss of an essential biological function of the vector, and into which a nucleic acid fragment can be spliced in order to bring about its replication and cloning. Vectors can further provide primer sites (e.g., for PCR), transcriptional and/or translational initiation and/or regulation sites, recombinational signals, replicons, selectable markers, etc. Clearly, methods of inserting a desired nucleic acid fragment which do not require the use of recombination, transpositions or restriction enzymes (such as, but not limited to, uracil N glycosylase (UDG) cloning of PCR fragments (U.S. Pat. Nos. 5,334,575 and 5,888,795, both of which are entirely incorporated herein by reference), T:A cloning, and the like) can also be applied to clone a fragment into a cloning vector to be used according to the present invention. The cloning vector can further contain one or more selectable markers (e.g., two, three, four, five, seven, ten, etc.) suitable for use in the identification of cells transformed with the cloning vector.

As used herein the term "nucleic acid targeting capability" refers to the ability of a molecule or a complex of molecule to recognize and/or associate with nucleic acid on a sequence specific basis. As an example, Hybridization Region 1 on a crRNA molecule confers nucleic acid targeting capability upon a CRISPR complex.

As used herein the term "target locus" refers to a site within a nucleic acid molecule for CRISPR system interaction (e.g., binding and cleavage). When a single CRISPR complex is designed to cleave double-stranded nucleic acid, then the target locus is the cut site and the surrounding region recognized by the CRISPR complex. When two CRISPR complexes are designed to nick double-stranded nucleic acid in close proximity to create a double-stranded break, then the region surrounding and including the break point is referred to as the target locus.

A "counter selectable" marker (also referred to herein a "negative selectable marker") or marker gene as used herein refers to any gene or functional variant thereof that allows for selection of wanted vectors, clones, cells or organisms by eliminating unwanted elements. These markers are often toxic or otherwise inhibitory to replication under certain conditions which often involve exposure to a specific substrates or shift in growth conditions. Counter selectable marker genes are often incorporated into genetic modification schemes in order to select for rare recombination or cloning events that require the removal of the marker or to selectively eliminate plasmids or cells from a given population. One example of a negative selectable marker system widely used in bacterial cloning methods is the ccdA/ccdB toxin-antitoxin system.

Overview:

The invention relates, in part, to compositions and methods for the preparation of nucleic acid molecules. In particular, the invention relates to combinations of proteins and nucleic acid molecules designed to interact with other nucleic acid molecules. More specifically, the invention relates to protein nucleic acid complexes, where the nucleic acid component has sequence complementarity to a target nucleic acid molecule. In these systems, sequence complementarity between the complexed nucleic acid and the target nucleic acid molecule is the used to bring the complex into association with the target nucleic acid. Once this occurs, functional activities associated with the complex may be used to modify the target nucleic acid molecule.

The invention is exemplified by CRISPR systems. The term "CRISPR" is a general term that applies to three type of systems, and system sub-types. In general, the term CRISPR refers to the repetitive regions that encode CRISPR system components (e.g., encoded crRNAs). Three types of CRISPR systems (see Table 2) have been identified, each with differing features.

TABLE 2

CRISPR System Types Overview

| System | Features | Example |
| --- | --- | --- |
| Type I | Multiple proteins (5-7 proteins typical), crRNA, requires PAM. DNA Cleavage is catalyzed by Cas3. | *S. epidermidis* (Type IA) |
| Type II | 3-4 proteins (one protein (Cas9) has nuclease activity) two RNAs, requires PAMs. Target DNA cleavage catalyzed by Cas9 and RNA components. | *Streptococcus pyogenes* CRISPR/Cas9 |
| Type III | Five or six proteins required for cutting, number of required RNAs unknown but expected to be 1, PAMs not required. Type IIIB systems have the ability to target RNA. | *S. epidermidis* (Type IIIA); *P. furiosus* (Type IIIB); |

While the invention has numerous aspects and variations associated with it, the Type II CRISPR/Cas9 system has been chosen as a port of reference for explanation herein.

In certain aspects, the invention provides:
1. Individual oligonucleotides to make crRNA/tracrRNAs and collections of such oligonucleotides, as well as methods for generating and using such oligonucleotides.
2. Compositions and methods for introducing CRISPR complex components into cells.

Figure 1:
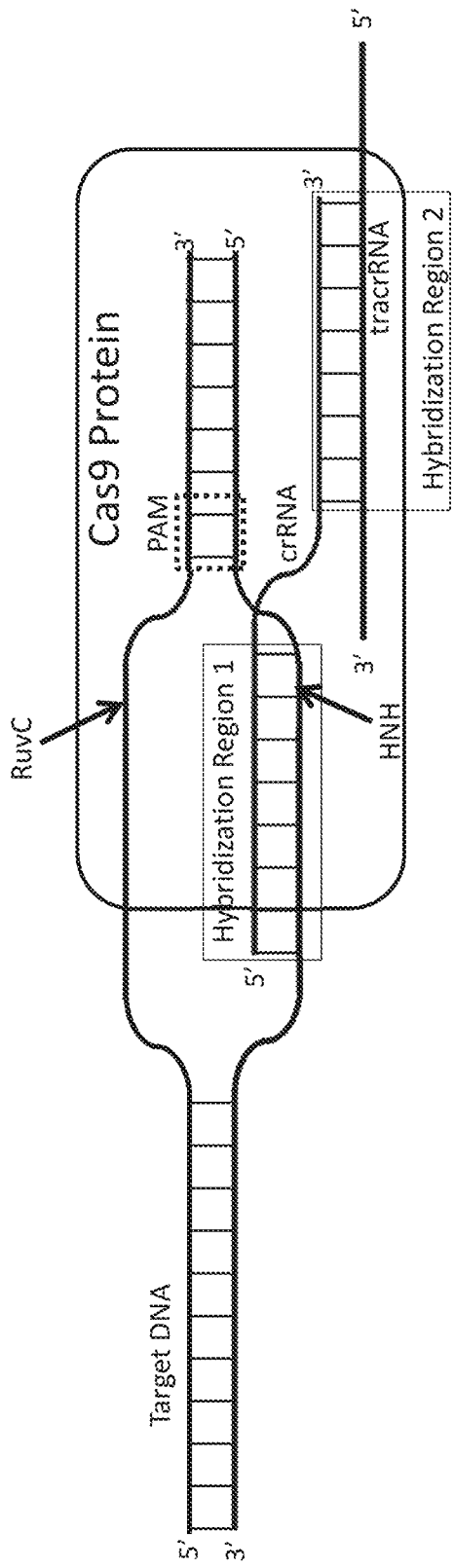
FIG. 1 is a representative diagram of a naturally occurring CRISPR system. In addition to the "Target DNA", three additional components are required: Cas9 protein (shaded rectangle), crRNA (CRISPR RNA), and tracrRNA (trans-activating crRNA). The arrows labeled "RuvC and "HNH" indicate cutting locations in the Target DNA. The dashed box labeled "PAM" refers to protospacer adjacent motif.
Figure 2:
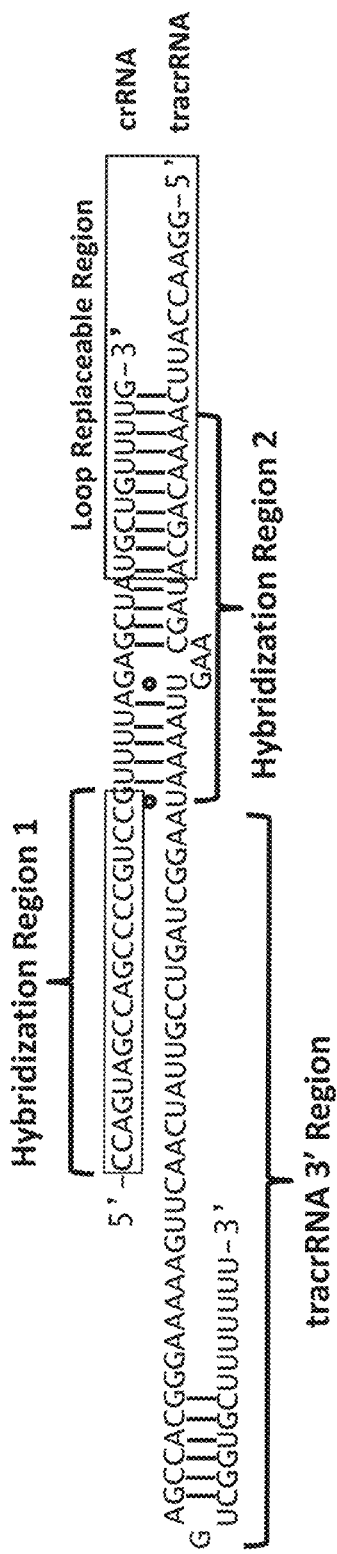
FIG. 2 shows the association between a crRNA molecule (SEQ ID NO: 56) and a tracrRNA molecule (SEQ ID NO: 57). Hybridization Region 1 (19 nucleotides, in this instance) is complementary to the target site. Hybridization Region 2 is a region of sequence complementarity between the crRNA (41 nucleotides) and the tracrRNA (85 nucleotides). The tracrRNA 3' region is the 3' region of the tracrRNA molecule that extends beyond Hybridization Region 2. The Loop Replaceable Region is roughly defined by the closed box and may be replaced with a hairpin loop to connect crRNA and tracrRNA molecules into a single entity, typically referred to as a guide RNA (see FIG. 3).

FIG. 1 shows components and molecular interactions associated with a Type II CRISPR system. In this instance, the Cas9 mediated *Streptococcus pyogenes* system is exemplified.

A crRNA is shown in FIG. 1 hybridizing to both target DNA (Hybridization Region 1) and tracrRNA (Hybridization Region 2). In this system, these two RNA molecules serve to bring the Cas9 protein to the target DNA sequence is a manner that allows for cutting of the target DNA. The target DNA is cut at two sites, to form a double-stranded break.

There appears to be substantial sequence variation in tracrRNA sequence. It has been postulated that tracrRNA function relates more to RNA structure, than RNA sequence.

The Cas9 protein of *Streptococcus pyogenes* is 1368 amino acids in length (NCBI Reference Sequence: WP_030126706.1) and contains a number of domains for the binding and cutting of nucleic acid molecules. This protein has two domains (RuvC and HNH), each of which has DNA nickase activity. When this protein nicks DNA on both strands, the nicks are in close enough proximity to result in the formation of a double-stranded break.

In some instances, CRISPR proteins will contain one or more of the following amino acid sequences: (1) YSIGLDIGTNSVG (SEQ ID NO: 2), (2) PTIYHLR (SEQ ID NO: 3), (3) RGHFLIE (SEQ ID NO: 4), (4) TKAPLSASM (SEQ ID NO: 5), (5) LRKQRTFDNG (SEQ ID NO: 6), (6) LTFRIPYYVGPLAR (SEQ ID NO: 7), (7) TLTLFEDREMI (SEQ ID NO: 8), (8) AGSPAIKKGILQ (SEQ ID NO: 9), (9) RQLVETRQITKHVA (SEQ ID NO: 10) and/or (10) QTGGFSKESIL (SEQ ID NO: 11).

While not wishing to be bound by theory, in brief, as shown in FIG. 1, crRNA hybridizes to target DNA, referred to as "Hybridization Region 1". Hybridization region 1 is typically in the range of 18 to 22 base pairs but can be longer or shorter. The crRNA thus "indentifies" the target DNA sequence. The crRNA also hybridizes to the tracrRNA, referred to as "Hybridization Region 2". Hybridization Region 1 is typically in the range of 15 to 25 base pairs but can be longer or shorter and often there is not have full sequence complementarity between the hybridized strands. The tracrRNA is believed to associate with the Cas9 protein, bringing the RuvC and HNH cleavage domains in contact with the target DNA.

A number of features of the CRISPR/Cas9 system, any or all of which may be used in the practice of the invention, have been identified:
1. crRNA and tracrRNA may be combined to form a guide RNA (gRNA).
2. Mutations may be introduced into Cas9 proteins that inactivate either the RuvC or HNH domains resulting in proteins with strand specific nickase activity.
3. Mutations may be introduced into Cas9 proteins that inactivate all nucleic acid cleavage activities but allow for these proteins to retain nucleic acid binding activity.
4. Sequence alterations, including truncations and multinucleotide deletions, can be made to the CRISPR system RNA components.

One limitation on Type II CRISPR systems is the requirement of a protospacer adjacent motif (PAM) for high level activity. Efficient binding and cleavage of DNA by Cas9-RNA requires recognition of a PAM. Typically, PAMs are three nucleotides in length.

In many instances, it will be desirable to make two nicks in close proximity to each other when cleaving nucleic acid using methods of the invention. This is especially so when the target locus is in a cellular genome. The use of CRISPR system components that nick nucleic acid is believed to limit "off-target effects" in that a single nick at a location other than the target locus is unlikely to result in single-stranded cleavage of the nucleic acid.

Figure 4:
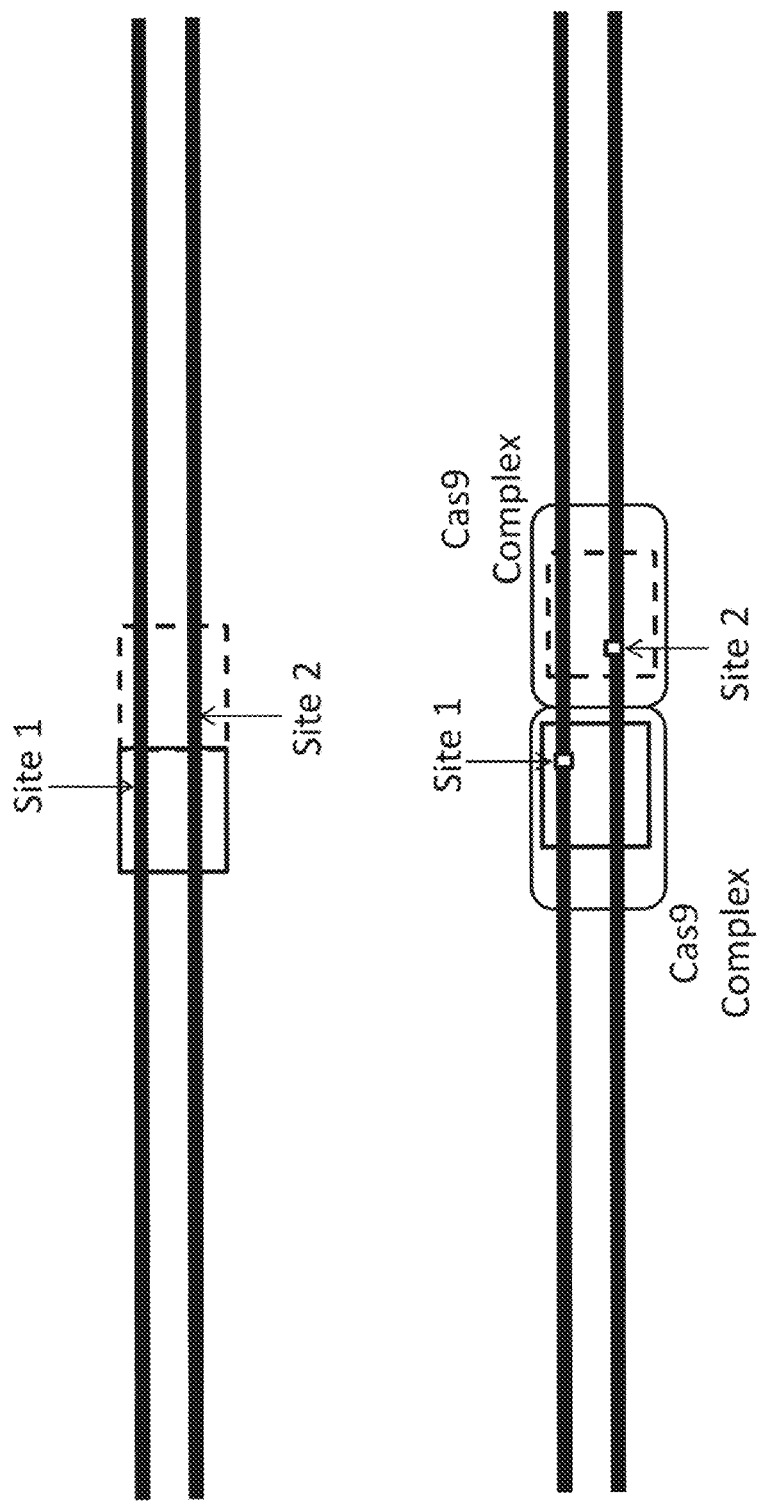
FIG. 4 is a schematic showing a nicking based nucleic acid cleavage strategy using a CRISPR system. In the top portion of the figure, two lines represent double-stranded nucleic acid. Two nick sites are indicated by Site 1 and Site 2. These sites are located within a solid or dashed box indicating the region of the nucleic acid that interacts with the CRISPR/Cas9 complex. The lower portion of the figure show nicking actions that result in two closely positioned nicks in both strands.

FIG. 4 shows the selection of two closely associated sites that form a target locus. Each of the sites (Site 1 and Site 2) binds a CRISPR complex with nickase activity.

The two sites exemplified in FIG. 4 will generally be located sufficiently close to each other so that the double-stranded nucleic acid containing the nick breaks. While this distance will vary with factors such as the AT/CG content of the region, the nick sites will generally be within 200 base pairs of each other (e.g., from about 1 to about 200, from about 10 to about 200, from about 25 to about 200, from about 40 to about 200, from about 50 to about 200, from about 60 to about 200, from about 1 to about 100, from about 10 to about 100, from about 20 to about 100, from about 30 to about 100, from about 40 to about 100, from about 50 to about 100, from about 1 to about 60, from about 10 to about 60, from about 20 to about 60, from about 30 to about 60, from about 40 to about 60, from about 1 to about 35, from about 5 to about 35, from about 10 to about 35, from about 20 to about 35, from about 25 to about 35, from about 1 to about 25, from about 10 to about 25, from about 15 to about 25, from about 2 to about 15, from about 5 to about 15, etc. base pairs).

In many instances, CRISPR complexes bind with high affinity to the target locus. In many such instances, when double-stranded breaks at the target locus are desired CRISPR complexes will be directed to the target locus in a manner such that they do not stericly interfere with each other. Thus, the invention includes methods in which CRISPR complex binding sites at a target locus are selected such that nicking activity on each strand is not significantly altered by the binding of a CRISPR complex directed to the nicking of the other strand. The invention further includes compositions for performing such methods.

TABLE 3

Predicted *S. pyogenes* Cas9 Functional Regions

| Description | Positions | Length |
|---|---|---|
| RuvC-I | 1-62 | 62 |
| Recognition lobe | 60-718 | 659 |
| RuvC-II | 718-765 | 48 |
| HNH | 810-872 | 63 |
| RuvC-III | 925-1102 | 178 |
| PAM-interacting domain | 1099-1368 | 270 |
| PAM substrate binding | 1125-1127 | 3 |

*S. pyogenes* Cas9 protein has a number of domains (see Table 3), two of which are nuclease domains. The discontinuous RuvC-like domain is encompassed by approximately amino acids 1-62, 718-765 and 925-1102. The HNH nuclease domain is encompassed by approximately amino acids residues 810-872. The recognition lobe, approximately amino acids 60-718, recognizes and binds regions of guide RNAs in a sequence-independent manner. Deletions of some parts of this lobe abolishes CRISPR activity. The PAM-interacting domain, approximately amino acids 1099-1368, recognizes the PAM motif.

The nicking activity may be accomplished in a number of ways. For example, the Cas9 protein has two domains, termed RuvC and HNH, that nick different strands of double-stranded nucleic acid. Cas9 proteins may be altered to inactivate one domain or the other. The result is that two Cas9 proteins are required to nick the target locus in order for a double-stranded break to occur. For example, an aspartate-to-alanine substitution (D10A) in the RuvC catalytic domain of Cas9 from *S. pyogenes* converts Cas9 from a nuclease that cleaves both strands to a nickase (cleaves a single strand). Other examples of mutations that render Cas9 a nickase include H840A, N854A, and N863A.

CRISPR proteins (e.g., Cas9) with nickase activities may be used in combination with guide sequences (e.g., two guide sequences) which target respectively sense and antisense strands of the DNA target.

Another way to generate double-stranded breaks in nucleic acid using nickase activity is by using CRISPR proteins that lack nuclease activity linked to a heterologous nuclease domain. One example of this is a mutated form of Cas9, referred to as dCas9, linked to FokI domain. FokI domains require dimerization for nuclease activity. Thus, in such instances, CRISPR RNA molecules are used to bring two dCas9-FokI fusion proteins into sufficiently close proximity to generate nuclease activity that results in the formation of a double-stranded cut. Methods of this type are set out in Tsai et al., "*Dimeric CRISPR RNA-guided FokI nucleases for highly specific genome editing,*" *Nature Biotech.*, 32:569-576 (2014) and Guilinger et al., "*Fusion of catalytically inactive Cas9 to FokI nuclease improves the specificity of genome modification,*" *Nature Biotech.*, 32:577-582 (2014).

Transient Activity

One need is for a genome editing system having transient or highly regulatable activity. Transient activity is important for a number of applications. For example, for construction of cells lines involving one or more nuclease activity. Once a cellular nucleic acid, for example, has been effectively exposed to a nuclease and appropriately cut, repair of the nucleic acid (e.g., via non-homologous end-joining) normally takes place. Repair of the cellular nucleic acid is generally required for the cell to remain viable. In many cases, the cell will either integrate nucleic acid into the repaired nucleic acid molecule or nucleic acid will be removed (e.g., from 1 base pair to about 100 base pairs) for the repaired nucleic acid molecule. In either instance, a heritable change occurs within the genome of the cell. Cells with genetic changes can then be screened to identify ones with a desired alteration. Once cells with desired changes are identified, for most applications, it is beneficial to maintain the cells without further nuclease induced genetic change. Thus, it is generally desirable that the nuclease activity used to facilitate the genetic changes not be active within the cells.

Figure 5:
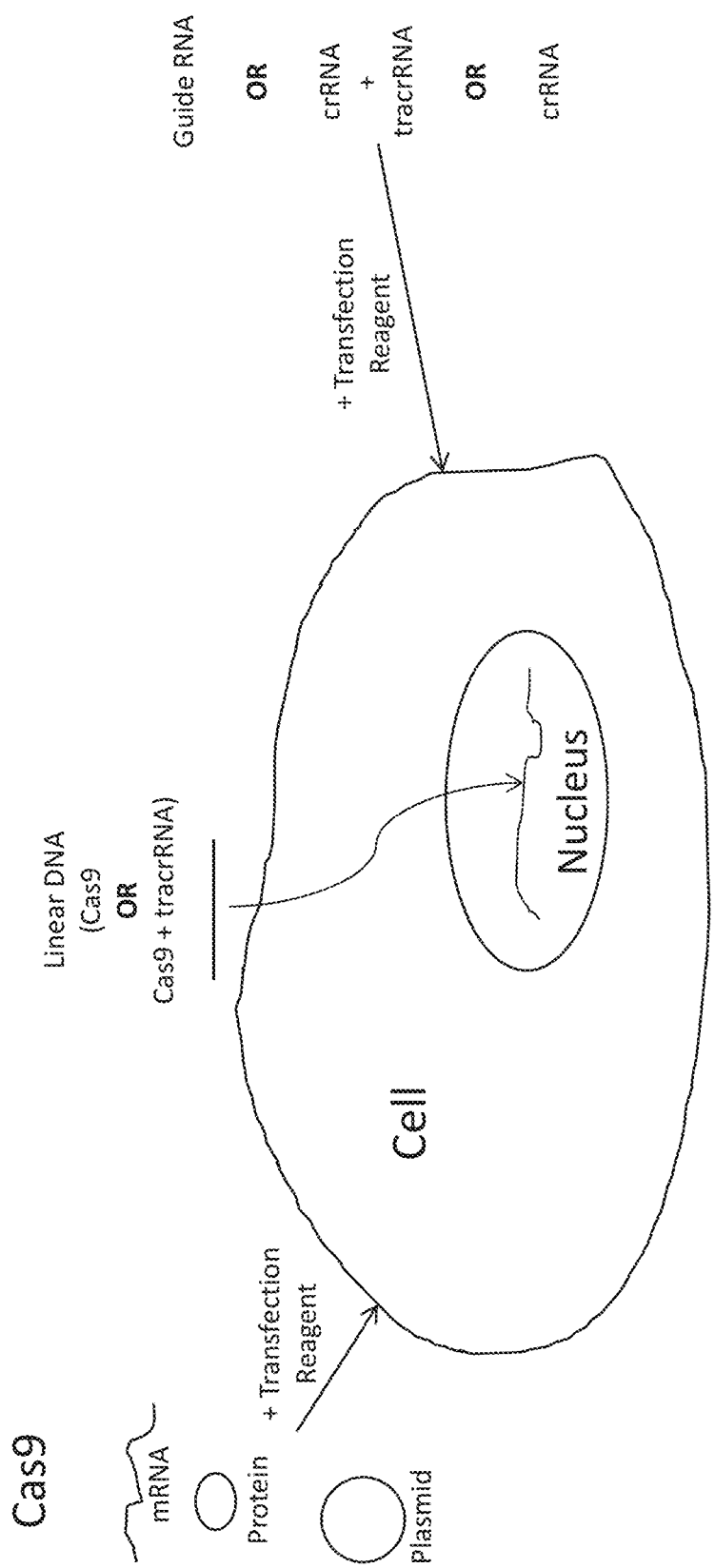
FIG. 5 is a schematic showing some methodologies for transient CRISPR activity within cells. The introduction of Cas9 proteins and/or nucleic acid encoding Cas9 is shown on the left. The introduction of guide RNA, crRNA plus tracrRNA, or crRNA alone is shown on the right. The middle shows the introduction of linear DNA encoding Cas9 or Cas9 plus tracrRNA. This DNA is designed to be stably maintained in the cell.

Transient activity can be achieved in a number of ways, some of which are represented in FIG. 5. CRISPR systems typically require that all necessary components be present for activity. Using a CRISPR/Cas9 system for reference, a target nucleic acid molecule must be contacted with a Cas9 protein and one or more CRISPR nucleic acid molecules (e.g., either (1) a crRNA molecule and a tracrRNA molecule or (2) a guide RNA molecule).

The invention thus includes compositions and methods for transient CRISPR mediate activities (e.g., nuclease activity). Transient activity may be the generated in any number of ways. One feature of CRISPR systems is that all components typically need to come together for activity. These components are (1) one or more CRISPR proteins (e.g., Cas9), (2) Hybridization Region 1 (e.g., crRNA), and (3) nucleic acid that associates with both Hybridization Region 1 and the one or more CRISPR proteins. Thus, if one or more components required for CRISPR mediate activity is removed, then the activity is inhibited.

Using the Cas9 based CRISPR system for purposes of illustration, three components are required for CRISP mediated activity: (1) Cas9 protein, (2) crRNA, and (3) tracrRNA. Thus, transient systems can be generated by the time limited presence of any one of these components. A number of variations are represented in FIG. 5.

TABLE 4

Exemplary CRISPR Components

| | | Format 1 | | Format 2 |
|---|---|---|---|---|
| Row No. | Cas9 Protein (Col. A) | crRNA (Col. B) | tracrRNA (Col. C) | Guide RNA (Col. D) |
| 1 | Integrated Coding Seq. | Integrated Coding Seq. | Integrated Coding Seq. | Integrated Coding Seq. |
| 2 | Protein | crRNA | tracrRNA | Guide RNA |
| 3 | Linear Coding Seq. | Linear Coding Seq. | Linear Coding Seq. | Linear Coding Seq. |
| 4 | Vector | Vector | Vector | Vector |
| 5 | mRNA | — | — | — |

As noted above, in Cas9 mediated system, Cas9 protein must be present for activity. Further, proteins normally are fairly stable molecules within cells. Cas9 proteins may be modified to enhance intracellular degradation (e.g., proteosome mediated degradation) by, for example, ubiquitination.

Cas9 protein may be either introduced into cells (Row 2, Column A) or produced intracellularly (Rows 1, 3, 4, and 5, Column A). Further, the duration of time that Cas9 protein is taken up or produced intracellularly and the amount that is present intracellularly may be controlled or regulated. As an example, a chromosomally integrated Cas9 protein coding sequence may be operably linked to a regulatable promoter. Further, the amount of mRNA encoding Cas9 protein introduced into cells may be regulated.

With respect to non-coding CRISPR RNA needed to high level CRISPR activity, at least two formats are possible: (1) separate crRNA and tracrRNA molecules and (2) Guide RNA (see Table 4).

The invention thus includes compositions and method for transient production of CRISPR mediated activities within cells. Such methods include, for example, the use of a combination of stable and unstable CRISPR system components. One example is a system where mRNA encoding wild-type Cas9 protein and a guide RNA are introduced into a cell in roughly equal amounts. In this example, the presence of Cas9 mRNA will result in the production of a stable Cas9 protein and the limiting factor on CRISPR mediated activity will typically be the determined by the amount of guide RNA present and guide RNA degradation.

The production and/or intracellular introduction of various components of CRISPR mediated systems in a number of ways. For example, a cell designed for convenient CRISPR system reconstitution could be produced. One example of such a cell would be a mammalian cell line (e.g., CHO, 293, etc.) that contains nucleic acid encoding Cas9 protein and tracrRNA integrated into the genome. CRISPR mediated activities can then be directed to a specific target sequence by the introduction into the cell line (e.g., via transfection) of crRNA. In such an exemplary cell line, Cas9 and/or tracrRNA coding sequences may be constitutively expressed or regulatably expressed (e.g., operably linked to an inducible or a repressible promoter).

The invention thus includes cell lines (e.g., eukaryotic cells lines) that contain one or more component of a CRISPR system, as well as methods for directing one or more CRISPR mediated activity to specific target loci within such cells. In many instances, this will result from the addition to or production of at least one additional component that results in target locus CRISPR mediated activities within the cell.

Hybridization Region 1 (Hr1)

HR1 (also referred to as Target Complementary crRNA) is believed to determine the target nucleic acid sequence to which the CRISPR complex associates with. HR1 may vary in length, nucleotide composition (e.g., AT/CG ratio), and level of sequence complementarity with the target sequence (e.g., 100%).

As noted above, the length of HR1 may vary. The length of HR1 is determined by the number of nucleotides of sequence complementarity to target nucleic acid, not including internal mismatches. For example, if the crRNA or guide RNA has a twenty-two nucleotide region where the ten 5' most terminal nucleotide and the ten 3' most terminal nucleotides are 100% complementary to the sequence of a target nucleic acid, then the HR1 region is twenty-two nucleotides in length with two internal mis-matches. In such an instance, HR1 would share about 91% sequence complementarity with the sequence of the target nucleic acid.

HR1 used in compositions and methods of the invention may vary from about 12 nucleotides to about 35 nucleotides (e.g., from about 13 nucleotides to about 33 nucleotides, from about 15 nucleotides to about 33 nucleotides, from about 17 nucleotides to about 33 nucleotides, from about 18 nucleotides to about 33 nucleotides, from about 19 nucleotides to about 33 nucleotides, from about 20 nucleotides to about 33 nucleotides, from about 21 nucleotides to about 33 nucleotides, from about 13 nucleotides to about 30 nucleotides, from about 15 nucleotides to about 30 nucleotides, from about 18 nucleotides to about 30 nucleotides, from about 20 nucleotides to about 30 nucleotides, from about 13 nucleotides to about 27 nucleotides, from about 15 nucleotides to about 27 nucleotides, from about 18 nucleotides to about 27 nucleotides, from about 20 nucleotides to about 27 nucleotides, from about 13 nucleotides to about 25 nucleotides, from about 15 nucleotides to about 25 nucleotides, from about 17 nucleotides to about 25 nucleotides, from about 18 nucleotides to about 25 nucleotides, from about 20 nucleotides to about 25 nucleotides, from about 13 nucleotides to about 23 nucleotides, from about 15 nucleotides to about 23 nucleotides, from about 18 nucleotides to about 23 nucleotides, from about 20 nucleotides to about 23 nucleotides, etc.).

HR1 may be designed with sequence complementarity to target nucleic acid with particular ratios AT/CG. AT/CG may be altered to adjust hybridization "affinity" between HR1 and the specific target nucleic acid. A-T pairs hybridize less tightly than C-G pairs. Thus, hybridization strength can be varied by altering the AT/CG ratio of HR1. In some instance, higher binding affinity and in some instances lower binding affinity may be desired.

Further, crRNA and guide RNA molecules may be designed with AT/CG contents for the reduction of off target effects. The human genome, for example, has an average CG content of around 41 to 42%. Thus, nucleic acids containing an HR1 with a CG content of greater or less than 41 to 42% are less likely to share significant sequence complementarity with nucleic acid other than intended the target nucleic acid. Also, fewer off target effects would be expected the further the AT/CG ratio of HR1 and the target nucleic acid are from the average AT/CG ratio of the genome or other nucleic acid molecule being altered.

TABLE 5

| Genomic CG Content of Select Eukaryotes | |
|---|---|
| Genome | Avg. CG Content |
| Homo sapiens | 41 to 42% |
| Arabidopsis thaliana | ~36% |
| Saccharomyces cerevisiae | ~38% |
| Plasmodium falciparum | ~20% |

HR1 used in compositions and methods of the invention thus may have AT/CG ratios in the range of from about 1:5 to about 5:1 (e.g., from about 1:4 to about 5:1, from about 1:3 to about 5:1, from about 1:2 to about 5:1, from about 1:1 to about 5:1, from about 1:5 to about 4:1, from about 1:4 to about 4:1, from about 1:3 to about 4:1, from about 1:2 to about 4:1, from about 1:1 to about 4:1, from about 1:5 to about 3:1, from about 1:4 to about 3:1, from about 1:3 to about 3:1, from about 1:2 to about 3:1, from about 1:1 to about 3:1, from about 1:5 to about 2:1, from about 1:4 to about 2:1, from about 1:3 to about 2:1, from about 1:2 to about 2:1, or from about 1:1 to about 2:1).

Binding affinity between HR1 and the target nucleic acid can be varied by a combination of HR1 length, AT/CG content, and percent sequence complementarity. In most instances, sequence between HR1 and the target nucleic acid will be 100% but this can vary between from about 80% to about 100%, from about 90% to about 100%, from about 95% to about 100%, from about 80% to about 95%, from about 85% to about 95%, or from about 90% to about 95%. HR1 used in compositions and methods of the invention may have sequence complementarity characteristics referred to above.

HR1 may also be designed using bioinformatic data to limit off-target effects. Complete genome sequence data is available for thousands of genomes. When a CRISPR system is engineered to modify the genome of a specific organism, the genome of that organism (assuming the genome sequence is known) may be analyzed the select a region that is unique and/or has no counter-part region with a sequence similar enough for substantial levels of CRISPR complex binding. This may be done through a combination of site selection and preparation of HR1 to binding to the selected site.

Hybridization Region 2 (Hr2)

Figure 3:
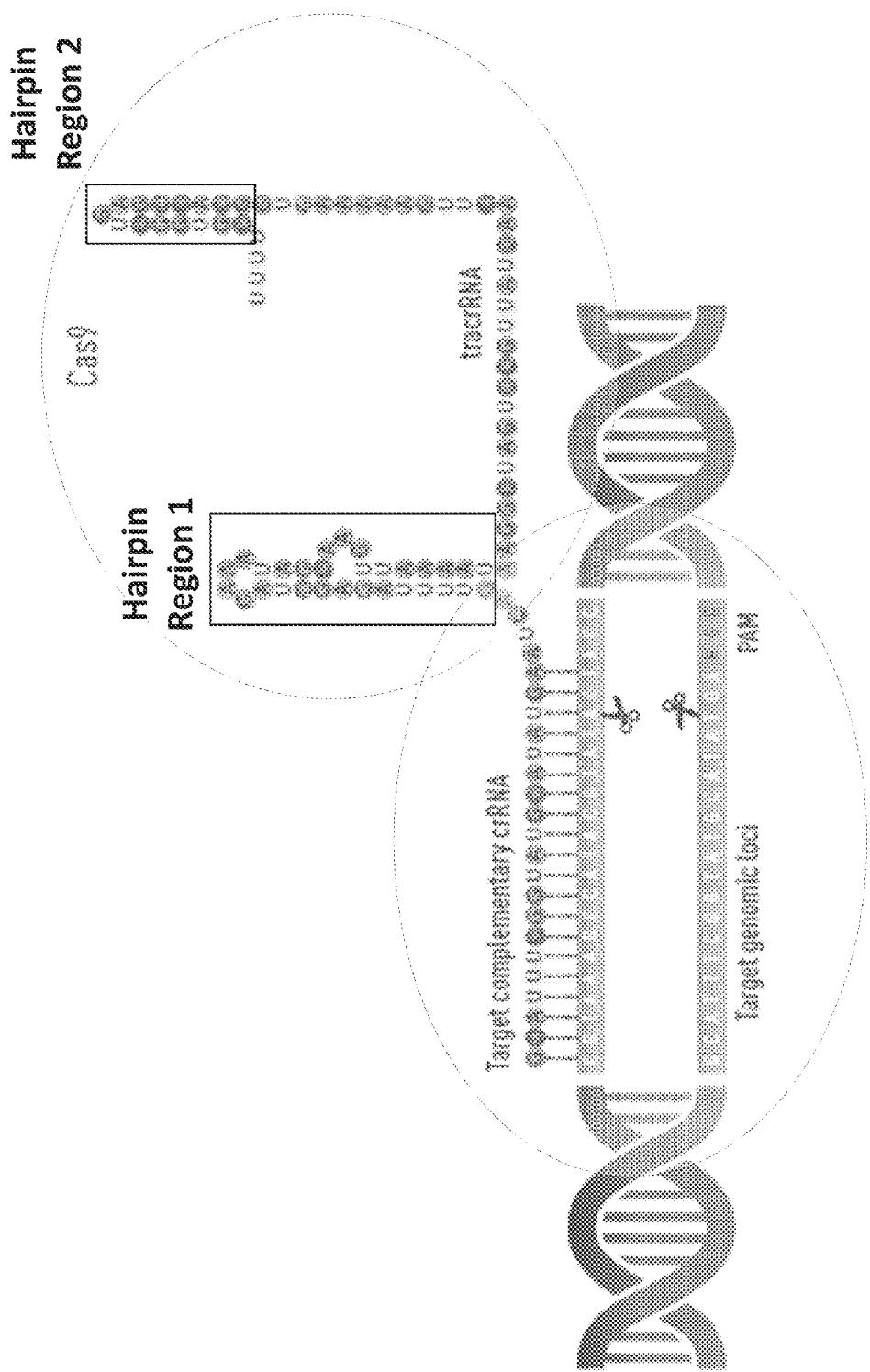
FIG. 3 is a schematic of a guide RNA molecule (104 nucleotides) showing the guide RNA bound to both Cas9 protein and a target genomic locus. Hairpin Region 1 is formed by the hybridization of complementary crRNA and tracrRNA regions joined by the nucleotides GAAA. Hairpin Region 2 is formed by a complementary region in the 3' portion of the tracrRNA.

HR2 is a region of sequence complementarity either (1) between the crRNA and the tracrRNA or (2) within the guide RNA. In a guide RNA, this region forms a hairpin (Hairpin Region 1 in FIG. 3).

CRISPR Proteins

Depending upon the type of CRISPR system, one or more CRISPR proteins (e.g., Cas9) may be used. These CRISPR proteins are targeted to a first nucleic acid of defined sequence (a target locus) by a second nucleic acid and function either alone or in conjunction with other proteins. Thus, the CRISPR complex is a nucleic acid guided, nucleic acid recognition system.

CRISPR proteins or protein complexes will typically have binding activity for one or more CRISPR oligonucleotides and a nucleic acid modification activity (e.g., recombinase activity, methylase activity, etc.). Further, a nuclear localization signal may be present in CRISPR proteins or protein complexes, especially when (1) generated in or (2) designed or produced for introduction into a eukaryotic cell.

Thus, CRISPR proteins may be fusion proteins comprising, for example, the CRISPR protein or fragment thereof and an effector domain. Suitable effector domains include, for example nucleic acid cleavage domains (e.g., heterologous cleavage domains such as the cleavage domain of the endonuclease FokI), epigenetic modification domains, transcriptional activation domains (e.g., a VP16 domain), and transcriptional repressor domains. Each fusion protein may be guided to a specific chromosomal locus, for example, by a specific guide RNA, wherein the effector domain mediates targeted genome modification or gene regulation.

In some aspects, the fusion proteins can function as dimers thereby increasing the length of the target site and increasing the likelihood of its uniqueness in the genome (thus, reducing off target effects). For example, endogenous CRISPR systems modify genomic locations based on DNA binding word lengths of approximately 13-20 bp (Cong et al., *Science*, 339:819-823 (2013).

CRISPR proteins may be synthesized and/or purified by any number of means. In many instances, CRISPR proteins will be produced within the cell in which activity is desired. In some instances, CRISPR proteins may be produced extracellular to the cell in which activity is desired and then introducing into the cell. Example of methods for producing such CRISPR proteins is by in vitro translation, extraction of the proteins from cell that express these proteins encoded by an expression vector, and extraction of these proteins from cell that normally express them.

CRISPR Oligonucleotides

CRISPR oligonucleotides may be produced by a number of methods and may be generated to have varying features. In many instances, CRISPR oligonucleotides will be one component or two components. By "one component" is meant that only one oligonucleotide (e.g., guide RNA) is necessary for CRISPR activity. By "two components" is meant that only two different oligonucleotides (e.g., crRNA and tracrRNA) are required for CRISPR activity. CRISPR systems with more than two components may also be designed, produced and used. Thus, the invention contemplates multi-components CRISPR oligonucleotides where functionality involves three, four, five, etc. oligonucleotides.

In some instances, two or more oligonucleotides may be generated separately and then joined to each other to form, for example, one oligonucleotide that functions as part of a CRISPR system. The number of components of a system is determined by interaction with Cas9. As an example, if two oligonucleotides are produced and then joined prior to introduction into a cell, where the joined oligonucleotide requires no additional oligonucleotides to facilitate a CRISPR mediated activity, then this is said to be a one component system.

Of course, the nucleotide sequences and other features of CRISPR oligonucleotides may vary with specific systems and desired functions. Common features of CRISPR oligonucleotides include association with one or more CRISPR complex protein (e.g., Cas9) and nucleic acid "targeting" capability.

The invention thus includes compositions and methods for the production of CRISPR oligonucleotides, as well as collections of oligonucleotides generated, for example, using such compositions and methods.

In some embodiments, compositions and methods of the invention are directed to one of or a combination of molecular biology synthesis (e.g., PCR) and/or chemical synthesis for the generation of CRISPR oligonucleotides. Using the schematic representation shown in FIG. 6 for reference, two chemically synthesized oligonucleotides encoding components of a guide RNA may be designed to hybridize with each other and be extended to form a fully double-stranded nucleic acid molecule (e.g., DNA).

Figure 6:
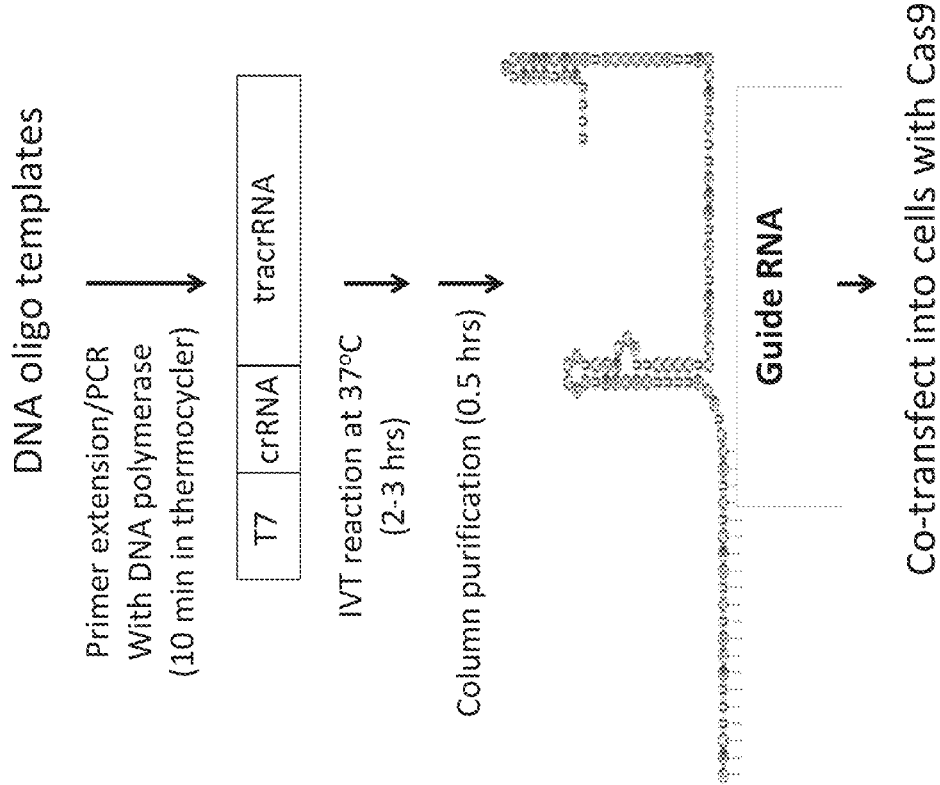
FIG. 6 shows a workflow for synthesizing guide RNA using DNA oligo templates. Guide RNA encoding DNA template is generated using assembly PCR. Components of this assembly reaction include 1) a target specific DNA oligo (encodes the crRNA region), 2) DNA oligo specific to the bacterial promoter used for in vitro transcription (in this case T7 promoter), and 3) overlapping PCR products encoding tracrRNA region. A fill in reaction followed by PCR amplification is performed in a Thermo cycler using DNA polymerase enzyme (in this case high fidelity PHUSION® Taq DNA polymerase) to generate full length gRNA encoding templates. Following PCR assembly the resulting DNA template is transcribed at 37° C. to generate target specific gRNA using in vitro transcription reagents for non-coding RNA synthesis (in this case MEGAshortscript™ T7 kit). Following synthesis the resulting gRNA is purified using a column or magnetic bead based method. Purified in vitro transcribed guide RNA is ready for co-transfection with Cas9 protein or mRNA delivery in a host system or cell line of interest.

FIG. 6 shows an exemplary workflow of the invention. The schematic in FIG. 6 shows oligonucleotides designed to generate a DNA molecule where the guide RNA coding region is operably linked to a T7 promoter. In this work flow DNA oligonucleotides either alone or in conjunction with double-stranded DNA are used to generate, via PCR, a DNA molecule encoding a guide RNA operably linked to a promoter suitable for in vitro transcription. The DNA molecule is then transcribed in vitro to generate guide RNA. The guide RNA may then be "cleaned up" by, for example, column purification or bead based methods. The guide RNA is then suitable for use by, as examples, (1) direct introduction into a cell or (2) introduction into a cell after being complexed with one or more CRISPR protein. Nucleic acid operably connected to a T7 promoter can be transcribed in mammalian cells when these cells contain T7 RNA polymerase (Lieber et al., *Nucleic Acids Res.*, 17: 8485-8493 (1989)). Of course, other promoters functional in eukaryotic cells (e.g., CMV promoter, U6 promoter, H1 promoter, etc.) could also be used for the intracellular production of guide RNA. The H1 promoter, for example, is about 300 base pairs in length. One advantage of the T7 promoter is its small size (20 base pairs). On specific T7 promoter that may be used in compositions and methods of the invention include those having the following nucleotide sequence: GAAAT-TAATACGACTCACTATAG (SEQ ID NO: 12).

The T7 promoter may also be used to generate guide RNA in an in vitro transcription system. In this instance, the double-stranded nucleic acid molecule would be used to generate guide RNA extracellularly for introduction into a cell.

Advantages of the guide RNA generation methods set out in FIG. 6 are speed and low cost of production. In particular, once a target sequence has been identified the Forward Oligo may be generated and combined with the Reverse Oligo in a reaction mixture designed to extend each of the oligonucleotides to form the double-stranded nucleic acid molecule (see FIG. 7). The Forward Oligo encodes the crRNA sequence designed with sequence complementarity to the target locus. Further, the Reverse Oligo has a sequence that is common to guide RNAs. The Reverse Oligo may be generated by any means and stored as a standard component. The Forward Oligo, however, is target sequence specific so it must be designed in view of the target locus.

Figure 7:
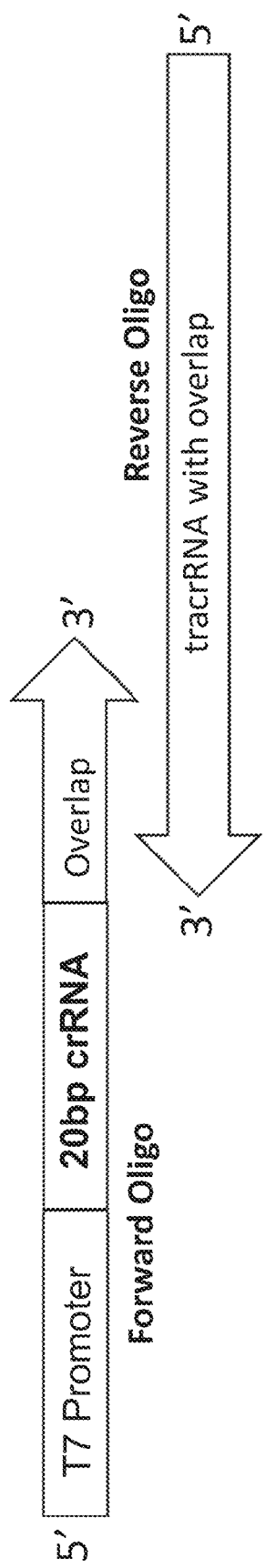
FIG. 7 shows overlapping DNA oligos as template for gRNA synthesis. The T7 promoter sequence and the overlap region are each about 20 nucleotides in length. Further, the box labeled "20 bp crRNA" is the target recognition component of the crRNA. Guide RNA is synthesized using 2 overlapping DNA oligonucleotides. 1) The forward DNA oligo contains the T7 promoter region (or other relevant in vitro transcription promoter), followed by target specific crRNA encoding region and a region that overlaps with the reverse oligonucleotide 2) Reverse DNA oligo encodes a tracrRNA sequence that is the constant component. These two overlapping oligonucleotides are annealed and extended to generate a DNA template for gRNA in vitro transcription (IVT) using high fidelity DNA polymerase enzyme (example PHUSION® Taq DNA polymerase). The assembly reaction also includes a 2-3 PCR cycling condition to enrich for the full length templates. The assembled DNA template is then used to generate guide RNA at 37° C. using in vitro transcription reagents for non-coding RNA synthesis (in this case MEGAshortscript™ T7 kit was used). Following gRNA synthesis the product is purified using a column or, alternatively, using bead based purification methods.

Two oligonucleotides suitable for the generation of double-stranded DNA suitable for transcription as set out in FIG. 6 are shown in FIG. 7. In the schematic of FIG. 7, the "Forward Oligo" is tailored for the target locus because it contains Hybridization Region 1 of the target specific crRNA. The "Reverse Oligo" contains regions of the tracrRNA and crRNA that are not target locus specific. Thus, the "Reverse Oligo" can be a "stock" component. The invention thus includes compositions and methods for the formation of guide RNA molecules. Methods of this aspect of the invention may comprise one or more of the following, a. identification of a target locus,
b. the in silico design of one or more CRISPR RNA molecules with sequence complementarity to that locus,
c. the production of a first oligonucleotide with a promoter sequence, a region of sequence complementarity (e.g., 15 to 25 nucleotides in length) to the target locus,
d. incubating the first oligonucleotide with (i) a second oligonucleotide and (ii) a polymerase under conditions suitable for performing polymerase chain reaction (PCR) to generate a double-stranded nucleic acid molecule, wherein the first oligonucleotide and the second oligonucleotide have a region of sequence complementarity of sufficient length to allow for hybridization between the two oligonucleotides, and
e. performing an in vitro transcription reaction on the PCR generated double-stranded nucleic acid molecule to produce a guide RNA molecule, and
f. purifying the guide RNA molecule from the other components of the reaction mixture.

Figure 8:
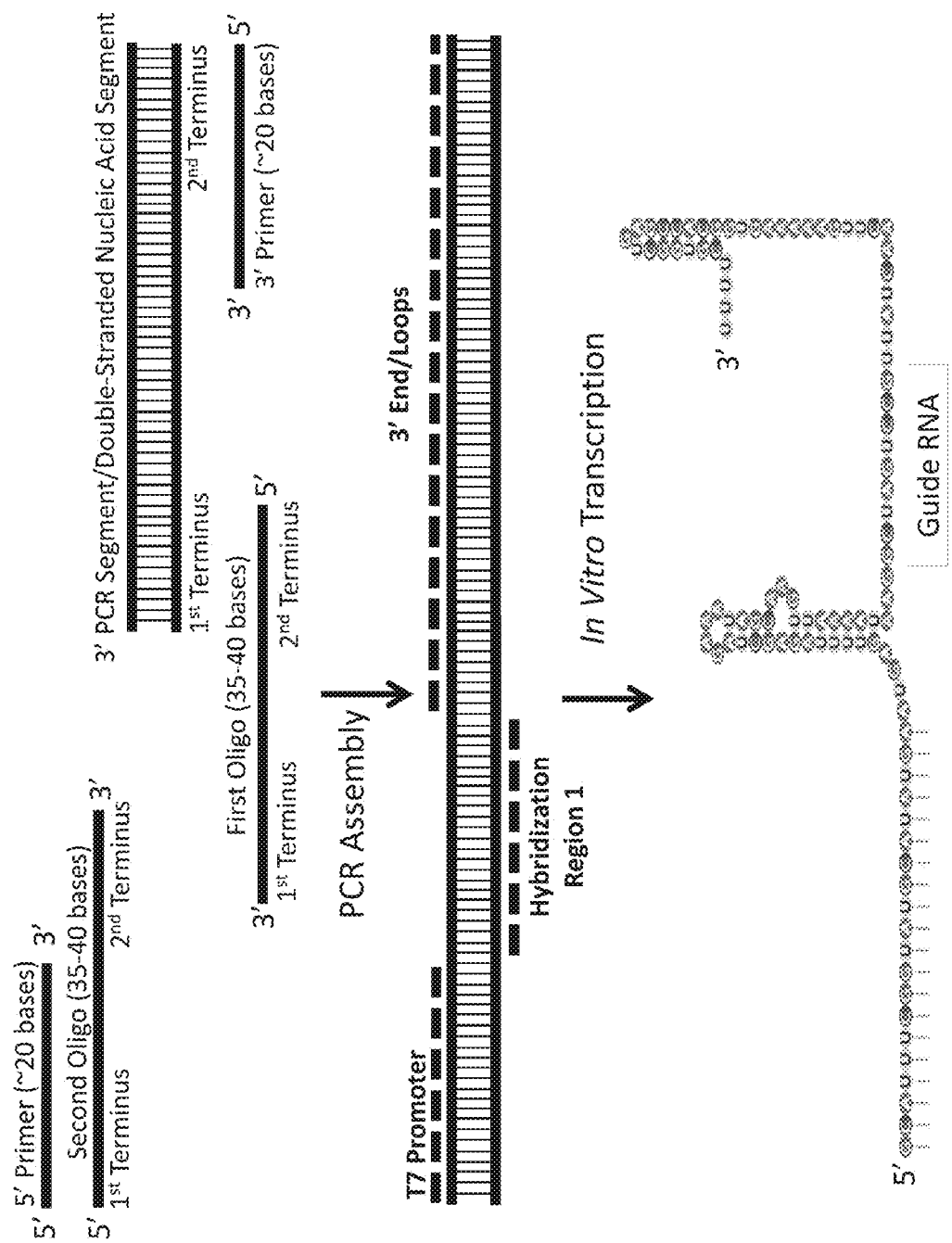
FIG. 8 shows a PCR assembly based method for producing DNA molecules that encode guide RNA molecules. In this schematic, "Oligo 1" encodes a T7 promoter and part of Hybridization Region 1 and "Oligo 2" encode part of Hybridization Region 1 and has overlapping sequence with the "3' PCR Segment". PCR is then used for assembly of these overlapping fragments, followed by amplification using the 5' and 3' primers, resulting in a double-stranded DNA molecule containing a T7 promoter operably connected to a target specific guide RNA coding sequence. RNA may be produced from this double-stranded DNA molecule by in vitro transcription.

In the work flow shown in FIG. 8, two oligonucleotides with the T7 promoter and Hybridization Region 1 nucleic acid and a Double-Stranded Nucleic Acid Segment are assembled by PCR. In this workflow, the Double-Stranded Nucleic Acid Segment has a constant sequence and, thus, can be a stock component.

The two oligonucleotides form the full length double-stranded nucleic acid segment via a polymerase mediated assembly reaction. Once the full length product molecule is assembled, further PCR reactions amplify the product. The primers prevent the two oligonucleotides from being PCR "limiting" components. In other words, once the product nucleic acid molecule has been generated, the primers allow for amplification to continue after the first and second oligonucleotides have been consumed.

Figure 9:
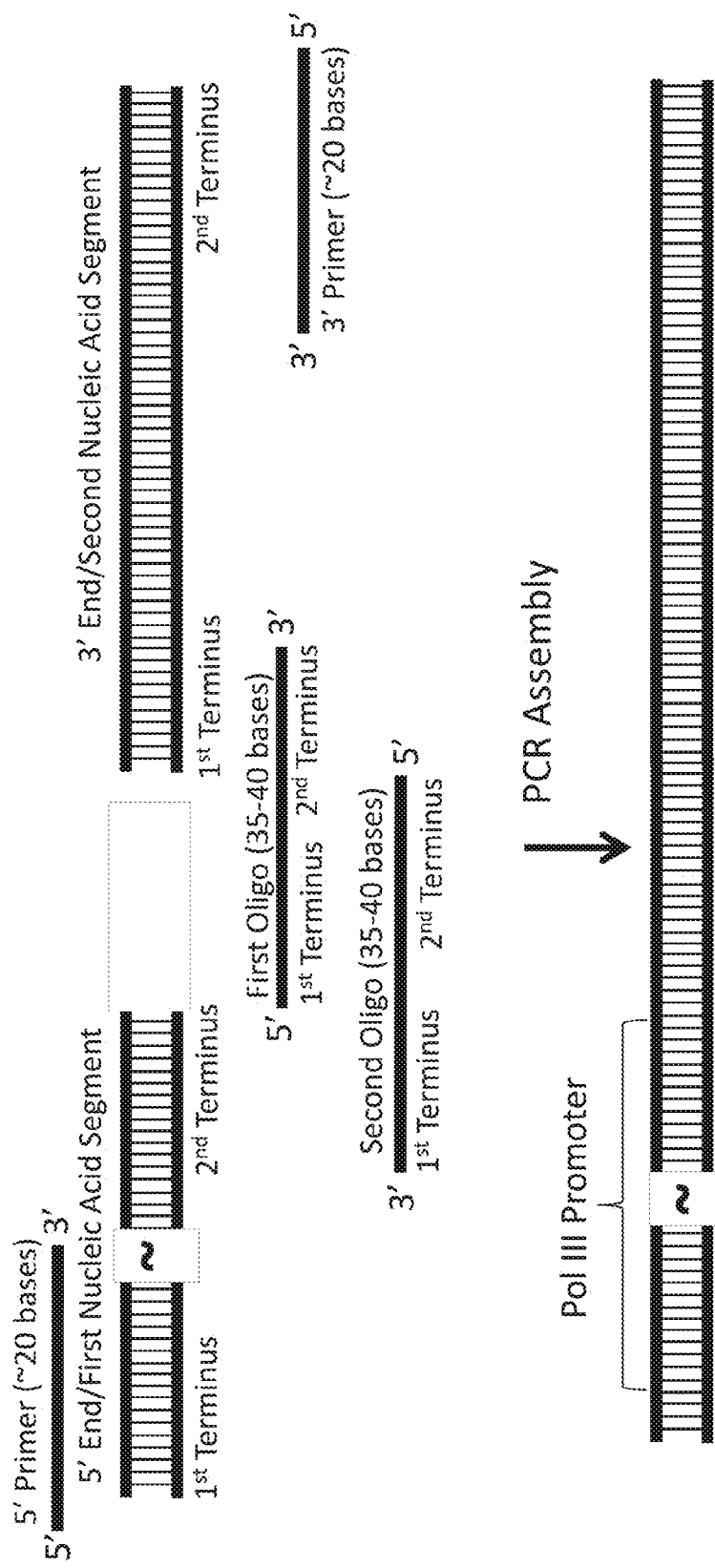
FIG. 9 shows PCR assembly method for synthesizing guide RNA expressing templates by PCR assembly. This method can be used to introduce other promoters and terminators in the context of the guide RNA. In this schematic, the overlap region between "First Oligo" and "Second Oligo" encode "Hybridization Region 1". The ~ in the RNA polymerase III promoter region represents an unrepresented segment of the nucleic acid molecule because these promoters can be several hundred bases in length. The RNA polymerase III terminator sequence is not shown in this figure. The 5' primer and 3' primer sequences extend beyond termini the nucleic acid segments that they hybridize to indicate that primers may be used to add additional functionalities to the amplified nucleic acid molecules.

FIG. 9 shows a process similar to that represented in FIG. 8 but the assembly reaction links two double-stranded nucleic acid segments and inserts specific nucleic acid in between them. Thus, the method represented in FIG. 9 is especially useful for the insertion of a nucleic acid segment of designed sequence between to selected nucleic acid molecules.

With respect to CRISPR RNA coding sequence construction, the First Oligonucleotide and the Second Oligonucleotide may be synthesized to hybridize with the First Nucleic Acid Segment and the Second Nucleic Acid Segment. Each of these oligonucleotides also encode all or part of Hybridization Region 1. Assembly reactions may thus be designed to generate, for example, a DNA molecule that encodes a target locus specific guide RNA operably linked to a promoter.

While only one oligonucleotide is required for assembly reactions of the type shown in FIG. 9, two will generally be used because crRNA Hybridization Region 1 is typically about 20 bases in length and about 15 bases of sequence identity is desired for efficient hybridization to the First Nucleic Acid Segment and the Second Nucleic Acid Segment. While oligonucleotides of 45 to 55 bases can be chemically synthesized, sequence fidelity often drops with length. The introduction of crRNA Hybridization Region 1 segment with low sequence results in two issues: (1) An increase in "off-target" effects can occur due to the Hybridization Region 1 associating with loci other that the desired target locus and (2) decreased target locus interaction efficiency of the encoded guide RNAs.

The second issue above occurs when heterogeneous PCR assembled nucleic acid (e.g., DNA) are transcribed (e.g., via in vitro transcription) and then introduced into cells. In general, the lower the level of sequence fidelity in the original assembly oligonucleotide population, the greater the variation in Hybridization Region 1 of the expressed guide RNA population. One way to address this problem is to use oligonucleotides generated with high sequence fidelity.

FIG. 9 represents a design for synthetic guide RNA expression cassette assembly. In this design, target specific variable crRNA region is encoded by the 35 to 40 base pair DNA oligo (represented here has first and second oligo). All the remaining DNA oligos and double stranded DNA segments may be constant components. These constant components include 1) a first double stranded nucleic acid segment encoding, for example, an RNA polymerase III promoter that can be leveraged for expressing the non-coding guide RNA component in vivo 2) a second double stranded nucleic acid segment encoding the tracrRNA component, and 3) 5' and 3' primers for amplification and enrichment of full length guide RNA expression templates containing the RNA polymerase III promoter. Full length guide RNA expression cassette containing relevant RNA polymerase III promoter is generated by assembly PCR using the double stranded nucleic acid segments, target specific overlapping oligos and flanking PCR primers. Assembly PCR is performed using a Taq DNA polymerase (e.g., PHUSION® Taq DNA polymerase), with the resulting product being column purified prior to delivery into host cell line of interest. Methods such as this can also be used to generate guide RNA expression cassettes containing any user defined promoter.

The invention further includes compositions and methods for the assembly of CRISPR RNA molecules (e.g., guide RNA molecules). CRISPR RNA molecules may be assembled by the connection of two or more (e.g., two, three, four, five, etc.) RNA segments with each other. In particular, the invention includes methods for producing nucleic acid molecules, these methods comprising contacting two or more linear RNA segments with each other under conditions that allow for the 5' terminus of a first RNA segment to be covalently linked with the 3' terminus of a second RNA segment.

Figure 10:
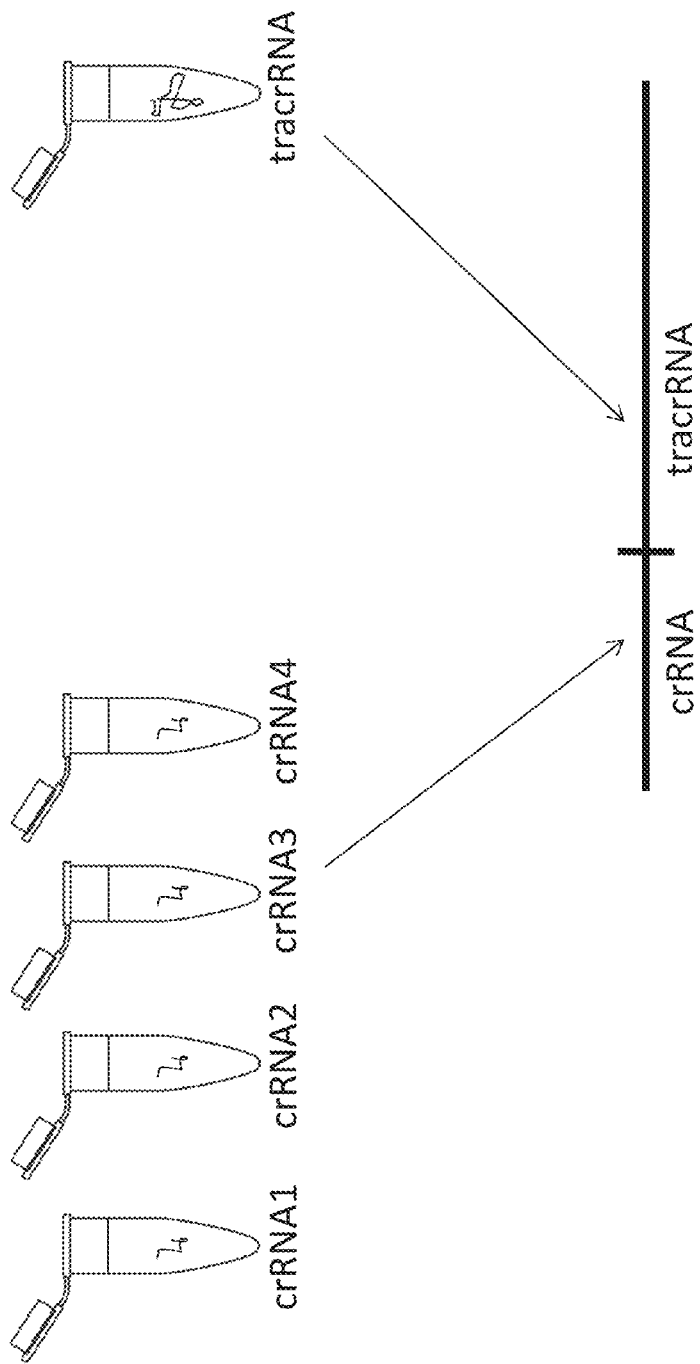
FIG. 10 shows a collection of variable crRNA molecules and a constant tracrRNA molecule. A specific crRNA molecule (crRNA3 in this instance) may be selected and then linked to a tracrRNA molecule.

This form of assembly has the advantage that it allows for rapid and efficient assembly of CRISPR RNA molecules. Using the schematic shown in FIG. 10 for purposes of illustration, guide RNA molecules with specificity for different target sites can be generated using a single tracrRNA molecule/segment connected to a target site specific crRNA molecule/segment. FIG. 10 shows four tubes with different crRNA molecules with crRNA molecule 3 being connected to a tracrRNA molecule to form a guide RNA molecule. Thus, FIG. 10 shows the connection of two RNA segments to for a product RNA molecule. Thus, the invention includes compositions and methods for the connection (e.g., covalent connection) of crRNA molecules and tracrRNA molecules.

The invention also includes compositions and methods for the production of guide RNA molecules with specificity for a target site, the method comprising: (1) identification of the target site, (2) production of a crRNA segment, and (3) connection of the crRNA segment with a tracrRNA segment. In such methods, the tracrRNA segment may be produced prior to connection with the crRNA and stored as a "stock" component or the tracrRNA segment may be generated from a DNA molecule that encodes the tracrRNA.

RNA molecules/segments connected to each other in the practice of the invention may be produced by any number of means, including chemical synthesis and transcription of DNA molecules. In some instances, RNA segments connected to each other may be produced by different methods. For example, a crRNA molecule produced by chemical synthesis may be connected to a tracrRNA molecule produced by in vitro transcription of DNA or RNA encoding the tracrRNA.

RNA segments may also be connected to each other by covalent coupling. RNA ligase, such as T4 RNA ligase, may be used to connect two or more RNA segments to each other. When a reagent such as an RNA ligase is used, a 5' terminus is typically linked to a 3' terminus. If two segments are connected, then there are two possible linear constructs that can be formed (i.e., (1) 5'-Segment 1-Segment 2-3' and (2) 5'-Segment 2-Segment 1-3'). Further, intramolecular circularization can also occur. Both of these issues can be addressed by blocking one 5' terminus or one 3' terminus so that RNA ligase cannot ligate the terminus to another terminus. Thus, if a construct of 5'-Segment 1-Segment 2-3' is desired, then placing a blocking group on either the 5' end of Segment 1 or the 3' end of Segment 2 will result in the formation of only the correct linear ligation product and will prevent intramolecular circularization. The invention thus includes compositions and methods for the covalent connection of two nucleic acid (e.g., RNA) segments. Methods of the invention include the use of an RNA ligase to directionally ligate two single-stranded RNA segments to each other.

One example of an end blocker that may be used in conjunction with, for example, T4 RNA ligase is a dideoxy terminator.

T4 RNA ligase catalyzes the ATP-dependent ligation of phosphodiester bonds between 5'-phosphate and 3'-hydroxyl termini. Thus, when one uses T4 RNA ligase, suitable termini must be present on the termini being ligated. One means for blocking T4 RNA ligase on a terminus is by failing to have the correct terminus format. In other words, termini of RNA segments with a 5-hydroxyl or a 3'-phosphate will not act as substrates for T4 RNA ligase.

Figure 11:
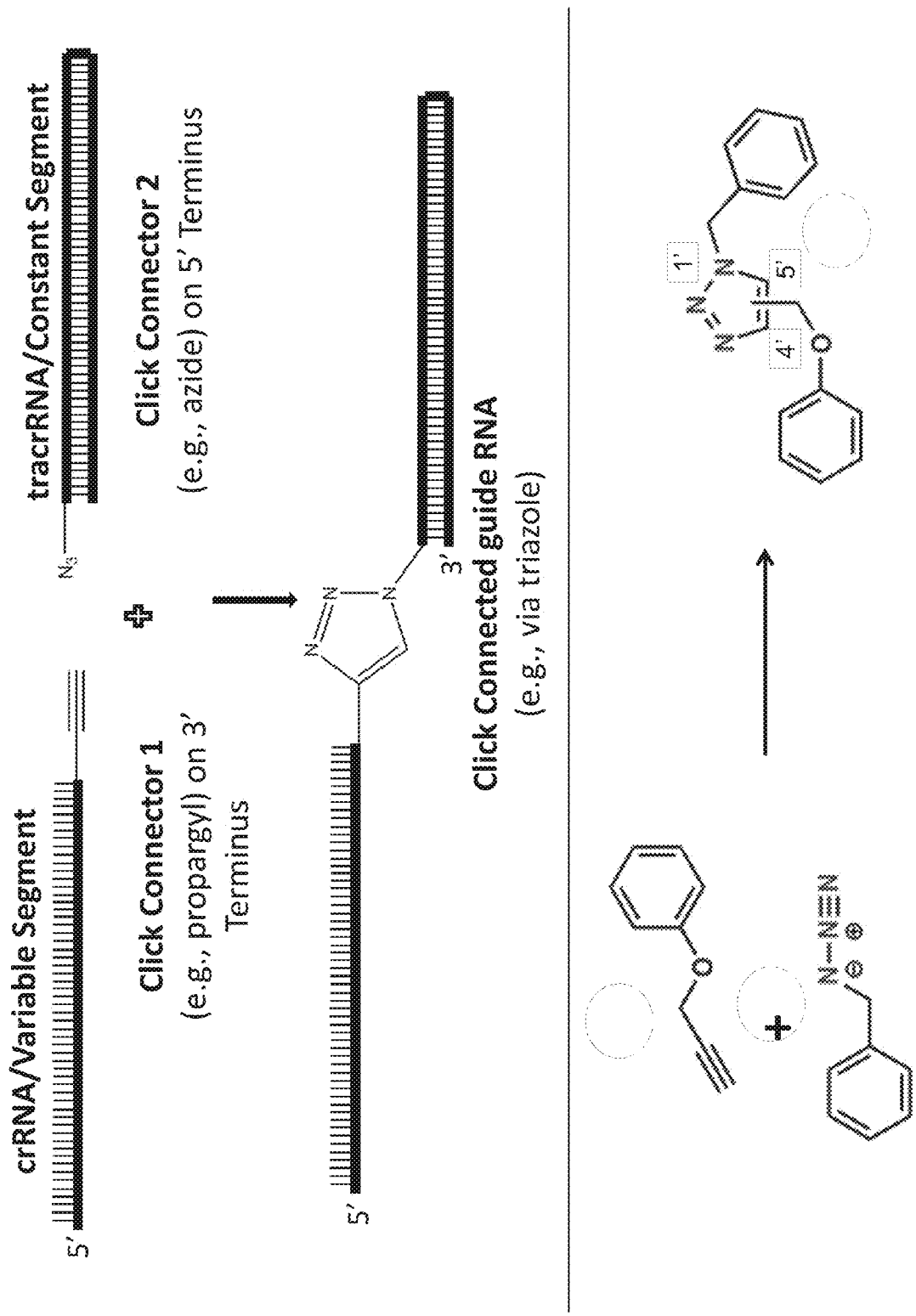
FIG. 11 shows an exemplary method for linking two RNA segments. The linking reaction shown in this figure using propargyl on one terminus and azide on the other terminus is unidirectional in that the termini with the chemical modifications are the only one that can link with each other.

Another method that may be used to connect RNA segments is by "click chemistry" (see, e.g., U.S. Pat. Nos. 7,375,234 and 7,070,941, and US Patent Publication No. 2013/0046084, the entire disclosures of which are incorporated herein by reference). For example, one click chemistry reaction is between an alkyne group and an azide group (see FIG. 11). Any click reaction can be used to link RNA segments (e.g., Cu-azide-alkyne, strain-promoted-azide-alkyne, staudinger ligation, tetrazine ligation, photo-induced tetrazole-alkene, thiol-ene, NHS esters, epoxides, isocyanates, and aldehyde-aminooxy). Ligation of RNA molecules using a click chemistry reaction is advantageous because click chemistry reactions are fast, modular, efficient, often do not produce toxic waste products, can be done with water as a solvent, and can be set up to be stereospecific.

In one embodiment the present invention uses the "Azide-Alkyne Huisgen Cycloaddition" reaction, which is a 1,3-dipolar cycloaddition between an azide and a terminal or internal alkyne to give a 1,2,3-triazole for the ligation of RNA segments. One advantage of this ligation method is that this reaction can initiated by the addition of required Cu(I) ions.

Other mechanism by which RNA segments may be connected include the use of halogens (F—, Br—, I—)/alkynes addition reactions, carbonyls/sulfhydryls/maleimide, and carboxyl/amine linkages.

For example, one RNA molecule may be modified with thiol at 3' (using disulfide amidite and universal support or disulfide modified support), and the other RNA molecule may be modified with acrydite at 5' (using acrylic phosphoramidite), then the two RNA molecules can be connected by Michael addition reaction. This strategy can also be applied to connecting multiple RAN molecules stepwise.

The invention also includes methods for linking more than two (e.g., three, four, five, six, etc.) RNA molecules to each other. One reason this may be done is when an RNA molecule longer than about 40 nucleotides is desired, as noted elsewhere herein, chemical synthesis efficiency degrades.

By way of example, a tracrRNA is typically around 80 nucleotides. Such RNA molecules may be produced by processes such as in vitro transcription or chemical synthesis. When chemical synthesis is used to produce such RNA molecules, they may be produced as a single synthesis product or by linking two or more synthesized RNA segments to each other. Further, when three or more RNA segments are connected to each other, different methods may be used to link the individual segments together. Also, the RNA segments may be connected to each other in one "pot", all at the same time, or in one "pot" at different times or in different "pots" at different times.

For purposes of illustration, assume one wishes to assemble RNA Segments 1, 2 and 3 in numerical order. RNA Segments 1 and 2 may be connected, 5' to 3', to each other. The reaction product may then be purified for reaction mixture components (e.g., by chromatography), then placed in a second vessel, "pot", for connection of the 3' terminus with the 5' terminus of RNA Segment 3. The final reaction product may then be connected to the 5' terminus of RNA Segment 3.

A second, more specific illustration of one embodiment of the invention is as follows. RNA Segment 1 (about 30 nucleotides) is the target locus recognition sequence of a crRNA and a portion of Hairpin Region 1. RNA Segment 2 (about 35 nucleotides) contains the remainder of Hairpin Region 1 and some of the linear tracrRNA between Hairpin Region 1 and Hairpin Region 2. RNA Segment 3 (about 35 nucleotides) contains the remainder of the linear tracrRNA between Hairpin Region 1 and Hairpin Region 2 and all of Hairpin Region 2. In this illustration, RNA Segments 2 and 3 are linked, 5' to 3', using click chemistry. Further, the 5' and 3' end termini of the reaction product are both phosphorylated. The reaction product is then contacted with RNA Segment 1, having a 3' terminal hydroxyl group, and T4 RNA ligase to produce a guide RNA molecule.

A number of additional linking chemistries may be used to connect RNA segments according to method of the invention. Some of these chemistries are set out in Table 6.

TABLE 6

Exemplary RNA Ligation Reactions

| Reaction Type | Reaction Summary |
|---|---|
| Thiol-yne | $R_1$—≡ + HS—$R_2$ → vinyl sulfide product |
| NHS esters | $R_1$-C(=O)-O-NHS + $H_2N$—$R_2$ → $R_1$-C(=O)-O-NH-$R_2$ |
| Thiol-ene | $R_1$-CH=CH$_2$ + HS-$R_2$ →(hv, cat.) $R_1$-CH$_2$-CH$_2$-S-$R_2$ |
| Isocyanates | $R_1$-NCO + HX-$R_2$ → $R_1$-NH-C(=O)-X-$R_2$   X = S or NH |
| Epoxy or aziridine | epoxide or aziridine ($R_1$) + HS-$R_2$ → HO-CH($R_1$)-CH$_2$-S-$R_2$ or H$_2$N-CH($R_1$)-CH$_2$-S-$R_2$ |
| Aldehyde-aminoxy | $R_1$-CHO + H$_2$N-O-$R_2$ → $R_1$-CH=N-O-$R_2$ |
| Cu-catalyzed-azid-alkyne | $R_1$-N$_3$ + alkyne-$R_2$ →(Cu⊕) 1,4-triazole ($R_1$, $R_2$) |
| Strain-promoted-azid-alkyne | Cyclooctyne cycloaddition (with azide or nitrile oxide or nitrone)<br>nitrone ($R_3$, $R_4$, $R_1$) or nitrile oxide ($R_1$) or azide $R_1$-N$_3$ + cyclooctyne-$R_2$ → fused triazole ($R_1$, $R_2$) or fused isoxazole ($R_1$, $R_2$) |

TABLE 6-continued
Exemplary RNA Ligation Reactions
| Reaction Type | Reaction Summary |
|---|---|
| | Norbornene cycloaddition (with azide or nitrile oxide or nitrone) 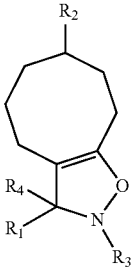 |
| | Oxanorbornadiene cycloaddition 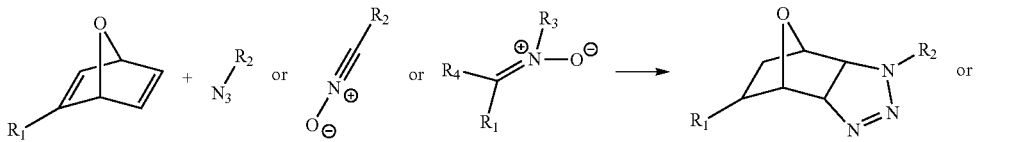 |
| Staudinger ligation | 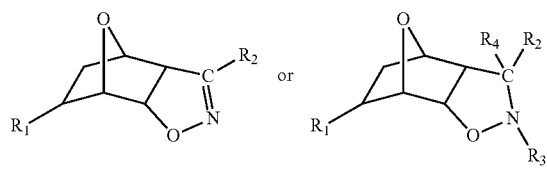 |
| Tetrazine ligation | 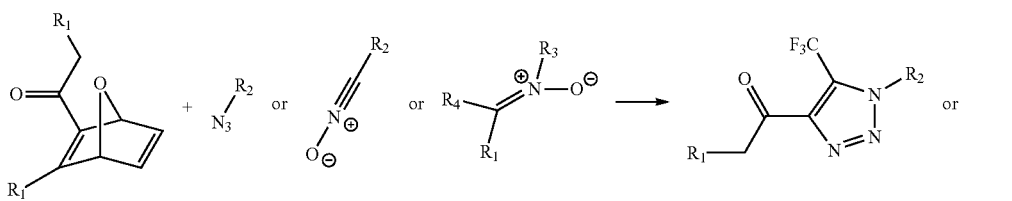 |

TABLE 6-continued

Exemplary RNA Ligation Reactions

| Reaction Type | Reaction Summary |
|---|---|
| Photo-induced tetrazole-alken | 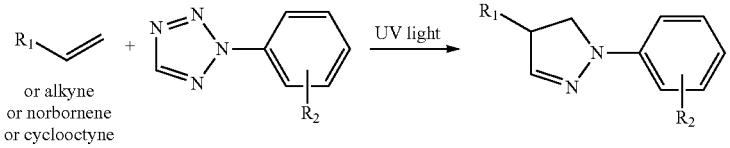 |
| [4 + 1] cyclo-addition | 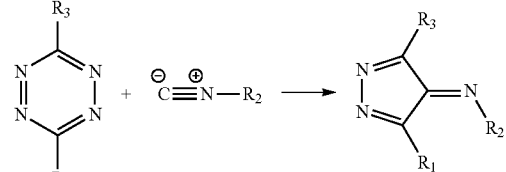 |
| Quadri-cyclane ligation | 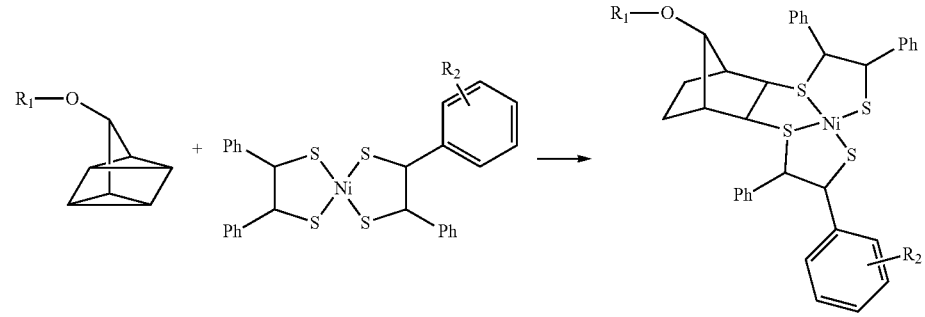 |

One issue with methods for linking RNA segments is that often they do not result in complete conversion of the segments to connected RNA molecules. For example, some chemical linkage reactions only result in 50% of the reactants forming the desired end product. In such instances, it will often be desirable to remove reagents and unreacted RNA segments. This may be done by any number of means such as dialysis, chromatography (e.g., HPLC), precipitation, electrophoresis, etc. Thus, the invention includes compositions and method for linking RNA segments, where the reaction products RNA molecules are separated from other reaction mixture components.

As noted above, CRISPR system components may be "generic" with respect to target loci (e.g., Cas9 protein) or may be specific for a particular target locus (e.g., crRNA). This allows for the production of "generic" components that may be used in conjunction with target sequence specific components. Thus, when a target locus of interest is identified, one need only produce a component or components specific for that target locus. In the instance where one seeks to make two closely associated "nicks" at the target sequence, then, for example, two crRNA molecules will typically need to be produced. These crRNA molecules may be produced when the target sequence of interest is identified or they may be produced in advance and stored until needed.

The invention further includes collections of crRNA molecules with specificity for individual target sites. For example, the invention includes collections of rRNA molecules with specificity for target sites within particular types of cell (e.g., human cells). The members of such collection of cells may be generated based upon sequence information for these particular types of cells. As an example, one such collection could be generated using the complete genome sequence of a particular type of cell. The genome sequence data can be used to generate a library of crRNA molecules with specificity for the coding region of each gene within the human genome. Parameters that could be used to generate such a library may include the location of protospacer adjacent motif (PAM) sites, off target effects (e.g., sequences unique to the target region), and, when gene "knockouts" are desired, locations within coding regions likely to render the gene expression product fully or partially non-functional (e.g., active site coding regions, intron/exon junctions, etc.).

Collections or libraries of crRNA molecules or the invention may include a wide variety of individual molecules such as from about five to about 100,000 (e.g., from about 50 to about 100,000, from about 200 to about 100,000, from about 500 to about 100,000, from about 800 to about 100,000, from about 1,000 to about 100,000, from about 2,000 to about 100,000, from about 4,000 to about 100,000, from about 5,000 to about 100,000, from about 50 to about 50,000, from about 100 to about 50,000, from about 500 to about 50,000, from about 1,000 to about 50,000, from about 2,000 to about 50,000, from about 4,000 to about 50,000, from about 50 to about 10,000, from about 100 to about 10,000, from about 200 to about 10,000, from about 500 to about 10,000, from about 1,000 to about 10,000, from about 2,000 to about 10,000, from about 4,000 to about 10,000, from about 50 to about 5,000, from about 100 to about 5,000, from about 500 to about 5,000, from about 1,000 to about 5,000, from about 50 to about 2,000, from about 100 to about 2,000, from about 500 to about 2,000, etc.).

RNA molecules generated by and used in the practice of the invention may be stored in a number of ways. RNA molecules are generally not as stable as DNA molecules and, thus, to enhance stability, RNA molecules may be stored at low temperature (e.g., −70° C.) and/or in the presence of one or more RNase inhibitor (e.g., RNAseOUT™, RNAsecure™ Reagent, both available from Thermo Fisher Scientific).

Further, RNA molecules may be chemically modified to be resistant to RNases by, for example, being generated using RNase-resistant ribonucleoside triphosphates. Examples of RNase-resistant modified ribonucleosides include, but are not limited to, 2-fluoro ribonucleosides, 2-amino ribonucleosides, and 2-methoxy ribonucleosides. Additional examples of RNase-resistant modified ribonucleosides are disclosed in U.S. Patent Publ. 2014/0235505 A1, the entire disclosure of which is incorporated herein by reference. 2'-O-allyl-ribonucleotides may also be incorporated into RNA molecules of the invention.

Chemical modification used in the practice of the invention will often be selected based upon a series of criteria, such as effectiveness for the purpose that the chemical modification is used (e.g., RNase resistance), level of toxicity to cells (low generally being better than high), ease of incorporation into the nucleic acid molecules, and minimal interference with the biological activities of the nucleic acid molecule (e.g., the activities of a guide RNA molecule).

Further, RNA molecules of and used in the practice of the invention may be stored in a number of different formats. For example, RNA molecules may be stored in tubes (e.g., 1.5 ml microcentrifuge tubes) or in the wells of plates (e.g., 96 well, 384 well, or 1536 well plates).

The invention thus includes compositions and methods for the production of libraries and/or collections of CRISPR system components, as well as the libraries and/or collections of CRISPR system components themselves.

The invention also includes compositions and methods for the isolation of gRNA molecules. Such methods will often be based upon hybridization of a gRNA region to another nucleic acid molecule, followed by separation of the hybridized complex from other molecules (e.g., nucleic acid molecules) present in a mixture.

As an example, beads containing a nucleic acid molecule with sequence homology to a gRNA molecule may be used to purify the gRNA from a solution. In some instances, the bead will be a magnetic bead. Further, the nucleic acid molecule designed to hybridize to the gRNA molecule may be designed with homology to a sequence present in gRNA molecules or gRNA molecules may be designed to contain a sequence that is used for hybridization. The invention thus includes gRNA molecules that are designed to contain what is effectively a hybridization "tag".

Such "tags" are particularly useful in high throughput applications. As an example, a 96 well plate may contain different gRNA molecules in each well, wherein each gRNA molecules contains the same tag. A magnetic bead may be placed in one or more well of the plate and then removed after a specified period of time to allow for gRNA/bead bound hybridization to take place. These beads may then be individually placed in wells of another plate containing cells and donor DNA under conditions that allow for release of gRNA molecules from the beads (e.g., competition with an oligonucleotide of identical or similar sequence to the tag).

As noted above, hybridization tags may be naturally resident with gRNA molecules or may be introduced into or added to gRNA molecules. Such tags may be added by the alteration of a region present in a gRNA molecule or may be added to the gRNA either internally or at a terminus. Further, tags may be generated during synthesis of gRNA molecules or added after gRNA molecules are produced (e.g., via "click chemistry").

Hybridization tags will typically be less than 25 (e.g., from about 10 to about 25, from about 15 to about 25, from about 16 to about 25, from about 10 to about 20, from about 15 to about 25, from about 15 to about 20, etc.) bases in length. Such tags will typically be able to hybridize to homologous sequences with sufficient affinity for association but will not associate so strongly that they do not efficiently release when desired. Further, shorter tags will often have a higher GC content. In many instances, tags will have a GC content of at least 45% (e.g., from about 45% to about 75%, from about 50% to about 75%, from about 55% to about 75%, from about 60% to about 75%, from about 65% to about 75%, etc.).

Also, tagged gRNA molecules may contain a label. This label may be used to quantify the amount of gRNA present. Labels may also be useful when seeking to determine the amount of gRNA transferred by hybridization based means. Such labels may also be used to measure cellular uptake as set out elsewhere herein.

CRISPR Activities

CRISPR complexes of the invention can have any number of activities. For example, CRISPR proteins may be fusion proteins comprising one or more heterologous protein domains (e.g., one, two, three, four, five, etc.). A CRISPR fusion protein may comprise any additional protein sequence, and optionally a linker sequence between any two domains. Examples of protein domains that may be fused to a CRISPR protein include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity, and nucleic acid binding activity.

Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP).

A CRISPR protein may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GALA DNA binding domain fusions, and herpes simplex virus (HSV) BP16 protein fusions. Additional domains that may form part of a fusion protein comprising a CRISPR protein are described in US 2011/0059502, incorporated herein by reference.

In particular, provided herein, in part, are CRISPR protein endonucleases, which comprise at least one nuclear localization signal, at least one nuclease domain, and at least one domain that interacts with a guide RNA to target the endonuclease to a specific nucleotide sequence for cleavage. Also provided are nucleic acids encoding CRISPR protein endonucleases, as well as methods of using CRISPR protein endonucleases to modify chromosomal sequences of eukaryotic cells or embryos. CRISPR protein endonucleases interacts with specific guide RNAs, each of which directs the endonuclease to a specific targeted site, at which site the CRISPR protein endonucleases introduces a double-stranded break that can be repaired by a DNA repair process such that the chromosomal sequence is modified. Since the specificity is provided by the guide RNA (or the crRNA), the CRISPR protein endonucleases are universal and can be used with different guide RNAs to target different genomic sequences. Methods disclosed herein can be used to target and modify specific chromosomal sequences and/or introduce exogenous sequences at targeted locations in the genome of cells or embryos.

CRISPR complexes may also be employed to activate or repress transcription. For example, a dCas9-transcriptional activator fusion protein (e.g., dCas9-VP64) may be used in conjunction with a guide RNA to activate transcription of nucleic acid associated with a target locus. Similarly, dCas9-repressor fusions (e.g., dCas9-KRAB transcriptional repressor) may be used to repress transcription of nucleic acid associated with a target locus. Transcriptional activation and repression such as the referred to above are discussed in, for example, Kearns et al., *Cas9 effector-mediated regulation of transcription and differentiation in human pluripotent stem cells, Development*, 141:219-223 (2014).

The invention thus includes compositions and methods for the production and use of CRISPR system components for the activation and repression of transcription.

CRISPR Systems

CRISPR systems that may be used in the practice of the invention vary greatly. These systems will generally have the functional activities of a being able to form complex comprising a protein and a first nucleic acid where the complex recognizes a second nucleic acid. CRISPR systems can be a type I, a type II, or a type III system (see Table 2). Non-limiting examples of suitable CRISPR proteins include Cas3, Cas4, Cas5, Cas5e (or CasD), Cash, Cas6e, Cas6f, Cas7, Cas8a1, Cas8a2, Cas8b, Cas8c, Cas9, Cas10, Cas1 Od, CasF, Cas6, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cul966.

In some embodiments, the CRISPR protein (e.g., Cas9) is derived from a type II CRISPR system. In specific embodiments, the CRISPR system is designed to acts as an oligonucleotide (e.g., DNA or RNA)-guided endonuclease derived from a Cas9 protein. The Cas9 protein for this and other functions set out herein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculumthermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.*

FIG. 12A-12F shows an alignment of Cas9 amino acid sequences. In many instances, the compositions and methods of the invention will be directed to Type II CRISPR systems. In such instances, a number of different Cas9 proteins may be employed. Cas9 proteins may be defined, to some extent, by their regions of sequence homology. Proteins suitable for use in compositions and methods of the invention will typically include those that have seven or more (e.g., from about seven to about fifteen, from about seven to about eleven, from about seven to about ten, from about seven to about eight, etc.) amino acids identical to the *S. pyogenes* Cas9 amino acid sequence shown in FIG. 12A-12F. Additional features of CRISPR proteins that fall within the scope of the invention are set out elsewhere herein.

Vector Components and Cells:

A number of functional nucleic acid components (e.g., promoters, polyA signal, origins of replication, selectable markers, etc.) may be used in the practice of the invention. The choice of functional nucleic acid components used in the practice of the invention, when employed, will vary greatly with the nature of the use and the specifics of the system (e.g., intracellular, extracellular, in vitro transcription, coupled in vitro transcription/translation, etc.).

Promoter choice depends upon a number of factors such as the expression products and the type of cell or system that is used. For example, non-mRNA molecules are often production using RNA polymerase I or III promoters. mRNA is generally transcribed using RNA polymerase II promoters. There are exceptions, however. One is microRNA expression systems where a microRNA can be transcribed from DNA using an RNA polymerase II promoter (e.g., the CMV promoter). While RNA polymerase II promoters do not have "sharp" stop and stop points, microRNAs tend to be processed by removal of 5' and 3' termini. Thus, "extra" RNA segments at the termini are removed. mRNA (e.g., cas9 mRNA) is normally produced via RNA polymerase II promoters.

The choice of a specific promoter varies with the particular application. For example, the T7, T3 and SP6 promoters are often used for in vitro transcription and in vitro transcription/translations systems. When intracellular expression in desired, the promoter or promoters used will generally be designed to function efficiently within the cells employed. The CMV promoter, for example, is a strong promoter for use within mammalian cells. The hybrid Hsp70A-Rbc S2 promoter is a constitutive promoter that functions well in eukaryotic algae such as *Chlamydomonas reinhardtii*. (see the product manual "GeneArt® Chlamydomonas Protein Expression Kit", cat. no. A24244, version B.0, from Life Technologies Corp., Carlsbad, Calif.). Additional promoters that may be used in the practice of the invention include AOX1, GAP, cauliflower mosaic virus 35S, pGC1, EF1α, and Hsp70 promoters.

The DNA segment in the expression vector is operatively linked to an appropriate expression control sequence(s) (promoter) to direct RNA synthesis. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter. Exemplary promoters suitable for use with the invention are from the type III class of RNA polymerase III promoters. Additionally, the promoters may be selected from the group consisting of the U6 and H1 promoters. The U6 and H1 promoters are both members of the type III class of RNA polymerase III promoters.

RNA polymerase III promoters are suitable for in vivo transcription of nucleic acid molecules produced by methods of the invention. For example, linear DNA molecules produced as set out in FIG. 9 may be introduced into cells and transcribed by, for example, naturally resident intracellular transcriptional processes.

Promoters in compositions and methods of the invention may also be inducible, in that expression may be turned "on" or "off." For example, a tetracycline-regulatable system employing the U6 promoter may be used to control the production of siRNA. Expression vectors may or may not contain a ribosome binding site for translation initiation and a transcription terminator. Vectors may also include appropriate sequences for amplifying expression.

A great variety of cloning/expression systems can be used to express proteins and nucleic acid molecules in the practice of the invention. Such vectors include, among others, chromosomal-, episomal- and viral-derived vectors, for example, vectors derived from plasmids, from bacteriophage, from transposons, from yeast episomes, from insertion elements, from yeast chromosomal elements, from viruses such as baculoviruses, papova viruses, such as SV40, vaccinia viruses, adenoviruses, adeno-associated viruses, avipox (e.g., fowl pox) viruses, suipox viruses, capripox viruses, pseudorabies viruses, picornaviruses and retroviruses, and vectors derived from combinations thereof, such as those derived from plasmid and bacteriophage genetic elements, such as cosmids and phagemids. The expression system constructs can contain control regions that regulate as well as engender expression. Generally, any system or vector suitable to maintain, propagate or express polynucleotides or to express a polypeptide in a host can be used for expression in this regard. The appropriate DNA sequence can be inserted into the expression system by any of a variety of well-known and routine techniques, such as, for example, those set forth in Sambrook et al., MOLECULAR CLONING: A LABORATORY MANUAL, 2nd Ed., Cold Spring Harbour Laboratory Press, Cold Spring Harbour. N.Y. (1989).

Cells suitable for use with the present invention include a wide variety of prokaryotic and eukaryotic cells. In many instances, the cells one or more CRISPR system component will not be naturally associated with the cell (i.e., will be exogenous to the cell).

Representative cells that may be used in the practice of the invention include, but are not limited to, bacterial cells, yeast cells, plant cells and animal cells. Exemplary bacterial cells include *Escherichia* spp. cells (particularly *E. coli* cells and most particularly *E. coli* strains DH10B, Stbl2, DH5□, DB3, DB3.1), *Bacillus* spp. cells (particularly *B. subtilis* and *B. megaterium* cells), *Streptomyces* spp. cells, *Erwinia* spp. cells, *Klebsiella* spp. cells, *Serratia* spp. cells (particularly *S. marcessans* cells), *Pseudomonas* spp. cells (particularly *P. aeruginosa* cells), and *Salmonella* spp. cells (particularly *S. typhimurium* and *S. typhi* cells). Exemplary animal cells include insect cells (most particularly *Drosophila melanogaster* cells, *Spodoptera frugiperda* Sf9 and Sf21 cells and *Trichoplusa* High-Five cells), nematode cells (particularly *C. elegans* cells), avian cells, amphibian cells (particularly *Xenopus laevis* cells), reptilian cells, and mammalian cells (more particularly NIH3T3, CHO, COS, VERO, BHK CHO-K1, BHK-21, HeLa, COS-7, HEK 293, HEK 293T, HT1080, PC12, MDCK, C2C12, Jurkat, NIH3T3, K-562, TF-1, P19 and human embryonic stem cells like clone H9 (Wicell, Madison, Wis., USA)). Exemplary yeast cells include *Saccharomyces cerevisiae* cells and *Pichia pastoris* cells. These and other cells are available commercially, for example, from Thermo-Fisher Scientific (Waltham, Mass.), the American Type Culture Collection, and Agricultural Research Culture Collection (NRRL; Peoria, Ill.). Exemplary plant cells include cells such as those derived from barley, wheat, rice, soybean, potato, arabidopsis and tobacco (e.g., *Nicotiana tabacum* SR1).

Introduction of CRISPR System Components into Cells:

The invention also includes compositions and methods for introduction of CRISPR system components into cells. Introduction of a molecules into cells may be done in a number of ways including by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbour Laboratory Press, Cold Spring Harbour. N.Y. (1989), such as, calcium phosphate transfection, DEAE-dextran mediated transfection, transfection, microinjection, cationic lipid-mediated transfection, electroporation, transduction, scrape loading, ballistic introduction, nucleoporation, hydrodynamic shock, and infection.

The invention includes methods in which different CRISPR system components are introduced into cells by different means, as well as compositions of matter for performing such methods. For example, a lentiviral vector may be used to introduce Cas9 coding nucleic acid operably linked to an suitable and guide RNA may be introduced by transfection.

CRISPR system components may be the functional CRISPR system molecules or they may be molecules encoding the functional molecules (e.g., DNA, RNA encoding Cas9, etc.) transfection of CRISPR system components into cells. Methods of the invention relate to the introduction into cells one or more of the following:

a. Guide RNA,
b. crRNA,
c. tracrRNA,
d. DNA encoding Cas9 or dCas9 (as well as fusion proteins of each), and
e. mRNA encoding Cas9 or dCas9 (as well as fusion proteins of each).

In most instances, CRISPR system components will be introduced into a cell in a manner that results in the generation of CRISPR activities within the cell. Thus, in instances where a cell expresses Cas9 protein (e.g., from chromosomally integrated CRISPR encoding nucleic acid operably linked to a promoter), crRNA and tracrRNA or guide may be introduced into the cell by transfection.

Transfection agents suitable for use with the invention include transfection agents that facilitate the introduction of RNA, DNA and proteins into cells. Exemplary transfection reagents include TurboFect Transfection Reagent (Thermo Fisher Scientific), Pro-Ject Reagent (Thermo Fisher Scientific), TRANSPASS™ P Protein Transfection Reagent (New England Biolabs), CHARIOT™ Protein Delivery Reagent (Active Motif), PROTEOJUICE™ Protein Transfection Reagent (EMD Millipore), 293fectin, LIPOFECTAMINE™ 2000, LIPOFECTAMINE™ 3000 (Thermo Fisher Scientific), LIPOFECTAMINE™ (Thermo Fisher Scientific), LIPOFECTIN™ (Thermo Fisher Scientific), DMRIE-C, CELLFECTIN™ (Thermo Fisher Scientific), OLIGOFECTAMINE™ (Thermo Fisher Scientific), LIPOFECTACE™, FUGENE™ (Roche, Basel, Switzerland), FUGENE™ HD (Roche), TRANSFECTAM™(Transfectam, Promega, Madison, Wis.), TFX-10™ (Promega), TFX-20™ (Promega), TFX-50™ (Promega), TRANSFECTIN™ (BioRad, Hercules, Calif.), SILENTFECT™ (Bio-Rad), Effectene™ (Qiagen, Valencia, Calif.), DC-chol (Avanti Polar Lipids), GENEPORTER™ (Gene Therapy Systems, San Diego, Calif.), DHARMAFECT 1™ (Dharmacon, Lafayette, Colo.), DHARMAFECT 2™ (Dharmacon), DHARMAFECT 3™ (Dharmacon), DHARMAFECT 4™ (Dharmacon), ESCORT™ III (Sigma, St. Louis, Mo.), and ESCORT™ IV (Sigma Chemical Co.).

The invention further includes methods in which one molecule is introduced into a cell, followed by the introduction of another molecule into the cell. Thus, more than one CRISPR system components molecule may be introduced into a cell at the same time or at different times. As an example, the invention includes methods in which Cas9 is introduced into a cell while the cell is in contact with a transfection reagent designed to facilitate the introduction of proteins in to cells (e.g., TurboFect Transfection Reagent), followed by washing of the cells and then introduction of guide RNA while the cell is in contact with LIPOFECTAMINE™ 2000.

Conditions will normally be adjusted on, for example, a per cell type basis for a desired level of CRISPR system component introduction into the cells. While enhanced conditions will vary, enhancement can be measure by detection of intracellular CRISPR system activity. Thus, the invention includes compositions and methods for measurement of the intracellular introduction of CRISPR system components in cells.

The invention also includes compositions and methods related to the formation and introduction of CRISPR complexes into cells. One exemplary method of the invention comprises:
  a. forming a complex comprising at least one CRISPR system protein with at least one CRISPR RNA,
  b. contacting the complexed CRISPR system protein and RNA with a cell,
  c. incubating or culturing the resulting cell for a period of time (e.g., from about 2 minutes to about 8 hours, from about 10 minutes to about 8 hours, from about 20 minutes to about 8 hours, from about 30 minutes to about 8 hours, from about 60 minutes to about 8 hours, from about 20 minutes to about 6 hours, from about 20 minutes to about 3 hours, from about 20 minutes to about 2 hours, from about 45 minutes to about 3 hours, etc.), and
  d. measuring CRISPR system activity within the cell.

In some instances, during the practice of methods of the invention, molecules introduced into cells may be labeled. One schematic example of this is set out in FIG. 24 where donor DNA labeled with ALEXA FLUOR® 647 dye (Thermo Fisher Scientific) and GFP-Cas9 RNP complexes are sequentially introduced into HEK293 cells, followed by cell sorting to obtain cells that contain both labels (lower right of FIG. 24). This is advantageous because cells containing specific amounts of both labels may be separated from other cells to obtain a population of cells having enhanced probabilities of undergoing genetic modification (e.g., homologous recombination). A similar workflow is set out in FIG. 25.

Labels may be attached to one or more CRISPR system component and/or other molecules (e.g., a donor nucleic acid molecule) for introduction in the cells. In many instances, labels will be detectable either visually or by cell sorting instruments. Exemplary labels include cyan florescent protein (CFP), green florescent protein (GFP), orange florescent protein (OFP), red florescent protein (RFP), and yellow florescent protein (YFP). Additional labels include AMCA-6-dUTP, DEAC-dUTP, dUTP-ATTO-425, dUTP-XX-ATTO-488, Fluorescein-12-dUTP, Rhodamine-12-dUTP, dUTP-XX-ATTO-532, dUTP-Cy3, dUTP-ATTO-550, dUTP-Texas Red, dUTP-J647, dUTP-Cy5, dUTP-ATTO-647N, dUTP-ATTO-655, Fluorescein-12-dCTP, Rhodamine-12-dCTP, dCTP-Cy3dCTP-ATTO-550, dCTP-Texas Red, dCTP-J647, dCTP-Cy5 and dCTP-ATTO-647N available from multiple sources including Jena Bioscience.

Labels may be located in nucleic acid molecules and proteins at one or both termini and/or interior portions of the particular molecules.

Figure 24:
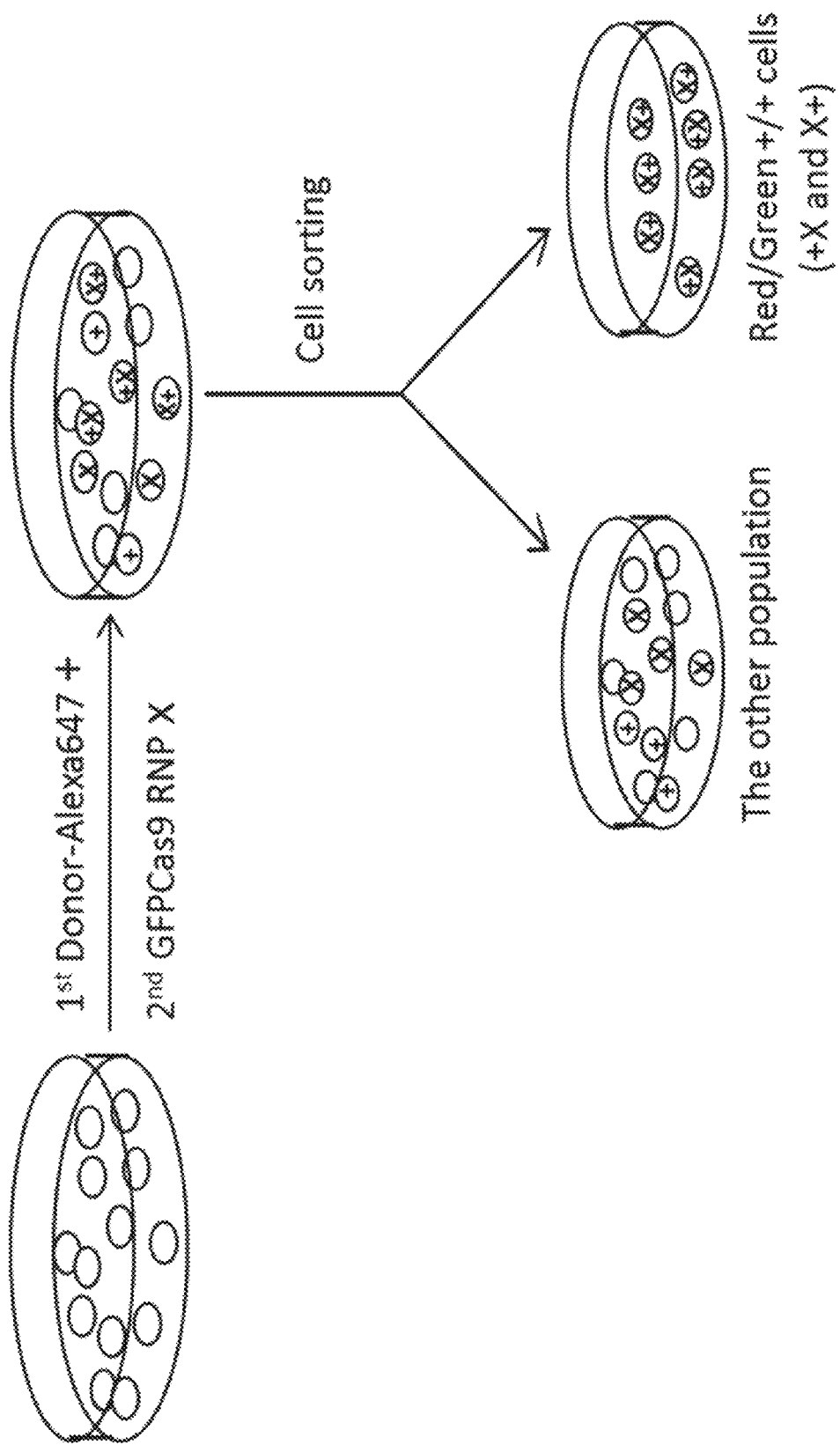
FIG. 24 shows a workflow for sequential delivery of CRISPR components and donor DNA into HEK293 cells and cell enrichment wherein donor DNA was labeled with Alexa647 dye and Cas9 was fused to GFP.
Figure 25:
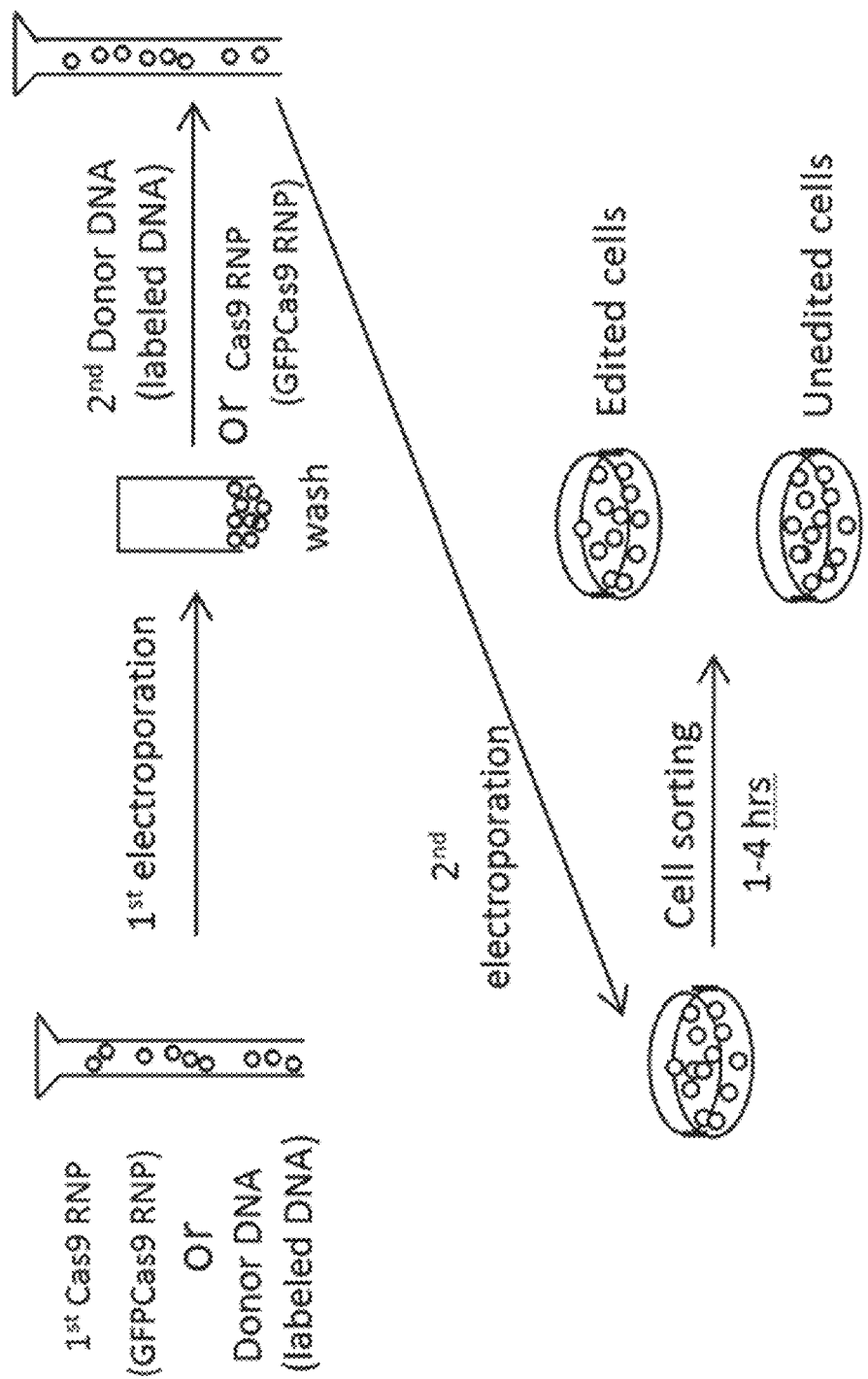
FIG. 25 shows a workflow for sequential delivery of CRISPR components and donor DNA and cell enrichment. In this work flow, cells are subjected to electroporation twice with donor DNA or Cas9 RNP introduced into the cells with each electroporation.

When cells are sorted, a number of separation parameters may be employed. In most instances, sorting may be designed to obtain cells having enhanced probability of undergoing genetic modification. For example, cells may be labeled as shown in FIG. 24 with different components required for genetic modification followed by cell sorting to obtain cells a specific amount of signal of each component. Using the schematic of FIG. 24 for purposes of illustration, cells may be selected based upon the number of donor DNA molecules and the number of GFP-Cas9 RNP complexes present within the cells. This may be done by choosing a minimum signal level for each the two labels, resulting in those cells being sorted as "positive" cells. Another sorting option is to score as "positive" cells that are in the top 3%, 5%, 8%, 10%, 15%, 20%, 25%, etc. for both signals as compared to all of the cells in a mixture. Assuming that two labels are equivalently and independently taken up, then scoring for the top 25% of cells for both labels would be expected to yield 6.25% of the original population being sorted. These would likely be the cells in the mixture that have the highest probabilities of undergoing genetic modification.

The invention thus includes methods, as well as compositions for performing such methods, for obtaining cell populations wherein the cells therein have an enhanced probabilities of undergoing genetic modification. In some instances, such methods will involve one or both of the following: (1) selection of cell (e.g., via cell sorting) of cells that have taken up one or more component necessary for genetic modification (e.g., one or more CRISPR system component and one or more donor DNA molecule) and (2) introduction of one or more one or more component necessary for genetic modification into cells by processes designed to result in high cellular uptake (e.g., sequence component introduction, as set out herein).

Figure 26:
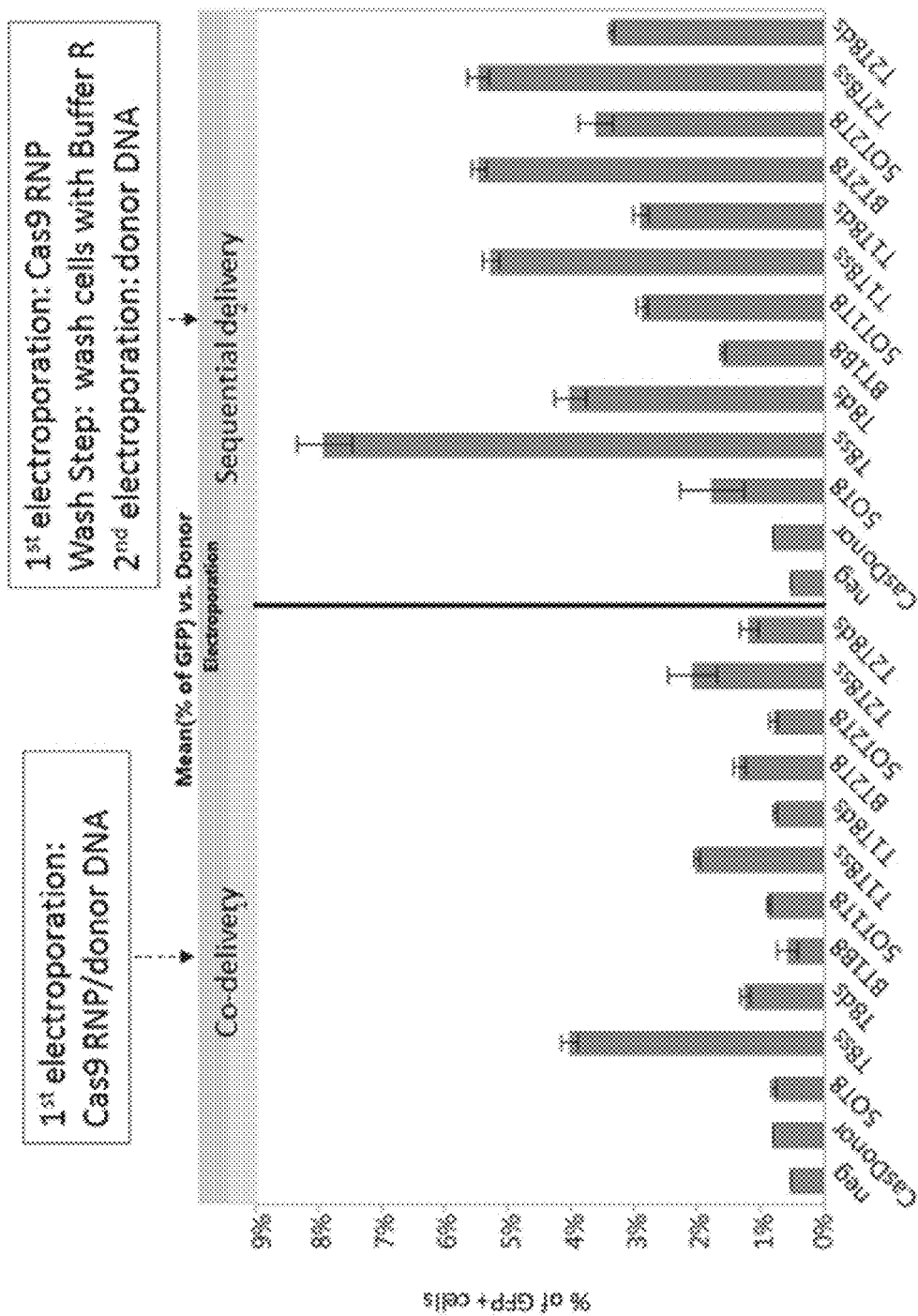
FIG. 26 shows data derived from two series of experiments using HEK293 cells involving either co-delivery of CRISPR system components and donor DNA or sequential delivery of CRISPR system components and donor DNA. In brief, 2 µg of Cas9 protein and 500 ng of the corresponding T1, T2 and/or T8 gRNA were added to Suspension Buffer R (Thermo Fisher Scientific, DPBS, cat no. #14287) to prepare the Cas9 RNP complexes. For co-delivery, 1 µl of 50 µM donor DNA with either blunt end (B) or 5' protrusion (5O) was added to the 10 µl reaction at this point. Alternatively, 1 µg of single strand (ss) DNA oligonucleotide and 500 ng double stranded DNA fragment was added. The mixture was then electroporated into a cell line having a disrupted GFP coding sequence using 1150 volts, 20 ms and 2 pulses. The cells were immediately transferred to a 24-well containing 500 µl medium, followed by incubation for 48 hours prior to flow cytometric analysis. For sequential electroporation, Cas9 RNP was delivered first into the cells, followed by a quick wash with 500 µl Suspension Buffer R. Upon centrifugation, the cell pellets were resuspended in 10 µl Suspension Buffer R. After addition of the corresponding donor DNA molecule, the cells were electroporated again using the same electroporation condition. The nucleotides sequences of nucleic acid molecules used in these experiment series are set out in Table 12.

As noted elsewhere herein, in some instances, sequential addition of components may be employed. As shown from the data set out in FIG. 26, sequential delivery of CRISPR system components and donor DNA generally results in higher efficiency levels of genetic modification than co-delivery. While not wishing to be bound by theory, this is possibly low uptake efficiency of combinations of CRISPR system components and non-CRISPR complex bound nucleic acid molecules when co-delivered.

When sequential delivery is employed, various components may be introduced into cells in a number of orders. For example, Cas9 protein, gRNA, or Cas9 RNP may be introduced into cells first followed by the introduction of donor DNA. Of course, the reverse order may be used too. Further, Cas9 protein may be expressed within cells and gRNA and donor DNA may be co-delivered or sequentially delivered to the cells in any order. Additionally, gRNA may be expressed within cells and Cas9 protein and donor DNA may be co-delivered or sequentially delivered to the cells in any order. In some instances, gRNA may be introduced into cells first, followed by Cas9 protein, then followed by donor DNA. Of course, other delivery orders may be used too, so long as all of the components required for genetic modification are not delivered simultaneously.

In some instances, methods of the invention include the contacting a cell with a linear DNA segment that has sequence homology at both termini to the target locus (e.g., a donor DNA molecule) under conditions that allow for uptake of the linear DNA segment by the cell (e.g., in conjunction with electroporation, contacting with a transfection reagent, etc.), followed by contacting the cell with one or more CRISPR system components (e.g., Cas9 mRNA, guide RNA, Cas9 mRNA and guide RNA, a Cas9 protein/guide RNA complex, etc.) under conditions that allow for uptake of the one or more CRISPR system components by the cell.

In specific aspects, the invention includes methods comprising steps (a), (b) and (c) below. Furthers, step (c) and step (a) may be swapped in order.

Step (a) involves contacting a cell with a linear DNA segment that has sequence homology at both termini to the target locus (e.g., a donor DNA molecule) under conditions that allow for uptake of the linear DNA segment by the cell. This may be done in any number of means. As examples, cell may be subjected to electroporation in the presence of the linear DNA segment or a transfection reagent may be used.

Step (b) involves waiting a period of time. This time period may be determined in a number of ways.

Step (c) involves contacting a cell with a Cas9 RNP complex under conditions that allow for uptake of the linear DNA segment by the cell.

As shown in FIGS. 27 and 28, the amount and characteristics of nucleic acid molecules introduced into cells in conjunction with CRISPR system components may be adjusted to enhance genetic modification.

Data in FIG. 27 shows that, under the particular conditions used, efficient homologous recombination occurs with 0.2 and 0.5 µg of donor DNA per 10 µl reaction volume. The number of cells was between 50,000 to 200,000. Further, homologous recombination decreases with donor DNA levels lower and higher than those amounts. The invention this includes compositions and methods and where donor DNA concentrations are in the range of 0.01 µg/10 µl to 500 µg/10 µl (e.g., from about 0.01 to about 400, from about 0.01 to about 200, from about 0.01 to about 100, from about 0.01 to about 50, from about 0.01 to about 30, from about 0.01 to about 20, from about 0.01 to about 15, from about 0.01 to about 10, from about 0.1 to about 50, from about 0.1 to about 25, from about 0.1 to about 15, from about 0.1 to about 10, from about 0.1 to about 50, from about 0.1 to about 5, from about 0.1 to about 1, from about 0.1 to about 0.8, etc. µg/10 µl.

Data in FIG. 27 shows that, under the particular conditions used, the efficient homologous recombination varies with the length, amount and presence or absence of certain chemical modifications. The length variation may be partially due to the sizes of regions of homology to the locus being modified. For example, about single-stranded donor nucleic acid molecules of about 80 bases in length appear to be sufficient for efficient homologous recombination. In many instances, such donor nucleic molecules will typically have terminal regions of homology to the target locus being modified with a central region containing nucleic acid for insertion at or substitution of nucleic acid at the target locus. In many instances, terminal homologous regions with be between 30 and 50 bases (e.g., from about 30 to about 45, from about 35 to about 45, from about 40 to about 45, from about 40 to about 48, etc.) in length with an intervening region of between 1 and 20 bases (e.g., one, two, three, four five, six, seven, etc.). Further, donor nucleic acid molecules may be used that contain regions of homology designed to hybridize the spatially separated regions of a target locus. In many instances, this spatial separation will be less than about 20 nucleotides. Homologous recombination using such donor nucleic acid molecules would be expected to result in deletion of nucleic acid at the target locus.

The invention further includes compositions and methods for the insertion and correction of single-nucleotide polymorphisms (SNPs). In some instances, such methods involve the use of single-stranded donor nucleic acid with terminal regions having homology to a target site in conjunction with CRISPR system components. Of course, double-stranded donor nucleic acid may also be used for SNP insertion or correction.

Data in FIG. 27 shows that, under the employed conditions used, efficiency of homologous recombination varies with the presence or absence of terminal chemical modifications to the donor nucleic acid. Phosphorothioate modifications were used at both termini of the modified donor molecules used to generate the data in FIG. 27. While not wishing to be bound by theory, one possibility is that the terminal chemical modifications used protect the donor nucleic acid from nuclease digestion.

The invention thus includes compositions containing and methods employing donor nucleic acid molecules having chemical modifications. In many instances, these chemical modifications will render nucleic acid molecules containing them resistant to one or more nuclease (e.g., exonuclease and/or endonuclease). Chemical modifications that may be used in the practice of the invention include the following: Phosphorothioate groups, 5' blocking groups (e.g., 5' diguanosine caps), 3' blocking groups, 2'-fluoro nucleosides, 2'-O-methyl-3'phosphorothioate, or 2'-O-methyl-3'thio-PACE, inverted dT, inverted ddT, and biotin. Further, a phosphoramidite C3 Spacer can be incorporated internally, or at either end of an oligo to introduce a long hydrophilic spacer arm for the attachment of fluorophores or other groups and can also be used to inhibit degradation by 3' exonucleases.

In some instances, the terminal base at one or each end of a donor DNA molecule will be chemically modified. In other instances, terminal two or three bases at one or each end will be chemically modified. In still other instances, internal bases will be chemically modified. In some instances, from about 1% to about 50% (e.g., from about 1% to about 45%, from about 1% to about 40%, from about 1% to about 35%, from about 1% to about 25%, from about 1% to about 15%, from about 5% to about 50%, from about 10% to about 50%, from about 15% to about 50%, from about 15% to about 35%, etc.) of the total number of bases present in donor nucleic acid molecules will be chemically modified.

FIG. 29 shows data generated using a series of electroporation conditions. It has been found that Cas9 RNP uptake is robust in some cell types (data not shown) but donor DNA uptake conditions often need to be adjusted with particular cell types in order to achieve efficient uptake. Further, it is believed that once efficient uptake conditions are identified for a particular cell type, those condition show low levels of variation when different donor DNA molecules are used. Thus, when electroporation is employed, one of the main factors for adjust of conditions for achieving efficient genetic modification is the selection of efficient condition of introduction of donor DNA into the particular cell being used. This is especially the case when large donor DNA molecules are used.

A number of compositions and methods may be used to form CRISPR complexes. For example, Cas9 mRNA and a guide RNA may be encapsulated in INVIVOFECTAMINE™ for, for example, later in vivo and in vitro delivery as follows. Cas9 mRNA is mixed (e.g., at a concentration of at 0.6 mg/ml) with guide RNA. The resulting mRNA/gRNA solution may be used as is or after addition of a diluents and then mixed with an equal volume of INVIVOFECTAMINE™ and incubated at 50° C. for 30 min. The mixture is then dialyzed using a 50 kDa molecular weight curt off for 2 hours in 1×PBS, pH7.4. The resulting dialyzed sample containing the formulated mRNA/gRNA is diluted to the desire concentration and applied directly on cells in vitro or inject tail vein or intraperitoneal for in vivo delivery. The formulated mRNA/gRNA is stable and can be stored at 4° C.

For Cas9 mRNA transfection with cell culture such as 293 cells, 0.5 μg mRNA was added to 25 μl of Opti-MEM, followed by addition of 50-100 ng gRNA. Meanwhile, two μl of LIPOFECTAMINE™ 3000 or RNAiMax was diluted into 25 μl of Opti-MEM and then mixed with mRNA/gRNA sample. The mixture was incubated for 15 minutes prior to addition to the cells.

A CRISPR system activity may comprise expression of a reporter (e.g., green fluorescent protein, β-lactamase, luciferase, etc.) or nucleic acid cleavage activity. Using nucleic acid cleavage activity for purposes of illustration, total nucleic acid can be isolated from cells to be tested for CRISPR system activity and then analyzed for the amount of nucleic acid that has been cut at the target locus. If the cell is diploid and both alleles contain target loci, then the data will often reflect two cut sites per cell. CRISPR systems can be designed to cut multiple target sites (e.g., two, three four, five, etc.) in a haploid target cell genome. Such methods can be used to, in effect, "amplify" the data for enhancement of CRISPR system component introduction into cells (e.g., specific cell types). Conditions may be enhanced such that greater than 50% of the total target loci in cells exposed to CRISPR system components (e.g., one or more of the following: Cas9 protein, Cas9 mRNA, crRNA, tracrRNA, guide RNA, complexed Cas9/guide RNA, etc.) are cleaved. In many instances, conditions may be adjusted so that greater than 60% (e.g., greater than 70%, greater than 80%, greater than 85%, greater than 90%, greater than 95%, from about 50% to about 99%, from about 60% to about 99%, from about 65% to about 99%, from about 70% to about 99%, from about 75% to about 99%, from about 80% to about 99%, from about 85% to about 99%, from about 90% to about 99%, from about 95% to about 99%, etc.) of the total target loci are cleaved.

Any number of conditions may be altered to enhance the introduction of CRISPR system components into cells. Exemplary incubation conditions are pH, ionic strength, cell type, energy charge of the cells, the specific CRISPR system components present, the ratio of CRISPR system components (when more than one CRISPR system component is present), the CRISPR system component/cell ratio, concentration of cells and CRISPR system components, incubation times, etc.

One factor that may be varied, especially when CRISPR complexes are formed, is ionic strength. Ionic strength is the total ion concentration in solution. CRISPR complexes are formed from the association of CRISPR protein with CRISPR RNA and this association is partially dependent upon the ionic strength of the surrounding environment. One method for calculating the ionic strength of a solution is by the Debye and Huckel formula. In many instances, the ionic strength of solutions used in the practice of the invention will be from about 0.001 to about 3 (e.g., from about 0.001 to about 2, from about 0.001 to about 1.5, from about 0.001 to about 1, from about 0.001 to about 0.7, from about 0.001 to about 0.5, from about 0.001 to about 0.25, from about 0.001 to about 0.1, from about 0.01 to about 1, from about 0.01 to about 0.5, from about 0.01 to about 0.2, from about 0.01 to about 0.1, etc.).

pH is another factor that may affect transfection efficiency. Typically, complexation and/or transfection will occur at near physiological pH (e.g., pHs from about 6.5 to about 7.5, pHs from about 6.8 to about 7.5, pHs from about 6.9 to about 7.5, pHs from about 6.5 to about 7.3, pHs from about 6.5 to about 7.1, pHs from about 6.8 to about 7.2, etc.). In some instances, transfection efficiency is known to be sensitive to small variations in pH (e.g., =/−0.2 pH units).

The ratio of CRISPR system components to each other and to other mixture components (e.g., cells) also affects the efficiency of CRISPR system component cellular update. Using Cas9 protein and guide RNA for purposes of illustration, Cas9 protein may be complexed with guide RNA before contact with a cell or simultaneously with cellular contact. In many instances, CRISPR protein and CRISPR RNA components will be present in set ratios (e.g., 1:1, 1.5:1, 2:1, 2.5:1, 3:1, 1:1.5, 1:2, 1:2.5, 1:3, from about 0.2:1 to about 4:1, from about 0.2:1 to about 3:1, from about 0.2:1 to about 2:1, from about 0.5:1 to about 6:1, from about 0.5:1 to about 4:1, etc.). One useful ratio for Cas9 protein to guide RNA is 1:1, where each Cas9 protein has available to it one guide RNA molecular partner for complex formation.

The uptake of CRISPR complexes by cells is partially determined by the concentration of the CRISPR complexes and the cell density and the ratio of the CRISPR complexes to the cells. Typically, high CRISPR complex concentrations will result in higher amounts of uptake by available cells. Exemplary CRISPR complex/cell density conditions include $10^7$ CRISPR complexes per cell. Additionally, CRISPR complexes per cell may be in the range of $10^2$ to $10^{12}$ complexes per cell (e.g., from about $10^2$ to about $10^{11}$, from about $10^2$ to about $10^{10}$, from about $10^2$ to about $10^9$, from about $10^2$ to about $10^8$, from about $10^2$ to about $10^7$, from about $10^2$ to about $10^6$, from about $10^3$ to about $10^{12}$, from about $10^4$ to about $10^{12}$, from about $10^5$ to about $10^{12}$, from about $10^6$ to about $10^{12}$, from about $10^7$ to about $10^{12}$, from about $10^8$ to about $10^{12}$, from about $10^3$ to about $10^{10}$, from about $10^4$ to about $10^{10}$, from about $10^5$ to about $10^{11}$, etc.). Also, the cell density will typically be about $10^5$ cells per ml. Typically, cell density will be in the range of $10^2$ to $10^8$ cells per ml (e.g., from about $10^2$ to about $10^7$, from about $10^2$ to about $10^6$, from about $10^2$ to about $10^5$, from about $10^2$ to about $10^4$, from about $10^3$ to about $10^8$, from about $10^3$ to about $10^7$, from about $10^4$ to about $10^7$, etc.).

The invention includes methods in which one or both of the CRISPR complex/cell density and/or the total cell density are adjusted such that, when double-stranded target locus cutting is assayed, the percentage of target loci cut are between 80 and 99.9% (e.g., from about 80% to about 99%, from about 85% to about 99%, from about 90% to about 99%, from about 95% to about 99%, from about 96% to about 99%, from about 80% to about 95%, from about 90% to about 97%, etc.).

One exemplary set of conditions that may be use is where $~5^5$ cells are contacted with 500 ng of Cas9 ($~2^{12}$ molecules) complexed with target locus specific guide RNA.

The invention also includes compositions and methods for storing reagent for intracellular genetic modification. FIGS. 30, 31, and 32 show the result of three month stability testing of CRISPR complexes stored at 4° C. and frozen. Data set out in FIG. 30 was generated using gRNA and Cas9 protein alone. Data set out in FIG. 31 was generated using gRNA, Cas9 protein and OPTI-MEM® culture medium. Data set out in FIG. 32 was generated using Cas9 protein and LIPOFECTAMINE® RNAiMax transfection reagent. In all cases, high levels of functional activity were retained for three months with freezing. Similar results were observed with Cas9 protein and OPTI-MEM® culture medium. Cas9 protein and LIPOFECTAMINE® RNAiMax transfection reagent data shows that functional activity appears to drop off relatively quickly at 4° C.

Data shown in FIGS. 30, 31, and 32 each show that CRISPR system component reagents are stable for a minimum of six months. This is particularly useful for high-throughput applications. The invention thus includes high-throughput reagents containing CRISPR system components. In some embodiments, such components comprise one or more of the following: one or more gRNA, one or more Cas9 protein, one or more cell culture medium (e.g., one or more mammalian cell culture medium), one or more transfection reagent, and one or more donor nucleic acid molecule.

For purposes of illustration, the invention includes multi-well plates, as well as high throughput methods employing such plates, in which different wells contain Cas9 protein and a transfection reagent. Further, different wells contain different gRNA molecules. Such plates may be used in high throughput methods for altering multiple genetic sites within cells. Each well may further contain, for example, donor DNA with termini homologous to the gRNA directed cleavage site for alteration of different loci within cells.

The invention also includes CRISPR system reagents that remain stable when stored for specified periods of time. For purposes of illustration, the invention provides CRISPR system reagents that retain at least 75% (e.g., from about 75% to about 100%, from about 80% to about 100%, from about 85% to about 100%, from about 90% to about 100%, from about 95% to about 100%, from about 75% to about 90%, from about 80% to about 90%, etc.) of their original CRISPR related activity after 3 months of storage at −20° C. Of course, CRISPR system reagents may be stored at different temperatures (e.g., 4° C., −20° C., −70° C., from about 4° C. to about −70° C., from about −20° C. to about −70° C., etc.). Further, the invention also includes CRISPR system reagents and method for storing such reagents where at least 75% of their original CRISPR related activity after up to 1 year (e.g., from about 1 month to about 12 months, from about 2 months to about 12 months, from about 3 months to about 12 months, from about 4 months to about 12 months, from about 5 months to about 12 months, from about 1 months to about 9 months, from about 3 months to about 9 months, from about 2 months to about 6 months, etc.).

In some instances, CRISPR complexes may not be stable during storage, especially under certain conditions. For example, under some conditions Cas9, gRNA and transfection reagents may be stable under one set of conditions but not under another set of conditions. It has been determined that under some conditions (e.g., in certain buffer formulations), Cas9, gRNA and transfection reagent mixtures are not stable upon freezing but are stable upon storage at 4° C. The invention this includes compositions that are stable under on set of storage conditions but not another set of storage conditions.

The data set out in FIGS. 30, 31, and 32 were generated using specific conditions. RNA was prepared in water but EDTA (e.g., 0.1 mM) and/or sodium acetate buffer may be used. Cas9 protein was prepared in 15 mM Tris HCl, 250 mM NaCl, 0.6 mM TCEP, 50% glycerol, pH 8.

Storage data was generated using reagent mixtures contained in wells of multiwall plates. Cas9 was present in wells in an amount of 500 ng/well (0.5 µl of a 0.5 µg/µl stock solution) and gRNA was present in an amount of 200 ng/well (0.7 µl of a 300 ng/µl stock solution). All reagents were stored as 4× solutions. Cas9/gRNA samples were placed under storage conditions as 1.2 µl aliquots in each well. Cas9/gRNA/OPTI-MEM® samples were placed under storage conditions as 20 µl aliquots in each well with 18.8 µl of OPTI-MEM® being present in each well. Cas9/OPTI-MEM® samples were placed under storage conditions as 10 µl aliquots in each well with 9.5 µl of OPTI-MEM® being present in each well. Cas9/RNAiMax samples were placed under storage conditions as 6.5 µl aliquots in each well with 6 µl of RNAiMax transfection reagent being present in each well.

The above reagents were then used after storage in cleavage assay after being combined with additional reagents and cells. The data set out in FIG. 30 was generated by combining the 1.2 µl of Cas9 protein and gRNA with 18.8 µl OPTI-MEM® which was incubated at room temperature for 5 minutes. 6 µl of LIPOFECTAMINE® RNAiMax was also mixed with 14 µl of OPTI-MEM® which was incubated at room temperature for 5 minutes. These two mixtures were then combined and incubated at room temperature for 5 minutes then contacted with cells. Cas9/gRNA/OPTI-MEM® samples (FIG. 31) were combined with 6 µl LIPOFECTAMINE® RNAiMax and 14 µl OPTI-MEM® that had been incubated at room temperature for 5 minutes. These two mixtures were then combined and incubated at room temperature for 5 minutes then contacted with cells. Cas9/OPTI-MEM® samples were mixed with both 0.7 µl or gRNA and 9.3 µl of OPTI-MEM® (incubated for 5 minutes at room temperature) and 6 µl LIPOFECTAMINE® RNAiMax and 14 µl OPTI-MEM® incubated for 5 minutes at room temperature), then contacted with cells after incubation for 5 minutes at room temperature. Cas9/LIPOFECTAMINE® RNAiMax samples (FIG. 32) were mixed with 0.7 µl gRNA and 32.8 µl OPTI-MEM® (incubated at room temperature for 5 minutes), then contacted with cells.

For transfection, 293FT cells were seeded one day prior to transfection at 20,000 cells per well in a 96 well plate format to get around 50% to 60% cell confluency on the day of transfection. Each well at the time of seeding has 100 µl of cell culture media (DMEM, 10% FBS, and 5% each of sodium pyruvate, non-essential amino acids and Gluta-MAX™). At the time of transfection 10 µl of final transfection mix (containing Cas9, gRNA, LIPOFECTAMINE® RNAiMAX and OPTIMEM®) was added to each well in 96 well format. Following incubation at 37° C. for 72 hours the cells were harvested for measuring % cleavage efficiency at the respective target loci (in this case HPRT gene target) using GENEART™ cleavage detection assay.

In one aspect, the invention relates to compositions and methods related to ready to use reagents. A ready to use reagent may be in any number of forms. For example, a ready to use reagent may contain one or more Cas9 protein, one or more gRNA, one or more transfection reagent, and one or more cell culture medium. As specific example is a reagent that contains a Cas9 protein, two gRNAs, and LIPOFECTAMINE® RNAiMax all in 2× concentration and OPTI-MEM® culture medium in a 1× concentration. A ready to use reagent of this type may be mixed 1:1 with cells contained in OPTI-MEM® culture medium to yield a transfection reaction mixture for the introduction of two gRNAs into the cells, where the gRNAs share sequence homology with two locations in the genome of the cells. If appropriate, the cells may simultaneously or subsequently be contacted with one or more nucleic acid molecules for insertion into the genomic cut sites.

Another example of a ready to use reagent includes a combination of one or more Cas9 protein, one or more gRNA, and one or more cell culture medium. As specific example is a reagent that contains a Cas9 protein and two gRNAs in 2× concentration and OPTI-MEM® culture medium in a 1× concentration. A ready to use reagent of this type may be mixed first with LIPOFECTAMINE® RNAiMax and then 1:1 with cells contained in OPTI-MEM® culture medium to yield a transfection reaction mixture for the introduction of two gRNAs into the cells.

Ready to use reagents such as those set out above may be stored at 4° C. for a period of time prior to use. As noted elsewhere herein, under some conditions, Cas9, gRNA and transfection reagent mixtures are not stable upon freezing but are stable upon storage at 4° C.

Ready to use reagents may be labeled with preferred storage conditions and expiration dates that are designed to reflect a specified decrease in activity (e.g., less than 80% of activity). For example, expiration dates may range from about two weeks to about one year (e.g., from about two weeks to about ten months, from about two weeks to about eight months, from about two weeks to about six months, from about two weeks to about four months, from about one month to about one year, from about one month to about ten months, from about one month to about six months, from about one month to about four months, from about three months to about one year, from about three months to about eight months, etc.).

It has also been found that, in some instances, higher concentrations of CRISPR system components result in higher stability upon storage. Thus, in some aspects, the invention includes reagents that contain greater than 50 ng/µl (e.g., from about 50 ng/µl to about 500 ng/µl, from about 100 ng/µl to about 500 ng/µl, from about 150 ng/µl to about 500 ng/µl, from about 200 ng/µl to about 500 ng/µl, from about 250 ng/µl to about 500 ng/µl, from about 300 ng/µl to about 500 ng/µl, from about 400 ng/µl to about 500 ng/µl, etc.) of gRNA. In many instances, the molar amount of Cas9 protein, when present, to gRNA will be in the range of from about 5:1 to about 1:5 (e.g., from about 5:1 to about 1:4, from about 5:1 to about 1:3, from about 5:1 to about 1:2, from about 5:1 to about 1:1, from about 5:1 to about 1:1, from about 4:1 to about 1:5, from about 5:1 to about 1:5, from about 2:1 to about 1:5, from about 1:2 to about 1:5, from about 4:1 to about 1:4, from about 3:1 to about 1:3, from about 2:1 to about 1:2, etc.).

Kits:

The invention also provides kits for, in part, the assembly and/or storage of nucleic acid molecules and for the editing of cellular genomes. As part of these kits, materials and instruction are provided for both the assembly of nucleic acid molecules and the preparation of reaction mixtures for storage and use of kit components.

Kits of the invention will often contain one or more of the following components:

1. One or more nucleic acid molecule (e.g., one or more primer, one or more DNA molecule encoding Cas9, dCas9, guide RNA, etc., one or more mRNA encoding a CRISPR system component, such as Cas9, dCas9, etc.), 2. One or more polymerase, 3. One or more protein (e.g., one or more CRISPR protein such as Cas9, dCas9, etc.), 4. One or more partial vector (e.g., one or more nucleic acid segment containing an origin of replication and/or a selectable marker) or complete vector, and 5. Instructions for how to use kits components.

In particular, some kits of the invention may include one or more of the following: (a) a double-stranded nucleic acid molecule encoding the 3'end of a guide RNA molecule (see FIG. 8), wherein this double-stranded nucleic acid molecule does not encode all or part of Hybridization Region 1, (b) a polymerase, and (c) at least one buffer.

In some embodiments, kits may comprise one or more reagents for use in a process utilizing one or more of the CRISPR system components discussed herein or for producing one or more CRISPR system component discussed herein.

Kit reagents may be provided in any suitable container. A kit may provide, for example, one or more reaction or storage buffers. Reagents may be provided in a form that is usable in a particular reaction, or in a form that requires addition of one or more other components before use (e.g., in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

EXAMPLES

Example 1

One Step Synthesis of gRNA Template and High Efficiency Cell Engineering Workflow Abstract CRISPR-Cas9 systems provide innovative applications in genome engineering. To edit the genome, expression of Cas9, mature crRNA and tracrRNA or a single guide RNA (gRNA) is required. Elements of the mature crRNA and tracrRNA or a gRNA are often built into a Cas9 expression plasmid or constructed in a standard plasmid driven by a U6 promoter for mammalian expression. A novel method for the rapid synthesis of gRNA template is described in this example, which combines gene synthesis and DNA fragment assembly technologies with an accuracy of assembly of >96%. In other words, over 96% of the assembled nucleic acid molecules are the desired assembly products. The method allows rapid synthesis of guide RNA (gRNA) via in vitro transcription using short DNA oligonucleotides. In conjunction with Cas9 protein delivery, Cas9/gRNA complexes can be transfected into the cells through processes such as lipid-mediated methods, electroporation, and cell penetrating peptide mediated delivery. Overall, cell engineering workflows can be reduced to at least four days and, in some instances, two days. Methods described herein are applicable for high throughput gRNA synthesis and genome-wide editing.

Introduction

CRISPR-Cas9 mediated genome engineering enables researchers to modify genomic DNA in vivo directly and efficiently. Three components (Cas9, mature crRNA and tracrRNA) are essential for efficient cell engineering. Although the mature crRNA and tracrRNA can be synthesized chemically, the quality of the synthetic RNA is often not sufficient for in vivo cell engineering due, for example, to the presence of truncated by-products. Thus, mature crRNA and tracrRNA or a combined single gRNA are often transcribed from a Cas9 expression plasmid or built into a separate plasmid driven by a U6 promoter. The resulting plasmids are then transfected or co-transfected into the cells. Because the constructs are relatively large, the delivery of plasmid DNA often becomes the limiting step, especially for suspension cells. Recently Cas9 mRNA has employed to increase the rate of DNA cleavage. To make gRNA, a pre-cloned all-in-one plasmid based upon, for example, a vector shown in FIG. 17 or FIG. 18 may serve as template to prepare a gRNA PCR fragment containing a T7 promoter, followed by gel extraction. Alternatively a synthetic DNA string may be used as a template.

Overall, it is time-consuming to prepare the gRNA template for in vitro transcription. A gRNA template can be assembled via PCR in about one hour. Further, gRNA can be generated in vitro transcription in about 3 hours. DNA oligonucleotides can be converted to into gRNA in about 4 hours. A workflow with the above timing elements was tested and. Furthermore, in combination with Cas9 protein transfection technology, cell engineering cycle was accomplished as described herein in four days.

Materials and Methods

Materials

293FT cells, DMEM medium, Fetal Bovine Serum (FBS), OPTI-MEM® Medium, LIPOFECTAMINE® 3000, RNAiMAX™, MESSENGERMAX™, GENEART® CRISPR Nuclease Vector with OFP Reporter, 2% E-GEL® EX Agarose Gels, PURELINK® PCR Micro Kit, TranscriptAid T7 High Yield Transcription Kit, MEGASHORTSCRIPT™ T7 Transcription Kit, MEGACLEAR™ Transcription Clean-Up Kit, ZERO BLUNT® TOPO® PCR Cloning Kit, PURELINK® Pro Quick96 Plasmid Purification Kit, Qubit® RNA BR Assay Kit, QUBIT® Protein Assay Kit, Pierce LAL Chromogenic Endotoxin Quantitation Kit, GENEART® Genomic Cleavage Detection Kit, and POROS® Heparin column were from Thermo Fisher Scientific. PHUSION® High-Fidelity DNA Polymerase was purchased from New England Biolabs. HIPREP™ 16/60 Sephacryl S-300 HR gel filtration column was purchased from GE Healthcare. All the DNA oligonucleotides used for gRNA synthesis were from Thermo Fisher Scientific.

Methods

One step synthesis of gRNA template

Figure 13:
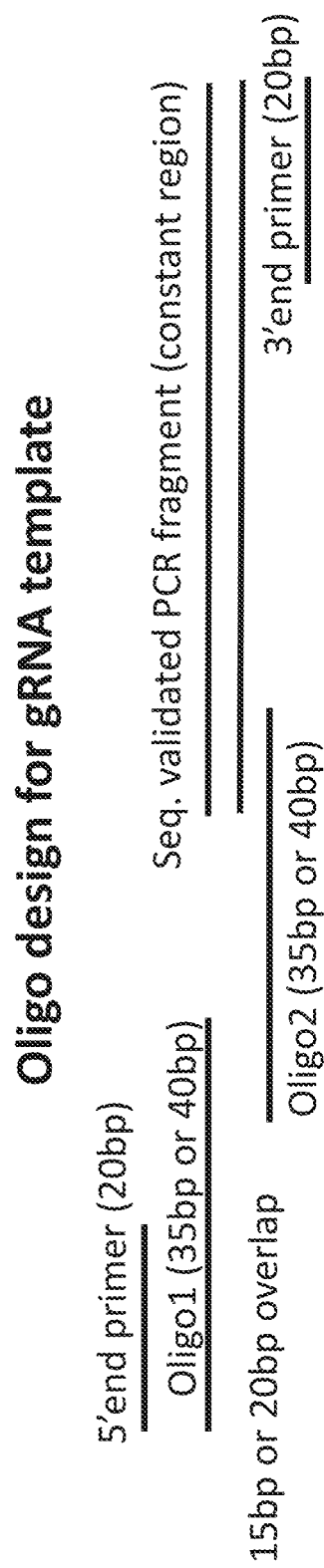
FIG. 13 shows oligonucleotide designs for a one-step synthesis of gRNA template workflow. Sequence validated PCR fragment refers to a PCR fragment of a sequence validated plasmid.

The design of oligonucleotides for the synthesis of gRNA template is depicted in FIG. 13. The forward primer:

5'-GTT TTA GAG CTA GAA ATA GCA AG-3' (SEQ ID NO: 13) and reverse primer:

5'-AAA AGC ACC GAC TCG GTG CCA C-3' (SEQ ID NO: 14) were used to amplify the 80 bp constant region of tracrRNA from a GENEART® CRISPR Nuclease Vector, followed by purification using agarose gel extraction. The concentration of PCR product was measured by Nanodrop (Thermo Fisher Scientific) and the molarity was calculated based on the molecular weight of 24.8 kd. To prepare a pool of oligonucleotides, an aliquot of the 80 bp PCR product was mixed with two end primers 5'-taatacgactcactatagg-3' (SEQ ID NO: 15) and 5'-AAA AGC ACC GAC TCG GTG CCA C-3' (SEQ ID NO: 14) with a final concentration of 0.3 µM for the 80 bp PCR product and 10 µM for each of the end primers. For a specific target, a 34 bp forward primer consisting of the 19 bp T7 promoter sequence taatacgactcactatagg (SEQ ID NO: 15) and 15 bp of the 5'end target sequence, and a 34 bp reverse primer consisting of 20 bp target sequence and 14 bp of the 5' end tracrRNA sequence gttttagagctaga (SEQ ID NO: 16) were chemically synthesized with 15 bp overlap. A working solution containing the two 34 bp oligonucleotides was prepared at a final concentration of 0.3 µM. Alternatively, a pair of 39 bp forward and reverse primers with 20 bp overlap was synthesized and tested. To set up the one step synthesis of gRNA template, 1.5 µl of pool oligonucleotides and 1.5 µl of the working solution were added to a PCR tube containing 10 µl of 5× Phusion HF buffer, 1 µl of 10 mM dNTP, 35.5 µl H2O, and 0.5 µl PHUSION® High-Fidelity DNA polymerase. The PCR program was set at 98° C. for 30 sec and then 30 cycles of 98° C. for 5 sec and 55° C. for sec, followed by incubation at 72° C. for 30 sec and 4° C. forever. The PCR product was analyzed by a 2% E-GEL® EX Agarose Gel, followed by purification using Purelink PCR micro column. The DNA concentration was determined by Nanodrop instrument.

To determine the error rate, the PCR product was cloned into ZERO BLUNT® TOPO® vector, followed by plasmid DNA isolation and sequencing.

In Vitro Transcription

The in vitro transcription of gRNA template was carried out using TRANSCRIPTAID™ T7 High Yield Transcription Kit. Briefly, 6 µl of gRNA template (250-500 ng) was added to a reaction mixture containing 8 µl of NTP, 4 µl of 5× reaction buffer and 2 µl of T7 enzyme mix. The reaction was carried out at 37° C. for 2 hrs, followed by incubation with DNase I (2 units per 120 ng DNA template) for 15 minutes. The gRNA product was purified using MEGACLEAR™ Transcription Clean-Up kit as described in the manual. The concentration of RNA was determined using QUBIT® RNA BR Assay Kit.

Expression and Purification of Cas9 Protein

A glycerol stock BL21(DE3) star $E.$ $coli$ strain expressing NLS Cas9 protein was inoculated in 20 ml BRM medium and grown overnight at 37° C. in a shaking incubator. The overnight culture was then added to 1 liter of BRM medium and grown cells to an $OD_{600}$ nm of 0.6-0.8 at 37° C. in a shaking incubator (~4-5 hours). An aliquot of un-induced sample was taken for monitoring protein induction with IPTG. 0.5 ml of 1 M IPTG was added to the culture and incubated overnight at room temperature in a shaking incubator. An aliquot of induced sample along with un-induced sample were analyzed by SDS-PAGE. Upon validation of protein induction, the culture medium was centrifuged at 5000 rpm for 15 minutes to harvest the cell pellets (~24 grams of wet weight). 100 ml of buffer A containing 20 mM Tris (pH7.5), 100 mM NaCl, 10% Glycerol, and 1 mM PMSF was used to resuspend the cell pellet. The cell suspension was sonicated on ice for 30 minutes with power level of medium tip set at 8, 10 sec "on", and 20 sec "off". The cell lysate was clarified by centrifugation at 16500 rpm for 30 minutes. The supernatant was filtered through a 0.2 µm filter device prior to loading to a 16 ml heparin column previously equilibrated with buffer A at a flow rate of 2 ml/min. The column was first washed with five column volume of buffer A and then gradually increased to 40% of buffer B containing 20 mM Tris (pH7.5), 1.2 M NaCl and 10% glycerol. The Cas9 protein was eluted with a 5 CV gradient from 40% to 100% buffer B. The fractions were analyzed by SDS-PAGE. Fractions containing Cas9 protein were combined and concentrated using two 15 ml Amicon Centrifugal filter units (EMD Millipore, Cat. No. UFC905024). The concentrated protein was filtered through a 0.2 μm filter device and loaded twice onto a 120 ml of HIPREP™ 16/60 Sephacryl S-300 HR column previously equilibrated with buffer C containing 20 mM Tris (pH 8), 250 mM KCl and 10% Glycerol. The fractions containing Cas9 protein were pooled and concentrated. The protein concentration was determined by QUBIT® Protein Assay Kit. The endotoxin level in the purified protein was measured by Endotoxin Quantitation Kit. The concentrated protein was adjusted to 50% glycerol and stored at −20° C.

Cell Culture

293FT cells were maintained in DMEM medium supplemented with 10% FBS in a 5% $CO_2$ incubator. One day prior to transfection, the cells were seeded in a 24-well plate at a cell density of $2.5 \times 10^5$ cells/0.5 ml medium. For transfection, 500 ng of purified Cas9 was added to 25 μl of OPTI-MEM® medium, followed by addition of 120 ng gRNA. The sample was mixed by gently tapping the tubes a few times and then incubated at room temperature for 10 minutes. To a separate test tube, 3 μl of RNAiMAX™ was added to 25 μl of OPTI-MEM® medium. The diluted transfection reagent was transferred to the tube containing Cas9 protein/gRNA complexes, followed by incubation at room temperature for 15 minutes. The entire solution was then added to the cells in a 24-well and mixed by gently swirling the plate a few times. The plate was incubated at 37° C. for 48 hours in a 5% $CO_2$ incubator. The percentage of genome editing was measured by GENEART® Genomic Cleavage Detection Kit.

Results and Discussion

One Step Synthesis of gRNA Template

Since gRNA synthesis is one of the limiting steps in genome engineering, an attempt was made to reduce the time for gRNA synthesis. As an example, HPRT-T1 target catttctcagtcctaaaca (SEQ ID NO: 17) was chosen, but these methods were also found to work for GFP and VEGFA-T3 targets (data not shown). Initially, a gene synthesis approach was utilized to assemble a gRNA template using a set of 6 synthetic DNA oligonucleotides (Set 1 oligonucleotides in Table 8). Through optimization of oligonucleotide pool concentration and PCR condition, a clean PCR product was obtained on an agarose gel (data not shown). An aliquot of the PCR product served as template to synthesize the gRNA via in vitro transcription. The quality of synthetic gRNA was analyzed by a denaturing gel.

Figure 15:
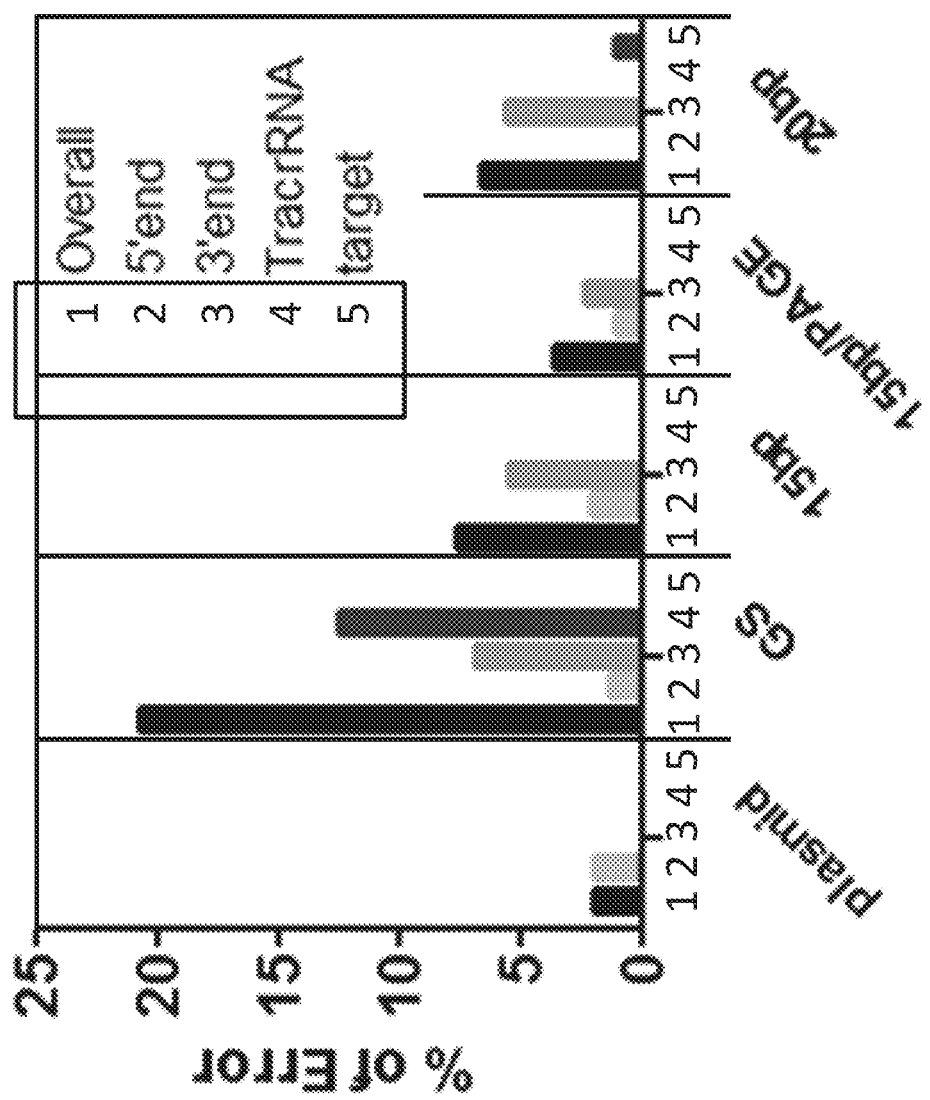
FIG. 15 shows data derived from synthetic gRNA templates that were cloned into a ZERO BLUNT® TOPO vector. Ninety-six colonies were randomly picked for sequencing analysis. The percentage of incorrect clones was calculated.

To test the functionality of synthetic gRNA, gRNA was associated with Cas9 protein. The resulting complexes were then delivered to the 293FT cells via lipid-based transfection. However, the evaluation of in vivo genome cleavage assay indicated that gRNA did not work well (data not shown). To determine the problem, gRNA templates were cloned into a ZERO BLUNT® TOPO vector and then sequenced. As shown in FIG. 15, it was observed that more than 20% of the gRNA templates harbored mutations, mostly deletions. To minimize the potential sources of errors, instead of using long synthetic oligos to create the complete T7 promoter/guide RNA template, the constant 80 bp tracrRNA region was amplified from a sequence-validated plasmid template, followed by gel purification to remove the template. Then to fuse the T7 promoter sequence and target sequence to the constant tracrRNA, a pair of 34 bp or 39 bp forward and reverse oligonucleotides that share 15 bp or 20 bp homology, respectively, across the variable target sequence were designed, wherein the middle oligo 2 also shared 19 bases of homology with the tracrRNA region (FIG. 13).

Figure 17:
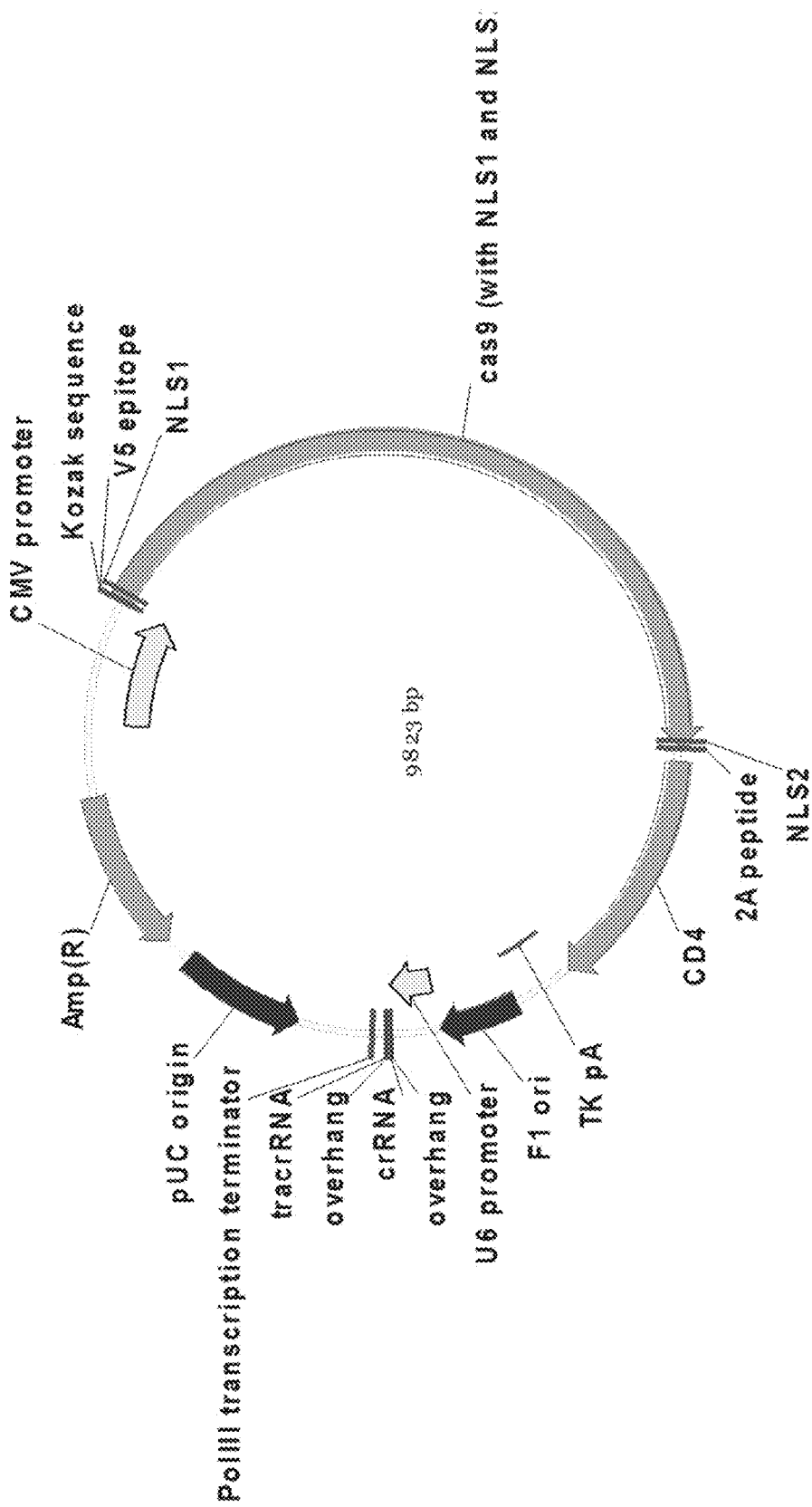
FIG. 17 shows an "all-in-one" vector containing a CD4 coding region. The nucleotide sequence for the vector is set out in Table 9.
Figure 18:
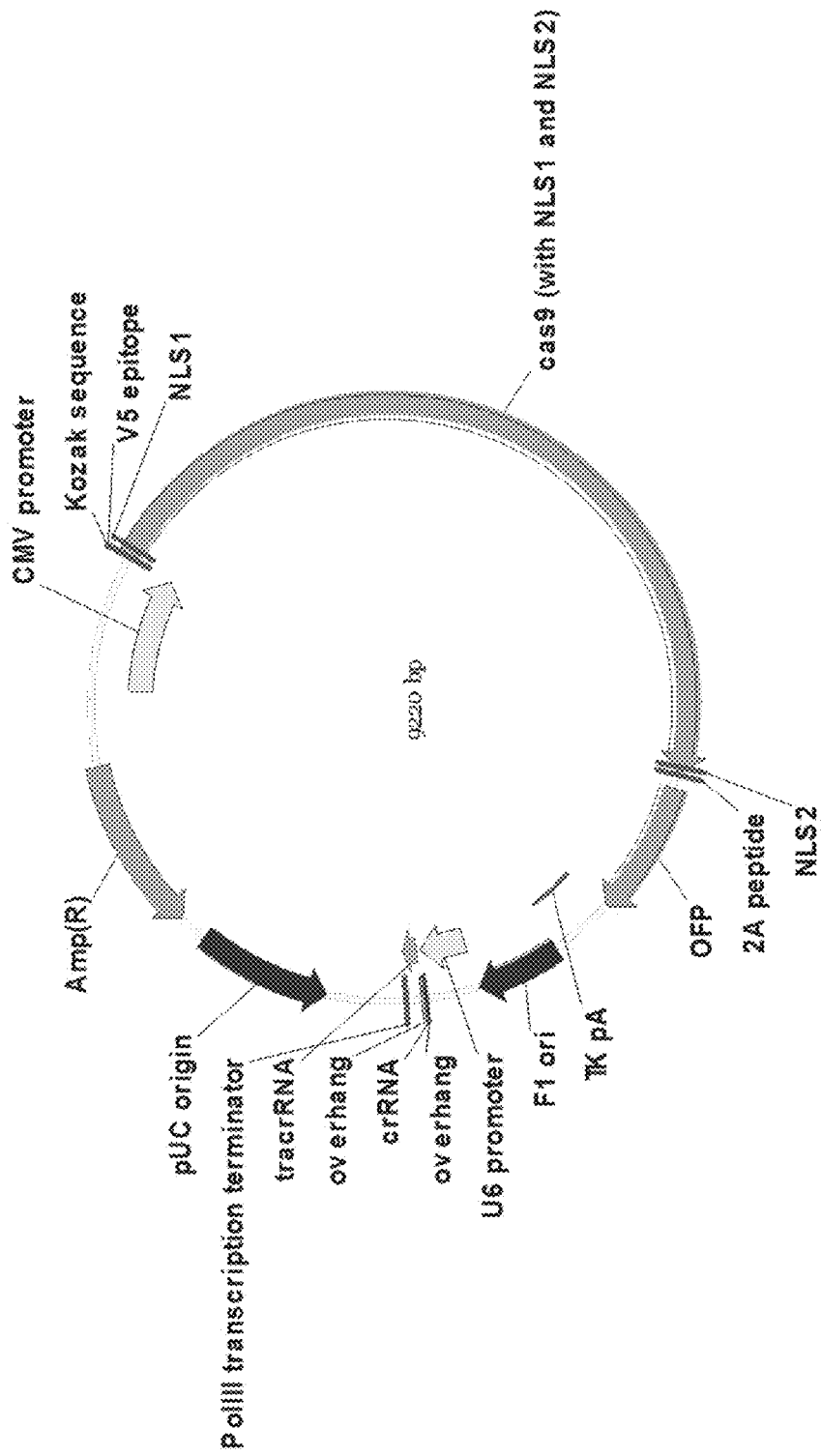
FIG. 18 shows an "all-in-one" vector containing an orange fluorescent protein (OFP) coding region. The nucleotide sequence for the vector is set out in Table 10.

As described in Materials and Methods, the gRNA template was assembled in a single PCR reaction using a pool of DNA oligonucleotides and tracrRNA fragment (FIG. 13). Upon PCR micro column purification, the gRNA template was used to prepare gRNA via in vitro transcription. The quality of gRNA was examined using a TBE-urea denaturing gel. gRNA prepared via PCR amplification from an all-in-one plasmid was used as positive control. An "all-in-one plasmid" is a plasmid that contains all of the components of a CRISPR system, such as guide RNA and Cas9 coding sequences. Vector maps of two similar all-in-one plasmids used in the experiments here are shown in FIG. 17 and FIG. 18.

Figure 14:
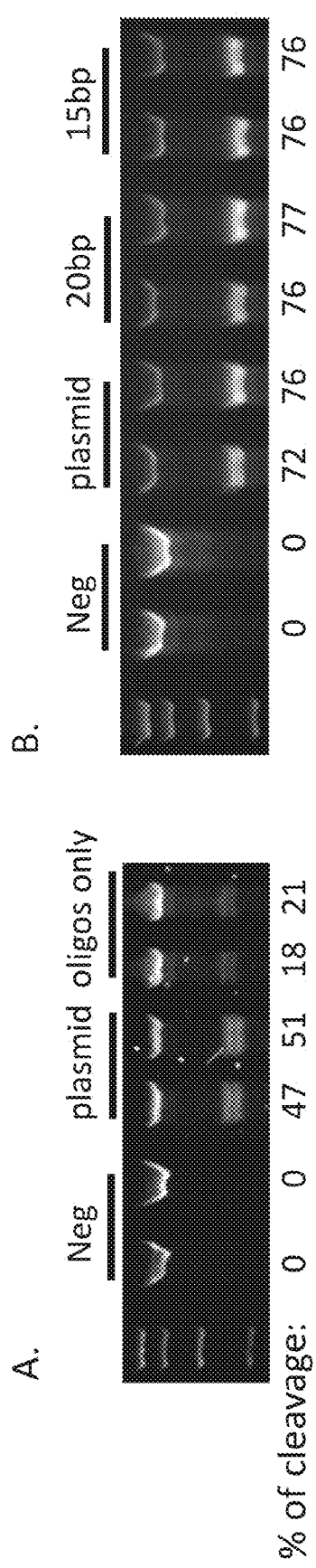
FIG. 14 shows data from in vivo genome cleavage and detection assays. Gel Image A: Original cleavage assay with gRNA amplified from a plasmid versus gRNA assembled from 6 overlapping oligos. Less than 50% cleavage activity compared to plasmid is seen. This is due to incorrect assembly. Gel Image B: New assembly method as outlined in FIG. 13, with either a 20 bp overlap or 15 bp overlap. An equivalent cleavage activity compared to the plasmid control is seen.

To examine in vivo functionality of synthesized gRNA, the Cas9 protein from *E. coli* was expressed and purified. The Cas9 protein was pre-incubated with synthetic gRNA to form the complexes prior to cell transfection. The gRNA prepared from an all-in-one plasmid served as a positive control. The genome modification was examined by Genome Cleavage and Detection assay. As depicted in Gel Image B of FIG. 14, the percentage of Indel for the newly synthesized gRNAs was similar to the positive control. To determine the error rate in the gRNA template, sequencing analysis was also performed. As depicted in FIG. 15, approximately 7% of gRNA template harbored mutation with most deletion occurred at 3' end and 5' end. One mutation was detected within the target region when longer 39 bp oligonucleotides were used. The use of PAGE-purified end primers (~20 bp each) further decreased the error rate to 3.6% with no mutation detected in the target region, which was similar to the control gRNA prepared from an all-in-one plasmid with a 2% error rate. These results indicated that the quality of gRNA were good enough for most of our applications.

Because the 80 bp tracrRNA contains a polyT at the 3' end, there was a possibility that the Poly T had no effect on genome editing. To test this, serial deletions of PolyT at the 3' end of gRNA (set 3 oligos in Table 8) were made. Based on in vivo genome cleavage assay, removal of the PolyT at 3' end of gRNA appeared to have no effect on the performance of gRNA. The addition of three extra Ts at the 3' end also did not affect the functionality of gRNA either (data not shown).

Figure 16:
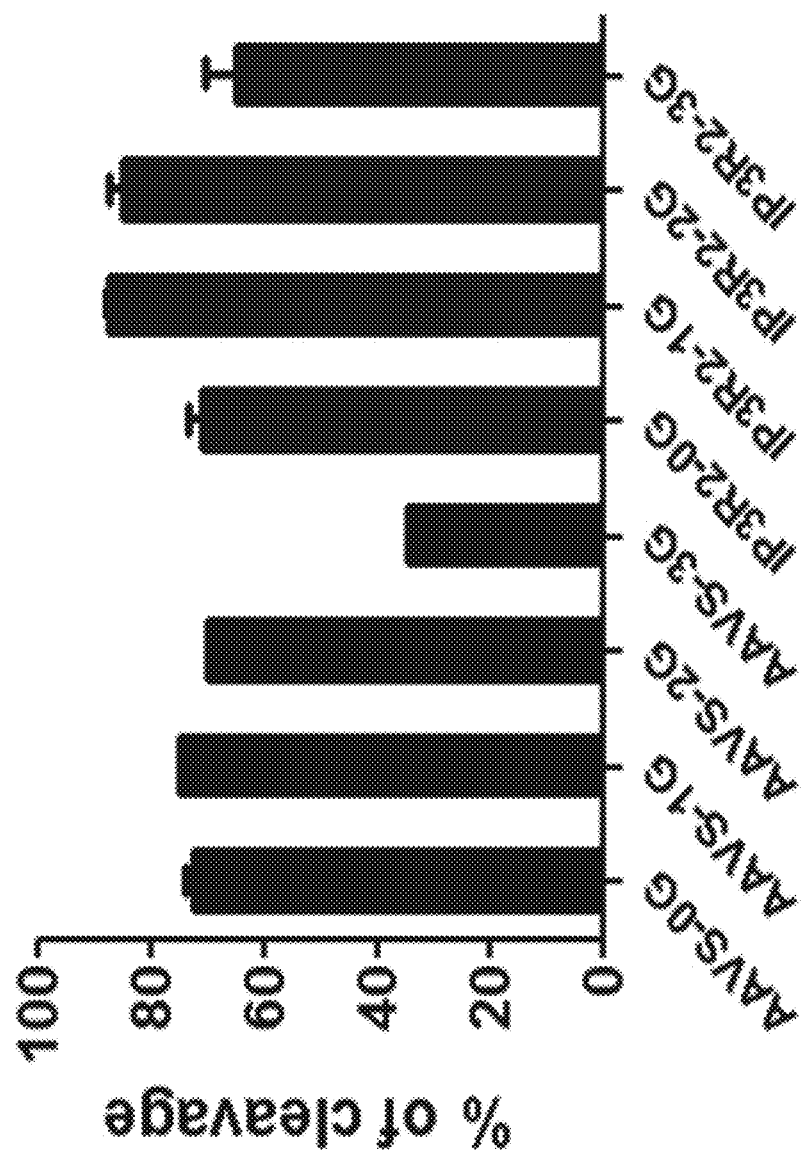
FIG. 16 shows data showing the effect of deletions of G's from the 3' terminus of a T7 promoter on in vitro transcription.

The standard T7 promoter sequence "taatacgactcactataggg" (SEQ ID NO: 18) contains GGG at the 3' end, which is thought to be essential for maximal production of gRNA via in vitro transcription. However, because the transcription starts from the first G, three extra G will be added to the gRNA sequence assuming the target does not have a G at the 5' end, which might affect the functionality of gRNA. To examine this, the AAVS target ccagtagccagccccgtcc (SEQ ID NO: 19) and the IP3R2 target tcgtgtccctgtacgcgga (SEQ ID NO: 20) were chosen and G deletions at the 3' end of T7 promoter were made (see FIG. 16 and Table 7). The addition of Gs, especially 3G in a row, significantly decreased the activity of gRNA. The addition of 1 G exhibited slightly better cleavage efficiency than that of 2 G, even although both produced similar amount of gRNA in in vitro transcription reaction. However, without any G, the yield of in vitro transcription reaction was dramatically reduced.

TABLE 7

Effect of G on gRNA synthesis

| Construct | PCR yield (ng/µl) | RNA yield (ng/µl) |
|---|---|---|
| AAVS-0G | 124 | 220 |
| AAVS-1G | 82 | 394 |
| AAVS-2G | 70 | 294 |
| AAVS-3G | 53 | 290 |
| IP3R2-0G | 100 | 65 |
| IP3R2-1G | 54 | 272 |
| IP3R2-2G | 46 | 300 |
| IP3R2-3G | 122 | 289 |
| EMX1-0G | 75 | 156 |
| EMX1-1G | 119 | 490 |
| EMX1-2G | 101 | 680 |
| EMX1-3G | 98 | 750 |

In conclusion, compositions and methods provided herein related to gRNA synthesis and associated workflows allow for four day cell engineering. On Day 1, the biologists (1) design and (2) synthesize or order short DNA oligonucleotides and seed the cells of interest. On Day 2, the biologists prepare the gRNA template by one pot PCR, followed by in vitro transcription for making gRNA. Upon association of gRNA with purified Cas9 protein, the Cas9 protein/gRNA complexes are transfected into the cells via lipid-mediated method or electroporation. On Day 4, the biologists harvest the cells to analyze genome modification. Thus, the invention provides compositions and methods related to improve workflows for genome engineering. In some aspects, these workflows allow for the genome modification experiments to occur in four days from concept to completion.

TABLE 8

| Oligonucleotides for gRNA synthesis | | SEQ ID NO |
|---|---|---|
| Set 1 oligos | | |
| gF1 | taatacgactcactatagggGcatttctcagtcctaaaca | 21 |
| gR1 | GCT ATT TCT AGC TCT AAA ACT GTT TAG GAC TGA GAA ATG C | 22 |
| gF2 | gttttagagctagaaatagcaagttaaaataaggctagtccgttatcaacttgaaaaagt | 23 |
| gR2 | AAA AGC ACC GAC TCG GTG CCA CTT TTT CAA GTT GAT AAC GGA CTA GCC TTA TTT TAA CTT | 24 |
| gEnd-F | taatacgactcactataggg | 18 |
| gEnd-R | AAA AGC ACC GAC TCG GTG CCA C | 14 |
| Set 2 oligos | | |
| Con-F | GTT TTA GAG CTA GAA ATA GCA AG | 13 |
| gEnd-R | AAA AGC ACC GAC TCG GTG CCA C | 14 |
| gR1-20bp | GCT ATT TCT AGC TCT AAA ACT GTT TAG GAC TGA GAA ATG | 25 |
| gR1-15bp | TTC TAG CTC TAA AAC TGT TTA GGA CTG AGA AAT G | 26 |
| gF1-20bp | taatacgactcactataggcatttctcagtcctaaacag | 27 |
| gF1-15bp | taatacgactcactataggcatttctcagtccta | 28 |
| gEnd-F-2G | taatacgactcactatagg | 15 |
| Set 3 oligos | | |
| gEnd-R4T | AAA AGC ACC GAC TCG GTG CCA C | 14 |
| gEnd-R3T | AA AGC ACC GAC TCG GTG CCA C | 29 |
| gEnd-R2T | A AGC ACC GAC TCG GTG CCA C | 30 |
| gEnd-R1T | AGC ACC GAC TCG GTG CCA C | 31 |
| gEnd-R0T | GC ACC GAC TCG GTG CCA C | 32 |
| Set 4 oligos | | |
| AAVS3G | taatacgactcactatagggCCAGTAGCCAGCCCC | 33 |
| AAVS2G | taatacgactcactataggCCAGTAGCCAGCCCC | 34 |
| AAVS1G | taatacgactcactatagCCAGTAGCCAGCCCC | 35 |

TABLE 9

Nucleotide sequence of the vector shown in FIG. 17. (SEQ ID NO: 36)

GTTAGGCGTTTGCGCTGCTTCGCGATGTACGGGCCAGATATACGCGTTGACATTGATTATTGACTAGTTATTA

ATAGTAATCAATTACGGGGTCATTAGTTCATAGCCCATATATGGAGTTCCGCGTTACATAACTTACGGTAAAT

GGCCCGCCTGGCTGACCGCCCAACGACCCCCGCCCATTGACGTCAATAATGACGTATGTTCCCATAGTAACGC

CAATAGGGACTTTCCATTGACGTCAATGGGTGGAGTATTTACGGTAAACTGCCCACTTGGCAGTACATCAAGT

GTATCATATGCCAAGTACGCCCCCTATTGACGTCAATGACGGTAAATGGCCCGCCTGGCATTATGCCCAGTAC

ATGACCTTATGGGACTTTCCTACTTGGCAGTACATCTACGTATTAGTCATCGCTATTACCATGGTGATGCGGTT

TTGGCAGTACATCAATGGGCGTGGATAGCGGTTTGACTCACGGGGATTTCCAAGTCTCCACCCCATTGACGTC

AATGGGAGTTTGTTTTGGCACCAAAATCAACGGGACTTTCCAAAATGTCGTAACAACTCCGCCCCATTGACGC

AAATGGGCGGTAGGCGTGTACGGTGGGAGGTCTATATAAGCAGAGCTCGTTTAGTGAACCGTCAGATCGCCT

TABLE 9-continued

Nucleotide sequence of the vector shown in FIG. 17. (SEQ ID NO: 36)

GGAGACGCCATCCACGCTGTTTTGACCTCCATAGAAGACACCGGGACCGATCCAGCCTCCGGAGCGGCCGCC

ACCATGGGCAAGCCCATCCCTAACCCCCTGTTGGGGCTGGACAGCACCGCTCCCAAAAAGAAAAGGAAGGTG

GGCATTCACGGCGTGCCTGCGGCCGACAAAAAGTACAGCATCGGCCTTGATATCGGCACCAATAGCGTGGGC

TGGGCCGTTATCACAGACGAATACAAGGTACCCAGCAAGAAGTTCAAGGTGCTGGGGAATACAGACAGGCAC

TCTATCAAGAAAAACCTTATCGGGGCTCTGCTGTTTGACTCAGGCGAGACCGCCGAGGCCACCAGGTTGAAGA

GGACCGCAAGGCGAAGGTACACCCGGAGGAAGAACAGGATCTGCTATCTGCAGGAGATCTTCAGCAACGAG

ATGGCCAAGGTGGACGACAGCTTCTTCCACAGGCTGGAGGAGAGCTTCCTTGTCGAGGAGGATAAGAAGCAC

GAACGACACCCCATCTTCGGCAACATAGTCGACGAGGTCGCTTATCACGAGAAGTACCCCACCATCTACCACC

TGCGAAAGAAATTGGTGGATAGCACCGATAAAGCCGACTTGCGACTTATCTACTTGGCTCTGGCGCACATGAT

TAAGTTCAGGGGCCACTTCCTGATCGAGGGCGACCTTAACCCCGACAACAGTGACGTAGACAAATTGTTCATC

CAGCTTGTACAGACCTATAACCAGCTGTTCGAGGAAAACCCTATTAACGCCAGCGGGGTGGATGCGAAGGCC

ATACTTAGCGCCAGGCTGAGCAAAAGCAGGCGCTTGGAGAACCTGATAGCCCAGCTGCCCGGTGAAAAGAAG

AACGGCCTCTTCGGTAATCTGATTGCCCTGAGCCTGGGCCTGACCCCCAACTTCAAGAGCAACTTCGACCTGG

CAGAAGATGCCAAGCTGCAGTTGAGTAAGGACACCTATGACGACGACTTGGACAATCTGCTCGCCCAAATCG

GCGACCAGTACGCTGACCTGTTCCTCGCCGCCAAGAACCTTTCTGACGCAATCCTGCTTAGCGATATCCTTAG

GGTGAACACAGAGATCACCAAGGCCCCCCTGAGCGCCAGCATGATCAAGAGGTACGACGAGCACCATCAGG

ACCTGACCCTTCTGAAGGCCCTGGTGAGGCAGCAACTGCCCGAGAAGTACAAGGAGATCTTTTTCGACCAGA

GCAAGAACGGCTACGCCGGCTACATCGACGGCGGAGCCAGCCAAGAGGAGTTCTACAAGTTCATCAAGCCCA

TCCTGGAGAAGATGGATGGCACCGAGGAGCTGCTGGTGAAGCTGAACAGGGAAGATTTGCTCCGGAAGCAGA

GGACCTTTGACAACGGTAGCATCCCCCACCAGATCCACCTGGGCGAGCTGCACGCAATACTGAGGCGACAGG

AGGATTTCTACCCCTTCCTCAAGGACAATAGGGAGAAAATCGAAAAGATTCTGACCTTCAGGATCCCCTACTA

CGTGGGCCCTCTTGCCAGGGGCAACAGCCGATTCGCTTGGATGACAAGAAAGAGCGAGGAGACCATCACCCC

CTGGAACTTCGAGGAAGTGGTGGACAAAGGAGCAAGCGCGCAGTCTTTCATCGAACGGATGACCAATTTCGA

CAAAAACCTGCCTAACGAGAAGGTGCTGCCCAAGCACAGCCTGCTTTACGAGTACTTCACCGTGTACAACGA

GCTCACCAAGGTGAAATATGTGACCGAGGGCATGCGAAAACCCGCTTTCCTGAGCGGCGAGCAGAAGAAGGC

CATCGTGGACCTGCTGTTCAAGACCAACAGGAAGGTGACCGTGAAGCAGCTGAAGGAGGACTACTTCAAGAA

GATCGAGTGCTTTGATAGCGTGGAAATAAGCGGCGTGGAGGACAGGTTCAACGCCAGCCTGGGCACCTACCA

CGACTTGTTGAAGATAATCAAAGACAAGGATTTCCTGGATAATGAGGAGAACGAGGATATACTCGAGGACAT

CGTGCTGACTTTGACCCTGTTTGAGGACCGAGAGATGATTGAAGAAAGGCTCAAAACCTACGCCCACCTGTTC

GACGACAAAGTGATGAAACAACTGAAGAGACGAAGATACACCGGCTGGGGCAGACTGTCCAGGAAGCTCAT

CAACGGCATTAGGGACAAGCAGAGCGGCAAGACCATCCTGGATTTCCTGAAGTCCGACGGCTTCGCCAACCG

AAACTTCATGCAGCTGATTCACGATGACAGCTTGACCTTCAAGGAGGACATCCAGAAGGCCCAGGTTAGCGG

CCAGGGCGACTCCCTGCACGAACATATTGCAAACCTGGCAGGCTCCCCTGCGATCAAGAAGGGCATACTGCA

GACCGTTAAGGTTGTGGACGAATTGGTCAAGGTCATGGGCAGGCACAAGCCCGAAAACATAGTTATAGAGAT

GGCCAGAGAGAACCAGACCACCCAAAAGGGCCAGAAGAACAGCCGGGAGCGCATGAAAAGGATCGAGGAG

GGTATCAAGGAACTCGGAAGCCAGATCCTCAAAGAGCACCCCGTGGAGAATACCCAGCTCCAGAACGAGAA

GCTGTACCTGTACTACCTGCAGAACGGCAGGGACATGTACGTTGACCAGGAGTTGGACATCAACAGGCTTTCA

GACTATGACGTGGATCACATAGTGCCCCAGAGCTTTCTTAAAGACGATAGCATCGACAACAAGGTCCTGACCC

GCTCCGACAAAAACAGGGGCAAAAGCGACAACGTGCCAAGCGAAGAGGTGGTTAAAAAGATGAAGAACTAC

TABLE 9-continued

Nucleotide sequence of the vector shown in FIG. 17. (SEQ ID NO: 36)

TGGAGGCAACTGCTCAACGCGAAATTGATCACCCAGAGAAAGTTCGATAACCTGACCAAGGCCGAGAGGGGC

GGACTCTCCGAACTTGACAAAGCGGGCTTCATAAAGAGGCAGCTGGTCGAGACCCGACAGATCACGAAGCAC

GTGGCCCAAATCCTCGACAGCAGAATGAATACCAAGTACGATGAGAATGACAAACTCATCAGGGAAGTGAAA

GTGATTACCCTGAAGAGCAAGTTGGTGTCCGACTTTCGCAAAGATTTCCAGTTCTACAAGGTGAGGGAGATCA

ACAACTACCACCATGCCCACGACGCATACCTGAACGCCGTGGTCGGCACCGCCCTGATTAAGAAGTATCCAA

AGCTGGAGTCCGAATTTGTCTACGGCGACTACAAAGTTTACGATGTGAGGAAGATGATCGCTAAGAGCGAAC

AGGAGATCGGCAAGGCCACCGCTAAGTATTTCTTCTACAGCAACATCATGAACTTTTTCAAGACCGAGATCAC

A0CTTGCCAACGGCGAAATCAGGAAGAGGCCGCTTATCGAGACCAACGGTGAGACCGGCGAGATCGTGTGGGA

CAAGGGCAGGGACTTCGCCACCGTGAGGAAAGTCCTGAGCATGCCCCAGGTGAATATTGTGAAAAAAACTGA

GGTGCAGACAGGCGGCTTTAGCAAGGAATCCATCCTGCCCAAGAGGAACAGCGACAAGCTGATCGCCCGGAA

GAAGGACTGGGACCCTAAGAAGTATGGAGGCTTCGACAGCCCCACCGTAGCCTACAGCGTGCTGGTGGTCGC

GAAGGTAGAGAAGGGGAAGAGCAAGAAACTGAAGAGCGTGAAGGAGCTGCTCGGCATAACCATCATGGAGA

GGTCCAGCTTTGAGAAGAACCCCATTGACTTTTTGGAAGCCAAGGGCTACAAAGAGGTCAAAAAGGACCTGA

TCATCAAACTCCCCAAGTACTCCCTGTTTGAATTGGAGAACGGCAGAAAGAGGATGCTGGCGAGCGCTGGGG

AACTGCAAAAGGGCAACGAACTGGCGCTGCCCAGCAAGTACGTGAATTTTCTGTACCTGGCGTCCCACTACG

AAAAGCTGAAAGGCAGCCCCGAGGACAACGAGCAGAAGCAGCTGTTCGTGGAGCAGCACAAGCATTACCTG

GACGAGATAATCGAGCAAATCAGCGAGTTCAGCAAGAGGGTGATTCTGGCCGACGCGAACCTGGATAAGGTC

CTCAGCGCCTACAACAAGCACCGAGACAAACCCATCAGGGAGCAGGCCGAGAATATCATACACCTGTTCACC

CTGACAAATCTGGGCGCACCTGCGGCATTCAAATACTTCGATACCACCATCGACAGGAAAAGGTACACTAGC

ACTAAGGAGGTGCTGGATGCCACCTTGATCCACCAGTCCATTACCGGCCTGTATGAGACCAGGATCGACCTGA

GCCAGCTTGGAGGCGACTCTAGGGCGGACCCAAAAAAGAAAAGGAAGGTGGAATTCTCTAGAGGCAGTGGA

GAGGGCAGAGGAAGTCTGCTAACATGCGGTGACGTCGAGGAGAATCCTGGCCCAATGAACCGGGGAGTCCCT

TTTAGGCACTTGCTTCTGGTGCTGCAACTGGCGCTCCTCCCAGCAGCCACTCAGGGAAAGAAAGTGGTGCTGG

GCAAAAAAGGGGATACAGTGGAACTGACCTGTACAGCTTCCCAGAAGAAGAGCATACAATTCCACTGGAAAA

ACTCCAACCAGATAAAGATTCTGGGAAATCAGGGCTCCTTCTTAACTAAAGGTCCATCCAAGCTGAATGATCG

CGCTGACTCAAGAAGAAGCCTTTGGGACCAAGGAAACTTCCCCCTGATCATCAAGAATCTTAAGATAGAAGA

CTCAGATACTTACATCTGTGAAGTGGAGGACCAGAAGGAGGAGGTGCAATTGCTAGTGTTCGGATTGACTGCC

AACTCTGACACCCACCTGCTTCAGGGGCAGAGCCTGACCCTGACCTTGGAGAGCCCCCCTGGTAGTAGCCCCT

CAGTGCAATGTAGGAGTCCAAGGGGTAAAAACATACAGGGGGGAAGACCCTCTCCGTGTCTCAGCTGGAGC

TCCAGGATAGTGGCACCTGGACATGCACTGTCTTGCAGAACCAGAAGAAGGTGGAGTTCAAAATAGACATCG

TGGTGCTAGCTTTCCAGAAGGCCTCCAGCATAGTCTATAAGAAAGAGGGGGAACAGGTGGAGTTCTCCTTCCC

ACTCGCCTTTACAGTTGAAAAGCTGACGGGCAGTGGCGAGCTGTGGTGGCAGGCGGAGAGGGCTTCCTCCTCC

AAGTCTTGGATCACCTTTGACCTGAAGAACAAGGAAGTGTCTGTAAAACGGGTTACCCAGGACCCTAAGCTCC

AGATGGGCAAGAAGCTCCCGCTCCACCTCACCCTGCCCCAGGCCTTGCCTCAGTATGCTGGCTCTGGAAACCT

CACCCTGGCCCTTGAAGCGAAAACAGGAAAGTTGCATCAGGAAGTGAACCTGGTGGTGATGAGAGCCACTCA

GCTCCAGAAAAATTTGACCTGTGAGGTGTGGGGACCCACCTCCCCTAAGCTGATGCTGAGCTTGAAACTGGAG

AACAAGGAGGCAAAGGTCTCGAAGCGGGAGAAGGCGGTGTGGGTGCTGAACCCTGAGGCGGGGATGTGGCA

GTGTCTGCTGAGTGACTCGGGACAGGTCCTGCTGGAATCCAACATCAAGGTTCTGCCCACATGGTCGACCCCG

GTGCAGCCAATGGCCCTGATTGTGCTGGGGGGCGTCGCCGGCCTCCTGCTTTTCATTGGGCTAGGCATCTTCTT

TABLE 9-continued

Nucleotide sequence of the vector shown in FIG. 17. (SEQ ID NO: 36)

CTGTGTCAGGTGCCGGCACACCGGTTAGTAATGAGTTTAAACGGGGGAGGCTAACTGAAACACGGAAGGAGA

CAATACCGGAAGGAACCCGCGCTATGACGGCAATAAAAAGACAGAATAAAACGCACGGGTGTTGGGTCGTTT

GTTCATAAACGCGGGGTTCGGTCCCAGGGCTGGCACTCTGTCGATACCCCACCGAGACCCCATTGGGGCCAAT

ACGCCCGCGTTTCTTCCTTTTCCCCACCCCACCCCCCAAGTTCGGGTGAAGGCCCAGGGCTCGCAGCCAACGT

CGGGGCGGCAGGCCCTGCCATAGCAGATCTGCGCAGCTGGGGCTCTAGGGGGTATCCCCACGCGCCCTGTAG

CGGCGCATTAAGCGCGGCGGGTGTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTCCCCGTCAAGCTCTAAATCGGGGGCT

CCCTTTAGGGTTCCGATTTAGTGCTTTACGGCACCTCGACCCCAAAAAACTTGATTAGGGTGATGGTTCACGTA

GTGGGCCATCGCCCTGATAGACGGTTTTTCGCCCTTTGACGTTGGAGTCCACGTTCTTTAATAGTGGACTCTTG

TTCCAAACTGGAACAACACTCAACCCTATCTCGGTCTATTCTTTTGATTTATAAGGGATTTTGCCGATTTCGGC

CTATTGGTTAAAAAATGAGCTGATTTAACAAAAATTTAACGCGAATTAATTAAGGTCGGGCAGGAAGAGGGC

CTATTTCCCATGATTCCTTCATATTTGCATATACGATACAAGGCTGTTAGAGAGATAATTAGAATTAATTTGAC

TGTAAACACAAAGATATTAGTACAAAATACGTGACGTAGAAAGTAATAATTTCTTGGGTAGTTTGCAGTTTTA

AAATTATGTTTTAAAATGGACTATCATATGCTTACCGTAACTTGAAAGTATTTCGATTTCTTGGCTTTATATAT

CTTGTGGAAAGGACGAAACACCGNNNNNNNNNNNNNNNNNNNNGTTTTAGAGCTAGAAATAGCAAGTTAAA

ATAAGGCTAGTCCGTTATCAACTTGAAAAAGTGGCACCGAGTCGGTGCTTTTTTCTAGTATACCGTCGACCTCT

AGCTAGAGCTTGGCGTAATCATGGTCATAGCTGTTTCCTGTGTGAAATTGTTATCCGCTCACAATTCCACACAA

CATACGAGCCGGAAGCATAAAGTGTAAAGCCTGGGGTGCCTAATGAGTGAGCTAACTCACATTAATTGCGTT

GCGCTCACTGCCCGCTTTCCAGTCGGGAAACCTGTCGTGCCAGCTGCATTAATGAATCGGCCAACGCGCGGGG

AGAGGCGGTTTGCGTATTGGGCGCTCTTCCGCTTCCTCGCTCACTGACTCGCTGCGCTCGGTCGTTCGGCTGCG

GCGAGCGGTATCAGCTCACTCAAAGGCGGTAATACGGTTATCCACAGAATCAGGGGATAACGCAGGAAAGAA

CATGTGAGCAAAAGGCCAGCAAAAGGCCAGGAACCGTAAAAAGGCCGCGTTGCTGGCGTTTTTCCATAGGCT

CCGCCCCCCTGACGAGCATCACAAAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCGACCCTGCCGCTTACCGGATACCTGT

CCGCCTTTCTCCCTTCGGGAAGCGTGGCGCTTTCTCATAGCTCACGCTGTAGGTATCTCAGTTCGGTGTAGGTC

GTTCGCTCCAAGCTGGGCTGTGTGCACGAACCCCCCGTTCAGCCCGACCGCTGCGCCTTATCCGGTAACTATC

GTCTTGAGTCCAACCCGGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACACTAGAAGAACAGTATT

TGGTATCTGCGCTCTGCTGAAGCCAGTTACCTTCGGAAAAAGAGTTGGTAGCTCTTGATCCGGCAAACAAACC

ACCGCTGGTAGCGGTGGTTTTTTTGTTTGCAAGCAGCAGATTACGCGCAGAAAAAAAGGATCTCAAGAAGATC

CTTTGATCTTTTCTACGGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAATCTAAAGTATATATGAG

TAAACTTGGTCTGACAGTTACCAATGCTTAATCAGTGAGGCACCTATCTCAGCGATCTGTCTATTTCGTTCATC

CATAGTTGCCTGACTCCCCGTCGTGTAGATAACTACGATACGGGAGGGCTTACCATCTGGCCCCAGTGCTGCA

ATGATACCGCGAGACCCACGCTCACCGGCTCCAGATTTATCAGCAATAAACCAGCCAGCCGGAAGGGCCGAG

CGCAGAAGTGGTCCTGCAACTTTATCCGCCTCCATCCAGTCTATTAATTGTTGCCGGGAAGCTAGAGTAAGTA

GTTCGCCAGTTAATAGTTTGCGCAACGTTGTTGCCATTGCTACAGGCATCGTGGTGTCACGCTCGTCGTTTGGT

ATGGCTTCATTCAGCTCCGGTTCCCAACGATCAAGGCGAGTTACATGATCCCCCATGTTGTGCAAAAAAGCGG

TTAGCTCCTTCGGTCCTCCGATCGTTGTCAGAAGTAAGTTGGCCGCAGTGTTATCACTCATGGTTATGGCAGCA

TABLE 9-continued

Nucleotide sequence of the vector shown in FIG. 17. (SEQ ID NO: 36)

CTGCATAATTCTCTTACTGTCATGCCATCCGTAAGATGCTTTTCTGTGACTGGTGAGTACTCAACCAAGTCATT
CTGAGAATAGTGTATGCGGCGACCGAGTTGCTCTTGCCCGGCGTCAATACGGGATAATACCGCGCCACATAGC
AGAACTTTAAAAGTGCTCATCATTGGAAAACGTTCTTCGGGGCGAAAACTCTCAAGGATCTTACCGCTGTTGA
GATCCAGTTCGATGTAACCCACTCGTGCACCCAACTGATCTTCAGCATCTTTTACTTTCACCAGCGTTTCTGGG
TGAGCAAAAACAGGAAGGCAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATATTTGAATGTAT
TTAGAAAAATAAACAAATAGGGGTTCCGCGCACATTTCCCCGAAAAGTGCCACCTGACGTCGACGGATCGGG
AGATCTCCCGATCCCCTATGGTGCACTCTCAGTACAATCTGCTCTGATGCCGCATAGTTAAGCCAGTATCTGCT
CCCTGCTTGTGTGTTGGAGGTCGCTGAGTAGTGCGCGAGCAAAATTTAAGCTACAACAAGGCAAGGCTTGACC
GACAATTGCATGAAGAATCTGCTTAGG

TABLE 10

Nucleotide sequence of the vector shown in FIG. 18. (SEQ ID NO: 37)

GTTAGGCGTTTTGCGCTGCTTCGCGATGTACGGGCCAGATATACGCGTTGACATTGATTATTGACTAGTTATTA
ATAGTAATCAATTACGGGGTCATTAGTTCATAGCCCATATATGGAGTTCCGCGTTACATAACTTACGGTAAAT
GGCCCGCCTGGCTGACCGCCCAACGACCCCCGCCCATTGACGTCAATAATGACGTATGTTCCCATAGTAACGC
CAATAGGGACTTTCCATTGACGTCAATGGGTGGAGTATTTACGGTAAACTGCCCACTTGGCAGTACATCAAGT
GTATCATATGCCAAGTACGCCCCCTATTGACGTCAATGACGGTAAATGGCCCGCCTGGCATTATGCCCAGTAC
ATGACCTTATGGGACTTTCCTACTTGGCAGTACATCTACGTATTAGTCATCGCTATTACCATGGTGATGCGGTT
TTGGCAGTACATCAATGGGCGTGGATAGCGGTTTGACTCACGGGGATTTCCAAGTCTCCACCCCATTGACGTC
AATGGGAGTTTGTTTTGGCACCAAAATCAACGGGACTTTCCAAAATGTCGTAACAACTCCGCCCCATTGACGC
AAATGGGCGGTAGGCGTGTACGGTGGGAGGTCTATATAAGCAGAGCTCGTTTAGTGAACCGTCAGATCGCCT
GGAGACGCCATCCACGCTGTTTTGACCTCCATAGAAGACACCGGGACCGATCCAGCCTCCGGAGCGGCCGCC
ACCATGGGCAAGCCCATCCCTAACCCCCTGTTGGGGCTGGACAGCACCGCTCCCAAAAAGAAAAGGAAGGTG
GGCATTCACGGCGTGCCTGCGGCCGACAAAAAGTACAGCATCGGCCTTGATATCGGCACCAATAGCGTGGGC
TGGGCCGTTATCACAGACGAATACAAGGTACCCAGCAAGAAGTTCAAGGTGCTGGGGAATACAGACAGGCAC
TCTATCAAGAAAAACCTTATCGGGGCTCTGCTGTTTGACTCAGGCGAGACCGCCGAGGCCACCAGGTTGAAGA
GGACCGCAAGGCGAAGGTACACCCGGAGGAAGAACAGGATCTGCTATCTGCAGGAGATCTTCAGCAACGAG
ATGGCCAAGGTGGACGACAGCTTCTTCCACAGGCTGGAGGAGAGCTTCCTTGTCGAGGAGGATAAGAAGCAC
GAACGACACCCCATCTTCGGCAACATAGTCGACGAGGTCGCTTATCACGAGAAGTACCCCACCATCTACCACC
TGCGAAAGAAATTGGTGGATAGCACCGATAAAGCCGACTTGCGACTTATCTACTTGGCTCTGGCGCACATGAT
TAAGTTCAGGGGCCACTTCCTGATCGAGGGCGACCTTAACCCCGACAACAGTGACGTAGACAAATTGTTCATC
CAGCTTGTACAGACCTATAACCAGCTGTTCGAGGAAAACCCTATTAACGCCAGCGGGTGGATGCGAAGGCC
ATACTTAGCGCCAGGCTGAGCAAAAGCAGGCGCTTGGAGAACCTGATAGCCCAGCTGCCCGGTGAAAAGAAG
AACGGCCTCTTCGGTAATCTGATTGCCCTGAGCCTGGGCCTGACCCCCAACTTCAAGAGCAACTTCGACCTGG
CAGAAGATGCCAAGCTGCAGTTGAGTAAGGACACCTATGACGACGACTTGGACAATCTGCTCGCCCAAATCG
GCGACCAGTACGCTGACCTGTTCCTCGCCGCCAAGAACCTTTCTGACGCAATCCTGCTTAGCGATATCCTTAG
GGTGAACACAGAGATCACCAAGGCCCCCCTGAGCGCCAGCATGATCAAGAGGTACGACGAGCACCATCAGG
ACCTGACCCTTCTGAAGGCCCTGGTGAGGCAGCAACTGCCCGAGAAGTACAAGGAGATCTTTTTCGACCAGA

TABLE 10-continued

Nucleotide sequence of the vector shown in FIG. 18. (SEQ ID NO: 37)

```
GCAAGAACGGCTACGCCGGCTACATCGACGGCGGAGCCAGCCAAGAGGAGTTCTACAAGTTCATCAAGCCCA

TCCTGGAGAAGATGGATGGCACCGAGGAGCTGCTGGTGAAGCTGAACAGGGAAGATTTGCTCCGGAAGCAGA

GGACCTTTGACAACGGTAGCATCCCCCACCAGATCCACCTGGGCGAGCTGCACGCAATACTGAGGCGACAGG

AGGATTTCTACCCCTTCCTCAAGGACAATAGGGAGAAAATCGAAAAGATTCTGACCTTCAGGATCCCCTACTA

CGTGGGCCCTCTTGCCAGGGGCAACAGCCGATTCGCTTGGATGACAAGAAAGAGCGAGGAGACCATCACCCC

CTGGAACTTCGAGGAAGTGGTGGACAAAGGAGCAAGCGCGCAGTCTTTCATCGAACGGATGACCAATTTCGA

CAAAAACCTGCCTAACGAGAAGGTGCTGCCCAAGCACAGCCTGCTTTACGAGTACTTCACCGTGTACAACGA

GCTCACCAAGGTGAAATATGTGACCGAGGGCATGCGAAAACCCGCTTTCCTGAGCGGCGAGCAGAAGAAGGC

CATCGTGGACCTGCTGTTCAAGACCAACAGGAAGGTGACCGTGAAGCAGCTGAAGGAGGACTACTTCAAGAA

GATCGAGTGCTTTGATAGCGTGGAAATAAGCGGCGTGGAGGACAGGTTCAACGCCAGCCTGGGCACCTACCA

CGACTTGTTGAAGATAATCAAAGACAAGGATTTCCTGGATAATGAGGAGAACGAGGATATACTCGAGGACAT

CGTGCTGACTTTGACCCTGTTTGAGGACCGAGAGATGATTGAAGAAAGGCTCAAAACCTACGCCCACCTGTTC

GACGACAAAGTGATGAAACAACTGAAGAGACGAAGATACACCGGCTGGGCGAGACTGTCCAGGAAGCTCAT

CAACGGCATTAGGGACAAGCAGAGCGGCAAGACCATCCTGGATTTCCTGAAGTCCGACGGCTTCGCCAACCG

AAACTTCATGCAGCTGATTCACGATGACAGCTTGACCTTCAAGGAGGACATCCAGAAGGCCCAGGTTAGCGG

CCAGGGCGACTCCCTGCACGAACATATTGCAAACCTGGCAGGCTCCCCTGCGATCAAGAAGGGCATACTGCA

GACCGTTAAGGTTGTGGACGAATTGGTCAAGGTCATGGGCAGGCACAAGCCCGAAAACATAGTTATAGAGAT

GGCCAGAGAGAACCAGACCACCCAAAAGGGCCAGAAGAACAGCCGGGAGCGCATGAAAAGGATCGAGGAG

GGTATCAAGGAACTCGGAAGCCAGATCCTCAAAGAGCACCCCGTGGAGAATACCCAGCTCCAGAACGAGAA

GCTGTACCTGTACTACCTGCAGAACGGCAGGGACATGTACGTTGACCAGGAGTTGGACATCAACAGGCTTTCA

GACTATGACGTGGATCACATAGTGCCCCAGAGCTTTCTTAAAGACGATAGCATCGACAACAAGGTCCTGACCC

GCTCCGACAAAAACAGGGGCAAAAGCGACAACGTGCCAAGCGAAGAGGTGGTTAAAAAGATGAAGAACTAC

TGGAGGCAACTGCTCAACGCGAAATTGATCACCCAGAGAAAGTTCGATAACCTGACCAAGGCCGAGAGGGGC

GGACTCTCCGAACTTGACAAAGCGGGCTTCATAAAGAGGCAGCTGGTCGAGACCCGACAGATCACGAAGCAC

GTGGCCCAAATCCTCGACAGCAGAATGAATACCAAGTACGATGAGAATGACAAACTCATCAGGGAAGTGAAA

GTGATTACCCTGAAGAGCAAGTTGGTGTCCGACTTTCGCAAAGATTTCCAGTTCTACAAGGTGAGGGAGATCA

ACAACTACCACCATGCCCACGACGCATACCTGAACGCCGTGGTCGGCACCGCCCTGATTAAGAAGTATCCAA

AGCTGGAGTCCGAATTTGTCTACGGCGACTACAAAGTTTACGATGTGAGGAAGATGATCGCTAAGAGCGAAC

AGGAGATCGGCAAGGCCACCGCTAAGTATTTCTTCTACAGCAACATCATGAACTTTTTCAAGACCGAGATCAC

ACTTGCCAACGGCGAAATCAGGAAGAGGCCGCTTATCGAGACCAACGGTGAGACCGGCGAGATCGTGTGGGA

CAAGGGCAGGGACTTCGCCACCGTGAGGAAAGTCCTGAGCATGCCCCAGGTGAATATTGTGAAAAAAACTGA

GGTGCAGACAGGCGGCTTTAGCAAGGAATCCATCCTGCCCAAGAGGAACAGCGACAAGCTGATCGCCCGGAA

GAAGGACTGGGACCCTAAGAAGTATGGAGGCTTCGACAGCCCCACCGTAGCCTACAGCGTGCTGGTGGTCGC

GAAGGTAGAGAAGGGGAAGAGCAAGAAACTGAAGAGCGTGAAGGAGCTGCTCGGCATAACCATCATGGAGA

GGTCCAGCTTTGAGAAGAACCCCATTGACTTTTTGGAAGCCAAGGGCTACAAAGAGGTCAAAAAGGACCTGA

TCATCAAACTCCCCAAGTACTCCCTGTTTGAATTGGAGAACGGCAGAAAGAGGATGCTGGCGAGCGCTGGGG

AACTGCAAAAGGGCAACGAACTGGCGCTGCCCAGCAAGTACGTGAATTTTCTGTACCTGGCGTCCCACTACG

AAAAGCTGAAAGGCAGCCCCGAGGACAACGAGCAGAAGCAGCTGTTCGTGGAGCAGCACAAGCATTACCTG

GACGAGATAATCGAGCAAATCAGCGAGTTCAGCAAGAGGGTGATTCTGGCCGACGCGAACCTGGATAAGGTC
```

TABLE 10-continued

Nucleotide sequence of the vector shown in FIG. 18. (SEQ ID NO: 37)

```
CTCAGCGCCTACAACAAGCACCGAGACAAACCCATCAGGGAGCAGGCCGAGAATATCATACACCTGTTCACC
CTGACAAATCTGGGCGCACCTGCGGCATTCAAATACTTCGATACCACCATCGACAGGAAAAGGTACACTAGC
ACTAAGGAGGTGCTGGATGCCACCTTGATCCACCAGTCCATTACCGGCCTGTATGAGACCAGGATCGACCTGA
GCCAGCTTGGAGGCGACTCTAGGGCGGACCCAAAAAAGAAAAGGAAGGTGGAATTCTCTAGAGGCAGTGGA
GAGGGCAGAGGAAGTCTGCTAACATGCGGTGACGTCGAGGAGAATCCTGGCCCAATGAACCTGAGCAAAAAC
GTGAGCGTGAGCGTGTATATGAAGGGGAACGTCAACAATCATGAGTTTGAGTACGACGGGGAAGGTGGTGGT
GATCCTTATACAGGTAAATATTCCATGAAGATGACGCTACGTGGTCAAAATTCCCTACCCTTTTCCTATGATAT
CATTACCACGGCATTTCAGTATGGTTTCCGCGTATTTACAAAATACCCTGAGGGAATTGTTGACTATTTTAAGG
ACTCGCTTCCCGACGCATTCCAGTGGAACAGACGAATTGTGTTTGAAGATGGTGGAGTACTAAACATGAGCAG
TGATATCACATATAAAGATAATGTTCTGCATGGTGACGTCAAGGCTGAGGGAGTGAACTTCCCGCCGAATGGG
CCAGTGATGAAGAATGAAATTGTGATGGAGGAACCGACTGAAGAAACATTTACTCCAAAAAACGGGGTTCTT
GTTGGCTTTTGTCCCAAAGCGTACTTACTTAAAGACGGTTCCTATTACTATGGAAATATGACAACATTTTACAG
ATCCAAGAAATCTGGCCAGGCACCTCCTGGGTATCACTTTGTTAAGCATCGTCTCGTCAAGACCAATGTGGGA
CATGGATTTAAGACGGTTGAGCAGACTGAATATGCCACTGCTCATGTCAGTGATCTTCCCAAGTTCGAAGCTT
GATAATGAGTTTAAACGGGGGAGGCTAACTGAAACACGGAAGGAGACAATACCGGAAGGAACCCGCGCTAT
GACGGCAATAAAAAGACAGAATAAAACGCACGGGTGTTGGGTCGTTTGTTCATAAACGCGGGGTTCGGTCCC
AGGGCTGGCACTCTGTCGATACCCCACCGAGACCCCATTGGGGCCAATACGCCCGCGTTTCTTCCTTTTCCCCA
CCCCACCCCCCAAGTTCGGGTGAAGGCCCAGGGCTCGCAGCCAACGTCGGGGCGGCAGGCCCTGCCATAGCA
GATCTGCGCAGCTGGGGCTCTAGGGGGTATCCCCACGCGCCCTGTAGCGGCGCATTAAGCGCGGCGGGTGTG
GTGGTTACGCGCAGCGTGACCGCTACACTTGCCAGCGCCCTAGCGCCCGCTCCTTTCGCTTTCTTCCCTTCCTT
TCTCGCCACGTTCGCCGGCTTTCCCCGTCAAGCTCTAAATCGGGGGCTCCCTTTAGGGTTCCGATTTAGTGCTT
TACGGCACCTCGACCCCAAAAAACTTGATTAGGGTGATGGTTCACGTAGTGGGCCATCGCCCTGATAGACGGT
TTTTCGCCCTTTGACGTTGGAGTCCACGTTCTTTAATAGTGGACTCTTGTTCCAAACTGGAACAACACTCAACC
CTATCTCGGTCTATTCTTTTGATTTATAAGGGATTTTGCCGATTTCGGCCTATTGGTTAAAAAATGAGCTGATTT
AACAAAAATTTAACGCGAATTAATTAAGGTCGGGCAGGAAGAGGGCCTATTTCCCATGATTCCTTCATATTTG
CATATACGATACAAGGCTGTTAGAGAGATAATTAGAATTAATTTGACTGTAAACACAAAGATATTAGTACAA
AATACGTGACGTAGAAAGTAATAATTTCTTGGGTAGTTTGCAGTTTTAAAATTATGTTTTAAAATGGACTATCA
TATGCTTACCGTAACTTGAAAGTATTTCGATTTCTTGGCTTTATATATCTTGTGGAAAGGACGAAACACCGNNN
NNNNNNNNNNNNNNNNGTTTTAGAGCTAGAAATAGCAAGTTAAAATAAGGCTAGTCCGTTATCAACTTGAA
AAAGTGGCACCGAGTCGGTGCTTTTTTCTAGTATACCGTCGACCTCTAGCTAGAGCTTGGCGTAATCATGGTC
ATAGCTGTTTCCTGTGTGAAATTGTTATCCGCTCACAATTCCACACAACATACGAGCCGGAAGCATAAAGTGT
AAAGCCTGGGGTGCCTAATGAGTGAGCTAACTCACATTAATTGCGTTGCGCTCACTGCCCGCTTTCCAGTCGG
GAAACCTGTCGTGCCAGCTGCATTAATGAATCGGCCAACGCGCGGGGAGAGGCGGTTTGCGTATTGGGCGCT
CTTCCGCTTCCTCGCTCACTGACTCGCTGCGCTCGGTCGTTCGGCTGCGGCGAGCGGTATCAGCTCACTCAAAG
GCGGTAATACGGTTATCCACAGAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCCGCCCCCCTGACGAGCATCACAAA
AATCGACGCTCAAGTCAGAGGTGGCGAAACCCGACAGGACTATAAAGATACCAGGCGTTTCCCCCTGGAAGC
TCCCTCGTGCGCTCTCCTGTTCCGACCCTGCCGCTTACCGGATACCTGTCCGCCTTTCTCCCTTCGGGAAGCGT
GGCGCTTTCTCATAGCTCACGCTGTAGGTATCTCAGTTCGGTGTAGGTCGTTCGCTCCAAGCTGGGCTGTGTGC
```

TABLE 10-continued

Nucleotide sequence of the vector shown in FIG. 18. (SEQ ID NO: 37)

```
ACGAACCCCCCGTTCAGCCCGACCGCTGCGCCTTATCCGGTAACTATCGTCTTGAGTCCAACCCGGTAAGACA
CGACTTATCGCCACTGGCAGCAGCCACTGGTAACAGGATTAGCAGAGCGAGGTATGTAGGCGGTGCTACAGA
GTTCTTGAAGTGGTGGCCTAACTACGGCTACACTAGAAGAACAGTATTTGGTATCTGCGCTCTGCTGAAGCCA
GTTACCTTCGGAAAAAGAGTTGGTAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCTTTGATCTTTTCTACGGGGTCTGA
CGCTCAGTGGAACGAAAACTCACGTTAAGGGATTTTGGTCATGAGATTATCAAAAAGGATCTTCACCTAGATC
CTTTTAAATTAAAAATGAAGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCTGACTCCCCGTCGTG
TAGATAACTACGATACGGGAGGGCTTACCATCTGGCCCCAGTGCTGCAATGATACCGCGAGACCCACGCTCA
CCCGGCTCCAGATTTATCAGCAATAAACCAGCCAGCCGGAAGGGCCGAGCGCAGAAGTGGTCCTGCAACTTTA
TCCGCCTCCATCCAGTCTATTAATTGTTGCCGGGAAGCTAGAGTAAGTAGTTCGCCAGTTAATAGTTTGCGCA
ACGTTGTTGCCATTGCTACAGGCATCGTGGTGTCACGCTCGTCGTTTGGTATGGCTTCATTCAGCTCCGGTTCC
CAACGATCAAGGCGAGTTACATGATCCCCCATGTTGTGCAAAAAAGCGGTTAGCTCCTTCGGTCCTCCGATCG
TTGTCAGAAGTAAGTTGGCCGCAGTGTTATCACTCATGGTTATGGCAGCACTGCATAATTCTCTTACTGTCATG
CCATCCGTAAGATGCTTTTCTGTGACTGGTGAGTACTCAACCAAGTCATTCTGAGAATAGTGTATGCGGCGAC
CGAGTTGCTCTTGCCCGGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAGTTCGATGTAACCCACT
CGTGCACCCAACTGATCTTCAGCATCTTTTACTTTCACCAGCGTTTCTGGGTGAGCAAAAACAGGAAGGCAAA
ATGCCGCAAAAAAGGGAATAAGGGCGACACGGAAATGTTGAATACTCATACTCTTCCTTTTTCAATATTATTG
AAGCATTTATCAGGGTTATTGTCTCATGAGCGGATACATATTTGAATGTATTTAGAAAAATAAACAAATAGGG
GTTCCGCGCACATTTCCCCGAAAAGTGCCACCTGACGTCGACGGATCGGGAGATCTCCCGATCCCCTATGGTG
CACTCTCAGTACAATCTGCTCTGATGCCGCATAGTTAAGCCAGTATCTGCTCCCTGCTTGTGTGTTGGAGGTCG
CTGAGTAGTGCGCGAGCAAAATTTAAGCTACAACAAGGCAAGGCTTGACCGACAATTGCATGAAGAATCTGC
TTAGG
```

Example 2

Rapid and Highly Efficient Mammalian Cell Engineering Via Cas9 Protein Transfection Abstract CRISPR-Cas9 systems provide a platform for high efficiency genome editing that are enabling innovative applications of mammalian cell engineering. However, the delivery of Cas9 and synthesis of guide RNA (gRNA) remain as steps that can limit overall efficiency and general ease of use. Described here are methods for rapid synthesis of gRNA and for delivery of Cas9 protein/gRNA ribonucleoprotein complexes (Cas9 RNPs) into a variety of mammalian cells through liposome-mediated transfection or electroporation. Using these methods, nuclease-mediated indel rates of up to 94% in Jurkat T cells and 87% in induced pluripotent stem cells (iPSC) for a single target are reported. When this approach is used for multigene targeting in Jurkat cells, it was found that two-locus and three-locus indels were achieved in approximately 93% and 65% of the resulting isolated cell lines, respectively. Further, in this study, it was found that the off-target cleavage rate is significantly reduced using Cas9 protein when compared to plasmid DNA transfection. Taken together, a streamlined cell engineering workflow is presented that enables gRNA design to analysis of edited cells in as little as four days and results in highly efficient genome modulation in hard-to-transfect cells. The reagent preparation and delivery to cells requires no plasmid manipulation, and is thus amenable to high throughput, multiplexed genome-wide cell engineering.

Introduction

CRISPR-Cas9 mediated genome engineering enables researchers to modify genomic DNA in vivo directly and efficiently (Cho et al., "Targeted genome engineering in human cells with the Cas9 RNA-guided endonuclease," Nat. Biotechnol. 31:230-232 (2013); Mali et al., "RNA-guided human genome engineering via Cas9," Science 339:823-826 (2013); Jiang et al., "RNA-guided editing of bacterial genomes using CRISPR-Cas systems," Nat. Biotechnol. 31:233-239 (2013); Wang et al., "One-step generation of mice carrying mutations in multiple genes by CRISPR/Cas-mediated genome engineering," Cell 153:910-918 (2013)). Three components (Cas9, mature crRNA and tracrRNA) are essential for functional activity. Although the mature crRNA and tracrRNA can be synthesized chemically, the quality of the synthetic RNA is not sufficient for in vivo cell engineering due to the presence of truncated by-products (data not shown). Therefore, templates for the mature crRNA and tracrRNA or a combined single gRNA are often cloned into a Cas9 expression plasmid or built into separate plasmids driven by either U6 or H1 promoters for transcription after transfection of mammalian cells. Because the constructs are relatively large, delivery rates can be low, which would limit genomic cleavage efficiency, especially for hard-to-transfect cells. Recently, the use of Cas9 delivered as mRNA has led to increases in the rate of genomic cleavage in some cells. For example, a mixture of Cas9 mRNA and a single species of gRNA were co-injected into mouse embryonic stem (ES) cells resulting in biallelic mutations in 95% of newborn mice (Wang et al., "*One-step generation of mice carrying mutations in multiple genes by CRISPR/Cas-mediated genome engineering,*" Cell 153:910-918 (2013)). To make guide RNA, often precloned plasmid is used directly or a linear template is created via PCR amplification of the targeting sequence from a plasmid. If a 5' T7 promoter does not appear in the plasmid, it is often added at this step and the resulting PCR product can be used in an in vitro transcription reaction. Alternatively, a synthetic DNA fragment containing a T7 promoter, crRNA and tracerRNA can be used as a template to prepare a gRNA by in vitro transcription. Overall, these represent a labor-intensive and time-consuming workflow, which led us to seek a simpler method to synthesize high quality gRNA. To that, describe here is a streamlined modular approach for gRNA production in vitro. Starting with two short single stranded oligos, the gRNA template is assembled in a 'one pot' PCR reaction. The product is then used as template in an in vitro transcription (IVT) reaction which is followed by a rapid purification step, yielding transfection-ready gRNA in as little as four hours.

To streamline the cell engineering workflow further, it was sought to eliminate any remaining cellular transcription or translation by directly introducing Cas9/gRNA ribonucleoprotein (RNP) complexes directly to the cells. Microinjection of Cas9 protein and gRNA complexes into *C. elegans* was first described in 2013 (Cho et al., "*Heritable gene knockout in Caenorhabditis elegans by direct injection of Cas9-sgRNA ribonucleoproteins,*" Genetics 195:1177-1180 (2013)) and was subsequently used to generate gene-knockout mice and zebrafish with mutation rates of up to 93% in newborn mice (Sung et al., "*Highly efficient gene knockout in mice and zebrafish with RNA-guided endonucleases,*" Genome Res. 24:125-131 (2014)). Following that report, Cas9 protein/gRNA complexes were delivered into cultured human fibroblasts and induced pluripotent stem cells (iPSC) via electroporation with high efficiency and relatively low off-target effects (Kim et al., "*Highly efficient RNA-guided genome editing in human cells via delivery of purified Cas9 ribonucleoproteins*" Genome Res. 24:1012-1019 (2014)). In that study, a large amount of Cas9 protein (4.5 to 45 μg) and gRNA (6 to 60 μg) were necessary for efficient genome modification (up to 79% indel efficiency). Most recently, delivery of Cas9 protein-associated gRNA complexes via liposomes was reported, in which RNAiMAX was used to deliver Cas9:sgRNA nuclease complexes into cultured human cells and into the mouse inner ear in vivo with up to 80% and 20% genome modification efficiency respectively (Zuris et al., "*Cationic lipid-mediated delivery of proteins enables efficient protein-based genome editing in vitro and in vivo*" Nat Biotechnol. October 30. doi: 10.1038/nbt.3081 (2014)).

The CRISPR/Cas system has been demonstrated as an efficient gene-targeting tool for multiplexed genome editing (Wang et al., "*One-step generation of mice carrying mutations in multiple genes by CRISPR/Cas-mediated genome engineering,*" Cell 153:910-918 (2013); Kabadi et al., "*Multiplex CRISPR/Cas9-based genome engineering from a single lentiviral vector*" Nucleic Acids Res. October 29; 42(19):e147. doi: 10.1093/nar/gku749 (2014); Sakuma et al., "*Multiplex genome engineering in human cells using all-in-one CRISPR/Cas9 vector system,*" Sci Rep. June 23; 4:5400. doi: 10.1038/srep05400 (2014); Cong et al., "*Multiplex genome engineering using CRISPR/Cas systems. Science.* 339: 819-823 (2013)). For example, co-transfections of mouse ES cells with constructs expressing Cas9 and three sgRNAs targeting Tet1, 2, and 3 resulted in 20% of cells having mutations in all six alleles of the three genes based on restriction fragment length polymorphism (RFLP) assay (Wang et al., "*One-step generation of mice carrying mutations in multiple genes by CRISPR/Cas-mediated genome engineering,*" Cell 153:910-918 (2013)). Lentiviral delivery of a single vector expressing Cas9 and four sgRNAs into primary human dermal fibroblasts resulted in about 30% simultaneous editing of four genomic loci among ten clonal populations based upon genomic cleavage detection assays (Kabadi et al., "*Multiplex CRISPR/Cas9-based genome engineering from a single lentiviral vector*" Nucleic Acids Res. October 29; 42(19):e147. doi: 10.1093/nar/gku749 (2014)). In one recent study, 'all-in-one' expression vectors containing seven guide RNA expression cassettes and a Cas9 nuclease/nickase expression cassette were delivered into 293T cells with genome cleavage efficiency ranging from 4 to 36% for each individual target (Sakuma et al., "*Multiplex genome engineering in human cells using all-in-one CRISPR/Cas9 vector system,*" Sci Rep. June 23; 4:5400. doi: 10.1038/srep05400 (2014)). In general, the efficiency of editing multiple genes in the human genome using plasmid-based delivery methods remains relatively low which subsequently increases the workload for downstream clonal isolation.

An in vitro gRNA production system has been developed and used a systematic approach to optimize the conditions for delivery of Cas9:gRNA complexes via lipid-mediated transfection or electroporation. A variety of mammalian cell lines were tested, including primary cells and other hard-to-transfect cells. Plasmid DNA, mRNA and Cas9 protein transfections were evaluated side by side. Using Cas9 protein transfection via electroporation, a superior genome editing efficiencies even in hard-to-transfect cells was achieved. In addition, the genome editing of multiple targets simultaneously using the Cas9 RNPs delivery system were assessed and are described here. It was found that delivery of Cas9 RNPs not only led to high indel production at single locus, but supports highly efficient biallelic modulation of at least two genes in a single transfection.

Materials and Methods

Materials:

293FT cells, The Gibco® Human Episomal iPSC Line, DMEM medium, RPMI 1640 medium, IMDM, DMEM/F-12, Fetal Bovine Serum (FBS), Knockout™ Serum Replacement, Non-Essential Amino Acid solution, basic fibroblast growth factor, Collagenase IV, TrypLE™ Express Enzyme, Geltrex, Opti-MEM Medium, FluoroBrite™ DMEM, Lipofectamine 2000, Lipofectamine 3000, RNAiMAX, Lipofectamine® MessengerMAX, GeneArt® CRISPR Nuclease Vector with OFP Reporter, 2% E-Gel® EX Agarose Gels, PureLink® PCR Micro Kit, TranscriptAid T7 High Yield Transcription Kit, MEGAclear™ Transcription Clean-Up Kit, Zero Blunt® TOPO® PCR Cloning Kit, PureLink® Pro Quick96 Plasmid Purification Kit, Endotoxin Quantitation Kit, Qubit® RNA BR Assay Kit, TRA-1-60 Alexa Fluor® 488 conjugated antibodies, SSEA4 Alexa Fluor®647, and Phusion Flash High-Fidelity PCR Master Mix were from Thermo Fisher Scientific. Jurkat T cells and K562 cells were obtained from the American Type Culture Collection (ATCC). MEF feeder cells and ROCK inhibitor Y-27632 were purchased from EMD Millipore. Monoclonal Cas9 antibody was ordered from Diagenode. Recombinant Cas9 protein was purified as described by Kim et al. (7). All oligonucleotides used for gRNA synthesis were from Thermo Fisher Scientific (Supplementary Table 1s).

One Step Synthesis of gRNA Template

The 80 nt constant region of tracrRNA from a GeneArt® CRISPR Nuclease Vector was amplified by PCR and purified via agarose gel extraction. The concentration of PCR product was measured by Nanodrop (Thermo Fisher Scientific) and the molarity was calculated based on the molecular weight of 49.6 kDa. To prepare a pool of oligonucleotides, an aliquot of the 80 nt PCR product was mixed with two end primers and target-specific forward and reverse primers, with a final concentration of 0.15 µM for the 80 nt PCR product and 10 µM for each of the end primers. For a specific target, a 34 nt forward primer consisting of the T7 promoter sequence and 5'end target sequence, and a 34 nt reverse primer consisting of the target sequence and 5' end tracrRNA sequence were chemically synthesized with a 15 nt overlap. To set up the synthesis of gRNA template, aliquots of the pooled oligonucleotides were added to a Phusion Flash High-Fidelity PCR Master Mix and amplified using manufacturer's recommended reaction conditions. The PCR product was analyzed by a 2% E-Gel® EX Agarose Gel, followed by purification using Purelink PCR micro column. The gRNA template was eluted with 13 µl water and the concentration was determined by Nanodrop instrument.

To determine the error rate, the PCR product was cloned into Zero Blunt® TOPO® vector, followed by plasmid DNA isolation and sequencing with a 3500xl DNA analyzer (Thermo Fisher Scientific).

In Vitro Transcription

The in vitro transcription of gRNA template was carried out using TranscriptAid T7 High Yield Transcription Kit using the manufacturer's recommended conditions. The gRNA product was purified using MEGAclear™ Transcription Clean-Up kit as described in the manual. The concentration of RNA was determined using Qubit® RNA BR Assay Kit.

Cell Culture

HEK 293FT cells were maintained in DMEM medium supplemented with 10% FBS. Jurkat T cells were propagated in RPMI medium containing 10% FBS, whereas K562 cells were cultured in IMDM medium supplemented with 10% FBS. Feeder-dependent human episomal iPSC were cultured on mitotically inactivated MEF feeder cells in human ESC (hESC) media containing 20% Knockout™ Serum Replacement, 10 µM Non-Essential Amino Acid solution, 55 µM 2-Mercaptoethanol, and 4 ng/ml basic fibroblast growth factor in DMEM/F-12. All cultures were maintained in a 5% $CO_2$, 37° C. humidified incubator. iPSC cultures were maintained with daily media changes and were passaged regularly using Collagenase IV.

Lipid-Mediated Cell Transfection

One day prior to transfection, the cells were seeded in a 24-well plate at a cell density of $2.5 \times 10^5$ cells per well. For plasmid DNA transfection, 0.5 µg DNA was added to 25 µl of Opti-MEM medium, followed by addition of 25 µl of Opti-MEM containing 2 µl of Lipofectamine 2000. The mixture was incubated at room temperature for 15 minutes and then added to the cells. For Cas9 mRNA tranfection, 0.5 µg Cas9 mRNA (Thermo Fisher Scientific) was added to 25 µl of Opti-MEM, followed by addition of 50-100 ng gRNA. Meanwhile, 2 µl of Lipofectamine 3000 was diluted into 25 µl of Opti-MEM and then mixed with mRNA/gRNA sample. The mixture was incubated for 15 minutes prior to addition to the cells. For Cas9 protein transfection, 500 ng of purified Cas9 protein (Thermo Fisher Scientific) was added to 25 µl of Opti-MEM medium, followed by addition of 120 ng gRNA. The molar ratio of gRNA over Cas9 protein was approximately 1:1.2. The sample was mixed by gently tapping the tubes a few times and then incubated at room temperature for 10 minutes. To a separate test tube, 2 µl of RNAiMAX or Lipofectamine 3000 was added to 25 µl of Opti-MEM medium. The diluted transfection reagent was transferred to the tube containing Cas9 protein/gRNA complexes, followed by incubation at room temperature for 15 minutes. The entire solution was then added to the cells in a 24-well plate and mixed by gently swirling the plate. The plate was incubated at 37° C. for 48 hours in a 5% $CO_2$ incubator. The percentage of locus-specific indel formation was measured by GeneArt® Genomic Cleavage Detection Kit. The band intensities were quantitated using built-in software in Alpha Imager (Bio-Rad).

Electroporation

For suspension cells, such as Jurkat T cells or K562 cells, $2 \times 10^5$ cells were used per electroporation using Neon® Transfection System 10 µL Kit (Thermo Fisher Scientific). To maximize the genome cleavage efficiency, the Neon 24 optimized protocol was applied according to the manufacturer's instruction. To set up a master mix, 24 µg of purified Cas9 protein was added to 240 µL of Resuspension Buffer R provided in the kit, followed by addition of 4.8 µg of gRNA. The mixture was incubated at room temperature for 10 minutes. Meanwhile, $4.8 \times 10^6$ cells were transferred to a sterile test tube and centrifuged at 500×g for 5 minutes. The supernatant was aspirated and the cell pellet was resuspended in 1 ml of PBS without $Ca^{2+}$ and $Mg^{2+}$. Upon centrifugation, the supernatant was carefully aspirated so that almost all the PBS buffer was removed with no or minimum loss of cells. The Resuspension Buffer R containing the Cas9 protein/gRNA complexes was then used to resuspend the cell pellets. A 10 µl cell suspension was used for each of the 24 optimized conditions, which varied in pulse voltage, pulse width and the number of pulses. The electroporated cells were transferred immediately to a 24 well containing 0.5 ml of the corresponding growth medium and then incubated for 48 hours in a 5% $CO_2$ incubator. The cells were harvested by centrifugation and then washed once with PBS, followed by Genomic Cleavage and Detection assay as described by the manual. Upon optimization of electroporation condition, a higher amount of Cas9 protein (1.5 to 2 µg) and gRNA (300 to 400 ng) could be applied to further increase the genome editing efficiency. For each target in the multiplexing assays, 1 to 2 µg of Cas9 protein and 200-400 ng of gRNA were pre-incubated separately prior to mixing with cell pellet for electroporation. For clonal isolation, the cell number of transfected cells was counted upon 48 hour incubation, followed by a serial of dilution to 96 well plates with a cell density of 10-20 cells per plate based on the cell count. After clonal expansion for three weeks, cells from each individual well were harvested, followed by PCR amplification of the target locus. The PCR fragments were then cloned using a TOPO vector and transformed into TOP10 competent cells. Approximately 8 E. coli colonies were randomly picked for sequencing for each individual target locus. The single cell population was determined by the homogeneity of sequences for each allele. Single cells containing bi-allelic mutations on all desired targets were considered homozygotic indels. Downstream sequence analysis to confirm frame-shift induced stop codon introduction was not done.

For transfection of feeder free adaptation of iPSC, feeder dependent iPSC were grown to 80% confluency prior to harvest with collagenase. Following removal of the cell clusters from the feeder layer, they were gravity sedimented to prevent MEF contamination. The cell clusters were then seeded on to tissue culture dishes coated with Geltrex® in MEF conditioned media supplemented with 4 ng/mL bFGF. MEF conditioned media was produced using inactivated feeder cells, which was harvested on 7 continuous days, sterile filtered and frozen until usage. The cultures were allowed to reach 80-90% confluence. The day prior to transfection, the cultures were pretreated with 5 µM ROCK inhibitor Y-27632. On the day of harvest the cultures were inspected for signs of differentiation and any contamination differentiated cells were removed via micro-dissection. The cultures were washed once with DPBS and then harvested using TrypLE™ Express Enzyme. Single cells suspensions were counted using the Countess® automated cell counter. Following transfections, the cells were seeded onto multi-well (24 well) tissue culture dish coated with Geltrex® and incubated overnight with MEF conditioned media containing 5 µM ROCK. Media was replaced daily, without ROCK inhibitor, prior to analysis.

Cell Surface Immunostaining

To ensure maintenance of pluripotency post transfection and genome editing, iPSC cells were tested for expression of cell surface markers of self-renewal. The wells to be probed were washed with DMEM/F12 basal media. TRA-1-60 Alexa Fluor® 488 conjugated antibodies and SSEA4 Alexa Fluor®647 were multiplexed in basal DMEM/F-12 media. Both antibodies were added at a concentration of 2 µl of each antibody into 0.5 mL of pre-warmed DMEM/F-12 media and incubated at 37° C. for 45 minutes. Following the incubation, the antibody solution was removed and the wells were washed twice with DMEM/F-12. Prior to observation the media was exchanged with pre-warmed FluoroBrite™ DMEM. Images were taken using a Zeiss Axiovision microscope using a FITC and Cy5 laser/filter combination.

Analysis of Pluripotency Markers

Cultures were detached and dissociated using TrypLE™ Select and trituration. Single cell suspensions were incubated with TRA-1-60 Alexa Fluor® 488 conjugated antibodies and SSEA4 Alexa Fluor®647 for 1 hour at room temperature with gentle agitation. Two microliters (50×) of each antibody were added to 0.5 mL of DMEM/F-12. Following the incubation, the cells were centrifuged and washed once with Dulbecco's Phosphate-Buffered Saline (DPBS). After the removal of the DPBS wash, the pelleted cells were gently re-suspended in 1 mL of DPBS and stained through a strainer capped tube. The cells were then measured for the expression of both markers using the ATTUNE® Acoustic Focusing Cytometer and the data was analyzed using FlowJo software.

Western Blot Analysis

293FT cells were transfected with either plasmid DNA, mRNA or Cas9 protein as described above. Cells were harvested at indicated times to perform both Genome Cleavage and Detection assay and Western Blot analysis. The cell lysate was fractionated using a 4-12% Novex Bis-tris gel. The proteins were transferred to a PVDF membrane using an iBlot following the manufacturer's protocol. Upon blocking, the membrane was incubated for 2 hours with monoclonal mouse Cas9 antibody at 1:3000 dilution. After washing, the membrane was incubated for 1 hour with rabbit anti-mouse antibody-HRP conjugate at 1:2000 dilution. Upon extensive washing, the membrane was developed with Pierce ECL reagent, followed by imaging using a Fuji imager LAS 4000 instrument.

Results

Three Day Cell Engineering Workflow

Figure 19:
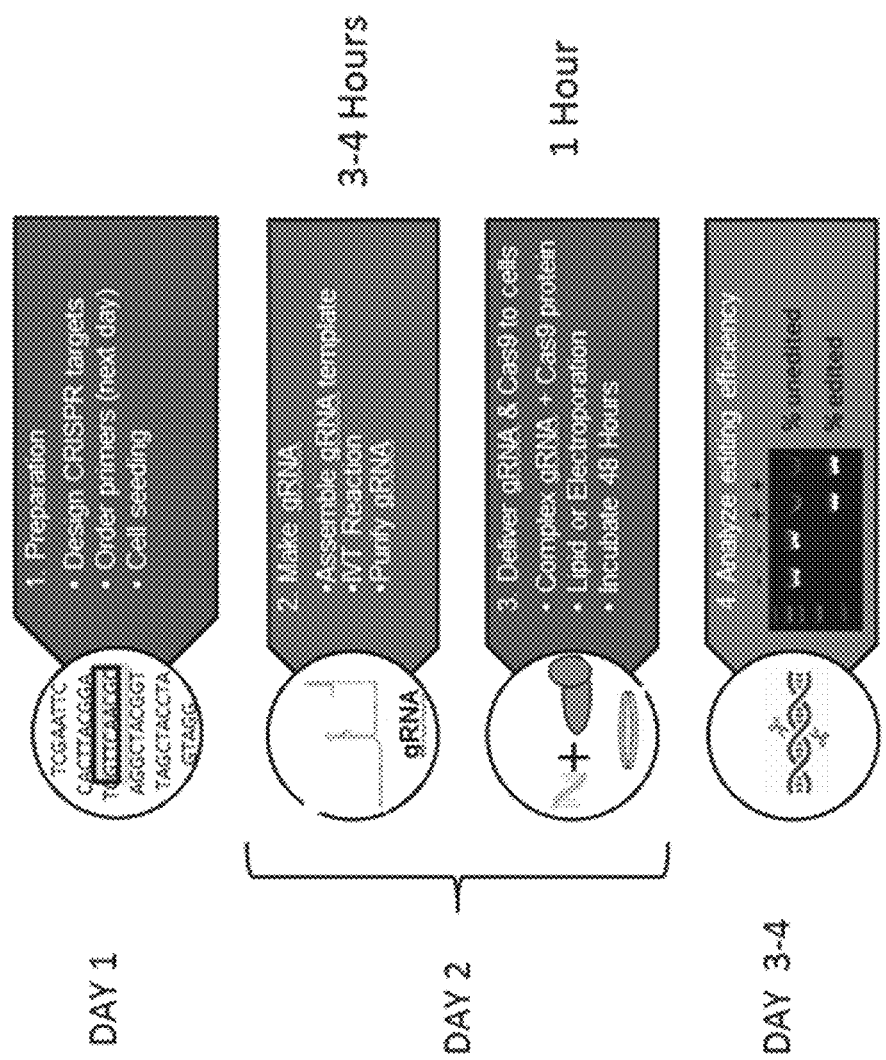
FIG. 19. Cell engineering workflow. On day 1, the researcher designs CRISPR targets and seeds cells. Synthesis of gRNA and cell transfection with Cas9 protein/gRNA complex (Cas9 RNP) are performed on day 2. Genome cleavage assays carried out on days 3-4.

To streamline the genome engineering workflow, it was sought to simplify the gRNA synthesis procedure and shorten the time from experimental design to initial analysis as much as possible. Presented herein is a process where on day 1, the researcher designs and orders short DNA oligonucleotides and seeds the cells of interest for next day transfection (FIG. 19). Upon receiving the oligonucleotides on day 2, the researcher assembles the gRNA template in less than 1 hour by 'one pot' PCR. The resulting PCR product is then subjected to in vitro transcription to synthesize gRNA in approximately 3 hours. Upon association of gRNA with purified Cas9 protein, the Cas9 protein/gRNA complexes (Cas9 RNPs) are used to transfect cells via lipid-mediated delivery or electroporation. As early as day 3 (24 hours post transfection), the cells can be harvested for analysis of locus-specific genome modification efficiency.

Figure 20D:
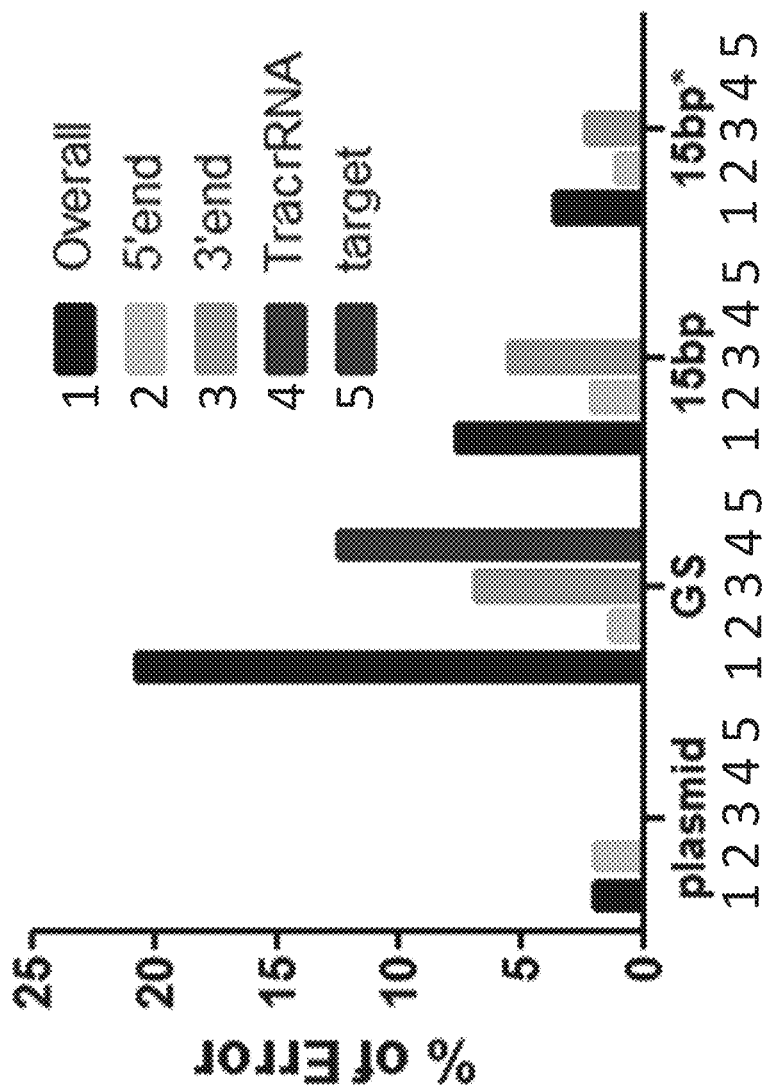

To assemble the DNA template for gRNA production, a total of 4 synthetic DNA oligonucleotides and a purified PCR product representing the constant (non-targeting) crRNA region and tracrRNA sequence (gRNA lacking target sequence) are used (FIG. 20A). A pair of 34 nt forward and reverse oligonucleotide primers were designed by an online web tool (Beta Testing Version, Thermo Fisher Scientific), and share 15 nt homology with the CRISPR and tracer RNA regions respectively. The oligonucleotide pool concentrations as well as the PCR conditions were optimized such that the template was amplified in less than 40 minutes in a single tube with no obvious by-products (FIG. 20B). The gRNA template was used directly to prepare gRNA via in vitro transcription (IVT). The resulting gRNA was purified yielding high levels of gRNA with no detectable by-products (FIG. 20C). This approach was validated by synthesis of more than 96 distinct gRNAs. To determine the error rate in the synthetic DNA template, the PCR fragments were cloned and sequenced and it was found that approximately 7% of gRNA templates harbored mutations, mainly small deletions occurring at the extreme 3' end and 5' ends of the mature template. The use of HPLC-purified end primers further decreased the error rate to 3.6% with no mutations detected in the target region, which was similar to what was observed with the control template prepared from an 'all-in-one' plasmid with a 2% error rate (FIG. 20D). Taken together, this optimized process facilitates the conversion of a small set of DNA oligonucleotides into purified gRNA in approximately 4 hours with an accuracy of 96% and no errors detected in the targeting or Cas9 complexing (cr/tracrRNA) regions. Given that the process consists solely of liquid handling PCR, transcription, and RNA isolation steps, it is well suited for high throughput gRNA production and screening.

Liposome-Mediated Cas9 Protein Transfection

To examine the activity of synthetic gRNA, pre-complexed purified synthetic IVT gRNA with Cas9 protein were produced. It was hypothesizing that creating complexes of purified gRNAs with Cas9 protein prior to delivery to the cells might lead to higher genome editing efficiency due to the protection of the gRNA as it transits to the nucleus during the transfection process. To examine in vivo functionality of the system, human embryonic kidney (HEK293) cells were transfected with pre-complexed Cas9/gRNA ribonucleoproteins (Cas9 RNPs) using a set of cationic lipid reagents, followed by a genomic cleavage detection assay. Interestingly, the commonly-used plasmid DNA or RNA transfection reagents were able to efficiently deliver Cas9 RNPs. Lipofectamine 3000 and RNAiMAX outperformed Lipofectamine 2000 in HEK 293 cells (data not shown), which is in agreement with the recent finding that RNAiMAX performed better than Lipofectamine 2000 for delivery of Cas9 mRNA (Zuris et al., "Cationic lipid-mediated delivery of proteins enables efficient protein-based genome editing in vitro and in vivo" Nat Biotechnol. October 30. doi: 10.1038/nbt.3081 (2014)). For protein transfection, serum-free medium is generally used to avoid serum protein inference. In this study however, it was observed that the complete medium containing 10% FBS facilitated protein transfection and genome modification (FIG. 21A). The efficiencies of genome editing via plasmid DNA, mRNA and Cas9 RNP transfection were evaluated using three different target loci, HPRT, AAVS and RelA. Plasmid DNA and mRNA were delivered into HEK293 cells by Lipofectamine 3000, whereas Cas9 RNPs were delivered with RNAiMAX. As shown in FIG. 21A, the efficiencies of genome modification were similar among three target loci in DNA, mRNA and Cas9 protein-transfected cells.

Next examined was the kinetics of genome cleavage by transfecting cells with either plasmid DNA, mRNA or Cas9 RNPs, followed by genome cleavage assays and Western Blot analysis of cell lysates. In this study, it was observed similar cleavage kinetics between Cas9 delivered as plasmid DNA, mRNA and protein with efficient cleavage seen at 24 hours plateauing at 48 to 72 hours post-transfection in HEK293 cells (FIG. 21B). It was found that the kinetics of Cas9 RNP and mRNA encoded Cas9 appearance and turnover inside the transfected cells was quite different from that seen with Cas9 delivered via plasmid DNA. Measuring by Western Blot (FIG. 21C), it was found that Cas9 protein accumulated over time as expected in plasmid DNA-transfected cells, whereas the relatively low expression of Cas9 in mRNA-transfected cells seemed to peak as early as four hours post transfection and remained relatively stable for approximately 44 hours before diminishing. In the Cas9 RNP-transfected cells, the level of Cas9 protein peaked in four hours or less then rapidly decreased and was barely detectable in our assay at 48 hours. As a control, the blot membrane was stripped and re-probed with anti-actin antibody. Similar levels of actin expression were observed among samples (data not shown).

Figure 21D:
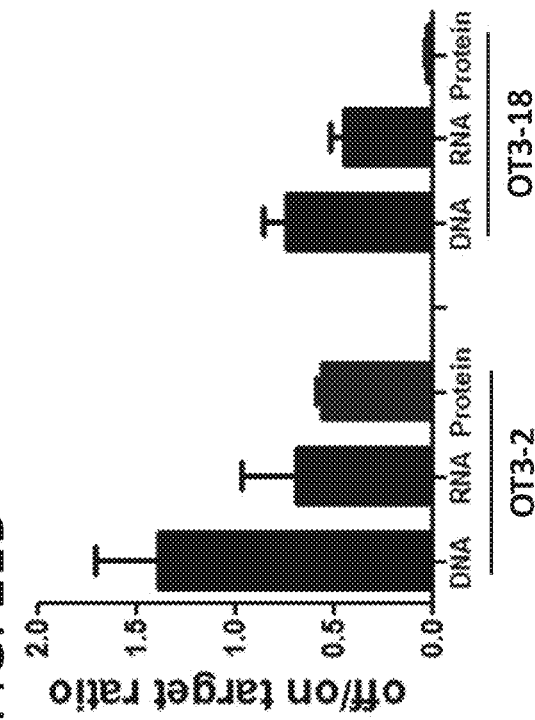
Figure 21C:
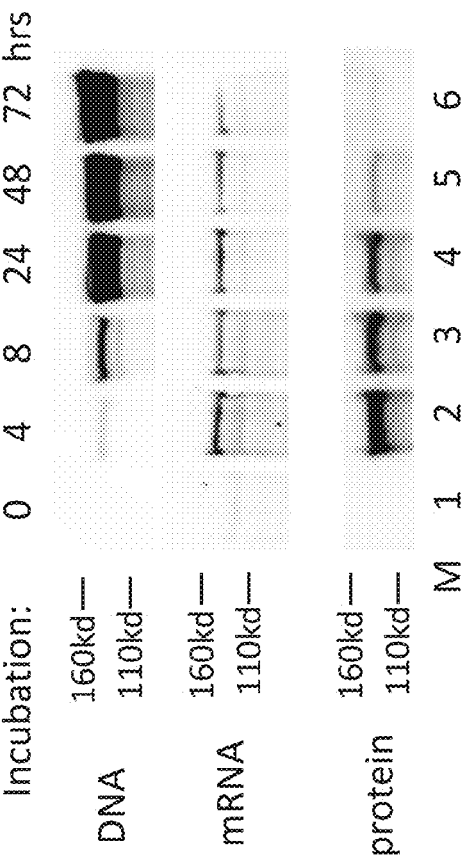

Because of the difference in protein appearance and apparent turnover rates, it was hypothesized that the off-target cleavage activity for Cas9 RNP transfection would be lower than that of plasmid DNA transfection. This was tested by targeting a locus in the VEGFA gene which has been identified as having several high activity off-target sites (Tsai et al., "GUIDE-seq enables genome-wide profiling of off-target cleavage by CRISPR-Cas nucleases," Nat Biotechnol. doi:10.1038/nbt.3117 (2014)) via DNA, mRNA, and Cas9 RNP protein transfection followed by genome cleavage and locus sequencing analysis. Among the six potential off-target sites that have been studied previously (OT3-1, OT3-2, OT3-4, OT3-9, OT3-17 and OT3-18), only OT3-2 and OT3-18 were detected to harbor off-target mutation based on genome cleavage analysis. Further analysis of locus OT3-2 by sequencing indicated that the ratio of indel mutation of OT3-2 over on target in mRNA and Cas9 RNP transfected cells was 2 fold and 2.5 fold lower than that in DNA-transfected cells, respectively. The ratio of indel mutation of OT3-18 over on on-target was 1.6 fold and 28 fold lower in mRNA or Cas9 RNP-transfected cells respectively than in DNA-transfected cells (FIG. 21D). The on-target editing efficiency increased with an increased dose of Cas9 RNP, reaching plateau at around 2 µg of Cas9 protein, while the off-target modification at the loci examined remained low and constant (data not shown). Taken together, these data suggest that Cas9 delivery as mRNA and pre-complexed protein supports increased genomic cleavage specificity compared with standard DNA plasmid transfection.

Electroporation-Mediated Cas9 Protein Transfection

Figure 22A:
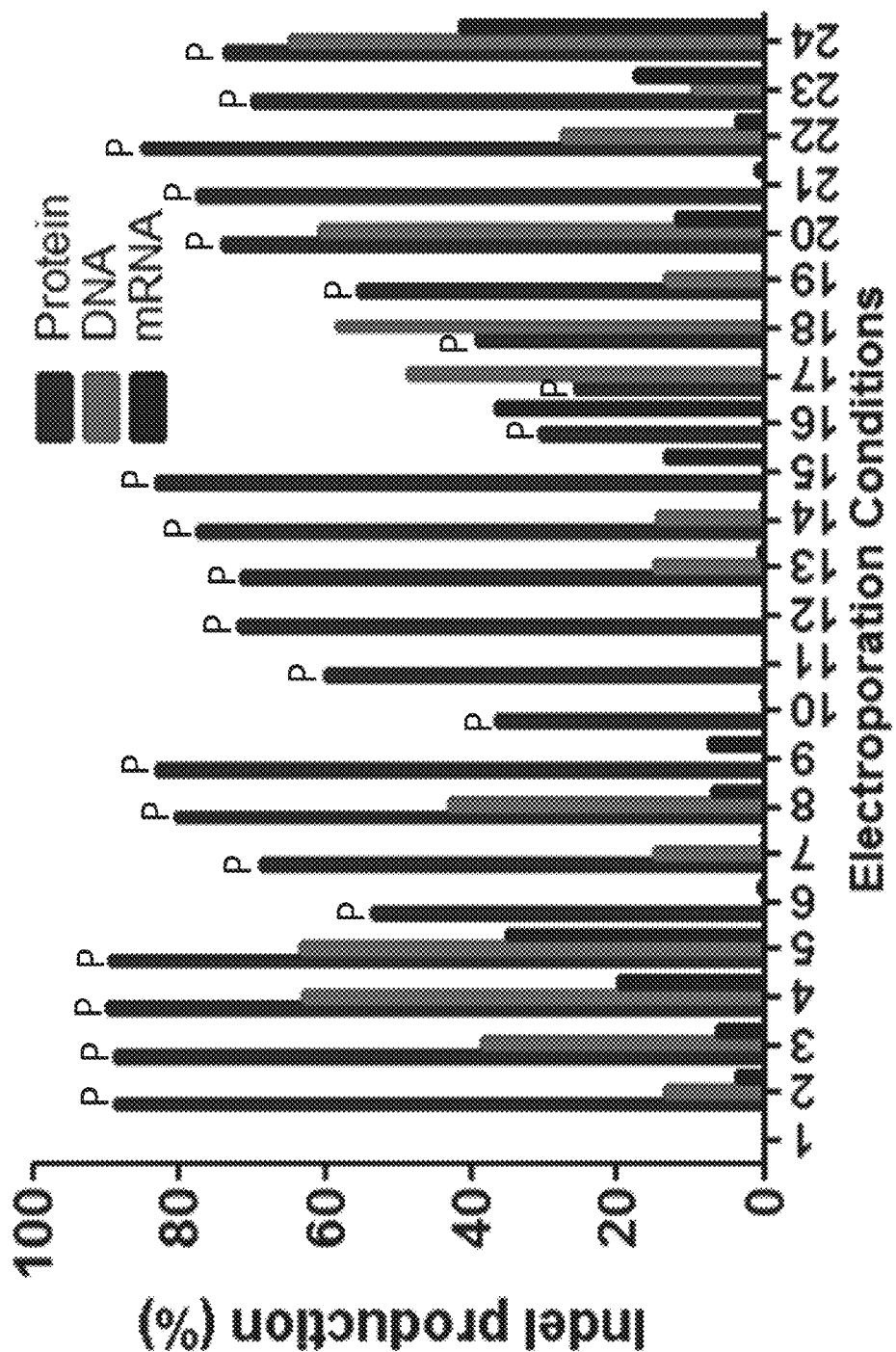
FIGS. 22A-22B. Electroporation-mediated transfection.
Figure 22B:
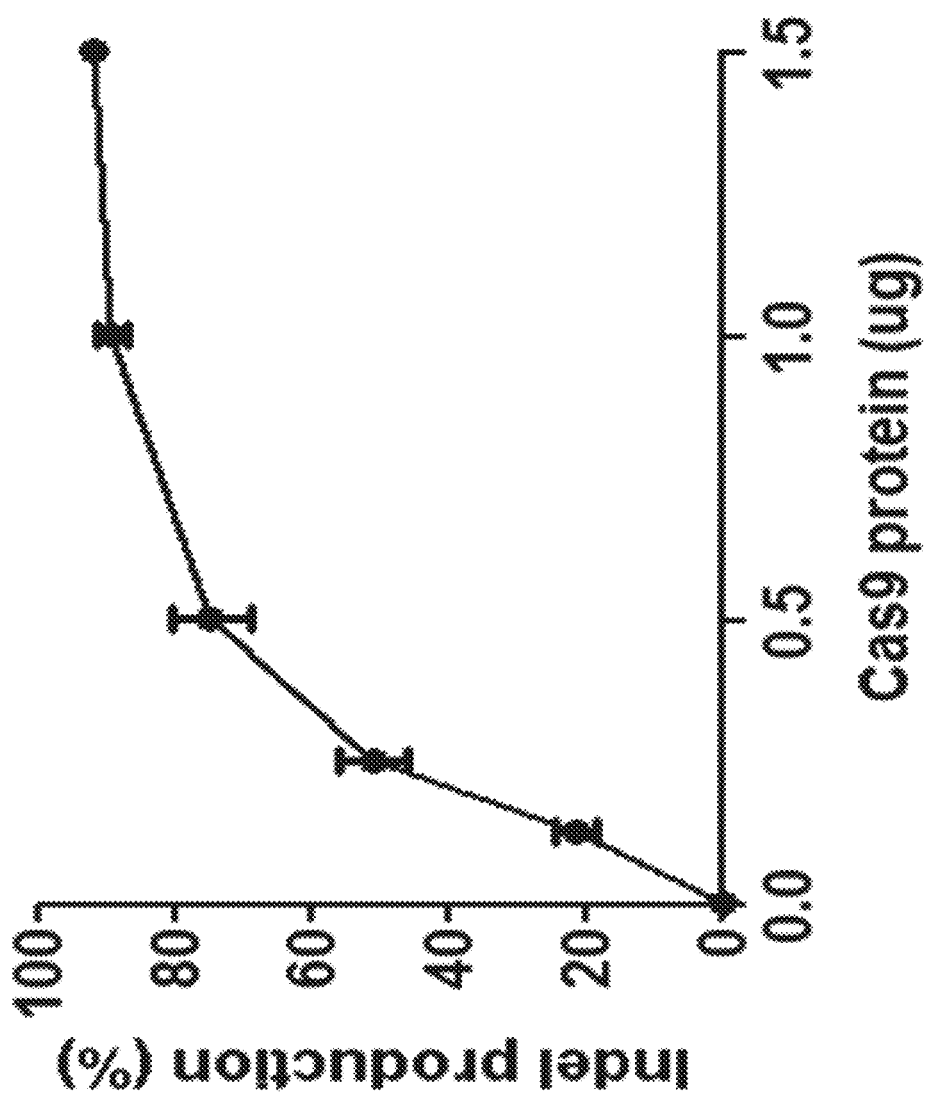
Figure 23A:
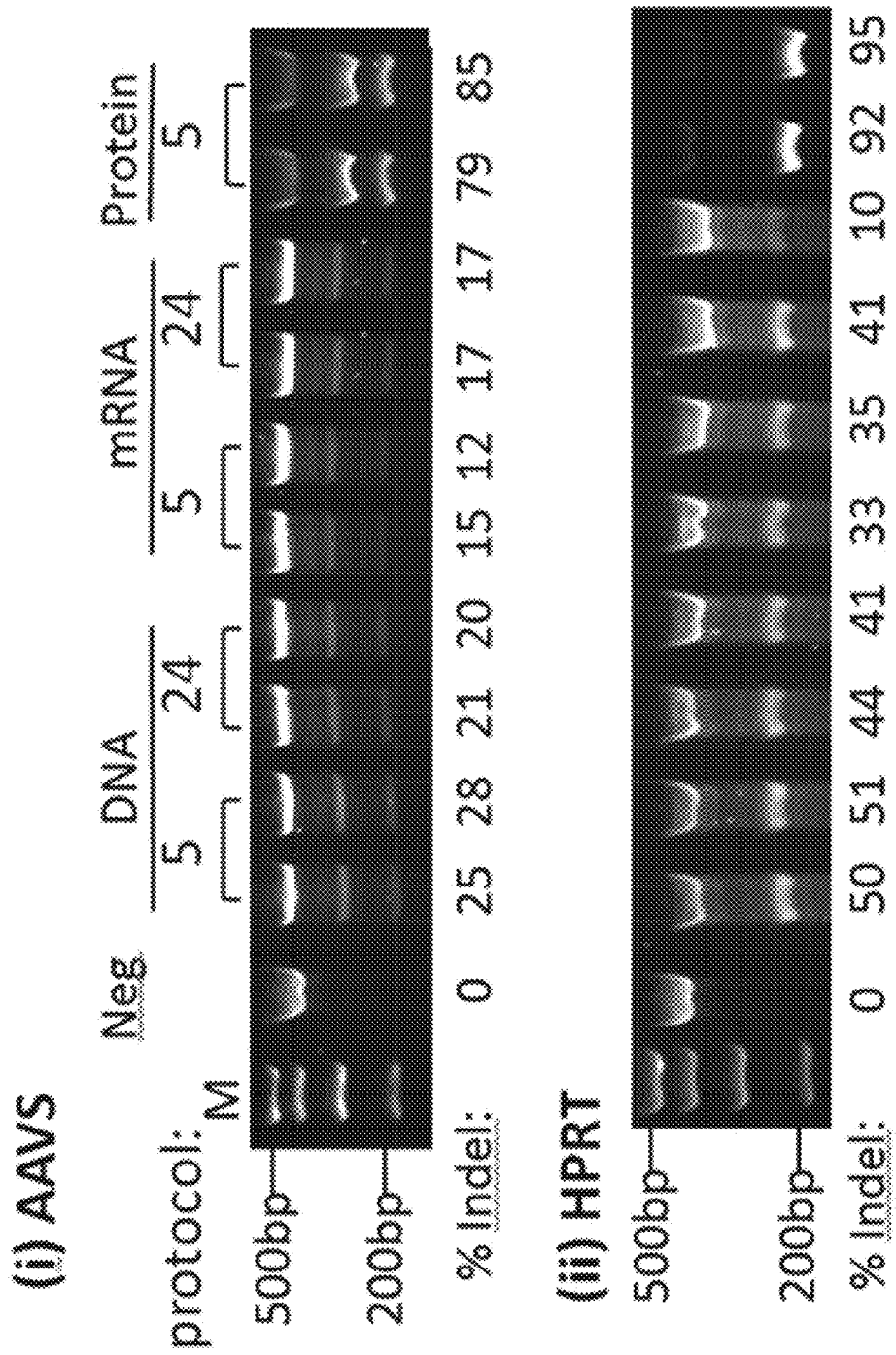
FIGS. 23A-23D. Multiple gene editing in the human genome. Jurkat T cells were cotransfected with either a Cas9 plasmid pool, a Cas9 mRNA/gRNA pool or Cas9 RNP complexes targeting AAVS1 and HPRT targets (FIG. 23A) or AAVS, RelA and HPRT gene targets (FIG. 23C). Genomic cleavage assays were performed for each locus at 48 hours post transfection. Cell aliquots were then subjected to clonal isolation by serial dilution. After clonal expansion, each locus was PCR-amplified from each clonal cell line. The PCR product was then cloned into a plasmid vector and the percentage of indel mutation was determined by sequencing of eight individual E. coli colonies. Quantitation of double mutants for AAVS1 and HPRT was based on 16 clonal cell lines (FIG. 23B: Efficiency of double mutant production), whereas quantitation of triple mutants of AAVS, RelA and HPRT was based on a total of 53 clonal cell lines derived from three independent experiments (FIG. 23D: Efficiency of triple mutant production).
Figure 23B:
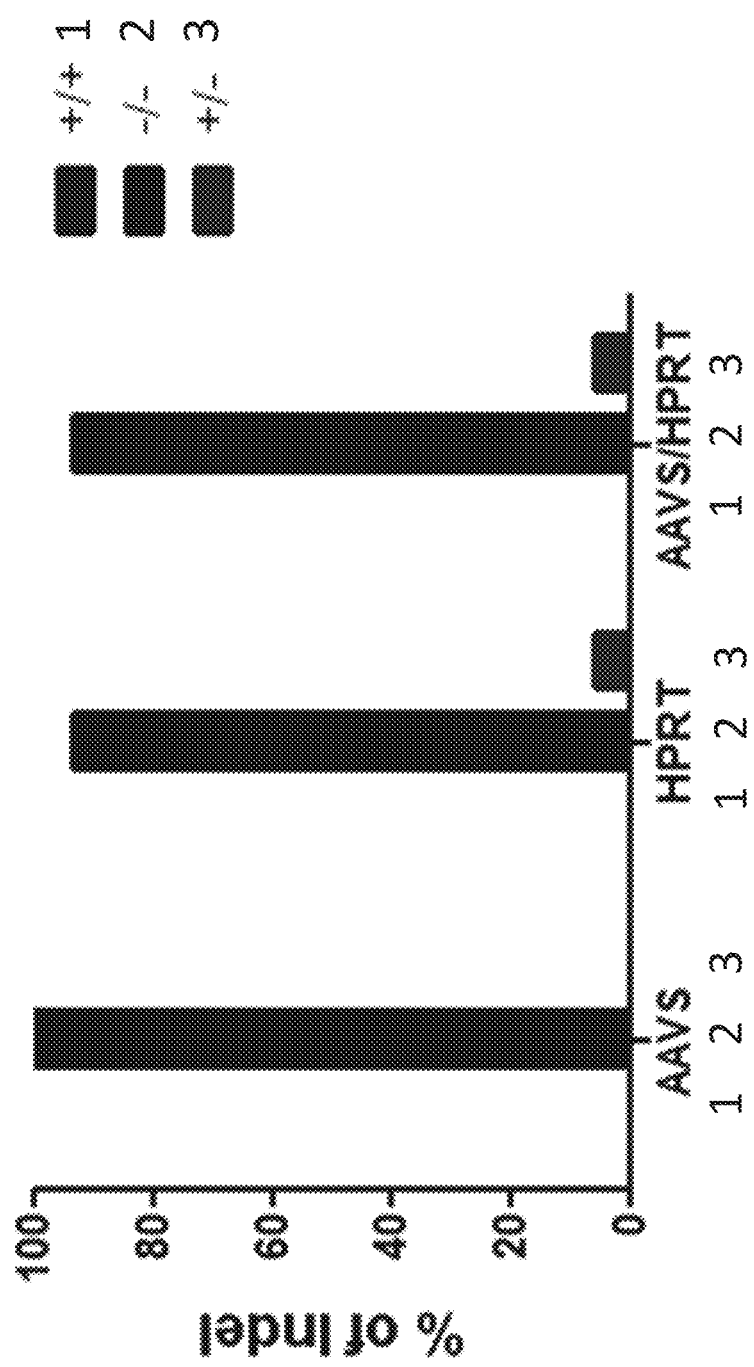
Figure 23C:
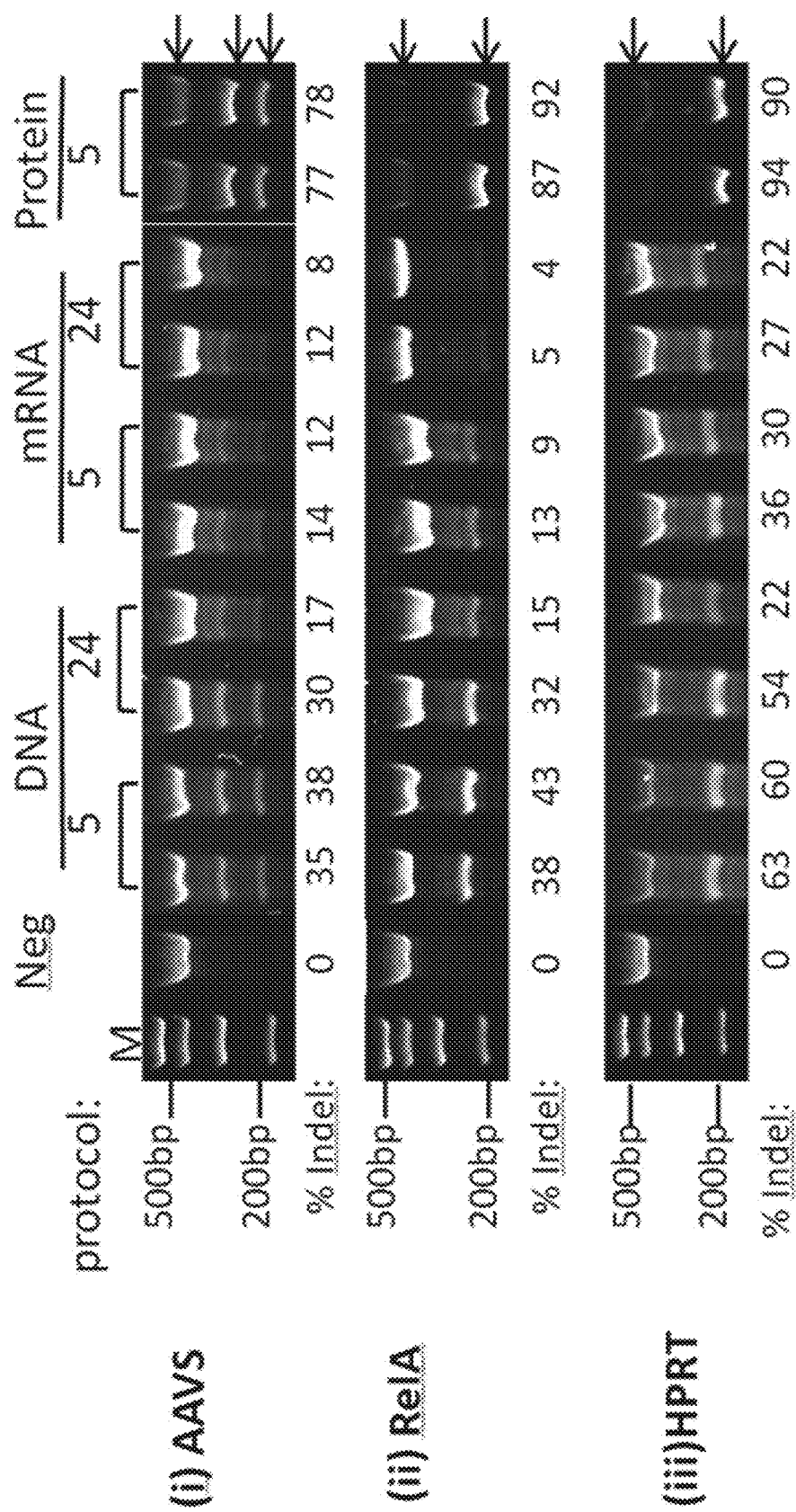
Figure 23D:
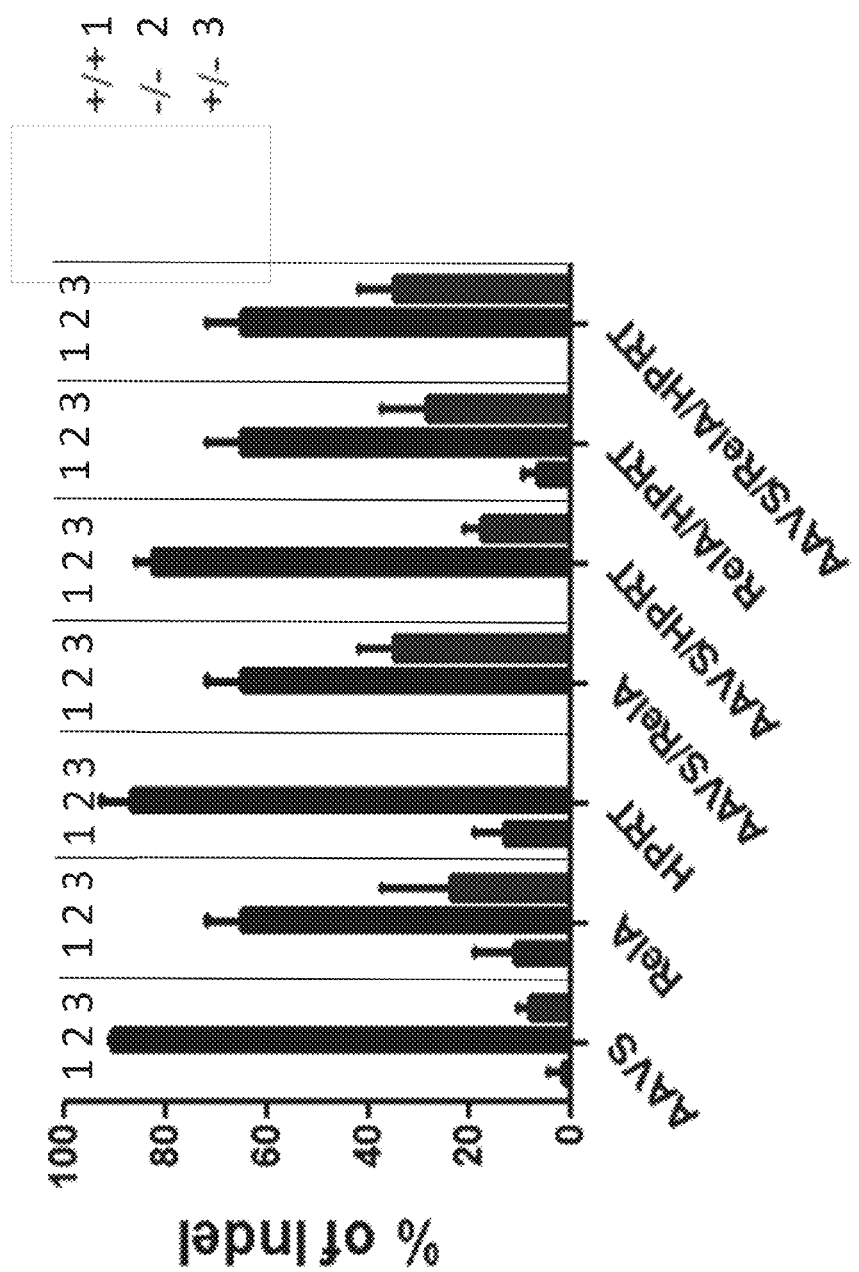

Many biologically and physiologically relevant cell lines, such as patient derived iPSC and progenitor cells, are refractory to efficient transfection by lipid-based reagents. Any improvement in the efficiency of genome modulation would facilitate isolation of appropriately engineered cells for experimentation and therapy so alternate means of delivering Cas9 RNPs and Cas9 mRNA/gRNA formulations and their effect on indel generation were explored. Using Jurkat T cells as an initial model, the delivery of Cas9 and gRNA plasmid DNA, Cas9 mRNA/gRNA formulations and Cas9 RNPs were compared using microporation (described in Materials and Methods, data not shown). Our results showed that, compared with plasmid DNA and mRNA deliveries, superior genome editing efficiency was achieved via delivery of Cas9 RNPs with approximately 90% HPRT locus-specific modification under several electroporation conditions (FIG. 22A). In general, Cas9 RNP delivery was more robust than DNA or mRNA delivery over most of the electroporation conditions tested. The cleavage efficiency was dose-dependent, reaching a maximum at approximately 1.5 µg Cas9 protein and 300 ng gRNA (~1:1 molar ratio) per transfection. After sequencing the cell pools it was found that 94% of target loci harbored mutations at a cleavage site located at 3 bases upstream of NGG PAM sequence (Supplementary sequencing data). In agreement with previous work, the majority of mutations were distinct from each other with 73% insertion, 18% deletion and 3% base substitution. Given the high single-locus cleavage efficiency measured with the Cas9 RNP system, the ability to efficiently lesion multiple genes in a single transfection was testes. Here the capability of multiplexing Cas9 RNP transfection at three loci (AAVS1, RelA and HPRT) were examined. After pooling and delivering multiple species of Cas9 RNP (differing only by gRNA target), it was found that the efficiency of simultaneous editing of AAVS1/HPRT or AAVS1/RelA/HPRT loci was significantly greater at all loci compared with either plasmid or mRNA delivery of Cas9 (FIGS. 23A and 23C). To gain insight into the molecular level of multiplexing, one round of clonal isolation by serial dilution was performed. After clonal expansion each of the loci was PCR amplified, followed by DNA cloning and sequencing. In the case of two gene editing, it was found that all of 16 isolated clonal cell lines harbored bi-allelic indel mutations on single AAVS1 loci and 93.7% (15 of 16) of clonal cells harbored one allelic indel mutation at the HPRT locus as the HPRT target was located on the X chromosome of a male Jurkat T cell line. Overall, 93.7% of the clonal cell populations carried indel mutations on both the AAVS1 and HPRT loci (FIG. 23B). For multiplexing of three genes, three individual cell transfections and clonal isolation were performed with a total of 53 single cell lines analyzed. In this experiment, 90% and 65% of the clonal cell lines analyzed harbored bi-allelic indel mutations at the AAVS1 and RelA loci respectively, whereas 80% of the clonal cells carried indel mutations at the HPRT locus. Approximately 65% of the clonal cells carried bi-allelic indel mutations on both AAVS1 and RelA loci, whereas 80% and 65% of the clonal cells harbored indel mutations on AAVS1/HPRT loci and RelA/HPRT loci respectively. Overall, 65% of the clonal cell lines harbored indel mutations on all three targets (FIG. 23D). Further, 100% of the Jurkat T cell clones were edited at least once, suggesting that the transfection efficiency reached nearly 100%. Taken together, Cas9 RNP delivery via electroporation under the conditions used here achieved exceptionally high mutagenesis frequencies. This represents a substantial improvement in Cas9-mediated genome editing and significantly reduces the workload needed for clonal isolation by substantially reducing the number of cells that must be screened in order to identify and isolate the desired cell line.

DISCUSSION

The ability to easily modulate the sequence specificity of the Cas9 nuclease by simply changing the 20 nucleotide targeting sequence of the gRNA offers significant versatility in delivery options over other nucleases that have been utilized for genome editing, such as zinc finger nucleases and TAL effectors. Now, researchers are able to choose from cost-effective and rapid design options by formulating the nuclease as either plasmid DNA, pre-made mRNA or purified protein. The design versatility is enabled by rapid production of the guide RNA component. Until recently, the gRNA was generally produced via cloning of a template sequence into a plasmid vector or vectors and expressing the Cas9 and gRNA in vivo. Described here is a streamlined protocol where gRNA design and template construction is facilitated by synthesis of two short single stranded oligonucleotides. The oligonucleotides are incorporated into gRNA templates via a short PCR reaction followed by conversion to gRNA by in vitro transcription. Target-specific oligos can be designed, ordered, and converted to purified gRNA in as little as two days. On the second day, the gRNA is formulated with either Cas9 mRNA or protein, and immediately used to transfect cells. The entire process consists completely of liquid handling and enzymatic reaction steps, which make it amenable to higher throughput gRNA production and transfection in multi-well plates.

The streamlined gRNA workflow was compared across the three delivery options and found that in general, Cas9/gRNA ribonucleoprotein complexes (Cas9 RNPs) offered superior indel production efficiency in most of the cell lines was used as a test bed. It is currently not clear why Cas9 RNP and total RNA formulations perform as they do but a factor could be overall size of the lipid complexes, the ability of Cas9 protein to protect the gRNA from cellular degradation, and the elimination of DNA-based cellular toxicity. In relation to plasmid delivery, Cas9 introduced as a Cas9 RNP or mRNA appears in the cell at low but evidently functional levels and is cleared rapidly which could also reduce the opportunity for off-target binding and cleavage. The data presented above suggests that this could be the case but a significantly more detailed evaluation is needed for confirmation.

Much progress has been made to reduce or eliminate off-target cleavage in CRISPR systems, such as use of paired Cas9 nickases and dimeric 'dead Cas9' FokI fusions, which has been shown to reduce off-target activity by 50- to 1,500-fold (Tsai et al., "GUIDE-seq enables genome-wide profiling of off-target cleavage by CRISPR-Cas nucleases," Nat Biotechnol. doi:10.1038/nbt.3117 (2014); Fu et al., "High frequency off-target mutagenesis induced by CRISPR-Cas nucleases in human cells," Nat. Biotechnol. 31:822-826 (2013)). Perhaps delivery of these tools via Cas9 RNPs would lead to even higher specificity while retaining high activity levels.

In this work, it was shown that it is possible to multiplex three Cas9 RNP species targeting separate loci in Jurkat T cells while achieving high levels indel production at all three loci. Further, it was observed high rates of biallelic modification at two diploid alleles (AAVS1 and RelA) in these experiments even when also modifying a haploid locus (HPRT) at similarly high levels. Taken together, the high rates of biallelic modification in cell populations suggest that employing Cas9 RNP delivery would significantly simplify the workflow by facilitating the selection of multigene knockout cell lines from a single experiment.

A survey was performed of eleven commonly used mammalian cell lines comparing CRISPR delivery via plasmid, Cas9 mRNA/gRNA, and Cas9 RNP (Table 11.) and found that Cas9 mRNA/gRNA or Cas9 RNPs were superior to plasmid delivery in all cell lines tested. Delivery of these reagents via microporation offered the highest target-specific indel production under the conditions tested. In all but one case (NHEK cells), Cas9 RNP out performed Cas9 mRNA/gRNA and in human CD34+ cord blood cells, Cas9 RNP delivered via microporation was the only method that yielded a significantly robust editing solution.

TABLE 11

Transfection efficiency in variety of cell lines

| Cell lines | DNA | | RNA | | Protein | |
|---|---|---|---|---|---|---|
|  | Lipid | Elect. | Lipid | Elect. | Lipid | Elect. |
| 293FT | 49.4 | 48.7 | 70 | 40.3 | 51.4 | 88 |
| U2OS | 15.0 | 50.3 | 21.4 | 23.6 # | 18.4 | 69.5 |
| Mouse ESCs | 30 | 45 | 45 | 20 | 25 | 70 |
| Human ESCs (H9) | 0 | 8 | 20 | 50 | 0 | 64 |
| Human iPSCs | 0 | 20 | 66 | 31.6 | 0 | 87* |
| N2A | 65.8 | 75.7 | 65.6 | 80.2 | 66.3 | 82.3 |
| Jurkat | 0 | 63 | 0 | 42 | 0 | 94* |
| K562 | 0 | 45 | 0 | 27 | 0 | 72 |
| A549 | 15.0 | 44.3 | 23.1 | 28.7 | 19.7 | 65.5 |
| Human keratin. (NHEK) | 0 | 30 | 0 | 50 | 0 | 35 |
| Human Cord blood cells CD34+ | n/a | 5 | n/a | 0 | n/a | 24 |

Notes:
1) HPRT for human cell lines and Rosa 26 for mouse cell lines
2) *confirmed by sequencing
3) # Cleavage efficiency could be increased to 68% when Lipid was added into reaction before electroporation.

Described here is a streamlined approach to the mammalian genome engineering workflow that takes as few three days to modify mammalian genomes from CRISPR target design to evaluation of genome editing. To achieve a high mutagenesis efficiency in hard-to-transfect cells, a systematic approach was used to optimize transfection conditions and compare delivery of CRISPR editing tools via plasmid DNA, Cas9 mRNA/purified guide RNA (gRNA) formulations, and pre-complexed Cas9 protein and gRNA ribonucleoproteins (Cas9 RNPs). It was found Cas9 mRNA/gRNA and Cas9 RNP performance superior to 'all-in-one' plasmid DNA constructs in the variety of cell lines analyzed in this work. Most likely due to the high efficiency of Cas9 RNP delivery, it was possible to efficiently modify the genome at multiple loci simultaneously, thereby reducing the workload for downstream clonal isolation in schemes where more than one gene knock-out is desired. Further, it was found that delivery of Cas9 RNPs to cell lines considered hard to transfect (Jurkat, iPSC, CD4+) via electroporation yielded high levels of locus specific modification.

TABLE 12

Structure of Donor DNA Molecules

| Oligo | Sequence | SEQ ID |
|---|---|---|
| BT1/ T8 | OOCTGGCCCACCCTCGTGACCAC<u>CTTCACCT</u>FOG | 38 |
| | GEEACCGGGTGGGAGCACTGGT<u>GAAGTGGA</u>TEO | 39 |
| 3OT1/ T8 | OOCTGGCCCACCCTCGTGACCAC<u>CTTCACC</u>TACGGCGZEC | 40 |
| | GEECACGGGACCGGGTGGGAGCACTGGTGG<u>AAGTGGA</u>TEO | 41 |
| 5OT1/ T8 | OOCGTGCCCTGGCCCACCCTCGTGACCACC<u>TTCACCT</u>FOG | 42 |
| | GEEACCGGGTGGGAGCACTGGTGG<u>AAGTGGA</u>TGCCGCAOE | 43 |
| 3O/ T8 | OZT<u>CACCT</u>ACGGCGZEC | 44 |
| | CFOTGGTGG<u>AAGTGGA</u>TEO | 45 |
| 5O/ T8 | EZGACCACCTT<u>CACCT</u>FOG | 46 |
| | GFF<u>GTGGA</u>TGCCGCAOE | 47 |
| BT2/ T8 | OFCCGGCAAGCTGCCCGTGCCCTGGCCCACCCTCGTGACCACCTT<u>CACCT</u>FOG | 48 |
| | GZEGCCGTTCGACGGGCACGGGACCGGGTGGGAGCACTGGTGGA<u>AGTGGA</u>TEO | 49 |
| 3OT/ T8 | OFCCGGCAAGCTGCCCGTGCCCTGGCCCACCCTCGTGACCACCTT<u>CACCT</u>ACGGCGZEC | 50 |
| | GFOGTGGTGGCCGTTCGACGGGCACGGGACCGGGTGGGAGCACTGGTGG<u>AAGTGGA</u>TEO | 51 |

TABLE 12-continued

Structure of Donor DNA Molecules

| Oligo | Sequence | SEQ ID |
|---|---|---|
| 5OT2/ T8 | OZGCACCACCGGCAAGCTGCCCGTGCCCTGGCCCACCCTCGTGACCACCTT<u>CACCT</u>FOG | 52 |
| | GZEGCCGTTCGACGGGCACGGGACCGGGTGGGAGCACTGGTGGA<u>AGTGGA</u>TGCCGCAOE | 53 |
| SS | P-OFTCTGCACCACCGGCAAGCTGCCCGTGCCCTGGCCCACCCTCGTGACCACCTT<u>CACCT</u>ACGGCGTGCAGTGCTTCGCCGCTACCCCGACCACFZG | 54 |
| DS DNA | ATGGTGAGCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATGCCACCTACGGCAAGCTGACCCTGAAGTTCATCTGCACCACCGGCAAGCTGCCCGTGCCCTGGCCCACCCTCGTGACCACCTTCACCTACGGCGTGCAGTGCTTCGCCCGCTACCCCGACCACATGAAGCAGCAGGACTTCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCCTGGTGAACCGCATCGAGCTGAAGGGCATCGACTTCAAGGAGG | 55 |

Legend:
F = Phosphorothioate-A, O = Phosphorothioate-C,
E = Phosphorothioate-G, Z = Phosphorothioate-T
Regions of sequence homology are underlined While the foregoing embodiments have been described in some detail for purposes of clarity and understanding, it will be clear to one skilled in the art from a reading of this disclosure that various changes in form and detail can be made without departing from the true scope of the embodiments disclosed herein. For example, all the techniques, apparatuses, systems and methods described above can be used in various combinations.

What is claimed is:

1. A method for producing a nucleic acid molecule, the method comprising performing polymerase chain reaction (PCR) in a reaction mixture comprising:
   (i) a double stranded nucleic acid segment comprising a first terminus and a second terminus,
   (ii) a first oligonucleotide comprising a first terminus and a second terminus, wherein the second terminus of the first oligonucleotide is capable of hybridizing to the first terminus of the double stranded nucleic acid segment, and
   (iii) a second oligonucleotide comprising a first terminus and a second terminus,
   wherein the second terminus of the second oligonucleotide is capable of hybridizing to the first terminus of the first oligonucleotide, to produce the nucleic acid molecule, wherein the product nucleic acid molecule contains a promoter suitable for in vitro transcription at or near one terminus and encodes a CRISPR RNA, and wherein the reaction mixture further comprises a first primer and a second primer, wherein the first primer is capable of hybridizing at or near the first terminus of the second oligonucleotide and the second primer is capable of hybridizing at or near the second terminus of the double stranded nucleic acid segment.

2. The method of claim 1, wherein the CRISPR RNA is a guide RNA.

3. The method of claim 2, wherein the nucleic acid molecule produced by the PCR reaction is from 70 to 150 base pairs in length.

4. The method of claim 1, wherein the CRISPR RNA is from 35 to 150 nucleotides in length.

5. The method of claim 1, wherein the CRISPR RNA has at least two hairpin turns.

6. The method of claim 1, wherein the CRISPR RNA is a crRNA.

7. The method of claim 1, wherein the CRISPR RNA is a tracrRNA.

8. The method of claim 1, wherein the promoter is a T7, T3 or SP6 promoter.

9. The method of claim 1, wherein the first oligonucleotide or the second oligonucleotide is between 35 and 40 nucleotides in length.

* * * * *

SEQUENCE LISTING

<160> NUMBER OF SEQ ID NOS: 65

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

-continued

```
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
            165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560
```

-continued

Val Lys Gln Leu Lys Glu Asp Tyr Phe Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
Thr Thr Gln Lys Gly Gln Lys Asn Ser Arg Glu Arg Met Lys Arg Ile
    770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
        835                 840                 845
Asp Asp Ser Ile Asp Asn Lys Val Leu Thr Arg Ser Asp Lys Asn Arg
    850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val 980             985             990
Val Gly Thr Ala Leu Ile Lys Lys Tyr Pro Lys Leu Glu Ser Glu Phe
            995             1000            1005
Val Tyr Gly Asp Tyr Lys Val Tyr Asp Val Arg Lys Met Ile Ala
    1010            1015            1020
Lys Ser Glu Gln Glu Ile Gly Lys Ala Thr Ala Lys Tyr Phe Phe
    1025            1030            1035
Tyr Ser Asn Ile Met Asn Phe Phe Lys Thr Glu Ile Thr Leu Ala
    1040            1045            1050
Asn Gly Glu Ile Arg Lys Arg Pro Leu Ile Glu Thr Asn Gly Glu
    1055            1060            1065
Thr Gly Glu Ile Val Trp Asp Lys Gly Arg Asp Phe Ala Thr Val
    1070            1075            1080
Arg Lys Val Leu Ser Met Pro Gln Val Asn Ile Val Lys Lys Thr
    1085            1090            1095
Glu Val Gln Thr Gly Gly Phe Ser Lys Glu Ser Ile Leu Pro Lys
    1100            1105            1110
Arg Asn Ser Asp Lys Leu Ile Ala Arg Lys Lys Asp Trp Asp Pro
    1115            1120            1125
Lys Lys Tyr Gly Gly Phe Asp Ser Pro Thr Val Ala Tyr Ser Val
    1130            1135            1140
Leu Val Val Ala Lys Val Glu Lys Gly Lys Ser Lys Lys Leu Lys
    1145            1150            1155
Ser Val Lys Glu Leu Leu Gly Ile Thr Ile Met Glu Arg Ser Ser
    1160            1165            1170
Phe Glu Lys Asn Pro Ile Asp Phe Leu Glu Ala Lys Gly Tyr Lys
    1175            1180            1185
Glu Val Lys Lys Asp Leu Ile Ile Lys Leu Pro Lys Tyr Ser Leu
    1190            1195            1200
Phe Glu Leu Glu Asn Gly Arg Lys Arg Met Leu Ala Ser Ala Gly
    1205            1210            1215
Glu Leu Gln Lys Gly Asn Glu Leu Ala Leu Pro Ser Lys Tyr Val
    1220            1225            1230
Asn Phe Leu Tyr Leu Ala Ser His Tyr Glu Lys Leu Lys Gly Ser
    1235            1240            1245
Pro Glu Asp Asn Glu Gln Lys Gln Leu Phe Val Glu Gln His Lys
    1250            1255            1260
His Tyr Leu Asp Glu Ile Ile Glu Gln Ile Ser Glu Phe Ser Lys
    1265            1270            1275
Arg Val Ile Leu Ala Asp Ala Asn Leu Asp Lys Val Leu Ser Ala
    1280            1285            1290
Tyr Asn Lys His Arg Asp Lys Pro Ile Arg Glu Gln Ala Glu Asn
    1295            1300            1305
Ile Ile His Leu Phe Thr Leu Thr Asn Leu Gly Ala Pro Ala Ala
    1310            1315            1320
Phe Lys Tyr Phe Asp Thr Thr Ile Asp Arg Lys Arg Tyr Thr Ser
    1325            1330            1335
Thr Lys Glu Val Leu Asp Ala Thr Leu Ile His Gln Ser Ile Thr
    1340            1345            1350
Gly Leu Tyr Glu Thr Arg Ile Asp Leu Ser Gln Leu Gly Gly Asp
    1355            1360            1365

<210> SEQ ID NO 2

```
<211> LENGTH: 13
<212> TYPE: PRT
<213> ORGANISM: Streptococcus sp.

<400> SEQUENCE: 2

Tyr Ser Ile Gly Leu Asp Ile Gly Thr Asn Ser Val Gly
1               5                   10

<210> SEQ ID NO 3
<211> LENGTH: 7
<212> TYPE: PRT
<213> ORGANISM: Streptococcus sp.

<400> SEQUENCE: 3

Pro Thr Ile Tyr His Leu Arg
1               5

<210> SEQ ID NO 4
<211> LENGTH: 7
<212> TYPE: PRT
<213> ORGANISM: Streptococcus sp.

<400> SEQUENCE: 4

Arg Gly His Phe Leu Ile Glu
1               5

<210> SEQ ID NO 5
<211> LENGTH: 9
<212> TYPE: PRT
<213> ORGANISM: Streptococcus sp.

<400> SEQUENCE: 5

Thr Lys Ala Pro Leu Ser Ala Ser Met
1               5

<210> SEQ ID NO 6
<211> LENGTH: 10
<212> TYPE: PRT
<213> ORGANISM: Streptococcus sp.

<400> SEQUENCE: 6

Leu Arg Lys Gln Arg Thr Phe Asp Asn Gly
1               5                   10

<210> SEQ ID NO 7
<211> LENGTH: 14
<212> TYPE: PRT
<213> ORGANISM: Streptococcus sp.

<400> SEQUENCE: 7

Leu Thr Phe Arg Ile Pro Tyr Tyr Val Gly Pro Leu Ala Arg
1               5                   10

<210> SEQ ID NO 8
<211> LENGTH: 11
<212> TYPE: PRT
<213> ORGANISM: Streptococcus sp.

<400> SEQUENCE: 8

Thr Leu Thr Leu Phe Glu Asp Arg Glu Met Ile
1               5                   10

<210> SEQ ID NO 9
<211> LENGTH: 12
<212> TYPE: PRT
```

<213> ORGANISM: Streptococcus sp.

<400> SEQUENCE: 9

Ala Gly Ser Pro Ala Ile Lys Lys Gly Ile Leu Gln
1               5                   10

<210> SEQ ID NO 10
<211> LENGTH: 14
<212> TYPE: PRT
<213> ORGANISM: Streptococcus sp.

<400> SEQUENCE: 10

Arg Gln Leu Val Glu Thr Arg Gln Ile Thr Lys His Val Ala
1               5                   10

<210> SEQ ID NO 11
<211> LENGTH: 11
<212> TYPE: PRT
<213> ORGANISM: Streptococcus sp.

<400> SEQUENCE: 11

Gln Thr Gly Gly Phe Ser Lys Glu Ser Ile Leu
1               5                   10

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gaaattaata cgactcacta tag                                              23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gttttagagc tagaaatagc aag                                              23

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaaagcaccg actcggtgcc ac                                               22

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
taatacgact cactatagg					19

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gttttagagc taga					14

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
catttctcag tcctaaaca					19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
taatacgact cactataggg					20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccagtagcca gccccgtcc					19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tcgtgtccct gtacgcgga					19

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
taatacgact cactataggg gcatttctca gtcctaaaca					40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gctatttcta gctctaaaac tgtttaggac tgagaaatgc                          40

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gttttagagc tagaaatagc aagttaaaat aaggctagtc cgttatcaac ttgaaaaagt    60

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aaaagcaccg actcggtgcc acttttcaa gttgataacg gactagcctt attttaactt     60

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gctatttcta gctctaaaac tgtttaggac tgagaaatg                           39

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttctagctct aaaactgttt aggactgaga aatg                                34

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
taatacgact cactataggc atttctcagt cctaaacag                           39

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
taatacgact cactataggc atttctcagt ccta                                 34

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aaagcaccga ctcggtgcca c                                               21

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aagcaccgac tcggtgccac                                                 20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
agcaccgact cggtgccac                                                  19

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcaccgactc ggtgccac                                                   18

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
taatacgact cactataggg ccagtagcca gcccc                                35

```
<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
taatacgact cactataggc cagtagccag cccc                                 34

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
taatacgact cactataggc agtagccagc ccc                                  33

<210> SEQ ID NO 36
<211> LENGTH: 9823
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (7336)..(7355)
<223> OTHER INFORMATION: a, c, t, g, unknown or other

<400> SEQUENCE: 36
gttaggcgtt ttgcgctgct tcgcgatgta cgggccagat atacgcgttg acattgatta    60
ttgactagtt attaatagta atcaattacg gggtcattag ttcatagccc atatatggag   120
ttccgcgtta cataacttac ggtaaatggc ccgcctggct gaccgcccaa cgacccccgc   180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgccccctat tgacgtcaat gacggtaaat ggcccgcctg gcattatgcc   360
cagtacatga ccttatggga ctttcctact tggcagtaca tctacgtatt agtcatcgct   420
attaccatgg tgatgcggtt ttggcagtac atcaatgggc gtggatagcg gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgttt tgacctccat agaagacacc gggaccgatc cagcctccgg   720
agcggccgcc accatgggca agcccatccc taacccctg ttggggctgg acagcaccgc   780
tcccaaaaag aaaggaagg tgggcattca cggcgtgcct gcggccgaca aaagtacag   840 catcggcctt gatatcggca ccaatagcgt gggctgggcc gttatcacag acgaatacaa   900
ggtacccagc aagaagttca aggtgctggg gaatacagac aggcactcta tcaagaaaaa   960
ccttatcggg gctctgctgt ttgactcagg cgagaccgcc gaggccacca ggttgaagag  1020
gaccgcaagg cgaaggtaca cccggaggaa gaacaggatc tgctatctgc aggagatctt  1080
cagcaacgag atggccaagg tggacgcaag cttcttccac aggctggagg agagcttcct  1140
tgtcgaggag gataagaagc acgaacgaca ccccatcttc ggcaacatag tcgacgaggt  1200
```

```
cgcttatcac gagaagtacc ccaccatcta ccacctgcga aagaaattgg tggatagcac    1260
cgataaagcc gacttgcgac ttatctactt ggctctggcg cacatgatta agttcagggg    1320
ccacttcctg atcgagggcg accttaaccc cgacaacagt gacgtagaca aattgttcat    1380
ccagcttgta cagacctata accagctgtt cgaggaaaac cctattaacg ccagcggggt    1440
ggatgcgaag gccatactta gcgccaggct gagcaaaagc aggcgcttgg agaacctgat    1500
agcccagctg cccggtgaaa agaagaacgg cctcttcggt aatctgattg ccctgagcct    1560
gggcctgacc cccaacttca gagcaacttc gacctggca gaagatgcca agctgcagtt    1620
gagtaaggac acctatgacg acgacttgga caatctgctc gcccaaatcg gcgaccagta    1680
cgctgacctg ttcctcgccg ccaagaacct ttctgacgca atcctgctta gcgatatcct    1740
tagggtgaac acagagatca ccaaggcccc cctgagcgcc agcatgatca agaggtacga    1800
cgagcaccat caggacctga cccttctgaa ggccctggtg aggcagcaac tgcccgagaa    1860
gtacaaggag atcttttttcg accagagcaa gaacggctac gccggctaca tcgacggcgg    1920
agccagccaa gaggagttct acaagttcat caagcccatc ctggagaaga tggatggcac    1980
cgaggagctg ctggtgaagc tgaacaggga agatttgctc cggaagcaga ggacctttga    2040
caacggtagc atcccccacc agatccacct gggcgagctg cacgcaatac tgaggcgaca    2100
ggaggatttc tacccttcc tcaaggacaa taggagaaa atcgaaaaga ttctgacctt    2160
caggatcccc tactacgtgg gccctcttgc caggggcaac agccgattcg cttggatgac    2220
aagaaagagc gaggagacca tcacccctg gaacttcgag gaagtggtgg acaaaggagc    2280
aagcgcgcag tctttcatcg aacggatgac caatttcgac aaaaacctgc taacgagaa    2340 ggtgctgccc aagcacagcc tgctttacga gtacttcacc gtgtacaacg agctcaccaa    2400
ggtgaaatat gtgaccgagg gcatgcgaaa acccgctttc ctgagcggcg agcagaagaa    2460
ggccatcgtg gacctgctgt tcaagaccaa caggaaggtg accgtgaagc agctgaagga    2520
ggactacttc aagaagatcg agtgctttga tagcgtggaa ataagcggcg tggaggacag    2580
gttcaacgcc agcctgggca cctaccacga cttgttgaag ataatcaaag acaaggattt    2640
cctggataat gaggagaacg aggatatact cgaggacatc gtgctgactt tgaccctgtt    2700
tgaggaccga gagatgattg aagaaaggct caaaacctac gcccacctgt tcgacgacaa    2760
agtgatgaaa caactgaaga acgaagata caccggctgg ggcagactgt ccaggaagct    2820
catcaacggc attagggaca agcagagcgg caagaccatc ctggatttcc tgaagtccga    2880
cggcttcgcc aaccgaaact tcatgcagct gattcacgat gacagcttga ccttcaagga    2940
ggacatccag aaggcccagg ttagcggcca gggcgactcc ctgcacgaac atattgcaaa    3000
cctggcaggc tcccctgcga tcaagaaggg catactgcag accgttaagg ttgtggacga    3060
attggtcaag gtcatgggca ggcacaagcc cgaaaacata gttatagaga tggccagaga    3120
gaaccagacc acccaaaagg ccagaagaa cagccgggag cgcatgaaaa ggatcgagga    3180
gggtatcaag gaactcggaa gccagatcct caaagagcac cccgtggaga tacccagct    3240 ccagaacgag aagctgtacc tgtactacct gcagaacggc agggacatgt acgttgacca    3300
ggagttggac atcaacaggc tttcagacta tgacgtggat cacatagtgc cccagagctt    3360
tcttaaagac gatagcatcg acaacaaggt cctgacccgc tccgacaaaa cagggcaa    3420 aagcgacaac gtgccaagcg aagaggtggt taaaaagatg aagaactact ggaggcaact    3480
gctcaacgcg aaattgatca cccagagaaa gttcgataac ctgaccaagg ccgagagggg    3540
```

```
cggactctcc gaacttgaca aagcgggctt cataaagagg cagctggtcg agacccgaca    3600
gatcacgaag cacgtggccc aaatcctcga cagcagaatg aataccaagt acgatgagaa    3660
tgacaaactc atcagggaag tgaaagtgat taccctgaag agcaagttgg tgtccgactt    3720
tcgcaaagat ttccagttct acaaggtgag ggagatcaac aactaccacc atgcccacga    3780
cgcatacctg aacgccgtgg tcggcaccgc cctgattaag aagtatccaa agctggagtc    3840
cgaatttgtc tacggcgact acaaagttta cgatgtgagg aagatgatcg ctaagagcga    3900
acaggagatc ggcaaggcca ccgctaagta tttcttctac agcaacatca tgaactttttt   3960 caagaccgag atcacacttg ccaacggcga aatcaggaag aggccgctta tcgagaccaa    4020
cggtgagacc ggcgagatcg tgtgggacaa gggcagggac ttcgccaccg tgaggaaagt    4080
cctgagcatg ccccaggtga atattgtgaa aaaaactgag gtgcagacag gcggctttag    4140
caaggaatcc atcctgccca gaggaacag cgacaagctg atcgcccgga agaaggactg    4200
ggaccctaag aagtatggag gcttcgacag ccccaccgta gcctacagcg tgctggtggt    4260
cgcgaaggta gagaagggga agagcaagaa actgaagagc gtgaaggagc tgctcggcat    4320
aaccatcatg gagaggtcca gctttgagaa gaaccccatt gactttttgg aagccaaggg    4380
ctacaaagag gtcaaaaagg acctgatcat caaactcccc aagtactccc tgtttgaatt    4440
ggagaacggc agaaagagga tgctggcgag cgctggggaa ctgcaaaagg gcaacgaact    4500
ggcgctgccc agcaagtacg tgaattttct gtacctggcg tcccactacg aaaagctgaa    4560
aggcagcccc gaggacaacg agcagaagca gctgttcgtg gagcagcaca agcattacct    4620
ggacgagata atcgagcaaa tcagcgagtt cagcaagagg gtgattctgg ccgacgcgaa    4680
cctggataag gtcctcagcg cctacaacaa gcaccgagac aaacccatca gggagcaggc    4740
cgagaatatc atacacctgt tcaccctgac aaatctgggc gcacctgcgg cattcaaata    4800
cttcgatacc accatcgaca ggaaaaggta cactagcact aaggaggtgc tggatgccac    4860
cttgatccac cagtccatta ccggcctgta tgagaccagg atcgacctga gccagcttgg    4920
aggcgactct agggcggacc caaaaaagaa aaggaaggtg gaattctcta gaggcagtgg    4980
agagggcaga ggaagtctgc taacatgcgg tgacgtcgag gagaatcctg gcccaatgaa    5040 ccgggggagtc ccttttaggc acttgcttct ggtgctgcaa ctggcgctcc tcccagcagc    5100
cactcaggga aagaaagtgg tgctgggcaa aaaaggggat acagtggaac tgacctgtac    5160
agcttcccag aagaagagca tacaattcca ctggaaaaac tccaaccaga taaagattct    5220
gggaaatcag ggctccttct taactaaagg tccatccaag ctgaatgatc gcgctgactc    5280
aagaagaagc ctttgggacc aaggaaactt ccccctgatc atcaagaatc ttaagataga    5340
agactcagat acttacatct gtgaagtgga ggaccagaag gaggaggtgc aattgctagt    5400
gttcggattg actgccaact ctgacaccca cctgcttcag gggcagagcc tgaccctgac    5460
cttggagagc ccccctggta gtagcccctc agtgcaatgt aggagtccaa ggggtaaaaa    5520
catacagggg gggaagaccc tctccgtgtc tcagctggag ctccaggata gtggcacctg    5580
gacatgcact gtcttgcaga accagaagaa ggtggagttc aaaatagaca tcgtggtgct    5640
agctttccag aaggcctcca gcatagtcta taagaaagag ggggaacagg tggagttctc    5700
cttcccactc gcctttacag ttgaaaagct gacgggcagt ggcgagctgt ggtggcaggc    5760
ggagagggct tcctcctcca gtcttggat caccttgac ctgaagaaca aggaagtgtc    5820
tgtaaaacgg gttacccagg accctaagct ccagatgggg aagaagctcc cgctccacct    5880
caccctgccc caggccttgc ctcagtatgc tggctctgga aacctcaccc tggcccttga    5940
```

```
agcgaaaaca ggaaagttgc atcaggaagt gaacctggtg gtgatgagag ccactcagct    6000
ccagaaaaat ttgacctgtg aggtgtgggg acccacctcc cctaagctga tgctgagctt    6060
gaaactggag aacaaggagg caaaggtctc gaagcgggag aaggcggtgt gggtgctgaa    6120
ccctgaggcg gggatgtggc agtgtctgct gagtgactcg ggacaggtcc tgctggaatc    6180
caacatcaag gttctgccca catggtcgac cccggtgcag ccaatggccc tgattgtgct    6240 gggggggcgtc gccggcctcc tgcttttcat tgggctaggc atcttcttct gtgtcaggtg    6300
ccggcacacc ggttagtaat gagtttaaac gggggaggct aactgaaaca cggaaggaga    6360
caataccgga aggaacccgc gctatgacgg caataaaaag acagaataaa acgcacgggt    6420
gttgggtcgt ttgttcataa acgcggggtt cggtcccagg gctggcactc tgtcgatacc    6480
ccaccgagac cccattgggg ccaatacgcc cgcgtttctt cctttteece accccacccc    6540 ccaagttcgg gtgaaggccc agggctcgca gccaacgtcg gggcggcagg ccctgccata    6600
gcagatctgc gcagctgggg ctctagggggg tatcccccacg cgccctgtag cggcgcatta    6660
agcgcggcgg gtgtggtggt tacgcgcagc gtgaccgcta cacttgccag cgccctagcg    6720
cccgctcctt tcgctttctt cccttccttt ctcgccacgt tcgccggctt tccccgtcaa    6780
gctctaaatc gggggctccc tttagggttc cgatttagtg ctttacggca cctcgacccc    6840
aaaaaacttg attagggtga tggttcacgt agtgggccat cgccctgata dacggttttt    6900
cgccctttga cgttggagtc cacgttcttt aatagtggac tcttgttcca aactggaaca    6960
acactcaacc ctatctcggt ctattctttt gatttataag gattttgcc gatttcggcc    7020 tattggttaa aaaatgagct gatttaacaa aaatttaacg cgaattaatt aaggtcgggc    7080
aggaagaggg cctatttccc atgattcctt catatttgca tatacgatac aaggctgtta    7140
gagagataat tagaattaat ttgactgtaa acacaaagat attagtacaa aatacgtgac    7200
gtagaaagta ataatttctt gggtagtttg cagttttaaa attatgtttt aaaatggact    7260
atcatatgct taccgtaact tgaaagtatt tcgatttctt ggctttatat atcttgtgga    7320
aaggacgaaa caccgnnnnn nnnnnnnnnn nnnnngtttt agagctagaa atagcaagtt    7380
aaaataaggc tagtccgtta tcaacttgaa aaagtggcac cgagtcggtg cttttttcta    7440
gtataccgtc gacctctagc tagagcttgg cgtaatcatg gtcatagctg tttcctgtgt    7500
gaaattgtta tccgctcaca attccacaca acatacgagc cggaagcata agtgtaaag    7560 cctggggtgc ctaatgagtg agctaactca cattaattgc gttgcgctca ctgcccgctt    7620
tccagtcggg aaacctgtcg tgccagctgc attaatgaat cggccaacgc gcggggagag    7680
gcggtttgcg tattgggcgc tcttccgctt cctcgctcac tgactcgctg cgctcggtcg    7740
ttcggctgcg gcgagcggta tcagctcact caaaggcggt aatacggtta tccacagaat    7800
caggggataa cgcaggaaag aacatgtgag caaaaggcca gcaaaggcc aggaaccgta    7860 aaaaggccgc gttgctggcg tttttccata ggctccgccc ccctgacgag catcacaaaa    7920
atcgacgctc aagtcagagg tggcgaaacc cgacaggact ataaagatac caggcgtttc    7980
cccctggaag ctccctcgtg cgctctcctg ttccgaccct gccgcttacc ggatacctgt    8040
ccgcctttct cccttcggga agcgtggcgc tttctcatag ctcacgctgt aggtatctca    8100
gttcggtgta ggtcgttcgc tccaagctgg gctgtgtgca cgaaccccc gttcagcccg    8160 accgctgcgc cttatccggt aactatcgtc ttgagtccaa cccggtaaga cacgacttat    8220
cgccactggc agcagccact ggtaacagga ttagcagagc gaggtatgta ggcggtgcta    8280
```

| | |
|---|---:|
| cagagttctt gaagtggtgg cctaactacg gctacactag aagaacagta tttggtatct | 8340 |
| gcgctctgct gaagccagtt accttcggaa aaagagttgg tagctcttga tccggcaaac | 8400 |
| aaaccaccgc tggtagcggt ggttttttg tttgcaagca gcagattacg cgcagaaaaa | 8460 |
| aaggatctca agaagatcct ttgatctttt ctacggggtc tgacgctcag tggaacgaaa | 8520 |
| actcacgtta agggattttg gtcatgagat tatcaaaaag gatcttcacc tagatccttt | 8580 |
| taaattaaaa atgaagtttt aaatcaatct aaagtatata tgagtaaact tggtctgaca | 8640 |
| gttaccaatg cttaatcagt gaggcaccta tctcagcgat ctgtctattt cgttcatcca | 8700 |
| tagttgcctg actccccgtc gtgtagataa ctacgatacg ggagggctta ccatctggcc | 8760 |
| ccagtgctgc aatgataccg cgagacccac gctcaccggc tccagattta tcagcaataa | 8820 |
| accagccagc cggaagggcc gagcgcagaa gtggtcctgc aactttatcc gcctccatcc | 8880 |
| agtctattaa ttgttgccgg gaagctagag taagtagttc gccagttaat agtttgcgca | 8940 |
| acgttgttgc cattgctaca ggcatcgtgg tgtcacgctc gtcgtttggt atggcttcat | 9000 |
| tcagctccgg ttcccaacga tcaaggcgag ttacatgatc ccccatgttg tgcaaaaaag | 9060 |
| cggttagctc cttcggtcct ccgatcgttg tcagaagtaa gttggccgca gtgttatcac | 9120 |
| tcatggttat ggcagcactg cataattctc ttactgtcat gccatccgta agatgctttt | 9180 |
| ctgtgactgg tgagtactca accaagtcat tctgagaata gtgtatgcgg cgaccgagtt | 9240 |
| gctcttgccc ggcgtcaata cgggataata ccgcgccaca tagcagaact ttaaaagtgc | 9300 |
| tcatcattgg aaaacgttct cggggcgaa aactctcaag gatcttaccg ctgttgagat | 9360 |
| ccagttcgat gtaacccact cgtgcaccca actgatcttc agcatctttt actttcacca | 9420 |
| gcgtttctgg gtgagcaaaa acaggaaggc aaaatgccgc aaaaaaggga ataagggcga | 9480 |
| cacggaaatg ttgaatactc atactcttcc tttttcaata ttattgaagc atttatcagg | 9540 |
| gttattgtct catgagcgga tacatatttg aatgtattta gaaaaataaa caaataggg | 9600 |
| ttccgcgcac atttccccga aaagtgccac ctgacgtcga cggatcggga gatccccga | 9660 |
| tcccctatgg tgcactctca gtacaatctg ctctgatgcc gcatagttaa gccagtatct | 9720 |
| gctcccgct tgtgtgttgg aggtcgctga gtagtgcgcg agcaaaattt aagctacaac | 9780 |
| aaggcaaggc ttgaccgaca attgcatgaa gaatctgctt agg | 9823 |

<210> SEQ ID NO 37
<211> LENGTH: 9220
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (6733)..(6752)
<223> OTHER INFORMATION: a, c, t, g, unknown or other

<400> SEQUENCE: 37

| | |
|---|---:|
| gttaggcgtt ttgcgctgct tcgcgatgta cgggccagat atacgcgttg acattgatta | 60 |
| ttgactagtt attaatagta atcaattacg gggtcattag ttcatagccc atatatggag | 120 |
| ttccgcgtta cataacttac ggtaaatggc ccgcctggct gaccgcccaa cgacccccgc | 180 |
| ccattgacgt caataatgac gtatgttccc atagtaacgc caatagggac tttccattga | 240 |
| cgtcaatggg tggagtattt acggtaaact gcccacttgg cagtacatca agtgtatcat | 300 |
| atgccaagta cgccccctat tgacgtcaat gacggtaaat ggcccgcctg gcattatgcc | 360 |

| | |
|---|---|
| cagtacatga ccttatggga ctttcctact tggcagtaca tctacgtatt agtcatcgct | 420 |
| attaccatgg tgatgcggtt ttggcagtac atcaatgggc gtggatacg gtttgactca | 480 |
| cggggatttc caagtctcca ccccattgac gtcaatggga gtttgttttg gcaccaaaat | 540 |
| caacgggact ttccaaaatg tcgtaacaac tccgccccat tgacgcaaat gggcggtagg | 600 |
| cgtgtacggt gggaggtcta tataagcaga gctcgtttag tgaaccgtca gatcgcctgg | 660 |
| agacgccatc cacgctgttt tgacctccat agaagacacc gggaccgatc cagcctccgg | 720 |
| agcggccgcc accatgggca agcccatccc taacccctg ttggggctgg acagcaccgc | 780 |
| tcccaaaaag aaaaggaagg tgggcattca cggcgtgcct gcggccgaca aaaagtacag | 840 |
| catcggcctt gatatcggca ccaatagcgt gggctgggcc gttatcacag acgaatacaa | 900 |
| ggtacccagc aagaagttca aggtgctggg aatacagac aggcactcta tcaagaaaaa | 960 |
| ccttatcggg gctctgctgt ttgactcagg cgagaccgcc gaggccacca ggttgaagag | 1020 |
| gaccgcaagg cgaaggtaca cccggaggaa gaacaggatc tgctatctgc aggagatctt | 1080 |
| cagcaacgag atggccaagg tggacgacag cttcttccac aggctggagg agagcttcct | 1140 |
| tgtcgaggag gataagaagc acgaacgaca ccccatcttc ggcaacatag tcgacgaggt | 1200 |
| cgcttatcac gagaagtacc ccaccatcta ccacctgcga aagaaattgg tggatagcac | 1260 |
| cgataaagcc gacttgcgac ttatctactt ggctctggcg cacatgatta agttcagggg | 1320 |
| ccacttcctg atcgagggcg accttaaccc cgacaacagt gacgtagaca aattgttcat | 1380 |
| ccagcttgta cagacctata accagctgtt cgaggaaaac cctattaacg ccagcggggt | 1440 |
| ggatgcgaag gccatactta gcgccaggct gagcaaaagc aggcgcttgg agaacctgat | 1500 |
| agcccagctg cccggtgaaa agaagaacgg cctcttcggt aatctgattg ccctgagcct | 1560 |
| gggcctgacc cccaacttca gagcaacttc gacctggca gaagatgcca agctgcagtt | 1620 |
| gagtaaggac acctatgacg acgacttgga caatctgctc gcccaaatcg gcgaccagta | 1680 |
| cgctgacctg ttcctcgccg ccaagaacct ttctgacgca atcctgctta gcgatatcct | 1740 |
| tagggtgaac acagagatca ccaaggcccc cctgagcgcc agcatgatca agaggtacga | 1800 |
| cgagcaccat caggacctga cccttctgaa ggccctggtg aggcagcaac tgcccgagaa | 1860 |
| gtacaaggag atcttttttcg accagagcaa gaacggctac gccggctaca tcgacggcgg | 1920 |
| agccagccaa gaggagttct acaagttcat caagcccatc ctggagaaga tggatggcac | 1980 |
| cgaggagctg ctggtgaagc tgaacaggga agatttgctc cggaagcaga ggacctttga | 2040 |
| caacggtagc atccccacc agatccacct gggcgagctg cacgcaatac tgaggcgaca | 2100 |
| ggaggatttc taccccttcc tcaaggacaa tagggagaaa atcgaaaaga ttctgacctt | 2160 |
| caggatcccc tactacgtgg gccctcttgc caggggcaac agccgattcg cttggatgac | 2220 |
| aagaaagagc gaggagacca tcacccctg gaacttcgag gaagtggtgg acaaaggagc | 2280 |
| aagcgcgcag tctttcatcg aacggatgac caatttcgac aaaaacctgc ctaacgagaa | 2340 |
| ggtgctgccc aagcacagcc tgctttacga gtacttcacc gtgtacaacg agctcaccaa | 2400 |
| ggtgaaatat gtgaccgagg gcatgcgaaa accgctttc ctgagcggcg agcagaagaa | 2460 |
| ggccatcgtg gacctgctgt tcaagaccaa caggaaggtg accgtgaagc agctgaagga | 2520 |
| ggactacttc aagaagatcg agtgctttga tagcgtggaa ataagcggcg tggaggacag | 2580 |
| gttcaacgcc agcctgggca cctaccacga cttgttgaag ataatcaaag acaaggattt | 2640 |
| cctggataat gaggagaacg aggatatact cgaggacatc gtgctgactt tgaccctgtt | 2700 |
| tgaggaccga gagatgattg aagaaaggct caaaacctac gcccacctgt tcgacgacaa | 2760 |

```
agtgatgaaa caactgaaga gacgaagata caccggctgg ggcagactgt ccaggaagct    2820
catcaacggc attagggaca agcagagcgg caagaccatc ctggatttcc tgaagtccga    2880
cggcttcgcc aaccgaaact tcatgcagct gattcacgat gacagcttga ccttcaagga    2940
ggacatccag aaggcccagg ttagcggcca gggcgactcc ctgcacgaac atattgcaaa    3000
cctggcaggc tcccctgcga tcaagaaggg catactgcag accgttaagg ttgtggacga    3060
attggtcaag gtcatgggca ggcacaagcc cgaaaacata gttatagaga tggccagaga    3120
gaaccagacc acccaaaagg ccagaagaa cagccgggag cgcatgaaaa ggatcgagga    3180
gggtatcaag gaactcggaa gccagatcct caaagagcac cccgtggaga tacccagct    3240 ccagaacgag aagctgtacc tgtactacct gcagaacggc agggacatgt acgttgacca    3300
ggagttggac atcaacaggc tttcagacta tgacgtggat cacatagtgc cccgagctt    3360 tcttaaagac gatagcatcg acaacaaggt cctgacccgc tccgacaaaa acaggggcaa    3420
aagcgacaac gtgccaagcg aagaggtggt taaaaagatg aagaactact ggaggcaact    3480
gctcaacgcg aaattgatca cccagagaaa gttcgataac ctgaccaagg ccgagagggg    3540
cggactctcc gaacttgaca aagcgggctt cataaagagg cagctggtcg agacccgaca    3600
gatcacgaag cacgtggccc aaatcctcga cagcagaatg aataccaagt acgatgagaa    3660
tgacaaactc atcagggaag tgaaagtgat taccctgaag agcaagttgg tgtccgactt    3720
tcgcaaagat ttccagttct acaaggtgag ggagatcaac aactaccacc atgcccacga    3780
cgcatacctg aacgccgtgg tcggcaccgc cctgattaag aagtatccaa agctggagtc    3840
cgaatttgtc tacggcgact acaaagttta cgatgtgagg aagatgatcg ctaagagcga    3900
acaggagatc ggcaaggcca ccgctaagta tttcttctac agcaacatca tgaacttttt    3960
caagaccgag atcacacttg ccaacggcga aatcaggaag aggccgctta tcgagaccaa    4020
cggtgagacc ggcgagatcg tgtgggacaa gggcagggac ttcgccaccg tgaggaaagt    4080
cctgagcatg ccccaggtga atattgtgaa aaaaactgag gtgcagacag gcggctttag    4140
caaggaatcc atcctgccca gaggaacag cgacaagctg atcgcccgga agaaggactg    4200
ggaccctaag aagtatggag gcttcgacag ccccaccgta gcctcagcg tgctggtggt    4260 cgcgaaggta gagaaggga agagcaagaa actgaagagc gtgaaggagc tgctcggcat    4320
aaccatcatg gagaggtcca gctttgagaa gaaccccatt gactttttgg aagccaaggg    4380
ctacaaagag gtcaaaaagg acctgatcat caaactcccc aagtactccc tgtttgaatt    4440
ggagaacggc agaaagagga tgctggcgag cgctggggaa ctgcaaaagg caacgaact    4500 ggcgctgccc agcaagtacg tgaattttct gtacctggcg tcccactacg aaaagctgaa    4560
aggcagcccc gaggacaacg agcagaagca gctgttcgtg gagcagcaca gcattacct    4620 ggacgagata tcgagcaaa tcagcgagtt cagcaagagg gtgattctgg ccgacgcgaa    4680
cctggataag gtcctcagcg cctacaacaa gcaccgagac aaacccatca gggagcaggc    4740
cgagaatatc atacacctgt tcaccctgac aaatctgggc gcacctgcgg cattcaaata    4800
cttcgatacc accatcgaca ggaaaaggta cactagcact aaggaggtgc tggatgccac    4860
cttgatccac cagtccatta ccggcctgta tgagaccagg atcgacctga gccagcttgg    4920
aggcgactct agggcggacc caaaaaagaa aaggaaggtg gaattctcta gaggcagtgg    4980
agagggcaga ggaagtctgc taacatgcgg tgacgtcgag gagaatcctg gcccaatgaa    5040
cctgagcaaa aacgtgagcg tgagcgtgta tatgaagggg aacgtcaaca atcatgagtt    5100
```

```
tgagtacgac ggggaaggtg gtggtgatcc ttatacaggt aaatattcca tgaagatgac    5160
gctacgtggt caaaattccc tacccttttc ctatgatatc attaccacgg catttcagta    5220
tggtttccgc gtatttacaa atacccctga gggaattgtt gactatttta aggactcgct    5280
tcccgacgca ttccagtgga acagacgaat tgtgtttgaa gatggtggag tactaaacat    5340
gagcagtgat atcacatata aagataatgt tctgcatggt gacgtcaagg ctgagggagt    5400
gaacttcccg ccgaatgggc cagtgatgaa gaatgaaatt gtgatggagg aaccgactga    5460
agaaacattt actccaaaaa acggggttct tgttggcttt tgtcccaaag cgtacttact    5520
taaagacggt tcctattact atggaaatat gacaacattt tacagatcca agaaatctgg    5580
ccaggcacct cctgggtatc actttgttaa gcatcgtctc gtcaagacca atgtgggaca    5640
tggatttaag acggttgagc agactgaata tgccactgct catgtcagtg atcttcccaa    5700
gttcgaagct tgataatgag tttaaacggg ggaggctaac tgaaacacgg aaggagacaa    5760
taccggaagg aacccgcgct atgacggcaa taaaaagaca gaataaaacg cacgggtgtt    5820
gggtcgtttg ttcataaacg cggggttcgg tcccagggct ggcactctgt cgataccccca    5880
ccgagacccc attggggcca atacgcccgc gtttcttcct tttccccacc ccaccccccca    5940
agttcgggtg aaggcccagg ctcgcagcc aacgtcgggg cggcaggccc tgccatagca    6000
gatctgcgca gctggggctc taggggtat ccccacgcgc cctgtagcgg cgcattaagc    6060
gcggcgggtg tggtggttac gcgcagcgtg accgctacac ttgccagcgc cctagcgccc    6120
gctccttttcg ctttcttccc ttcctttctc gccacgttcg ccggctttcc ccgtcaagct    6180
ctaaatcggg ggctcccttt agggttccga tttagtgctt tacggcacct cgaccccaaa    6240
aaacttgatt agggtgatgg ttcacgtagt gggccatcgc cctgatagac ggttttttcgc    6300
cctttgacgt tggagtccac gttctttaat agtggactct tgttccaaac tggaacaaca    6360
ctcaacccta tctcggtcta ttcttttgat ttataaggga ttttgccgat ttcggcctat    6420
tggttaaaaa atgagctgat ttaacaaaaa tttaacgcga attaattaag gtcgggcagg    6480
aagagggcct atttcccatg attccttcat atttgcatat acgatacaag gctgttagag    6540
agataattag aattaatttg actgtaaaca caaagatatt agtacaaaat acgtgacgta    6600
gaaagtaata atttcttggg tagtttgcag ttttaaaatt atgttttaaa atggactatc    6660
atatgcttac cgtaacttga agtatttcg atttcttggc tttatatatc ttgtggaaag    6720
gacgaaacac cgnnnnnnnn nnnnnnnnnn nngttttaga gctagaaata gcaagttaaa    6780
ataaggctag tccgttatca acttgaaaaa gtggcaccga tcggtgcttt ttttctagta    6840
taccgtcgac ctctagctag agcttggcgt aatcatggtc atagctgttt cctgtgtgaa    6900
attgttatcc gctcacaatt ccacacaaca tacgagccgg aagcataaag tgtaaagcct    6960
ggggtgccta atgagtgagc taactcacat taattgcgtt gcgctcactg cccgctttcc    7020
agtcgggaaa cctgtcgtgc cagctgcatt aatgaatcgg ccaacgcgcg gggagaggcg    7080
gtttgcgtat tgggcgctct tccgcttcct cgctcactga ctcgctgcgc tcggtcgttc    7140
ggctgcggcg agcggtatca gctcactcaa aggcggtaat acggttatcc acagaatcag    7200
gggataacgc aggaaagaac atgtgagcaa aaggccagca aaaggccagg aaccgtaaaa    7260
aggccgcgtt gctggcgttt ttccataggc tccgcccccc tgacgagcat cacaaaaatc    7320
gacgctcaag tcagaggtgg cgaaacccga caggactata aagataccag gcgtttcccc    7380
ctggaagctc cctcgtgcgc tctcctgttc cgaccctgcc gcttaccgga tacctgtccg    7440
cctttctccc ttcgggaagc gtggcgcttt ctcatagctc acgctgtagg tatctcagtt    7500
```

```
cggtgtaggt cgttcgctcc aagctgggct gtgtgcacga accccccgtt cagcccgacc    7560
gctgcgcctt atccggtaac tatcgtcttg agtccaaccc ggtaagacac gacttatcgc    7620
cactggcagc agccactggt aacaggatta gcagagcgag gtatgtaggc ggtgctacag    7680
agttcttgaa gtggtggcct aactacggct acactagaag aacagtattt ggtatctgcg    7740
ctctgctgaa gccagttacc ttcggaaaaa gagttggtag ctcttgatcc ggcaaacaaa    7800
ccaccgctgg tagcggtggt ttttttgttt gcaagcagca gattacgcgc agaaaaaaag    7860
gatctcaaga agatcctttg atcttttcta cggggtctga cgctcagtgg aacgaaaact    7920
cacgttaagg gattttggtc atgagattat caaaaaggat cttcacctag atccttttaa    7980
attaaaaatg aagttttaaa tcaatctaaa gtatatatga gtaaacttgg tctgacagtt    8040
accaatgctt aatcagtgag gcacctatct cagcgatctg tctatttcgt tcatccatag    8100
ttgcctgact ccccgtcgtg tagataacta cgatacggga gggcttacca tctggcccca    8160
gtgctgcaat gataccgcga gacccacgct caccggctcc agatttatca gcaataaacc    8220
agccagccgg aagggccgag cgcagaagtg gtcctgcaac tttatccgcc tccatccagt    8280
ctattaattg ttgccgggaa gctagagtaa gtagttcgcc agttaatagt ttgcgcaacg    8340
ttgttgccat tgctacaggc atcgtggtgt cacgctcgtc gtttggtatg gcttcattca    8400
gctccggttc ccaacgatca aggcgagtta catgatcccc catgttgtgc aaaaaagcgg    8460
ttagctcctt cggtcctccg atcgttgtca gaagtaagtt ggccgcagtg ttatcactca    8520
tggttatggc agcactgcat aattctctta ctgtcatgcc atccgtaaga tgcttttctg    8580
tgactggtga gtactcaacc aagtcattct gagaatagtg tatgcggcga ccgagttgct    8640
cttgcccggc gtcaatacgg gataataccg cgccacatag cagaacttta aaagtgctca    8700
tcattggaaa acgttcttcg gggcgaaaac tctcaaggat cttaccgctg ttgagatcca    8760
gttcgatgta acccactcgt gcacccaact gatcttcagc atcttttact ttcaccagcg    8820
tttctgggtg agcaaaaaca ggaaggcaaa atgccgcaaa aagggaata agggcgacac    8880 ggaaatgttg aatactcata ctcttccttt tcaatatta ttgaagcatt tatcagggtt    8940
attgtctcat gagcggatac atatttgaat gtatttagaa aaataaacaa ataggggttc    9000
cgcgcacatt tccccgaaaa gtgccacctg acgtcgacgg atcgggagat ctcccgatcc    9060
cctatggtgc actctcagta caatctgctc tgatgccgca tagttaagcc agtatctgct    9120
ccctgcttgt gtgttggagg tcgctgagta gtgcgcgagc aaaatttaag ctacaacaag    9180
gcaaggcttg accgacaatt gcatgaagaa tctgcttagg                          9220
```

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 38
ccctggccca ccctcgtgac caccttcacc tacg                                 34

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
gggaccgggt gggagcactg gtggaagtgg atgc                                   34

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ccctggccca ccctcgtgac caccttcacc tacggcgtgc                             40

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gggcacggga ccgggtggga gcactggtgg aagtggatgc                             40

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cccgtgccct ggcccaccct cgtgaccacc ttcacctacg                             40

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gggaccgggt gggagcactg gtggaagtgg atgccgcacg                             40

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cttcacctac ggcgtgc                                                      17

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cactggtgga agtggatgc                                                19

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gtgaccacct tcacctacg                                                19

<210> SEQ ID NO 47
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gaagtggatg ccgcacg                                                  17

<210> SEQ ID NO 48
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
caccggcaag ctgcccgtgc cctggcccac cctcgtgacc accttcacct acg          53

<210> SEQ ID NO 49
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gtggccgttc gacgggcacg ggaccgggtg ggagcactgg tggaagtgga tgc          53

<210> SEQ ID NO 50
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
caccggcaag ctgcccgtgc cctggcccac cctcgtgacc accttcacct acggcgtgc    59

<210> SEQ ID NO 51
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 51
gacgtggtgg ccgttcgacg ggcacgggac cgggtgggag cactggtgga agtggatgc      59

<210> SEQ ID NO 52
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ctgcaccacc ggcaagctgc ccgtgccctg gcccaccctc gtgaccacct tcacctacg      59

<210> SEQ ID NO 53
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gtggccgttc gacgggcacg ggaccgggtg ggagcactgg tggaagtgga tgccgcacg      59

<210> SEQ ID NO 54
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
catctgcacc accggcaagc tgcccgtgcc ctggcccacc ctcgtgacca ccttcaccta      60
cggcgtgcag tgcttcgccc gctaccccga ccacatg                              97

<210> SEQ ID NO 55
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcaccta cggcgtgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg                           400

<210> SEQ ID NO 56
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 56
ccaguagcca gccccguccg uuuuagagcu augcuguuuu g                          41

<210> SEQ ID NO 57
<211> LENGTH: 85
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ggaaccauuc aaaacagcau agcaaguuaa aauaaggcua guccguuauc aacuugaaaa      60
agggcaccga gucggugcuu uuuuu                                            85

<210> SEQ ID NO 58
<211> LENGTH: 104
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 58
gcauuucggu augcauauga augaguuuua gagcuagaaa uagcaaguua aaauaaggcu      60
aguccguuau caacuugaaa aaguggcacc gagucggugc uuuu                      104

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ccatcatatg cataccgaaa tgc                                              23

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(21)
<223> OTHER INFORMATION: a, c, t, g, unknown or other

<400> SEQUENCE: 60
gcatttcggt atgcatatga ngg                                              23

<210> SEQ ID NO 61
<211> LENGTH: 1370
<212> TYPE: PRT
<213> ORGANISM: Streptococcus agalactiae

<400> SEQUENCE: 61

Met Asn Lys Pro Tyr Ser Ile Gly Leu Asp Ile Gly Thr Asn Ser Val
1               5                   10                  15

Gly Trp Ser Ile Ile Thr Asp Asp Tyr Lys Val Pro Ala Lys Lys Met
            20                  25                  30

Arg Val Leu Gly Asn Thr Asp Lys Glu Tyr Ile Lys Lys Asn Leu Ile
```

-continued

```
                35                  40                  45
Gly Ala Leu Leu Phe Asp Gly Asn Thr Ala Ala Asp Arg Arg Leu
            50                  55                  60
Lys Arg Thr Ala Arg Arg Tyr Thr Arg Arg Asn Arg Ile Leu
65                  70                  75                  80
Tyr Leu Gln Glu Ile Phe Ala Glu Glu Met Ser Lys Val Asp Asp Ser
                85                  90                  95
Phe Phe His Arg Leu Glu Asp Ser Phe Leu Val Glu Glu Asp Lys Arg
                100                 105                 110
Gly Ser Lys Tyr Pro Ile Phe Ala Thr Met Gln Glu Glu Lys Tyr Tyr
                115                 120                 125
His Glu Lys Phe Pro Thr Ile Tyr His Leu Arg Lys Glu Leu Ala Asp
                130                 135                 140
Lys Lys Glu Lys Ala Asp Leu Arg Leu Ile Tyr Leu Ala Leu Ala His
145                 150                 155                 160
Ile Ile Lys Phe Arg Gly His Phe Leu Ile Glu Asp Asp Arg Phe Asp
                165                 170                 175
Val Arg Asn Thr Asp Ile Gln Lys Gln Tyr Gln Ala Phe Leu Glu Ile
                180                 185                 190
Phe Asp Thr Thr Phe Glu Asn Asn Asp Leu Leu Ser Gln Asn Val Asp
                195                 200                 205
Val Glu Ala Ile Leu Thr Asp Lys Ile Ser Lys Ser Ala Lys Lys Asp
                210                 215                 220
Arg Ile Leu Ala Arg Tyr Pro Asn Gln Lys Ser Thr Gly Ile Phe Ala
225                 230                 235                 240
Glu Phe Leu Lys Leu Ile Val Gly Asn Gln Ala Asp Phe Lys Lys His
                245                 250                 255
Phe Asn Leu Glu Asp Lys Thr Pro Leu Gln Phe Ala Lys Asp Ser Tyr
                260                 265                 270
Asp Glu Asp Leu Glu Asn Leu Leu Gly Gln Ile Gly Asp Glu Phe Ala
                275                 280                 285
Asp Leu Phe Ser Ala Ala Lys Lys Leu Tyr Asp Ser Val Leu Leu Ser
                290                 295                 300
Gly Ile Leu Thr Val Thr Asp Leu Ser Thr Lys Ala Pro Leu Ser Ala
305                 310                 315                 320
Ser Met Ile Gln Arg Tyr Asp Glu His Arg Glu Asp Leu Lys Gln Leu
                325                 330                 335
Lys Gln Phe Val Lys Ala Ser Leu Pro Glu Lys Tyr Gln Glu Ile Phe
                340                 345                 350
Ala Asp Ser Ser Lys Asp Gly Tyr Ala Gly Tyr Ile Glu Gly Lys Thr
                355                 360                 365
Asn Gln Glu Ala Phe Tyr Lys Tyr Leu Ser Lys Leu Leu Thr Lys Gln
                370                 375                 380
Glu Gly Ser Glu Tyr Leu Leu Glu Lys Ile Lys Asn Glu Asp Phe Leu
385                 390                 395                 400
Arg Lys Gln Arg Thr Phe Asp Asn Gly Ser Ile Pro His Gln Val His
                405                 410                 415
Leu Thr Glu Leu Arg Ala Ile Ile Arg Arg Gln Ser Glu Tyr Tyr Pro
                420                 425                 430
Phe Leu Lys Glu Asn Leu Asp Arg Ile Glu Lys Ile Leu Thr Phe Arg
                435                 440                 445
Ile Pro Tyr Tyr Val Gly Pro Leu Ala Arg Glu Lys Ser Asp Phe Ala
450                 455                 460
```

```
Trp Met Thr Arg Lys Thr Asp Asp Ser Ile Arg Pro Trp Asn Phe Glu
465                 470                 475                 480

Asp Leu Val Asp Lys Glu Lys Ser Ala Glu Ala Phe Ile His Arg Met
            485                 490                 495

Thr Asn Asn Asp Leu Tyr Leu Pro Glu Glu Lys Val Leu Pro Lys His
        500                 505                 510

Ser Leu Ile Tyr Glu Lys Phe Thr Val Tyr Asn Glu Leu Thr Lys Val
    515                 520                 525

Arg Phe Leu Ala Glu Gly Phe Lys Asp Phe Gln Phe Leu Asn Arg Lys
530                 535                 540

Gln Lys Glu Thr Ile Phe Asn Ser Leu Phe Lys Glu Lys Arg Lys Val
545                 550                 555                 560

Thr Glu Lys Asp Ile Ile Ser Phe Leu Asn Lys Val Asp Gly Tyr Glu
            565                 570                 575

Gly Ile Ala Ile Lys Gly Ile Glu Lys Gln Phe Asn Ala Ser Leu Ser
        580                 585                 590

Thr Tyr His Asp Leu Lys Lys Ile Leu Gly Lys Asp Phe Leu Asp Asn
    595                 600                 605

Thr Asp Asn Glu Leu Ile Leu Glu Asp Ile Val Gln Thr Leu Thr Leu
610                 615                 620

Phe Glu Asp Arg Glu Met Ile Arg Lys Arg Leu Asp Ile Tyr Lys Asp
625                 630                 635                 640

Phe Phe Thr Glu Ser Gln Leu Lys Lys Leu Tyr Arg Arg His Tyr Thr
            645                 650                 655

Gly Trp Glu Arg Leu Ser Ala Lys Leu Ile Asn Gly Ile Arg Asn Lys
        660                 665                 670

Glu Asn Gln Lys Thr Ile Leu Asp Tyr Leu Ile Asp Asp Gly Ser Ala
    675                 680                 685

Asn Arg Asn Phe Met Gln Leu Ile Lys Asp Ala Gly Leu Ser Phe Lys
690                 695                 700

Pro Ile Ile Asp Lys Ala Arg Thr Gly Ser His Leu Asp Asn Leu Lys
705                 710                 715                 720

Glu Val Val Gly Glu Leu Ala Gly Ser Pro Ala Ile Lys Lys Gly Ile
            725                 730                 735

Leu Gln Ser Leu Lys Ile Val Asp Glu Leu Val Lys Val Met Gly Tyr
        740                 745                 750

Glu Pro Glu Gln Ile Val Val Glu Met Ala Arg Glu Asn Gln Thr Thr
    755                 760                 765

Ala Lys Gly Leu Ser Arg Ser Arg Gln Arg Leu Thr Thr Leu Arg Glu
770                 775                 780

Ser Leu Ala Asn Leu Lys Ser Asn Ile Leu Glu Glu Lys Lys Pro Lys
785                 790                 795                 800

Tyr Val Lys Asp Gln Val Glu Asn His His Leu Ser Asp Asp Arg Leu
            805                 810                 815

Phe Leu Tyr Tyr Leu Gln Asn Gly Lys Asp Met Tyr Thr Asp Asp Glu
        820                 825                 830

Leu Asp Ile Asp Asn Leu Ser Gln Tyr Asp Ile Asp His Ile Ile Pro
    835                 840                 845

Gln Ala Phe Ile Lys Asp Asp Ser Ile Asp Asn Arg Val Leu Val Ser
850                 855                 860

Ser Ala Lys Asn Arg Gly Lys Ser Asp Asp Val Pro Ser Leu Glu Ile
865                 870                 875                 880
```

-continued

Val Lys Asp Cys Lys Val Phe Trp Lys Lys Leu Leu Asp Ala Lys Leu
                885                 890                 895

Met Ser Gln Arg Lys Tyr Asp Asn Leu Thr Lys Ala Glu Arg Gly Gly
            900                 905                 910

Leu Thr Ser Asp Asp Lys Ala Arg Phe Ile Gln Arg Gln Leu Val Glu
            915                 920                 925

Thr Arg Gln Ile Thr Lys His Val Ala Arg Ile Leu Asp Glu Arg Phe
        930                 935                 940

Asn Asn Glu Leu Asp Ser Lys Gly Arg Arg Ile Arg Lys Val Lys Ile
945                 950                 955                 960

Val Thr Leu Lys Ser Asn Leu Val Ser Asn Phe Arg Lys Glu Phe Gly
                965                 970                 975

Phe Tyr Lys Ile Arg Glu Val Asn Asn Tyr His His Ala His Asp Ala
            980                 985                 990

Tyr Leu Asn Ala Val Val Ala Lys Ala Ile Leu Thr Lys Tyr Pro Gln
        995                 1000                1005

Leu Glu Pro Glu Phe Val Tyr Gly Asp Tyr Pro Lys Tyr Asn Ser
    1010                1015                1020

Tyr Lys Thr Arg Lys Ser Ala Thr Glu Lys Leu Phe Phe Tyr Ser
    1025                1030                1035

Asn Ile Met Asn Phe Phe Lys Thr Lys Val Thr Leu Ala Asp Gly
    1040                1045                1050

Thr Val Val Lys Asp Asp Ile Glu Val Asn Asn Asp Thr Gly
    1055                1060                1065

Glu Ile Val Trp Asp Lys Lys His Phe Ala Thr Val Arg Lys
    1070                1075                1080

Val Leu Ser Tyr Pro Gln Val Asn Ile Val Lys Lys Thr Glu Val
    1085                1090                1095

Gln Thr Gly Gly Phe Ser Lys Glu Ser Ile Leu Ala His Gly Asn
    1100                1105                1110

Ser Asp Lys Leu Ile Pro Arg Lys Thr Lys Asp Ile Tyr Leu Asp
    1115                1120                1125

Pro Lys Lys Tyr Gly Gly Phe Asp Ser Pro Ile Val Ala Tyr Ser
    1130                1135                1140

Val Leu Val Val Ala Asp Ile Lys Lys Gly Lys Ala Gln Lys Leu
    1145                1150                1155

Lys Thr Val Thr Glu Leu Leu Gly Ile Thr Ile Met Glu Arg Ser
    1160                1165                1170

Arg Phe Glu Lys Asn Pro Ser Ala Phe Leu Glu Ser Lys Gly Tyr
    1175                1180                1185

Leu Asn Ile Arg Thr Asp Lys Leu Ile Ile Leu Pro Lys Tyr Ser
    1190                1195                1200

Leu Phe Glu Leu Glu Asn Gly Arg Arg Arg Leu Leu Ala Ser Ala
    1205                1210                1215

Gly Glu Leu Gln Lys Gly Asn Glu Leu Ala Leu Pro Thr Gln Tyr
    1220                1225                1230

Met Lys Phe Leu Tyr Leu Ala Ser Arg Tyr Asn Glu Leu Lys Gly
    1235                1240                1245

Lys Pro Glu Glu Ile Glu Gln Lys Gln Glu Phe Val Val Gln His
    1250                1255                1260

Val Ser Tyr Phe Asp Asp Ile Leu Gln Ile Ile Asn Asp Phe Ser
    1265                1270                1275

Asn Arg Val Ile Leu Ala Asp Ala Asn Leu Glu Lys Ile Asn Lys

-continued

```
                1280                1285                1290
Leu Tyr Gln Asp Asn Lys Glu Asn Ile Pro Val Asp Glu Leu Ala
        1295                1300                1305
Asn Asn Ile Ile Asn Leu Phe Thr Phe Thr Ser Leu Gly Ala Pro
        1310                1315                1320
Ala Ala Phe Lys Phe Phe Asp Lys Ile Val Asp Arg Lys Arg Tyr
        1325                1330                1335
Thr Ser Thr Lys Glu Val Leu Asn Ser Thr Leu Ile His Gln Ser
        1340                1345                1350
Ile Thr Gly Leu Tyr Glu Thr Arg Ile Asp Leu Gly Lys Leu Gly
        1355                1360                1365
Glu Gly
    1370

<210> SEQ ID NO 62
<211> LENGTH: 1345
<212> TYPE: PRT
<213> ORGANISM: Streptococcus mutans

<400> SEQUENCE: 62

Met Lys Lys Pro Tyr Ser Ile Gly Leu Asp Ile Gly Thr Asn Ser Val
1               5                   10                  15

Gly Trp Ala Val Val Thr Asp Asp Tyr Lys Val Pro Ala Lys Lys Met
            20                  25                  30

Lys Val Leu Gly Asn Thr Asp Lys Ser His Ile Lys Lys Asn Leu Leu
        35                  40                  45

Gly Ala Leu Leu Phe Asp Ser Gly Asn Thr Ala Glu Asp Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Glu Glu Met Gly Lys Val Asp Asp Ser
                85                  90                  95

Phe Phe His Arg Leu Glu Asp Ser Phe Leu Val Thr Glu Asp Lys Arg
            100                 105                 110

Gly Glu Arg His Pro Ile Phe Gly Asn Leu Glu Glu Val Lys Tyr
        115                 120                 125

His Glu Asn Phe Pro Thr Ile Tyr His Leu Arg Gln Tyr Leu Ala Asp
    130                 135                 140

Asn Pro Glu Lys Val Asp Leu Arg Leu Val Tyr Leu Ala Leu Ala His
145                 150                 155                 160

Ile Ile Lys Phe Arg Gly His Phe Leu Ile Glu Gly Lys Phe Asp Thr
                165                 170                 175

Arg Asn Asn Asp Val Gln Arg Leu Phe Gln Glu Phe Leu Ala Val Tyr
            180                 185                 190

Asp Asn Thr Phe Glu Asn Ser Ser Leu Gln Glu Gln Asn Val Gln Val
        195                 200                 205

Glu Glu Ile Leu Thr Asp Lys Ile Ser Lys Ser Ala Lys Lys Asp Arg
    210                 215                 220

Val Leu Lys Leu Phe Pro Asn Glu Lys Ser Asn Gly Arg Phe Ala Glu
225                 230                 235                 240

Phe Leu Lys Leu Ile Val Gly Asn Gln Ala Asp Phe Lys Lys His Phe
                245                 250                 255

Glu Leu Glu Glu Lys Ala Pro Leu Gln Phe Ser Lys Asp Thr Tyr Glu
            260                 265                 270
```

-continued

```
Glu Glu Leu Glu Val Leu Leu Ala Gln Ile Gly Asp Asn Tyr Ala Glu
            275                 280                 285
Leu Phe Leu Ser Ala Lys Lys Leu Tyr Asp Ser Ile Leu Leu Ser Gly
            290                 295                 300
Ile Leu Thr Val Thr Asp Val Ser Thr Lys Ala Pro Leu Ser Ala Ser
305                 310                 315                 320
Met Ile Gln Arg Tyr Asn Glu His Gln Met Asp Leu Ala Gln Leu Lys
                325                 330                 335
Gln Phe Ile Arg Gln Lys Leu Ser Asp Lys Tyr Asn Glu Val Phe Ser
            340                 345                 350
Asp Val Ser Lys Asp Gly Tyr Ala Gly Tyr Ile Asp Gly Lys Thr Asn
            355                 360                 365
Gln Glu Ala Phe Tyr Lys Tyr Leu Lys Gly Leu Leu Asn Lys Ile Glu
370                 375                 380
Gly Ser Gly Tyr Phe Leu Asp Lys Ile Glu Arg Glu Asp Phe Leu Arg
385                 390                 395                 400
Lys Gln Arg Thr Phe Asp Asn Gly Ser Ile Pro His Gln Ile His Leu
                405                 410                 415
Gln Glu Met Arg Ala Ile Ile Arg Arg Gln Ala Glu Phe Tyr Pro Phe
            420                 425                 430
Leu Ala Asp Asn Gln Asp Arg Ile Glu Lys Ile Leu Thr Phe Arg Ile
            435                 440                 445
Pro Tyr Tyr Val Gly Pro Leu Ala Arg Gly Lys Ser Asp Phe Ala Trp
            450                 455                 460
Leu Ser Arg Lys Ser Ala Asp Lys Ile Thr Pro Trp Asn Phe Asp Glu
465                 470                 475                 480
Ile Val Asp Lys Glu Ser Ser Ala Glu Ala Phe Ile Asn Arg Met Thr
                485                 490                 495
Asn Tyr Asp Leu Tyr Leu Pro Asn Gln Lys Val Leu Pro Lys His Ser
            500                 505                 510
Leu Leu Tyr Glu Lys Phe Thr Val Tyr Asn Glu Leu Thr Lys Val Lys
            515                 520                 525
Tyr Lys Thr Glu Gln Gly Lys Thr Ala Phe Phe Asp Ala Asn Met Lys
            530                 535                 540
Gln Glu Ile Phe Asp Gly Val Phe Lys Val Tyr Arg Lys Val Thr Lys
545                 550                 555                 560
Asp Lys Leu Met Asp Phe Leu Glu Lys Glu Phe Asp Glu Phe Arg Ile
                565                 570                 575
Val Asp Leu Thr Gly Leu Asp Lys Glu Asn Lys Val Phe Asn Ala Ser
            580                 585                 590
Tyr Gly Thr Tyr His Asp Leu Cys Lys Ile Leu Asp Lys Asp Phe Leu
            595                 600                 605
Asp Asn Ser Lys Asn Glu Lys Ile Leu Glu Asp Ile Val Leu Thr Leu
610                 615                 620
Thr Leu Phe Glu Asp Arg Glu Met Ile Arg Lys Arg Leu Glu Asn Tyr
625                 630                 635                 640
Ser Asp Leu Leu Thr Lys Glu Gln Val Lys Lys Leu Glu Arg His
                645                 650                 655
Tyr Thr Gly Trp Gly Arg Leu Ser Ala Glu Leu Ile His Gly Ile Arg
            660                 665                 670
Asn Lys Glu Ser Arg Lys Thr Ile Leu Asp Tyr Leu Ile Asp Asp Gly
            675                 680                 685
Asn Ser Asn Arg Asn Phe Met Gln Leu Ile Asn Asp Asp Ala Leu Ser
```

```
            690             695             700
        Phe Lys Glu Glu Ile Ala Lys Ala Gln Val Ile Gly Glu Thr Asp Asn
        705             710             715             720

Leu Asn Gln Val Val Ser Asp Ile Ala Gly Ser Pro Ala Ile Lys Lys
                    725             730             735

Gly Ile Leu Gln Ser Leu Lys Ile Val Asp Glu Leu Val Lys Ile Met
                    740             745             750

Gly His Gln Pro Glu Asn Ile Val Val Glu Met Ala Arg Glu Asn Gln
                    755             760             765

Phe Thr Asn Gln Gly Arg Gln Asn Ser Gln Gln Arg Leu Lys Gly Leu
                    770             775             780

Thr Asp Ser Ile Lys Glu Phe Gly Ser Gln Ile Leu Lys Glu His Pro
        785             790             795             800

Val Glu Asn Ser Gln Leu Gln Asn Asp Arg Leu Phe Leu Tyr Tyr Leu
                    805             810             815

Gln Asn Gly Arg Asp Met Tyr Thr Gly Glu Glu Leu Asp Ile Asp Tyr
                    820             825             830

Leu Ser Gln Tyr Asp Ile Asp His Ile Ile Pro Gln Ala Phe Ile Lys
                    835             840             845

Asp Asn Ser Ile Asp Asn Arg Val Leu Thr Ser Ser Lys Glu Asn Arg
        850             855             860

Gly Lys Ser Asp Val Pro Ser Glu Asp Val Val Arg Lys Met Lys
        865             870             875             880

Ser Tyr Trp Ser Lys Leu Leu Ser Ala Lys Leu Ile Thr Gln Arg Lys
                    885             890             895

Phe Asp Asn Leu Thr Lys Ala Glu Arg Gly Gly Leu Thr Asp Asp Asp
                    900             905             910

Lys Ala Gly Phe Ile Lys Arg Gln Leu Val Glu Thr Arg Gln Ile Thr
                    915             920             925

Lys His Val Ala Arg Ile Leu Asp Glu Arg Phe Tyr Thr Glu Thr Asp
                    930             935             940

Glu Asn Asn Lys Lys Ile Arg Gln Val Lys Ile Val Thr Leu Lys Ser
        945             950             955             960

Asn Leu Val Ser Asn Phe Arg Lys Glu Phe Glu Leu Tyr Lys Val Arg
                    965             970             975

Glu Ile Asn Asp Tyr His His Ala His Asp Ala Tyr Leu Asn Ala Val
                    980             985             990

Ile Gly Lys Ala Leu Leu Gly Val Tyr Pro Gln Leu Glu Pro Glu Phe
                    995            1000            1005

Val Tyr Gly Asp Tyr Pro His Phe His Gly His Lys Glu Asn Lys
        1010            1015            1020

Ala Thr Ala Lys Lys Phe Phe Tyr Ser Asn Ile Met Asn Phe Phe
                    1025            1030            1035

Lys Lys Asp Asp Val Arg Thr Asp Lys Asn Gly Glu Ile Ile Trp
                    1040            1045            1050

Lys Lys Asp Glu His Ile Ser Asn Ile Lys Lys Val Leu Ser Tyr
                    1055            1060            1065

Pro Gln Val Asn Ile Val Lys Lys Val Glu Glu Gln Thr Gly Gly
                    1070            1075            1080

Phe Ser Lys Glu Ser Ile Leu Pro Lys Gly Asn Ser Asp Lys Leu
                    1085            1090            1095

Ile Pro Arg Lys Thr Lys Lys Phe Tyr Trp Asp Thr Lys Lys Tyr
                    1100            1105            1110
```

```
Gly Gly Phe Asp Ser Pro Ile Val Ala Tyr Ser Ile Leu Val Ile
    1115                1120                1125

Ala Asp Ile Glu Lys Gly Lys Ser Lys Leu Lys Thr Val Lys
    1130                1135                1140

Ala Leu Val Gly Val Thr Ile Met Glu Lys Met Thr Phe Glu Arg
    1145                1150                1155

Asp Pro Val Ala Phe Leu Glu Arg Lys Gly Tyr Arg Asn Val Gln
    1160                1165                1170

Glu Glu Asn Ile Ile Lys Leu Pro Lys Tyr Ser Leu Phe Lys Leu
    1175                1180                1185

Glu Asn Gly Arg Lys Arg Leu Leu Ala Ser Ala Arg Glu Leu Gln
    1190                1195                1200

Lys Gly Asn Glu Ile Val Leu Pro Asn His Leu Gly Thr Leu Leu
    1205                1210                1215

Tyr His Ala Lys Asn Ile His Lys Val Asp Glu Pro Lys His Leu
    1220                1225                1230

Asp Tyr Val Asp Lys His Lys Asp Glu Phe Lys Glu Leu Leu Asp
    1235                1240                1245

Val Val Ser Asn Phe Ser Lys Lys Tyr Thr Leu Ala Glu Gly Asn
    1250                1255                1260

Leu Glu Lys Ile Lys Glu Leu Tyr Ala Gln Asn Asn Gly Glu Asp
    1265                1270                1275

Leu Lys Glu Leu Ala Ser Ser Phe Ile Asn Leu Leu Thr Phe Thr
    1280                1285                1290

Ala Ile Gly Ala Pro Ala Thr Phe Lys Phe Phe Asp Lys Asn Ile
    1295                1300                1305

Asp Arg Lys Arg Tyr Thr Ser Thr Thr Glu Ile Leu Asn Ala Thr
    1310                1315                1320

Leu Ile His Gln Ser Ile Thr Gly Leu Tyr Glu Thr Arg Ile Asp
    1325                1330                1335

Leu Ser Lys Leu Gly Gly Asp
    1340                1345

<210> SEQ ID NO 63
<211> LENGTH: 1347
<212> TYPE: PRT
<213> ORGANISM: Streptococcus plurextorum

<400> SEQUENCE: 63

Met Gln Lys Thr Tyr Ser Ile Gly Leu Asp Ile Gly Thr Asn Ser Val
1               5                   10                  15

Gly Phe Ser Val Val Thr Asp Asp Tyr Lys Val Pro Ser Lys Lys Met
                20                  25                  30

Lys Val Asn Gly Asn Thr Asp Lys Lys Tyr Leu Lys Lys Asn Leu Leu
            35                  40                  45

Gly Thr Leu Leu Phe Asp Ser Gly Glu Thr Ala Ala Gly Thr Arg Met
        50                  55                  60

Arg Arg Thr Thr Arg Arg Tyr Val Arg Arg Asn Asn Arg Leu Arg
65                  70                  75                  80

Tyr Leu Gln Glu Ile Phe Ala Asp Gln Met Glu Gln Ile Asp Pro Asn
                85                  90                  95

Phe Phe His Arg Leu Lys Glu Ser Phe Leu Asp Glu Asp Lys Gln
                100                 105                 110

Phe Glu Gln His Pro Ile Phe Gly Thr Leu Ala Glu Glu Val Ala Tyr
```

```
            115                 120                 125
His Gln Gln Phe Pro Thr Ile Tyr His Leu Arg Lys His Leu Ala Asp
    130                 135                 140

Ser Lys Glu Gln Val Asp Leu Arg Leu Val Tyr Met Ala Leu Ala His
145                 150                 155                 160

Ile Ile Lys Tyr Arg Gly His Phe Leu Ile Glu Gly Gly Leu Glu Ser
                165                 170                 175

Gln Ala Val Gly Ile Gln Gln Leu Phe Asp Glu Phe Val Gln Val Tyr
            180                 185                 190

Asp Ser Val Phe Glu Gly Ser Asp Leu Val Ser Ile His Ala Glu Val
        195                 200                 205

Glu Pro Ile Leu Val Asp Lys Leu Ser Lys Ser Val Lys Lys Asp Arg
    210                 215                 220

Val Met Gln Leu Phe Pro Thr Glu Lys Ser Asn Gly Asn Phe Ala Glu
225                 230                 235                 240

Phe Met Lys Leu Ile Val Gly Asn Gln Ala Asp Phe Lys Lys Val Phe
                245                 250                 255

Ser Leu Asp Glu Lys Ala Val Leu Gln Leu Ser Lys Asp Thr Tyr Glu
            260                 265                 270

Glu Glu Leu Ala Asp Leu Leu Gly Lys Val Gly Asp Asp Tyr Leu Asp
        275                 280                 285

Leu Phe His Ala Ala Lys Arg Leu Tyr Asp Ala Val Leu Leu Ala Gly
    290                 295                 300

Ile Ile Thr Ser Gln Asp Ile Ala Thr Lys Ala Pro Leu Ser Ala Ser
305                 310                 315                 320

Met Val Gln Arg Tyr Glu Glu His Gln Ser Asp Leu Lys Ala Leu Lys
                325                 330                 335

Lys His Ile Pro Asn Tyr Lys Pro Asp Glu Arg Lys Leu Tyr Lys Glu
            340                 345                 350

Met Phe Asn Asp Ser Thr Lys Asn Gly Tyr Ala Gly Tyr Ile Glu Gly
        355                 360                 365

Gly Val Lys Gln Glu Glu Phe Tyr Lys Tyr Thr Lys Ala Leu Leu Ser
    370                 375                 380

Glu Ile Glu Asn Ser Gln Tyr Phe Ile Asp Lys Ile Glu Arg Glu Asp
385                 390                 395                 400

Phe Leu Arg Lys Gln Arg Thr Phe Asp Asn Gly Ala Ile Pro His Gln
                405                 410                 415

Ile His Leu Gln Glu Leu Lys Ala Ile Val Arg Arg Gln Gly Glu His
            420                 425                 430

Tyr Pro Phe Leu Lys Glu Glu Gln His Lys Ile Glu Ala Leu Leu Thr
        435                 440                 445

Phe Arg Ile Pro Tyr Tyr Val Gly Pro Leu Ala Arg Gly Asn Ser Arg
    450                 455                 460

Phe Ala Trp Ala Val Arg Lys Ser Asn Glu Lys Ile Thr Pro Trp Asn
465                 470                 475                 480

Phe Glu Glu Ile Ile Asp Lys Glu Ser Ala Arg Lys Phe Ile Glu
                485                 490                 495

Arg Met Thr Asn Val Asp Leu Tyr Leu Pro Asp Glu Lys Val Leu Pro
            500                 505                 510

Lys His Ser Phe Leu Tyr Glu Lys Phe Ala Val Phe Asn Glu Leu Thr
        515                 520                 525

Lys Val Lys Tyr Ile Thr Glu Gln Gly Lys Glu Glu Phe Phe Asp Cys
    530                 535                 540
```

```
His Leu Lys Arg Glu Ile Phe Glu Gln Val Phe Lys Asn Ser Arg Lys
545                 550                 555                 560

Val Lys Lys Lys Asp Leu Leu Asn Phe Leu Asp Lys Glu Phe Glu Glu
                565                 570                 575

Phe Arg Ile Val Asp Ile Thr Gly Leu Asp Ser Glu Lys Gln Glu Phe
            580                 585                 590

Asn Ala Ser Leu Gly Thr Tyr His Asp Leu Lys Lys Ile Leu Asp Lys
        595                 600                 605

Asp Phe Leu Asp Asp Val Ala Asn Glu His Leu Leu Glu Glu Leu Ile
    610                 615                 620

Leu Thr Leu Thr Leu Phe Glu Asp Arg Glu Met Ile Arg Lys Arg Leu
625                 630                 635                 640

Ser Lys Tyr Ser Glu Ala Leu Thr Lys Glu Gln Leu Lys Lys Leu Glu
                645                 650                 655

Arg Arg His Tyr Thr Gly Trp Gly Arg Leu Ser Ala Lys Leu Leu Asn
            660                 665                 670

Gly Ile Arg His Lys Ala Thr Asn Lys Thr Ile Leu Asp Tyr Leu Met
        675                 680                 685

Asp Asp Gly Gln Ile Asn Arg Asn Phe Met Gln Leu Ile His Asp Asp
    690                 695                 700

Gly Leu Asp Phe Lys Thr Ile Ile Ser Glu Ala Gln Val Ile Gly Glu
705                 710                 715                 720

Arg Asp Asp Leu Lys Ala Ile Val Asp Asp Ile Ala Gly Ser Pro Ala
                725                 730                 735

Ile Lys Lys Gly Ile Leu Gln Ser Leu Lys Val Val Glu Glu Leu Val
            740                 745                 750

Ser Ile Met Gly His Asn Pro Glu Ser Ile Ile Glu Met Ala Arg
        755                 760                 765

Glu Asn Gln Thr Thr Gln Lys Gly Arg Lys Asn Ser Gln Gln Arg Leu
    770                 775                 780

Thr Gly Leu Thr Asn Ser Ile Arg Glu Leu Gly Ser Asp Ile Leu Lys
785                 790                 795                 800

Glu Phe Pro Val Asp Asn Ser Gln Leu Gln Asn Asp Arg Leu Tyr Leu
                805                 810                 815

Tyr Tyr Leu Gln Asn Gly Lys Asp Met Tyr Thr Gly Glu Thr Leu Asn
            820                 825                 830

Ile Asp Gln Leu Ser His Tyr Asp Ile Asp His Ile Ile Pro Gln Ser
        835                 840                 845

Phe Ile Lys Asp Asp Ser Leu Asp Asn Arg Val Leu Thr Ser Ser Lys
    850                 855                 860

Ser Asn Arg Gly Lys Ser Asp Ser Val Pro Ser Gln Glu Ile Val Gln
865                 870                 875                 880

Lys Met Lys Pro Phe Trp Lys Leu Arg Asp Ala Gln Leu Ile Ser
                885                 890                 895

Lys Arg Lys Phe Asp Asn Leu Thr Lys Ser Glu Arg Gly Gly Leu Ser
            900                 905                 910

Gln Glu Asp Lys Ala Gly Phe Ile Lys Arg Gln Leu Val Glu Thr Arg
        915                 920                 925

Gln Ile Thr Lys His Val Ala Arg Ile Leu Asp Glu Arg Phe Asn Gln
    930                 935                 940

Lys Arg Asp Asp Asn Asn Lys Leu Ile Arg Asp Val Lys Ile Ile Thr
945                 950                 955                 960
```

-continued

```
Leu Lys Ser Asn Leu Val Ser Gln Phe Arg Lys Glu Phe Glu Leu Tyr
            965                 970                 975
Lys Ile Arg Glu Leu Asn Asp Tyr His His Ala His Asp Ala Tyr Leu
            980                 985                 990
Asn Ala Val Val Gly Lys Ala Leu  Leu Ala Lys Tyr Pro  Gln Leu Glu
            995                 1000                1005
Ala Glu Phe Val Phe Gly Asp  Tyr Pro Lys Tyr Asn  Ser Tyr Lys
       1010                 1015                1020
Glu Arg Met Thr Ala Thr Gln  Lys Val Leu Phe Tyr  Ser Asn Ile
       1025                 1030                1035
Leu Asn Phe Leu Lys Asp Gly  Asn Lys His Gly Asn  Glu Asp Gly
       1040                 1045                1050
Glu Val Ile Trp Asp Pro Asn  Tyr His Leu Pro Met  Ile Lys Lys
       1055                 1060                1065
Val Leu Ser Tyr Pro Gln Val  Asn Ile Val Lys Lys  Thr Glu Ile
       1070                 1075                1080
Gln Thr Gly Gly Phe Ser Lys  Glu Ser Ile Leu Pro  Lys Gly Asp
       1085                 1090                1095
Ser Asp Lys Leu Ile Arg Arg  Lys Asn Asn Trp Asp  Pro Lys Lys
       1100                 1105                1110
Tyr Gly Gly Phe Asp Ser Pro  Thr Val Ala Tyr Ser  Val Leu Val
       1115                 1120                1125
Ile Ala Asp Val Ala Lys Gly  Lys Ala Gln Lys Leu  Lys Thr Val
       1130                 1135                1140
Lys Glu Leu Val Gly Ile Thr  Ile Met Glu Arg Ser  Ala Phe Glu
       1145                 1150                1155
Lys Asn Pro Ile Val Phe Leu  Glu Ser Lys Gly Tyr  Gln Asn Ile
       1160                 1165                1170
Gln Glu Lys Asn Ile Ile Lys  Leu Pro Lys Tyr Ser  Leu Phe Glu
       1175                 1180                1185
Leu Glu Glu Gly Arg Arg Arg  Leu Leu Ala Ser Ala  Ile Glu Leu
       1190                 1195                1200
Gln Lys Gly Asn Gln Leu Val  Leu Ser Gln Glu Gln  Ile Asn Leu
       1205                 1210                1215
Leu Tyr His Ala Gln Arg Val  Lys Asn Leu Glu Gln  Pro Glu His
       1220                 1225                1230
Leu Arg Tyr Val Glu Glu His  Lys Ala Glu Phe Glu  Val Ile Leu
       1235                 1240                1245
Asn Thr Leu Leu Ile Ala Ala  Glu Arg Tyr Ile Leu  Lys Pro Lys
       1250                 1255                1260
Val Ile Glu Met Ile Lys Lys  Ala Leu Glu Ser Asn  Gln Leu Asp
       1265                 1270                1275
Ile Thr Gln Tyr Ala Glu Ser  Phe Val Asn Leu Leu  Lys Phe Thr
       1280                 1285                1290
Ala Phe Gly Ala Pro Gly Gly  Phe Lys Cys Phe Gly  Ile Glu Ile
       1295                 1300                1305
Lys Gln Ala Asn Leu Arg Tyr  Gln Thr Val Thr Glu  Cys Leu Asn
       1310                 1315                1320
Ala Thr Leu Ile His Gln Tyr  Val Thr Gly Leu Tyr  Glu Thr Arg
       1325                 1330                1335
Ile Asp Leu Ser Lys Leu Gly  Gly Glu
       1340                 1345
```

```
<210> SEQ ID NO 64
<211> LENGTH: 1388
<212> TYPE: PRT
<213> ORGANISM: Streptococcus thermophilus

<400> SEQUENCE: 64
```

| Met | Thr | Lys | Pro | Tyr | Ser | Ile | Gly | Leu | Asp | Ile | Gly | Thr | Asn | Ser | Val |
|---|---|---|---|---|---|---|---|---|---|---|---|---|---|---|---|
| 1 | | | | 5 | | | | | 10 | | | | | 15 | |

| Gly | Trp | Ala | Val | Ile | Thr | Asp | Asn | Tyr | Lys | Val | Pro | Ser | Lys | Lys | Met |
|  |  | 20 |  |  |  |  | 25 |  |  |  |  | 30 |  |  |  |

| Lys | Val | Leu | Gly | Asn | Thr | Ser | Lys | Lys | Tyr | Ile | Lys | Lys | Asn | Leu | Leu |
|  |  |  | 35 |  |  |  |  | 40 |  |  |  |  | 45 |  |  |

| Gly | Val | Leu | Leu | Phe | Asp | Ser | Gly | Ile | Thr | Ala | Glu | Gly | Arg | Arg | Leu |
|  | 50 |  |  |  |  |  | 55 |  |  |  |  | 60 |  |  |  |

| Lys | Arg | Thr | Ala | Arg | Arg | Arg | Tyr | Thr | Arg | Arg | Arg | Asn | Arg | Ile | Leu |
| 65 |  |  |  |  | 70 |  |  |  |  | 75 |  |  |  |  | 80 |

| Tyr | Leu | Gln | Glu | Ile | Phe | Ser | Thr | Glu | Met | Ala | Thr | Leu | Asp | Asp | Ala |
|  |  |  |  | 85 |  |  |  |  | 90 |  |  |  |  | 95 |  |

| Phe | Phe | Gln | Arg | Leu | Asp | Asp | Ser | Phe | Leu | Val | Pro | Asp | Asp | Lys | Arg |
|  |  |  | 100 |  |  |  |  | 105 |  |  |  |  | 110 |  |  |

| Asp | Ser | Lys | Tyr | Pro | Ile | Phe | Gly | Asn | Leu | Val | Glu | Glu | Lys | Ala | Tyr |
|  |  | 115 |  |  |  |  | 120 |  |  |  |  | 125 |  |  |  |

| His | Asp | Glu | Phe | Pro | Thr | Ile | Tyr | His | Leu | Arg | Lys | Tyr | Leu | Ala | Asp |
| 130 |  |  |  |  | 135 |  |  |  |  | 140 |  |  |  |  |  |

| Ser | Thr | Lys | Lys | Ala | Asp | Leu | Arg | Leu | Val | Tyr | Leu | Ala | Leu | Ala | His |
| 145 |  |  |  |  | 150 |  |  |  |  | 155 |  |  |  |  | 160 |

| Met | Ile | Lys | Tyr | Arg | Gly | His | Phe | Leu | Ile | Glu | Gly | Glu | Phe | Asn | Ser |
|  |  |  |  | 165 |  |  |  |  | 170 |  |  |  |  | 175 |  |

| Lys | Asn | Asn | Asp | Ile | Gln | Lys | Asn | Phe | Gln | Asp | Phe | Leu | Asp | Thr | Tyr |
|  |  |  | 180 |  |  |  |  | 185 |  |  |  |  | 190 |  |  |

| Asn | Ala | Ile | Phe | Glu | Ser | Asp | Leu | Ser | Leu | Glu | Asn | Ser | Lys | Gln | Leu |
|  |  |  | 195 |  |  |  |  | 200 |  |  |  |  | 205 |  |  |

| Glu | Glu | Ile | Val | Lys | Asp | Lys | Ile | Ser | Lys | Leu | Glu | Lys | Lys | Asp | Arg |
|  | 210 |  |  |  |  | 215 |  |  |  |  | 220 |  |  |  |  |

| Ile | Leu | Lys | Leu | Phe | Pro | Gly | Glu | Lys | Asn | Ser | Gly | Ile | Phe | Ser | Glu |
| 225 |  |  |  |  | 230 |  |  |  |  | 235 |  |  |  |  | 240 |

| Phe | Leu | Lys | Leu | Ile | Val | Gly | Asn | Gln | Ala | Asp | Phe | Arg | Lys | Cys | Phe |
|  |  |  |  | 245 |  |  |  |  | 250 |  |  |  |  | 255 |  |

| Asn | Leu | Asp | Glu | Lys | Ala | Ser | Leu | His | Phe | Ser | Lys | Glu | Ser | Tyr | Asp |
|  |  |  | 260 |  |  |  |  | 265 |  |  |  |  | 270 |  |  |

| Glu | Asp | Leu | Glu | Thr | Leu | Leu | Gly | Tyr | Ile | Gly | Asp | Asp | Tyr | Ser | Asp |
|  |  | 275 |  |  |  |  | 280 |  |  |  |  | 285 |  |  |  |

| Val | Phe | Leu | Lys | Ala | Lys | Lys | Leu | Tyr | Asp | Ala | Ile | Leu | Leu | Ser | Gly |
|  | 290 |  |  |  |  | 295 |  |  |  |  | 300 |  |  |  |  |

| Phe | Leu | Thr | Val | Thr | Asp | Asn | Glu | Thr | Glu | Ala | Pro | Leu | Ser | Ser | Ala |
| 305 |  |  |  |  | 310 |  |  |  |  | 315 |  |  |  |  | 320 |

| Met | Ile | Lys | Arg | Tyr | Asn | Glu | His | Lys | Glu | Asp | Leu | Ala | Leu | Leu | Lys |
|  |  |  |  | 325 |  |  |  |  | 330 |  |  |  |  | 335 |  |

| Glu | Tyr | Ile | Arg | Asn | Ile | Ser | Leu | Lys | Thr | Tyr | Asn | Glu | Val | Phe | Lys |
|  |  |  | 340 |  |  |  |  | 345 |  |  |  |  | 350 |  |  |

| Asp | Asp | Thr | Lys | Asn | Gly | Tyr | Ala | Gly | Tyr | Ile | Asp | Gly | Lys | Thr | Asn |
|  |  | 355 |  |  |  |  | 360 |  |  |  |  | 365 |  |  |  |

| Gln | Glu | Asp | Phe | Tyr | Val | Tyr | Leu | Lys | Asn | Leu | Leu | Ala | Glu | Phe | Glu |
|  | 370 |  |  |  |  | 375 |  |  |  |  | 380 |  |  |  |  |

```
Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
            405                 410                 415

Gln Glu Met Arg Ala Ile Leu Asp Lys Gln Ala Lys Phe Tyr Pro Phe
        420                 425                 430

Leu Ala Lys Asn Lys Glu Arg Ile Glu Lys Ile Leu Thr Phe Arg Ile
            435                 440                 445

Pro Tyr Tyr Val Gly Pro Leu Ala Arg Gly Asn Ser Asp Phe Ala Trp
        450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
            485                 490                 495

Ser Phe Asp Leu Tyr Leu Pro Glu Glu Lys Val Leu Pro Lys His Ser
        500                 505                 510

Leu Leu Tyr Glu Thr Phe Asn Val Tyr Asn Glu Leu Thr Lys Val Arg
            515                 520                 525

Phe Ile Ala Glu Ser Met Arg Asp Tyr Gln Phe Leu Asp Ser Lys Gln
        530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
            565                 570                 575

Ile Glu Leu Lys Gly Ile Glu Lys Gln Phe Asn Ser Ser Leu Ser Thr
        580                 585                 590

Tyr His Asp Leu Leu Asn Ile Ile Asn Asp Lys Glu Phe Leu Asp Asp
        595                 600                 605

Ser Ser Asn Glu Ala Ile Ile Glu Glu Ile Ile His Thr Leu Thr Ile
        610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
            645                 650                 655

Gly Trp Gly Lys Leu Ser Ala Lys Leu Ile Asn Gly Ile Arg Asp Glu
        660                 665                 670

Lys Ser Gly Asn Thr Ile Leu Asp Tyr Leu Ile Asp Asp Gly Ile Ser
        675                 680                 685

Asn Arg Asn Phe Met Gln Leu Ile His Asp Asp Ala Leu Ser Phe Lys
690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
            725                 730                 735

Gly Ile Leu Gln Ser Ile Lys Ile Val Asp Glu Leu Val Lys Val Met
        740                 745                 750

Gly Gly Arg Lys Pro Glu Ser Ile Val Val Glu Met Ala Arg Glu Asn
            755                 760                 765

Gln Tyr Thr Asn Gln Gly Lys Ser Asn Ser Gln Arg Leu Lys Arg
        770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
```

```
                805                 810                 815
Arg Leu Tyr Leu Tyr Leu Gln Asn Gly Lys Asp Met Tyr Thr Gly
            820                 825                 830

Asp Asp Leu Asp Ile Asp Arg Leu Ser Asn Tyr Asp Ile Asp His Ile
        835                 840                 845

Ile Pro Gln Ala Phe Leu Lys Asp Asn Ser Ile Asp Asn Lys Val Leu
    850                 855                 860

Val Ser Ser Ala Ser Asn Arg Gly Lys Ser Asp Asp Phe Pro Ser Leu
865                 870                 875                 880

Glu Val Val Lys Lys Arg Lys Thr Phe Trp Tyr Gln Leu Leu Lys Ser
                885                 890                 895

Lys Leu Ile Ser Gln Arg Lys Phe Asp Asn Leu Thr Lys Ala Glu Arg
            900                 905                 910

Gly Gly Leu Leu Pro Glu Asp Lys Ala Gly Phe Ile Gln Arg Gln Leu
        915                 920                 925

Val Glu Thr Arg Gln Ile Thr Lys His Val Ala Arg Leu Leu Asp Glu
    930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Cys Glu Ile Asn Asp Phe His His Ala His
            980                 985                 990

Asp Ala Tyr Leu Asn Ala Val Ile Ala Ser Ala Leu Leu Lys Lys Tyr
        995                 1000                1005

Pro Lys Leu Glu Pro Glu Phe Val Tyr Gly Asp Tyr Pro Lys Tyr
    1010                1015                1020

Asn Ser Phe Arg Glu Arg Lys Ser Ala Thr Glu Lys Val Tyr Phe
    1025                1030                1035

Tyr Ser Asn Ile Met Asn Ile Phe Lys Lys Ser Ile Ser Leu Ala
    1040                1045                1050

Asp Gly Arg Val Ile Glu Arg Pro Leu Ile Glu Val Asn Glu Glu
    1055                1060                1065

Thr Gly Glu Ser Val Trp Asn Lys Glu Ser Asp Leu Ala Thr Val
    1070                1075                1080

Arg Arg Val Leu Ser Tyr Pro Gln Val Asn Val Val Lys Lys Val
    1085                1090                1095

Glu Glu Gln Asn His Gly Leu Asp Arg Gly Lys Pro Lys Gly Leu
    1100                1105                1110

Phe Asn Ala Asn Leu Ser Ser Lys Pro Lys Pro Asn Ser Asn Glu
    1115                1120                1125

Asn Leu Val Gly Ala Lys Glu Tyr Leu Asp Pro Lys Lys Tyr Gly
    1130                1135                1140

Gly Tyr Ala Gly Ile Ser Asn Ser Phe Ala Val Leu Val Lys Gly
    1145                1150                1155

Thr Ile Glu Lys Gly Ala Lys Lys Lys Ile Thr Asn Val Leu Glu
    1160                1165                1170

Phe Gln Gly Ile Ser Ile Leu Asp Arg Ile Asn Tyr Arg Lys Asp
    1175                1180                1185

Lys Leu Asn Phe Leu Leu Glu Lys Gly Tyr Lys Asp Ile Glu Leu
    1190                1195                1200

Ile Ile Glu Leu Pro Lys Tyr Ser Leu Phe Glu Leu Ser Asp Gly
    1205                1210                1215
```

```
Ser Arg  Arg Met Leu Ala Ser  Ile Leu Ser Thr Asn  Asn Lys Arg
    1220                 1225             1230

Gly Glu  Ile His Lys Gly Asn  Gln Ile Phe Leu Ser  Gln Lys Phe
    1235                 1240             1245

Val Lys  Leu Leu Tyr His Ala  Lys Arg Ile Ser Asn  Thr Ile Asn
    1250                 1255             1260

Glu Asn  His Arg Lys Tyr Val  Glu Asn His Lys Lys  Glu Phe Glu
    1265                 1270             1275

Glu Leu  Phe Tyr Tyr Ile Leu  Glu Phe Asn Glu Asn  Tyr Val Gly
    1280                 1285             1290

Ala Lys  Lys Asn Gly Lys Leu  Leu Asn Ser Ala Phe  Gln Ser Trp
    1295                 1300             1305

Gln Asn  His Ser Ile Asp Glu  Leu Cys Ser Ser Phe  Ile Gly Pro
    1310                 1315             1320

Thr Gly  Ser Glu Arg Lys Gly  Leu Phe Glu Leu Thr  Ser Arg Gly
    1325                 1330             1335

Ser Ala  Ala Asp Phe Glu Phe  Leu Gly Val Lys Ile  Pro Arg Tyr
    1340                 1345             1350

Arg Asp  Tyr Thr Pro Ser Ser  Leu Leu Lys Asp Ala  Thr Leu Ile
    1355                 1360             1365

His Gln  Ser Val Thr Gly Leu  Tyr Glu Thr Arg Ile  Asp Leu Ala
    1370                 1375             1380

Lys Leu  Gly Glu Gly
    1385

<210> SEQ ID NO 65
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tcgaattcca cttacggatc gttcaacgca ggctacggtt agctacctag tagg          54
```